United States Patent
Tada et al.

(10) Patent No.: US 12,421,201 B2
(45) Date of Patent: Sep. 23, 2025

(54) ORGANIC COMPOUND, OPTICAL DEVICE, LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Anna Tada, Kanagawa (JP); Sachiko Kawakami, Kanagawa (JP); Takumu Okuyama, Tokyo (JP); Tsunenori Suzuki, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 799 days.

(21) Appl. No.: 17/640,843

(22) PCT Filed: Sep. 16, 2020

(86) PCT No.: PCT/IB2020/058589
§ 371 (c)(1),
(2) Date: Mar. 7, 2022

(87) PCT Pub. No.: WO2021/059086
PCT Pub. Date: Apr. 1, 2021

(65) Prior Publication Data
US 2022/0367816 A1    Nov. 17, 2022

(30) Foreign Application Priority Data
Sep. 27, 2019  (JP) .................................. 2019-177516

(51) Int. Cl.
*C09K 11/06*    (2006.01)
*C07D 307/77*   (2006.01)
(Continued)

(52) U.S. Cl.
CPC ............ *C07D 307/77* (2013.01); *C09K 11/06* (2013.01); *F21V 31/005* (2013.01);
(Continued)

(58) Field of Classification Search
CPC .. H01K 85/636; H01K 85/633; C07D 307/77; C09K 11/06; F21V 31/005
See application file for complete search history.

(56) References Cited

U.S. PATENT DOCUMENTS

| 2014/0183500 A1 | 7/2014 | Ikeda et al. |
| 2015/0031900 A1 | 1/2015 | Kawakami et al. |

(Continued)

FOREIGN PATENT DOCUMENTS

| CN | 108689972 A | 10/2018 |
| CN | 109400560 A | 3/2019 |

(Continued)

OTHER PUBLICATIONS

International Search Report (Application No. PCT/IB2020/058589) Dated Dec. 15, 2020.
Written Opinion (Application No. PCT/IB2020/058589) Dated Dec. 15, 2020.

*Primary Examiner* — Timothy R Rozof
(74) *Attorney, Agent, or Firm* — NIXON PEABODY LLP; Jeffrey L. Costellia

(57) ABSTRACT

A novel organic compound is provided. An organic compound represented by General Formula (G1) below is provided. Note that in General Formula (G1), one of A and B represents a group represented by General Formula (g1) below, and the other of A and B, R1 to R8, and R11 to R14 each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. R9 and R10 each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. Ar represents a substituted or unsubstituted aryl group having 6 to 13 carbon atoms.

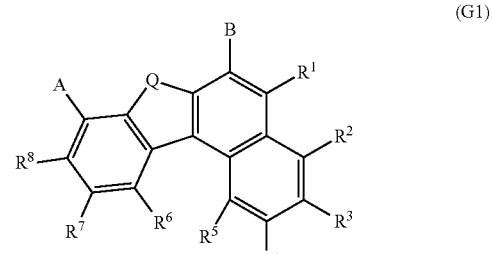

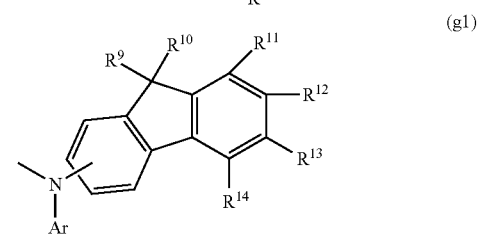

20 Claims, 66 Drawing Sheets

(51) Int. Cl.
  *F21V 31/00*   (2006.01)
  *H10K 85/60*   (2023.01)
  *H10K 50/11*   (2023.01)
  *H10K 50/17*   (2023.01)
  *H10K 59/12*   (2023.01)

(52) U.S. Cl.
  CPC ......... *H10K 85/633* (2023.02); *H10K 85/636* (2023.02); *C09K 2211/1018* (2013.01); *H10K 50/11* (2023.02); *H10K 50/17* (2023.02); *H10K 59/12* (2023.02); *H10K 85/615* (2023.02); *H10K 85/6574* (2023.02)

(56) References Cited

U.S. PATENT DOCUMENTS

| | | |
|---|---|---|
| 2017/0040535 A1 | 2/2017 | Ogita et al. |
| 2017/0125689 A1 | 5/2017 | Lee et al. |
| 2017/0222156 A1 | 8/2017 | Kawakami et al. |

FOREIGN PATENT DOCUMENTS

| | | | |
|---|---|---|---|
| CN | 209400560 | * | 3/2019 |
| CN | 110818675 | * | 2/2020 |
| CN | 110818675 A | | 2/2020 |
| CN | 110835304 A | | 2/2020 |
| KR | 2019-0007789 A | | 1/2019 |
| KR | 201900789 | * | 1/2019 |

* cited by examiner

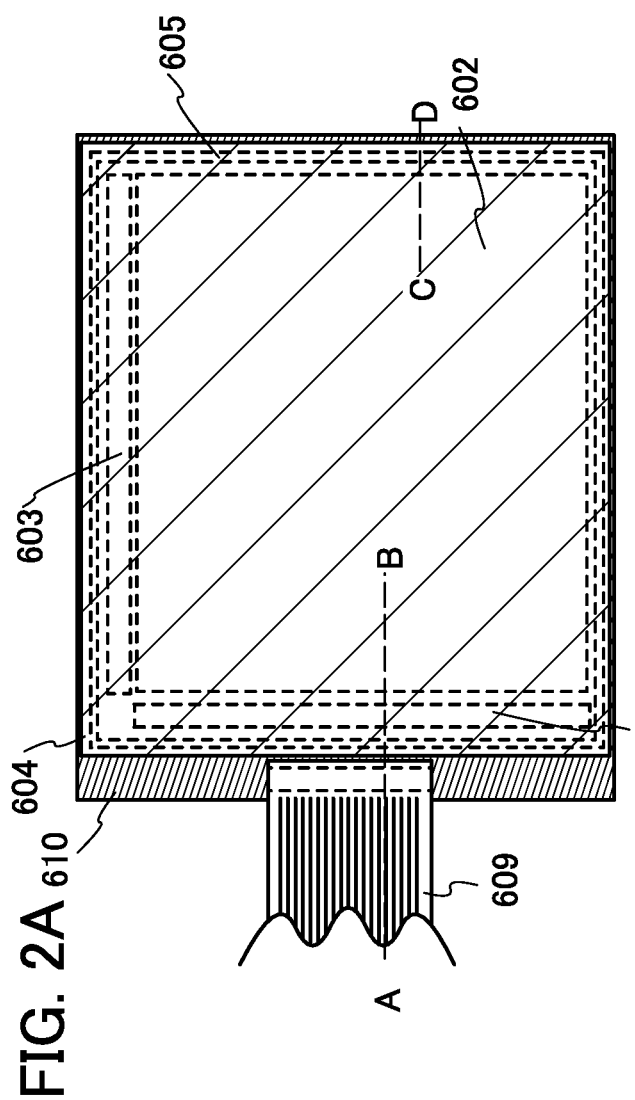
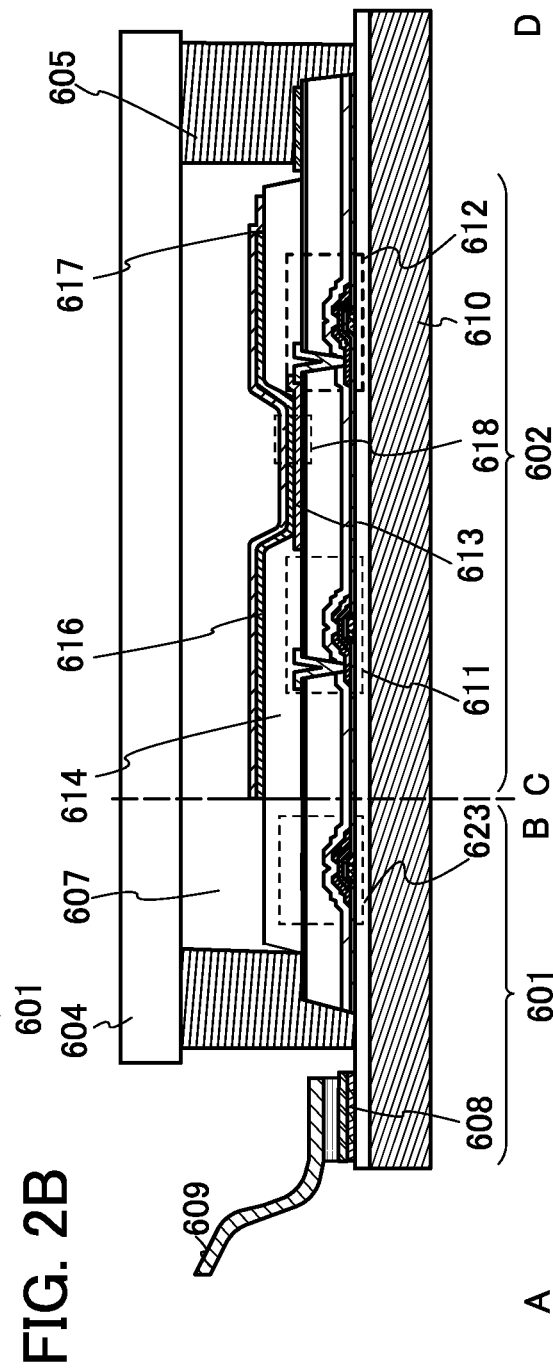
FIG. 2A
FIG. 2B

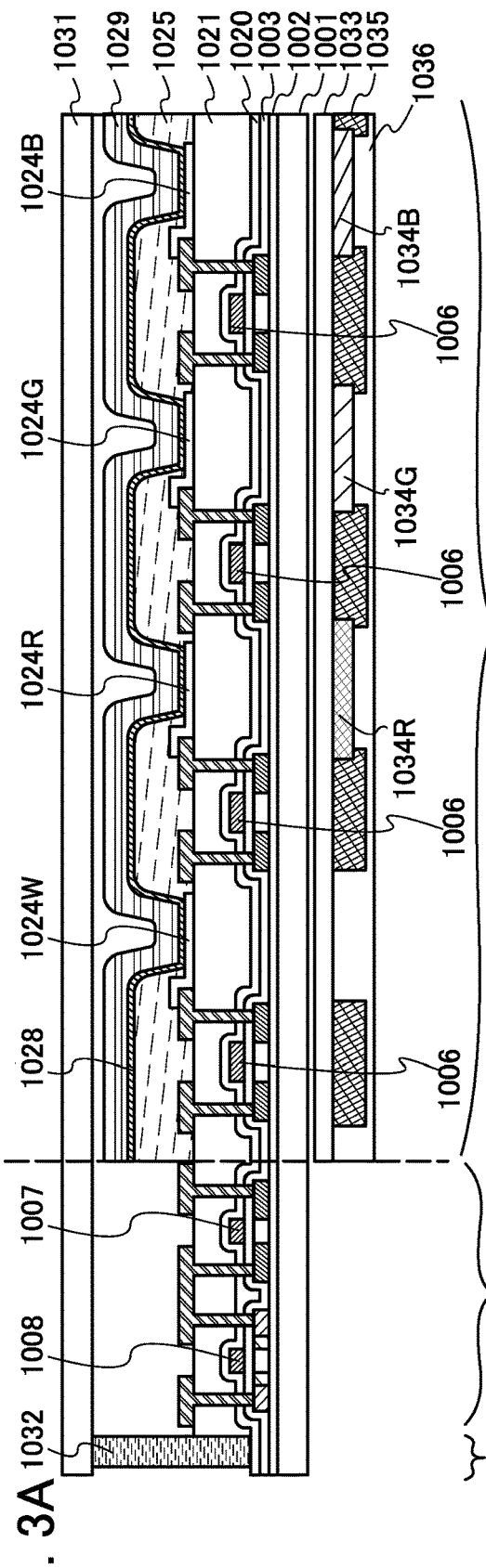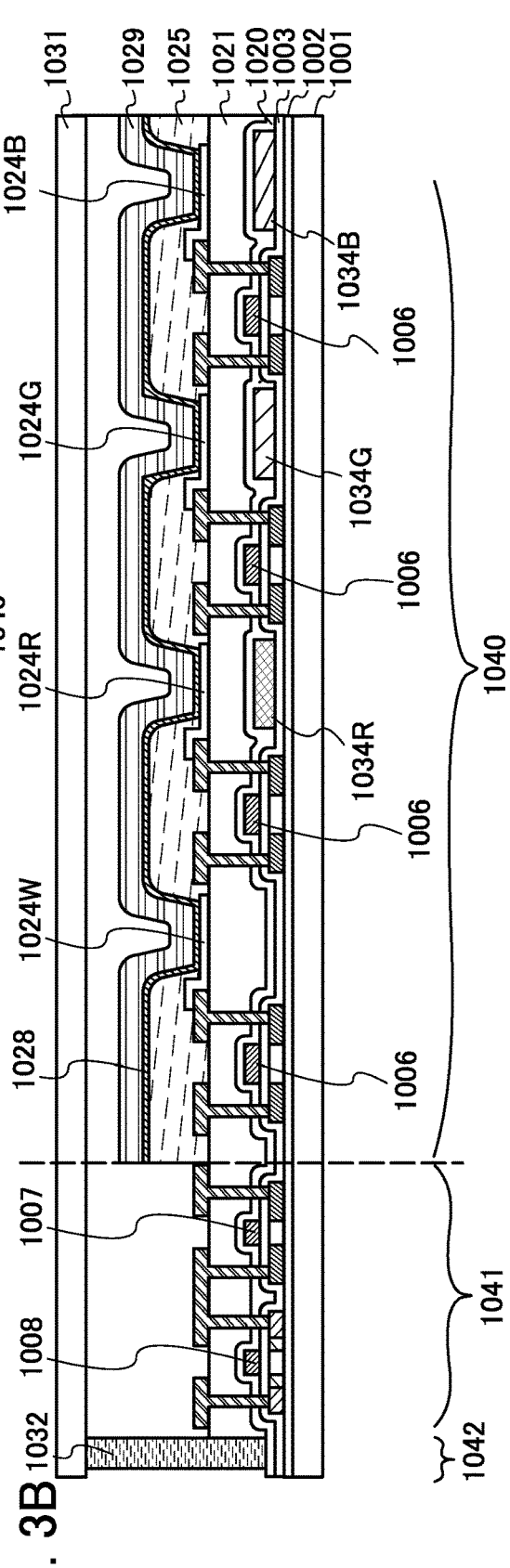

FIG. 7A
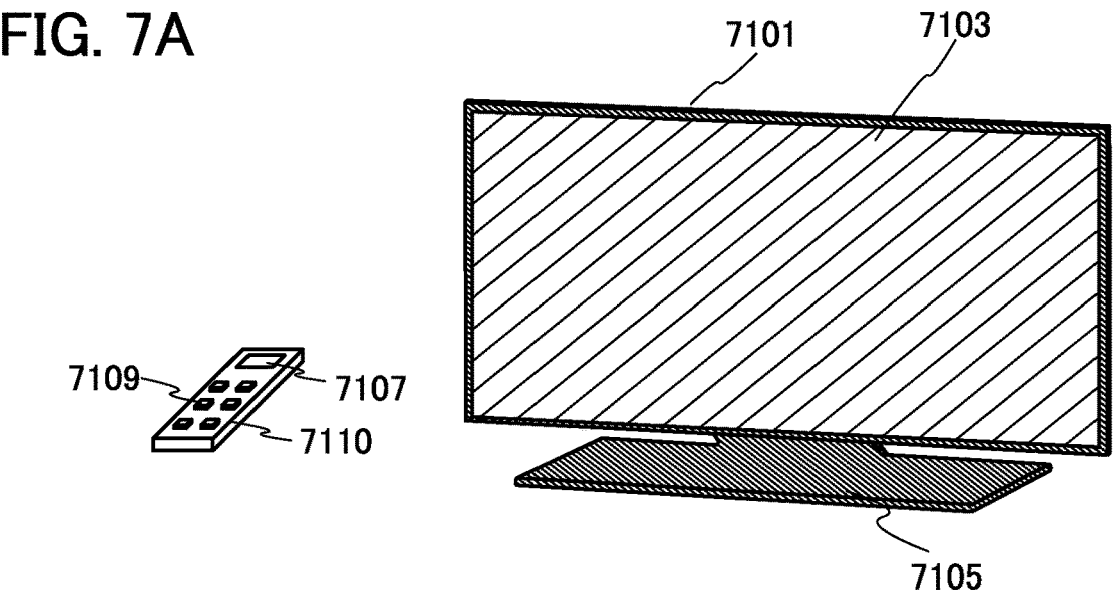
FIG. 7B1
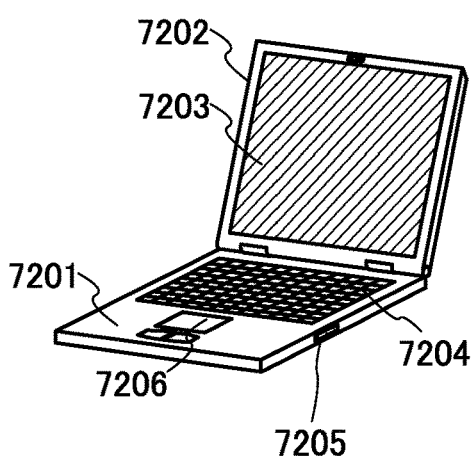
FIG. 7B2
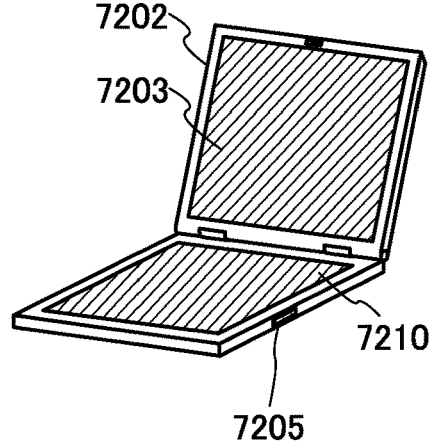
FIG. 7C
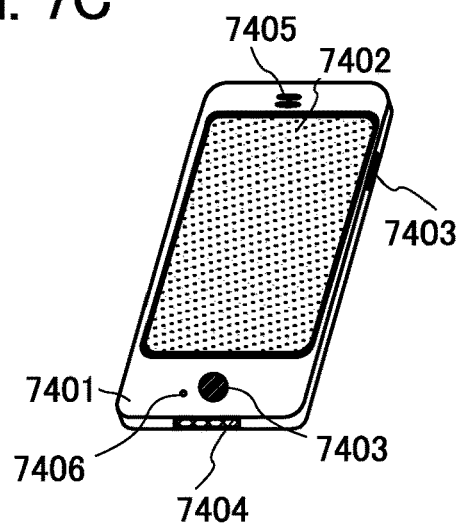

ORGANIC COMPOUND, OPTICAL DEVICE, LIGHT-EMITTING DEVICE, LIGHT-EMITTING APPARATUS, ELECTRONIC DEVICE, AND LIGHTING DEVICE

TECHNICAL FIELD

One embodiment of the present invention relates to an organic compound, a light-emitting element, a light-emitting device, a display module, a lighting module, a display device, a light-emitting apparatus, an electronic device, a lighting device, and an electronic appliance. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

Light-emitting devices (organic EL devices) including organic compounds and utilizing electroluminescence (EL) have been put into practical use. In the basic structure of such light-emitting devices, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

Such light-emitting devices are of self-light-emitting type and thus have advantages over liquid crystal, such as high visibility and no need for backlight when used for pixels of a display, and are suitable as flat panel display elements. Displays including such light-emitting devices are also highly advantageous in that they can be thin and lightweight. Moreover, an extremely fast response speed is also a feature.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting and the like.

Displays or lighting devices using light-emitting devices can be suitably used for a variety of electronic devices as described above, and research and development of light-emitting devices have progressed for more favorable characteristics.

REFERENCE

Patent Document

[Patent Document 1] Chinese Patent Application Publication No. 108689972

SUMMARY OF THE INVENTION

Problems to be Solved by the Invention

An object of one embodiment of the present invention is to provide a novel organic compound. Another object of one embodiment of the present invention is to provide a novel carrier-transport material. Another object of one embodiment of the present invention is to provide a novel hole-transport material.

An object of another embodiment of the present invention is to provide a light-emitting device with a low driving voltage. Another object of one embodiment of the present invention is to provide a light-emitting device, a light-emitting apparatus, an electronic device, a display device, and an electronic appliance each with low power consumption.

Note that the description of these objects does not preclude the existence of other objects. In one embodiment of the present invention, there is no need to achieve all of these objects. Other objects will be apparent from the descriptions of the specification, the drawings, the claims, and the like, and other objects can be derived from the descriptions of the specification, the drawings, the claims, and the like.

It is only necessary that at least one of the above-described objects be achieved in the present invention.

Means for Solving the Problems

One embodiment of the present invention is an organic compound represented by General Formula (G1) below.

[Chemical Formula 1]

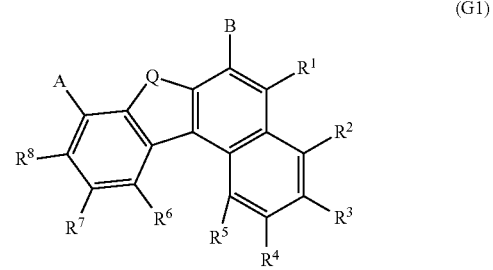

(G1)

Note that in General Formula (G1) above, Q represents an oxygen atom or a sulfur atom. One of A and B represents a group represented by General Formula (g1) below, and the other represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. $R^1$ to $R^8$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

[Chemical Formula 2]

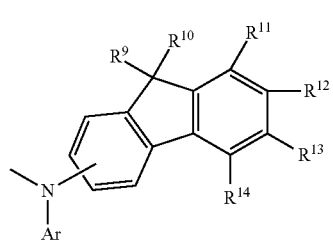

(g1)

Note that in General Formula (g1) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. $R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Ar represents a substituted or unsubstituted aryl group having 6 to 13 carbon atoms.

Alternatively, another embodiment of the present invention is the organic compound in the above structure, in which the General Formula (G1) is represented by General Formula (G1-1) below.

[Chemical Formula 3]

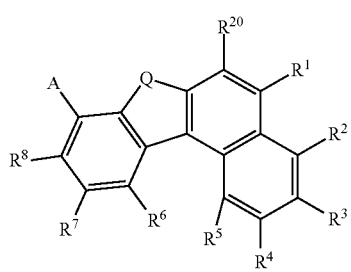

(G1-1)

Note that in General Formula (G1-1) above, Q represents an oxygen atom or a sulfur atom. A represents a group represented by General Formula (g1) below, and $R^{20}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. $R^1$ to $R^8$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and an alkyl group of a substituted or unsubstituted aromatic hydrocarbon group having 6 to 60 carbon atoms.

[Chemical Formula 4]

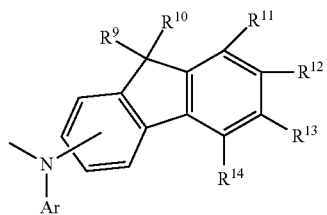

(g1)

Note that in General Formula (g1) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. $R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Ar represents a substituted or unsubstituted aryl group having 6 to 13 carbon atoms.

Alternatively, another embodiment of the present invention is the organic compound in the above structure, in which the General Formula (G1) is represented by General Formula (G1-2) below.

[Chemical Formula 5]

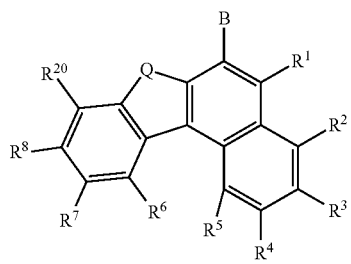

(G1-2)

Note that in General Formula (G1-2) above, Q represents an oxygen atom or a sulfur atom. B represents a group represented by General Formula (g1) above, and $R^{20}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. $R^1$ to $R^8$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and an alkyl group of a substituted or unsubstituted aromatic hydrocarbon group having 6 to 60 carbon atoms.

[Chemical Formula 6]

(g1)

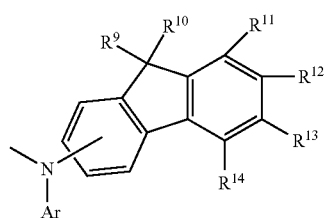

Note that in General Formula (g1) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. $R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Ar represents a substituted or unsubstituted aryl group having 6 to 13 carbon atoms.

Alternatively, another embodiment of the present invention is the organic compound in the above structure, in which $R^{20}$ represents hydrogen.

Alternatively, another embodiment of the present invention is the organic compound in the above structures, in which the group represented by the General Formula (g1) is a group represented by General Formula (g1-1) below.

[Chemical Formula 7]

(g1-1)

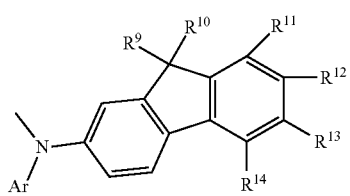

Note that in General Formula (g1-1) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. R11 to R14 each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Ar represents a substituted or unsubstituted aryl group having 6 to 13 carbon atoms.

Alternatively, another embodiment of the present invention is the organic compound in the above structures, in which the group represented by the General Formula (g1) is a group represented by General Formula (g1-2) below.

[Chemical Formula 8]

(g1-2)

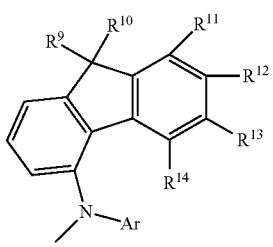

Note that in General Formula (g1-2) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. $R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Ar represents a substituted or unsubstituted aryl group having 6 to 13 carbon atoms.

Another embodiment of the present invention is the organic compound in the above structure, in which the Ar is represented by General Formulae (Ar-1) to (Ar-3) below.

[Chemical Formulae 9]

(Ar-1)

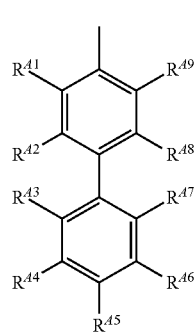

(Ar-2)

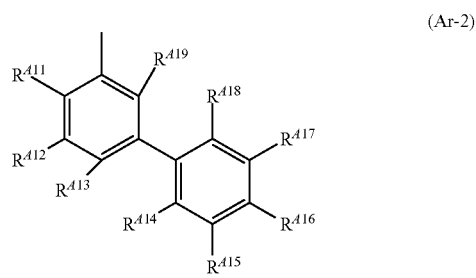

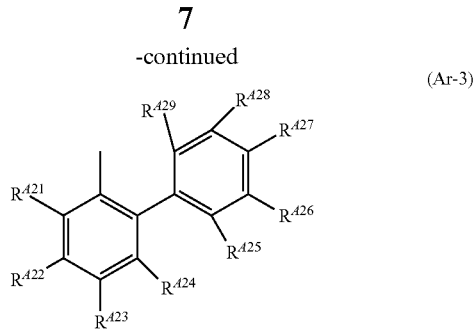

(Ar-3)

Note that in General Formulae (Ar-1) to (Ar-3) above, $R^{A1}$ to $R^{A9}$, $R^{A11}$ to $R^{A19}$, and $R^{A21}$ to $R^{A29}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

Alternatively, another embodiment of the present invention is the organic compound in the above structure, in which $R^{A1}$ to $R^{A9}$, $R^{A11}$ to $R^{A19}$, and $R^{A21}$ to $R^{A29}$ each represent hydrogen.

Alternatively, another embodiment of the present invention is the organic compound in the above structure, in which $R^9$ and $R^{10}$ each represent a methyl group.

Alternatively, another embodiment of the present invention is the organic compound in the above structure, in which $R^1$ and $R^8$ each represent hydrogen.

Alternatively, another embodiment of the present invention is the organic compound in the above structure, in which $R^{11}$ to $R^{14}$ each represent hydrogen.

Alternatively, another embodiment of the present invention is an optical device including the organic compound described in any of the above.

Alternatively, another embodiment of the present invention is a light-emitting device including the organic compound described in any of the above.

Another embodiment of the present invention is an electronic device including the above optical device, and a sensor, an operation button, a speaker, or a microphone.

Another embodiment of the present invention is a light-emitting apparatus including the above optical device, and a transistor or a substrate.

Another embodiment of the present invention is a lighting device including the above optical device and a housing.

Note that the light-emitting apparatus in this specification includes, in its category, an image display device that uses a light-emitting device. A module in which a light-emitting device is provided with a connector such as an anisotropic conductive film or a TCP (Tape Carrier Package), a module in which a printed wiring board is provided on the tip of a TCP, and a module in which an IC (integrated circuit) is directly mounted on a light-emitting device by a COG (Chip On Glass) method include the light-emitting apparatus in some cases. Furthermore, in some cases, lighting equipment or the like includes the light-emitting apparatus.

Effect of the Invention

One embodiment of the present invention can provide a novel organic compound. One embodiment of the present invention can provide a novel material for an electron-transport layer. One embodiment of the present invention can provide a novel host material for a phosphorescent light-emitting device.

Another embodiment of the present invention can provide a light-emitting device with high emission efficiency. One embodiment of the present invention can provide a light-emitting device, a light-emitting apparatus, an electronic device, a display device, and an electronic appliance each with low power consumption.

Note that the description of these effects does not preclude the existence of other effects. One embodiment of the present invention does not have to have all of these effects. Other effects will be apparent from the descriptions of the specification, the drawings, the claims, and the like, and other effects can be derived from the descriptions of the specification, the drawings, the claims, and the like.

BRIEF DESCRIPTION OF THE DRAWINGS

FIG. 2A and FIG. 2B are conceptual diagrams of an active matrix light-emitting apparatus.

FIG. 3A and FIG. 3B are conceptual diagrams of an active matrix light-emitting apparatus.

FIG. 7A, FIG. 7B1, FIG. 7B2, and FIG. 7C are diagrams illustrating electronic devices.

MODE FOR CARRYING OUT THE INVENTION

Figure 1A:
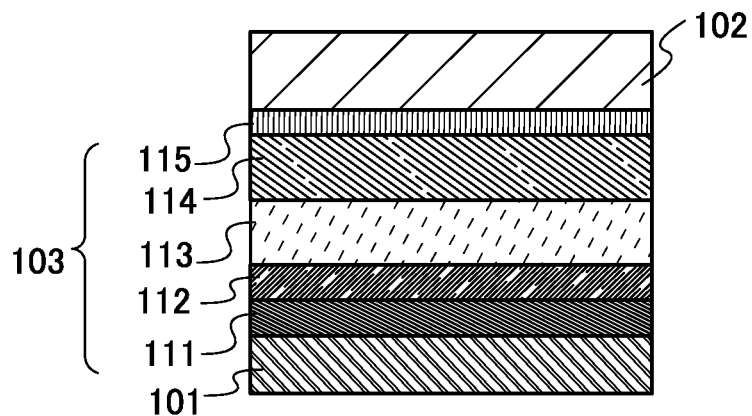
FIG. 1A, FIG. 1B, and FIG. 1C are schematic diagrams of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

In this embodiment, an organic compound of one embodiment of the present invention will be described.

An organic compound of one embodiment of the present invention is an organic compound represented by General Formula (G1) below.

[Chemical Formula 10]

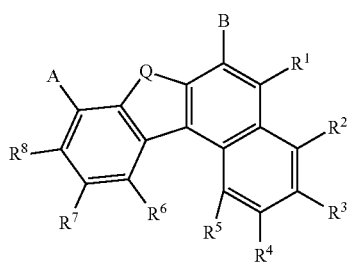

(G1)

General Formula (G1) above can also be represented by either General Formula (G1-1) or General Formula (G1-2) below.

[Chemical Formula 11]

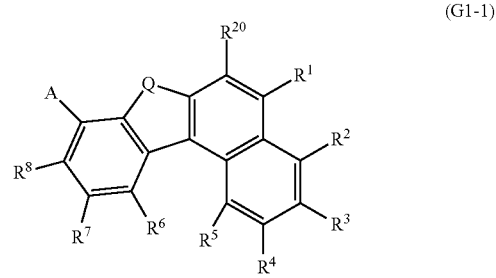

(G1-1)

[Chemical Formula 12]

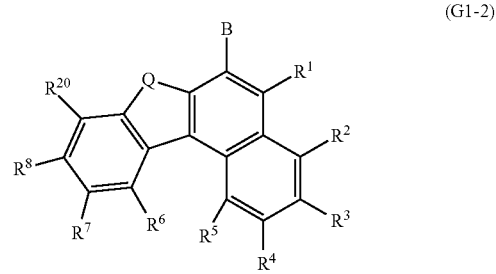

(G1-2)

In the organic compounds represented by General Formula (G1), General Formula (G1-1), and General Formula (G1-2) above, Q represents an oxygen atom or a sulfur atom. Note that Q preferably represents an oxygen atom, in which case the refractive index is lower than that of a compound containing a sulfur atom, an element using a compound with a lower refractive index can achieve the effect of higher light extraction efficiency, and a light-emitting device with high efficiency can be provided.

In addition, A or B in General Formula (G1) above, A in General Formula (G1-1) above, and B in General Formula (G1-2) above each represent a group represented by General Formula (g1) below.

[Chemical Formula 13]

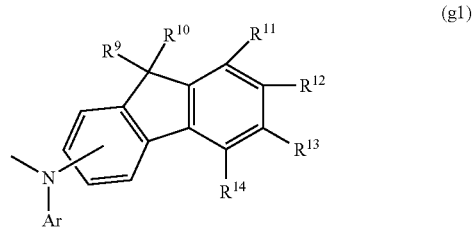

(g1)

In the group represented by General Formula (g1) above, the positon of a fluorenyl group where nitrogen of amine is bonded is preferably the 2-position or the 4-position. That is, in the case where the group represented by General Formula (g1) above is a group represented by General Formula (g1-1) below, the compound includes a fluoren-2-amine skeleton; thus, a compound with a relatively shallow HOMO and a high transport property can be provided, and as a result, a light-emitting device with low power consumption can be provided. In the case of the group represented by General Formula (g1-1) below, the compound is easily synthesized, which is an advantage in terms of cost. Alternatively, General Formula (g1) above is preferably a group represented by General Formula (g1-2) below, in which case a device with high emission efficiency can be provided.

[Chemical Formula 14]

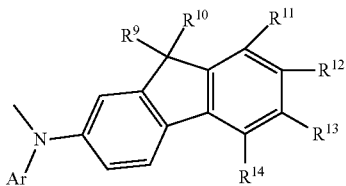
(g1-1)

[Chemical Formula 15]

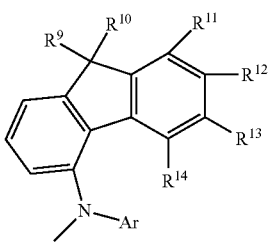
(g1-2)

In the groups represented by General Formula (g1), General Formula (g1-1), and General Formula (g1-2) above, Ar represents a substituted or unsubstituted aryl group having 6 to 13 carbon atoms. Note that Ar preferably represents any of groups represented by General Formulae (Ar-1) to (Ar-3) below in order to provide a device with high efficiency and high reliability. In the case where Ar in General Formula (g1-2) is any of the groups represented by General Formulae (Ar-1) to (Ar-3) below, synthesis is easy, which is an advantage in terms of the providing cost of the compound.

[Chemical Formulae 16]

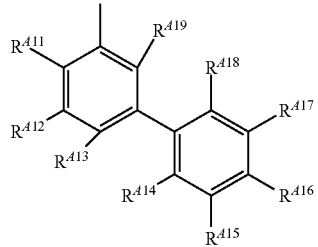
(Ar-1)

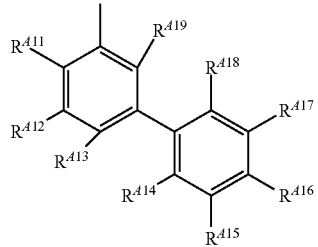
(Ar-2)

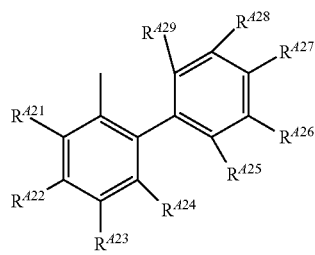
(Ar-3)

Note that in General Formulae (Ar-1) to (Ar-3) above, $R^{A1}$ to $R^{A9}$, $R^{A11}$ to $R^{A19}$, and $R^{A21}$ to $R^{A29}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. Note that $R^{A1}$ to $R^{A9}$, $R^{A11}$ to $R^{A19}$, and $R^{A21}$ to $R^{A29}$ each preferably represent hydrogen, a phenyl group, a biphenyl group, or a fluorenyl group, in which case a compound and a device that can be easily synthesized and have high heat resistance, high reliability, and low power consumption and whose raw materials can be easily prepared can be provided.

In the groups represented by General Formula (g1), General Formula (g1-1), and General Formula (g1-2) above, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group. In the case where $R^9$ and $R^{10}$ each represent an alkyl group having 1 to 6 carbon atoms, $R^9$ and $R^{10}$ may be bonded to each other to form a ring and have a spiro structure as in General Formula (g3-1) to General Formula (g3-4) below.

[Chemical Formulae 17]

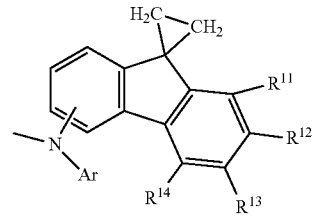
(g3-1)

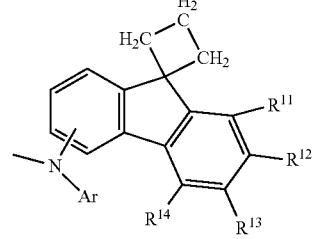
(g3-2)

-continued (g3-3)
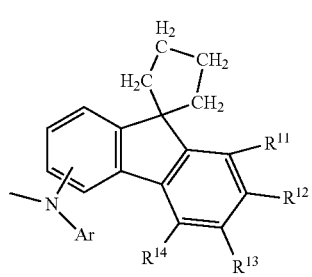

(g3-4)
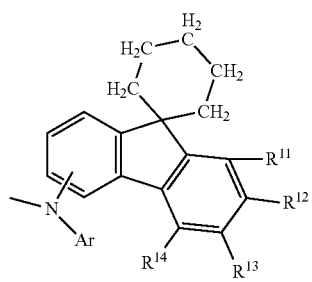

In the groups represented by General Formula (G1), General Formula (G1-1), General Formula (G1-2), General Formula (g1), General Formula (g1-1), and General Formula (g1-2) above, the other of A and B, $R^1$ to $R^8$, $R^{11}$ to $R^{14}$, and $R^{20}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

Note that in this specification, when the substituted or unsubstituted group includes a substituent, any of an alkyl group having 1 to 6 carbon atoms, a phenyl group, a biphenyl group (an o-biphenyl group, an m-biphenyl group, and a p-biphenyl group), and a naphthyl group can be used as the substituent.

Structural Formula (1-1) to Structural Formula (1-40) below can be given as specific examples of the hydrocarbon group having 1 to 6 carbon atoms, the cyclic hydrocarbon group having 3 to 6 carbon atoms, the alkoxy group having 1 to 6 carbon atoms, the cyano group, the halogen, and the haloalkyl group having 1 to 6 carbon atoms.

[Chemical Formulae 18]

(1-1)
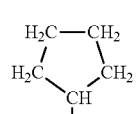

(1-2)
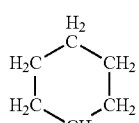

(1-3)
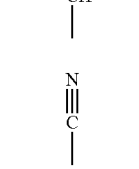

(1-4)
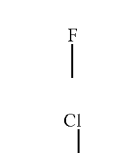

(1-5)
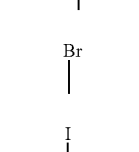

(1-6)
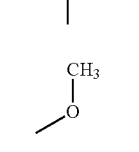

(1-7)
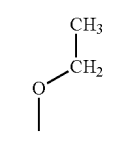

(1-8)
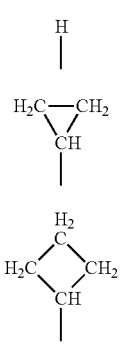

(1-9)

(1-10)

(1-11)
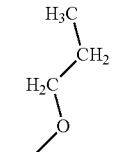

(1-12)
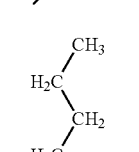

(1-13)
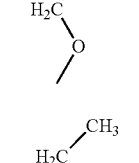

(1-14)
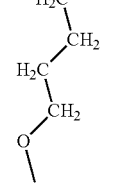

(1-15)
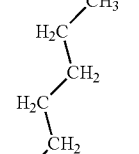

-continued
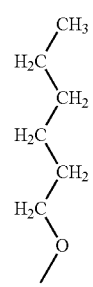 (1-16)
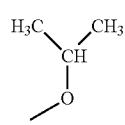 (1-17)
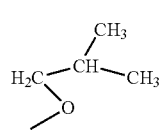 (1-18)
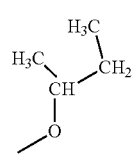 (1-19)
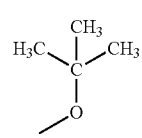 (1-20)
 (-21)
 (1-22)
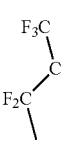 (1-23)
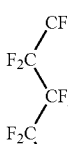 (1-24)
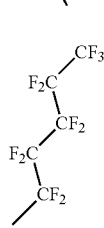 (1-25)
-continued
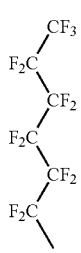 (1-26)
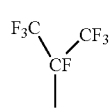 (1-27)
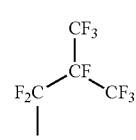 (1-28)
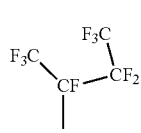 (1-29)
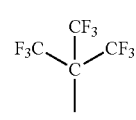 (1-30)
 (1-31)
 (1-32)
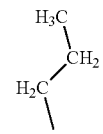 (1-33)
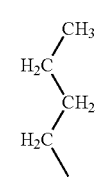 (1-34)
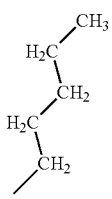 (1-35)

-continued
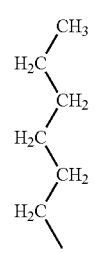 (1-36)
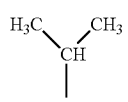 (1-37)
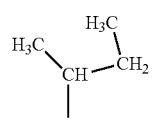 (1-38)
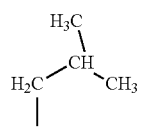 (1-39)
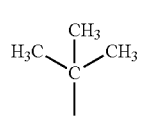 (1-40)
As specific examples of the aromatic hydrocarbon group having 6 to 60 carbon atoms, substituents represented by Structural Formulae (2-1) to (2-13) below and the like can be given. Note that there is no limitation on the substitution position of Structural Formulae (2-1) to (2-13) below. Furthermore, they may have a substituent.
[Chemical Formulae 19]
 (2-1)
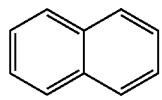 (2-2)
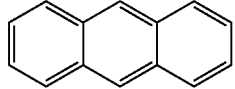 (2-3)
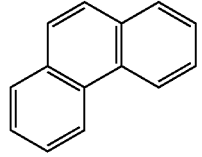 (2-4)
-continued
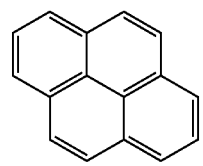 (2-5)
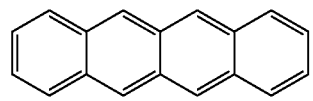 (2-6)
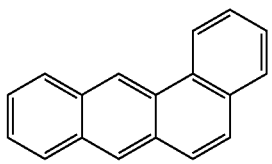 (2-7)
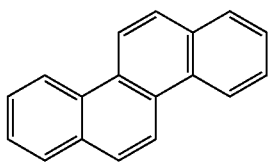 (2-8)
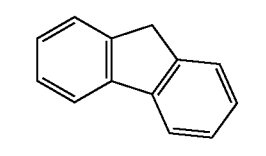 (2-9)
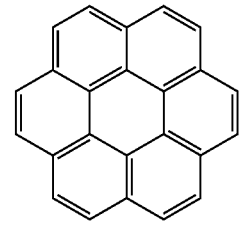 (2-10)
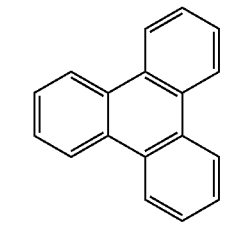 (2-11)
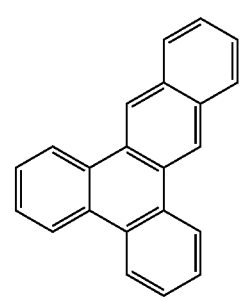 (2-12)

(2-13)

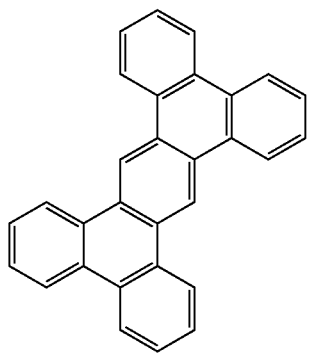

In the case where $R^1$ to $R^8$ and $R^{11}$ to $R^{14}$ each represent an aromatic hydrocarbon group, Structural Formula (2-1) to Structural Formula (2-3) and Structural Formula (2-9) are preferable among Structural Formulae (2-1) to (2-13) above and Structural Formulae below. There is no limitation on the substitution position of each of the aromatic hydrocarbon groups. Specific examples of such an aromatic hydrocarbon group and a hydrocarbon group each having a substituent are shown in Structural Formula (1-41) to Structural Formula (1-50) below.

[Chemical Formulae 20]

(1-41)

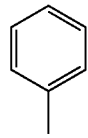

(1-42)

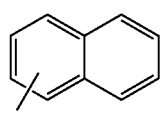

(1-43)

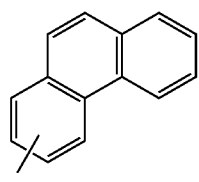

(1-44)

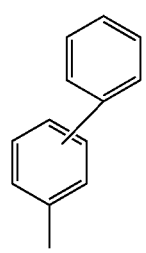

(1-45)

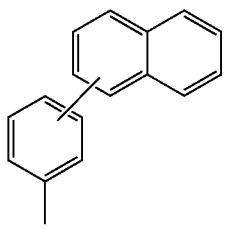

(1-46)

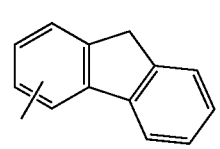

(1-47)

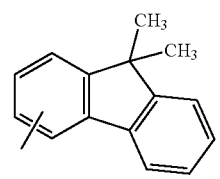

(1-48)

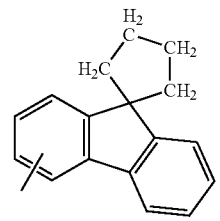

(1-49)

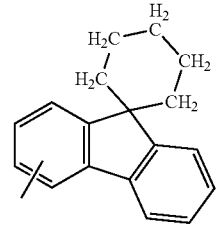

(1-50)

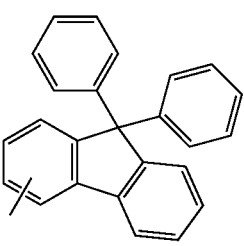

Here, specific examples of the groups represented by General Formula (g1), General Formula (g1-1), General Formula (g1-2), and General Formula (g3-1) to General Formula (g3-4) above are given below.

[Chemical Formulae 21]
(4-1)
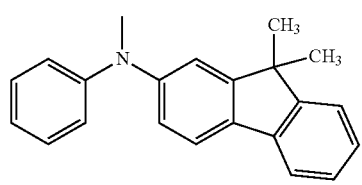
(4-2)
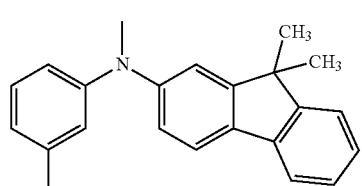
(4-3)
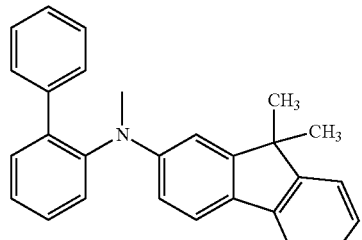
(4-4)
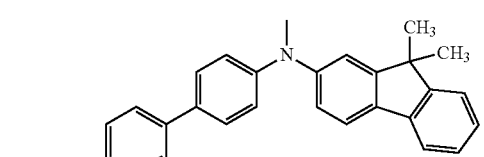
(4-5)
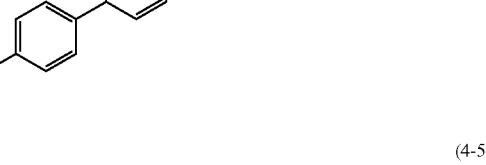
(4-6)
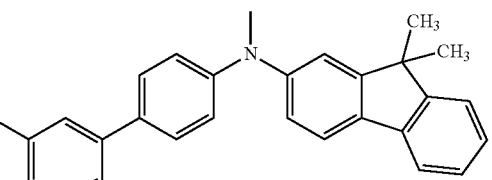
-continued
(4-7)
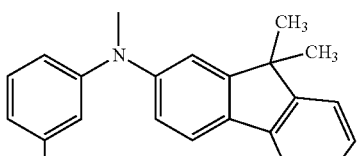
(4-8)
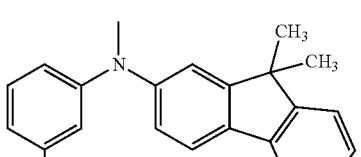
(4-9)
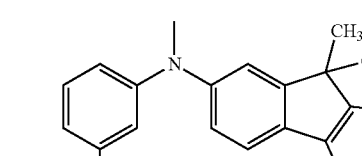
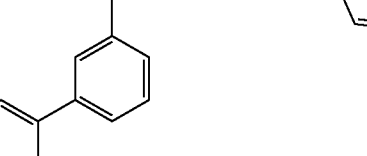
(4-10)
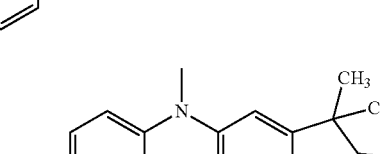

(4-11)
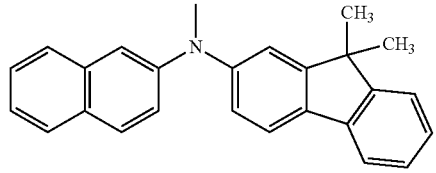
(4-12)
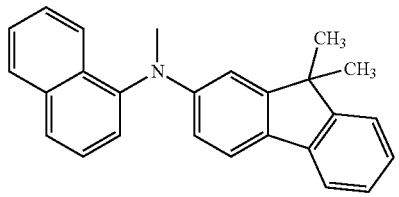
(4-13)
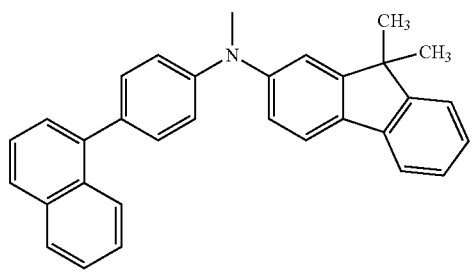
(4-14)
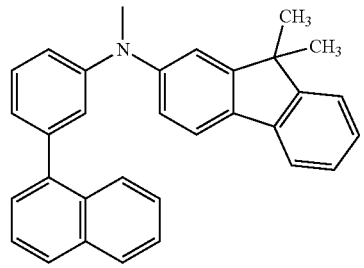
(4-15)
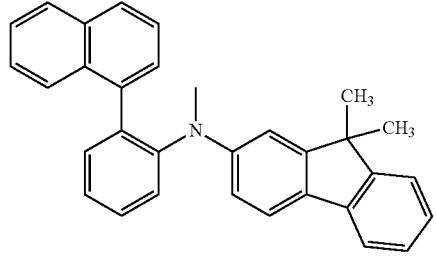
(4-16)
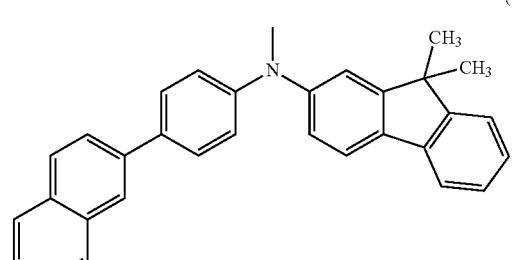
(4-17)
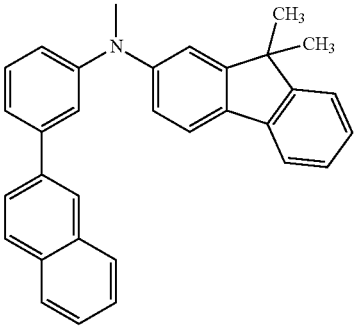
[Chemical Formulae 22]
(4-18)
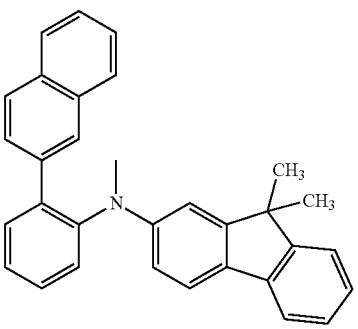
(4-19)
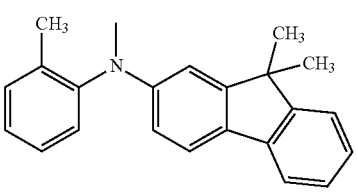
(4-20)
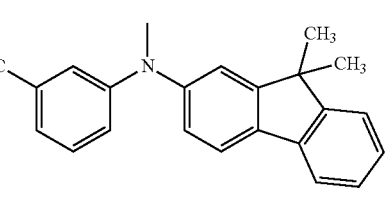
(4-21)
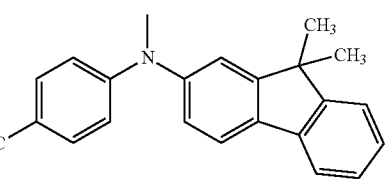
(4-22)
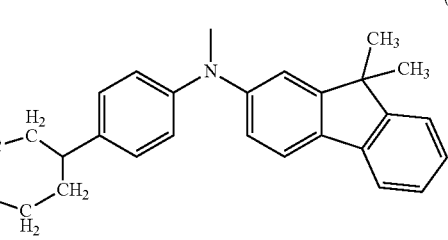

-continued
(4-23)
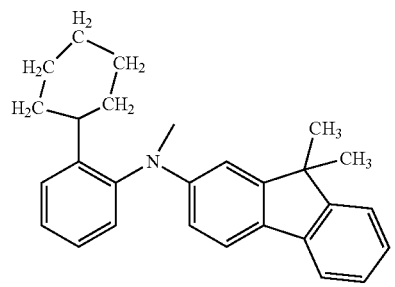
(4-24)
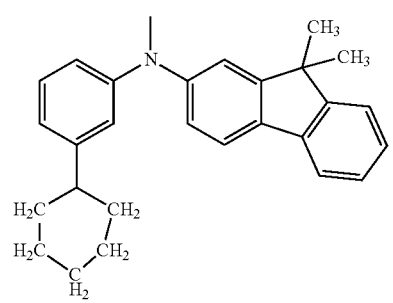
(4-25)
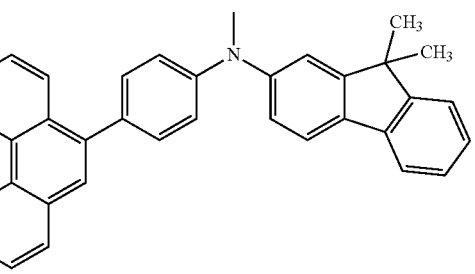
(4-26)
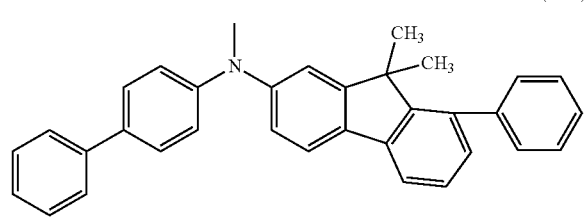
(4-27)
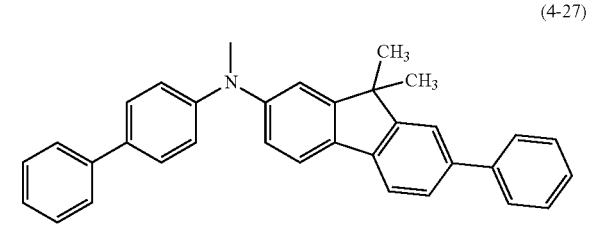
(4-28)
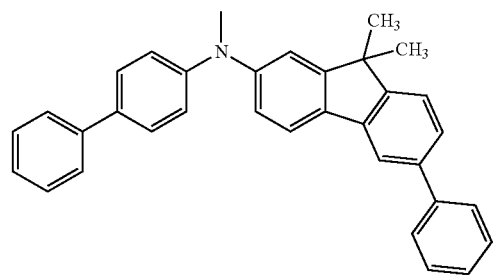
-continued
(4-29)
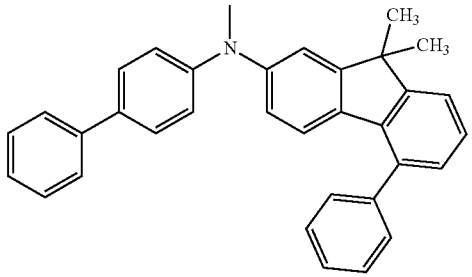
(4-30)
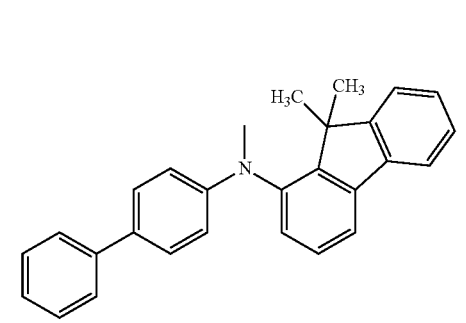
(4-31)
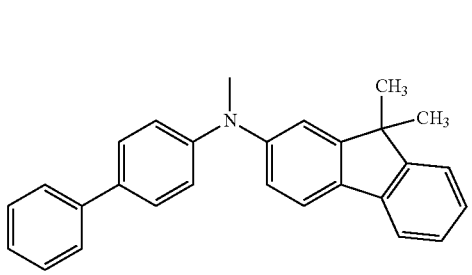
(4-32)
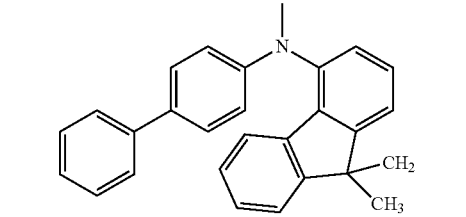
(4-33)
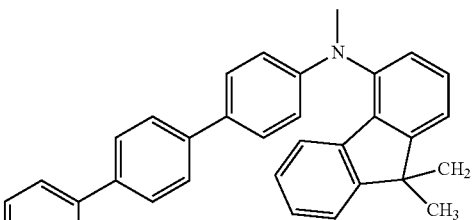
(4-34)
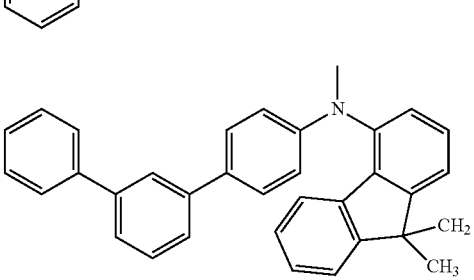

(4-35)
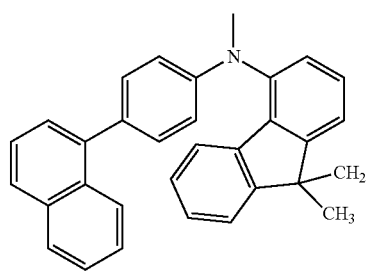
(4-36)
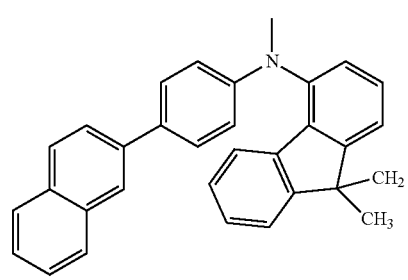
[Chemical Formulae 23]
(4-37)
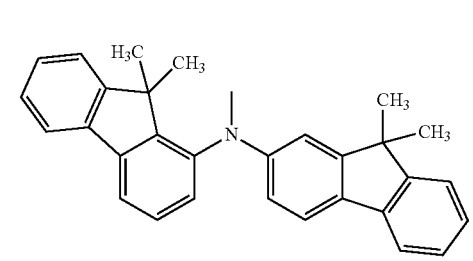
(4-38)
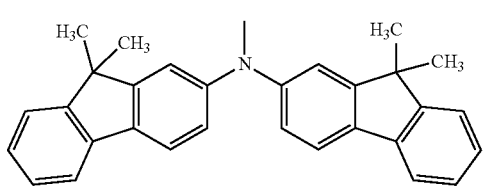
(4-39)
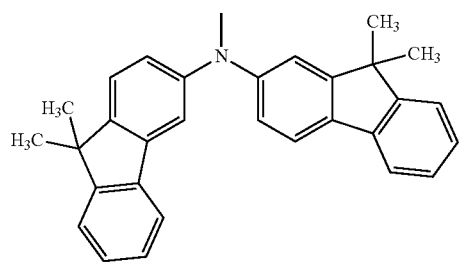
(4-40)
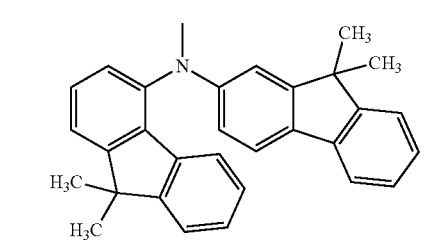
(4-41)
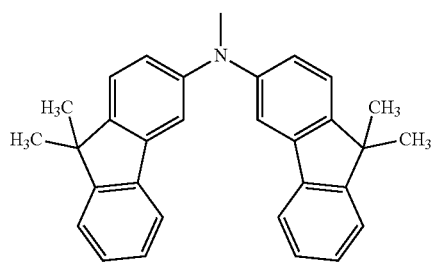
(4-42)
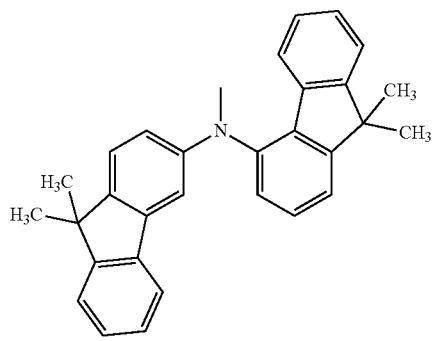
(4-43)
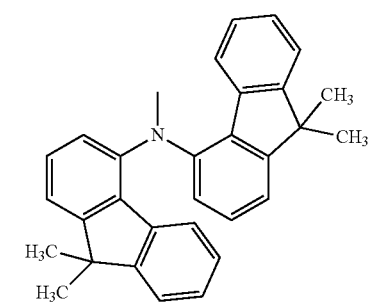
(4-44)
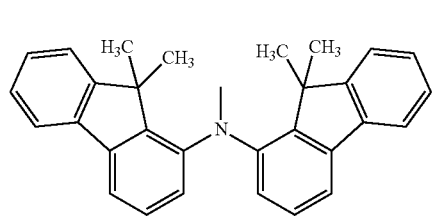
(4-45)
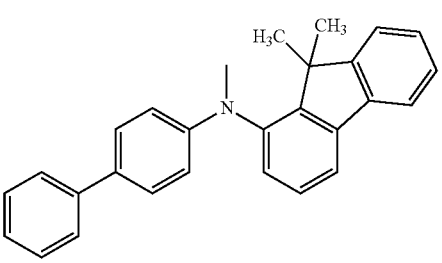
(4-46)
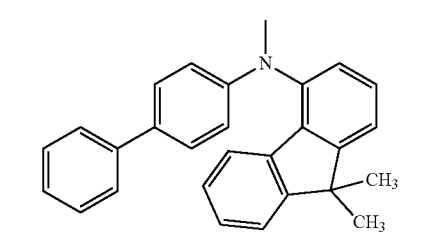

(4-47)
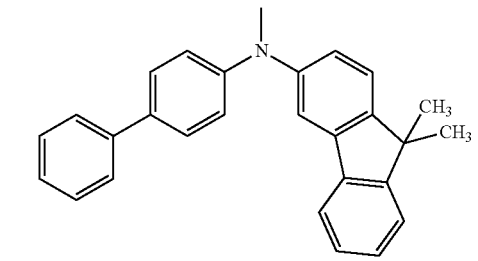

(4-48)
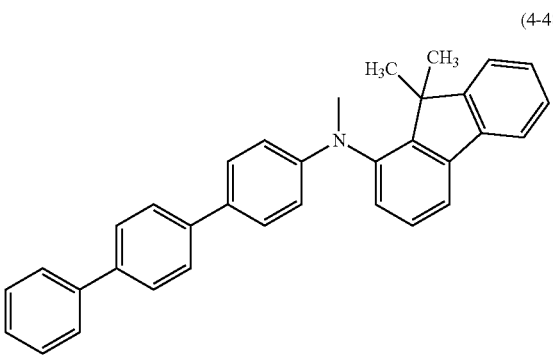

(4-49)
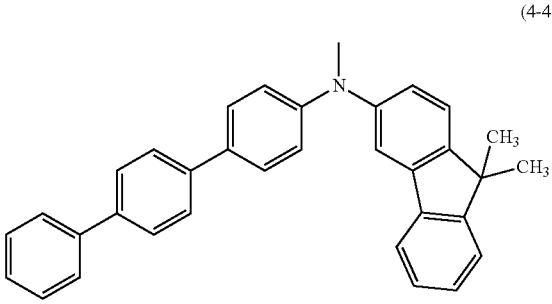

(4-50)
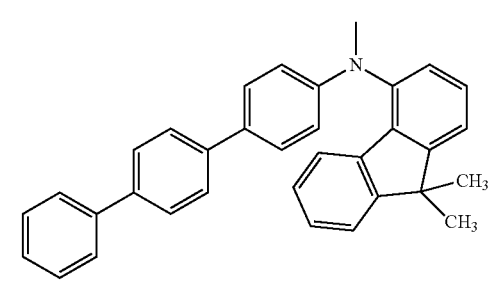

(4-51)
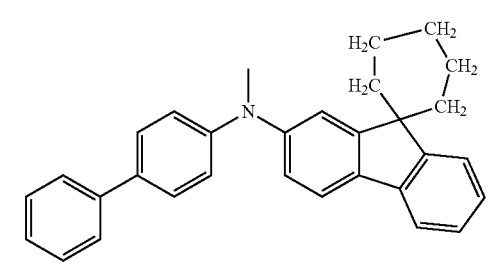

(4-52)
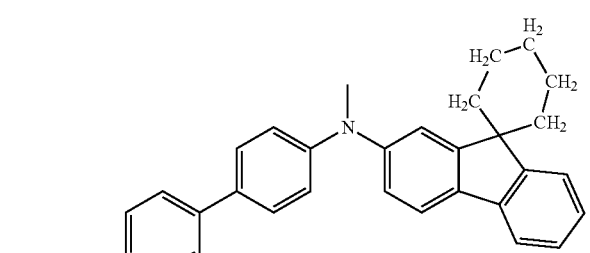

(4-53)
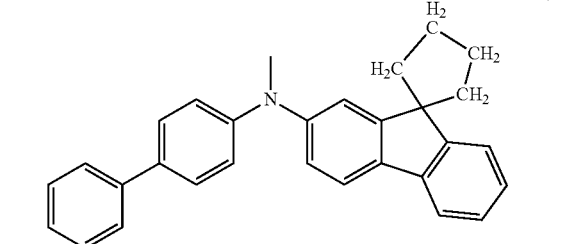

(4-54)
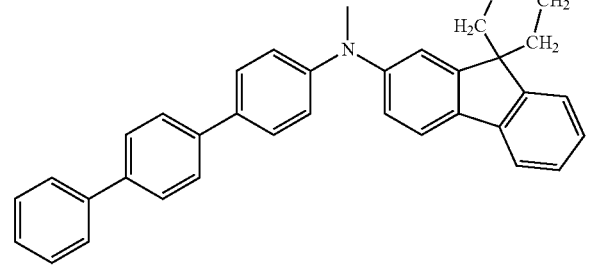

The organic compound of one embodiment of the present invention with the above structure is an organic compound having a high carrier-transport property. In particular, a light-emitting device that has a high hole-transport property, has a small increase in driving voltage even when formed as a thick film, and has favorable characteristics can be obtained. The organic compound with the above structure can be suitably used for a hole-injection layer and a hole-transport layer of a light-emitting device.

Specific examples of the organic compound with the above structure are shown below.

[Chemical Formulae 21]

(5-1)
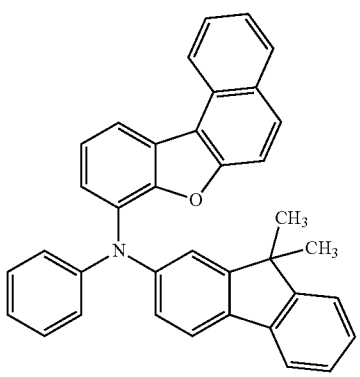

(5-2)
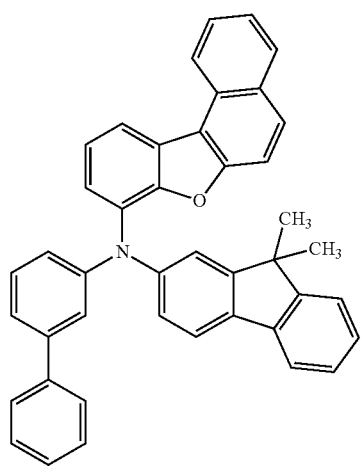
(5-3)
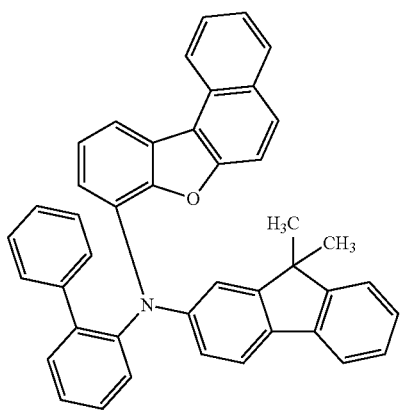
(5-4)
(5-5)
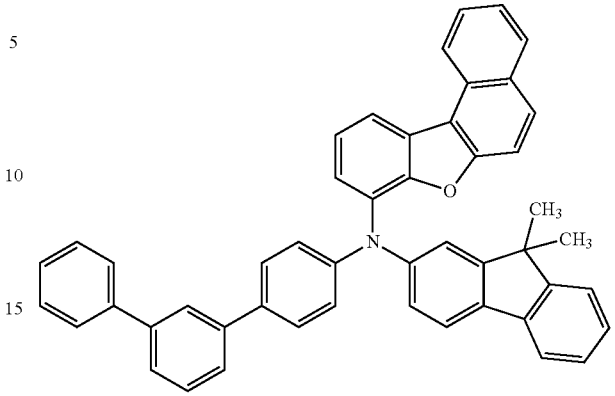
(5-6)
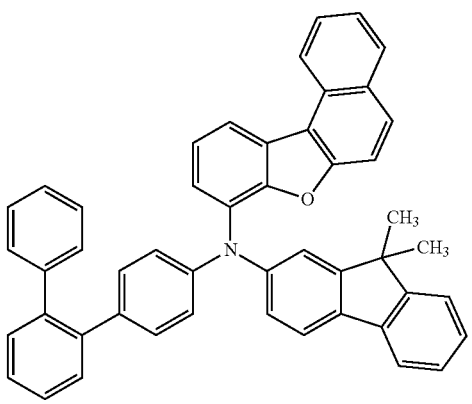
(5-7)
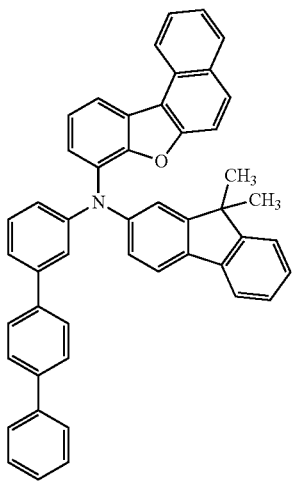

(5-8) 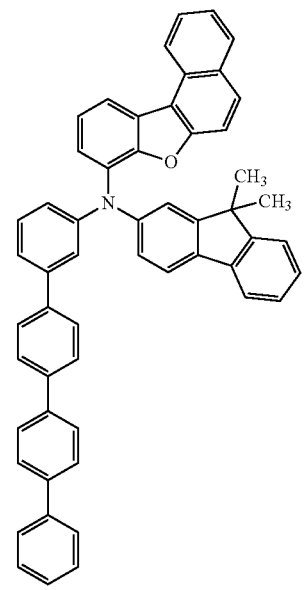
(5-9) 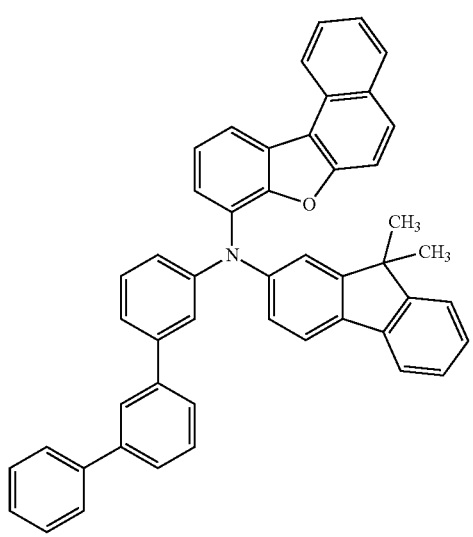
(5-10) 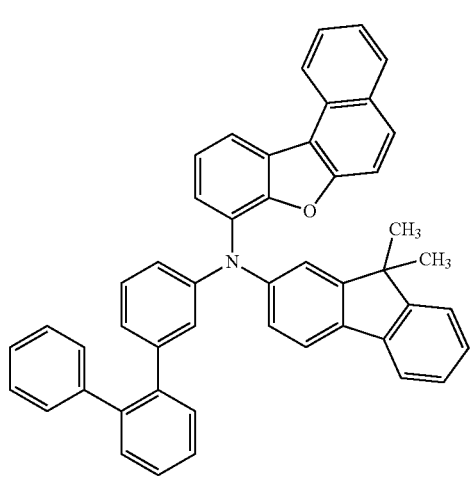
(5-11) 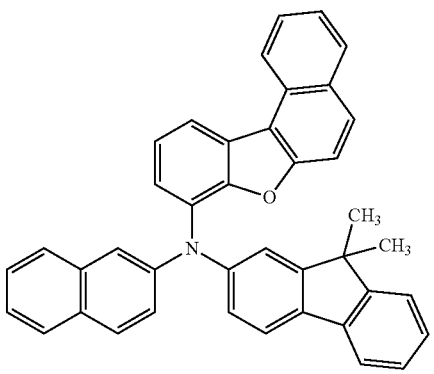
(5-12) 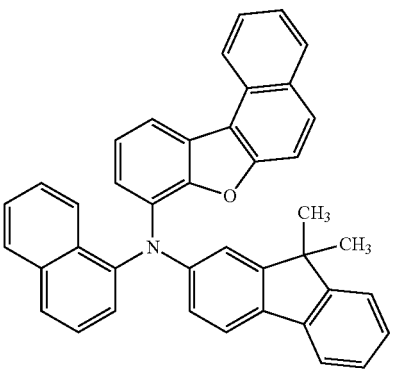
[Chemical Formulae 25]
(513) 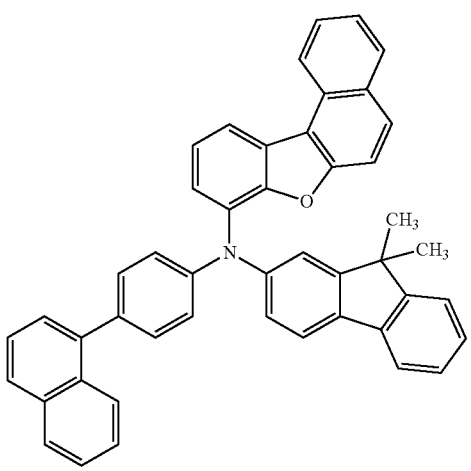

(5-14)
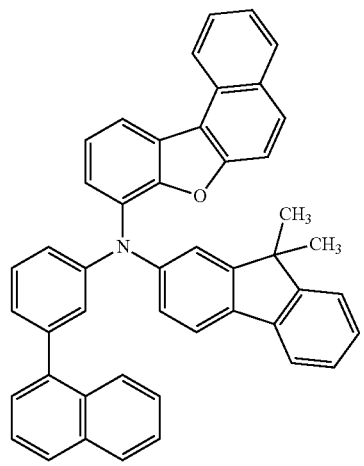
(5-15)
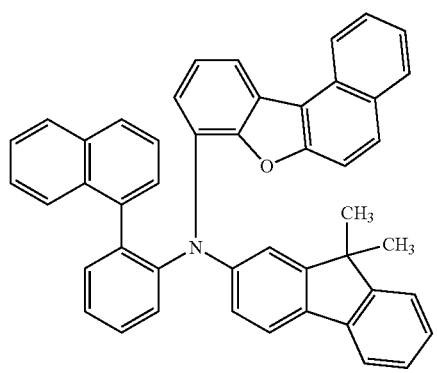
(5-16)
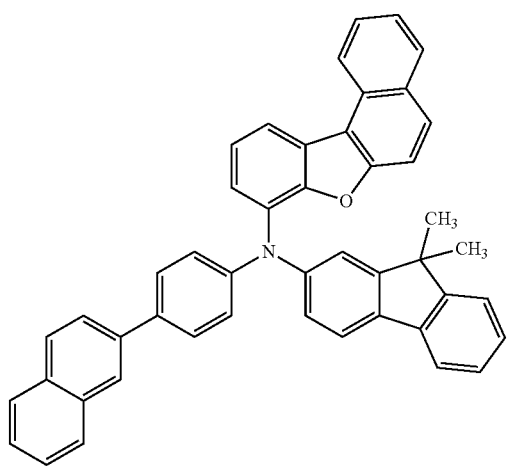
(5-17)
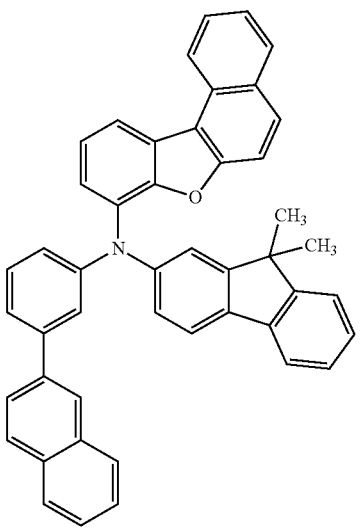
(5-18)
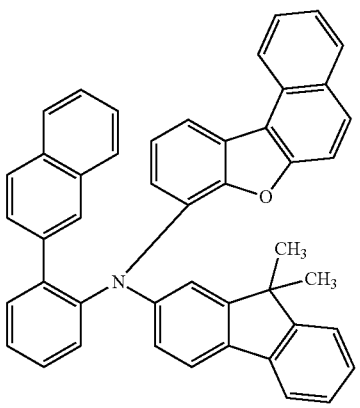
(5-19)
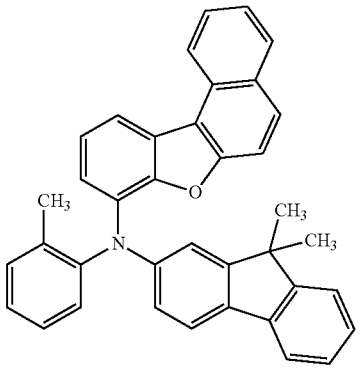

(5-20)
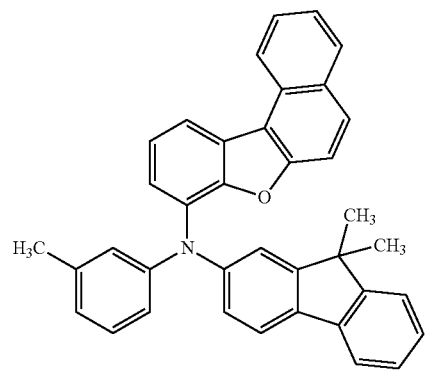
(5-21)
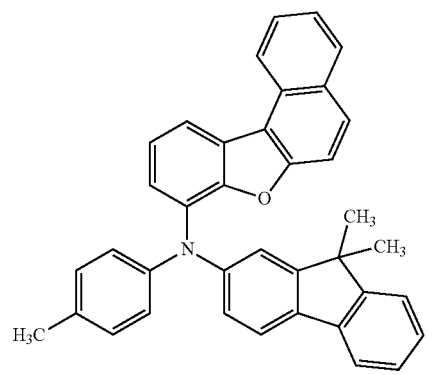
(5-22)
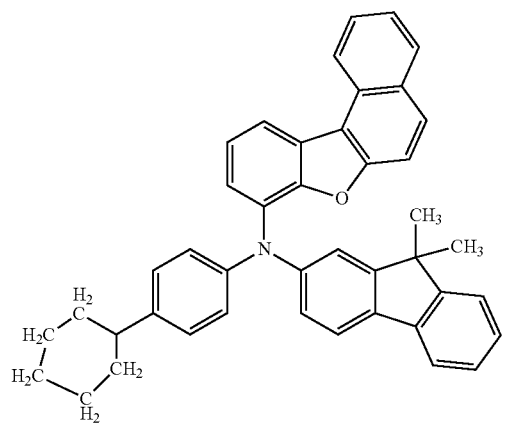
(5-23)
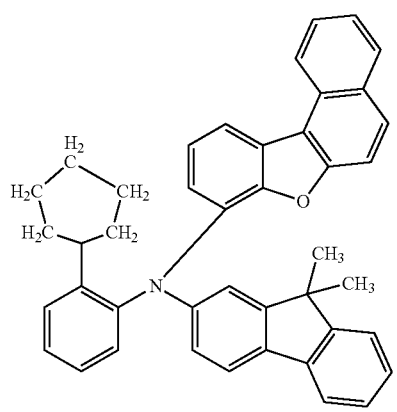
(5-24)
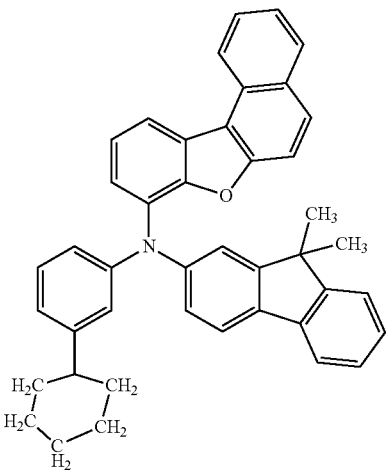
(5-25)
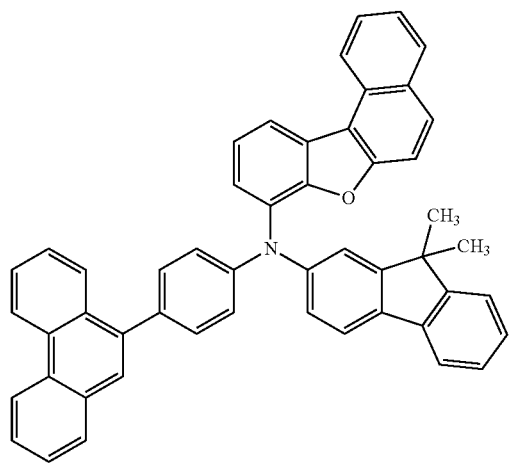
(5-26)
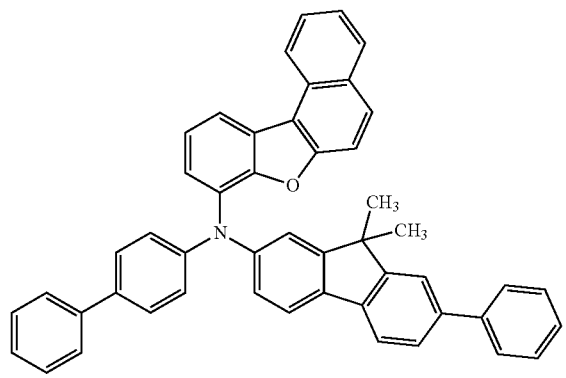

[Chemical Formulae 26]
(5-27)
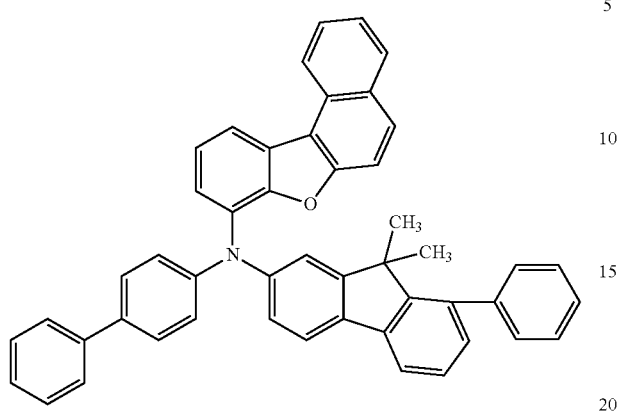
(5-30)
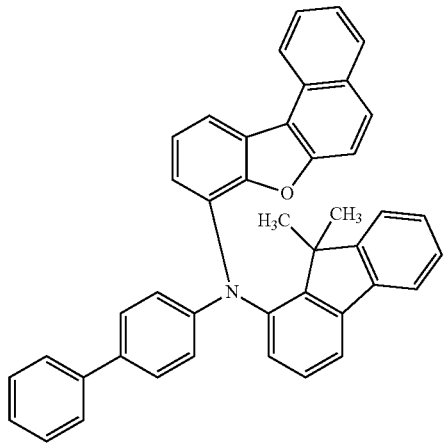
(5-28)
(5-31)
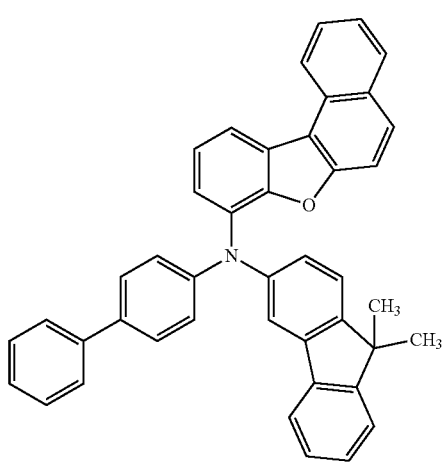
(5-29)
(5-32)
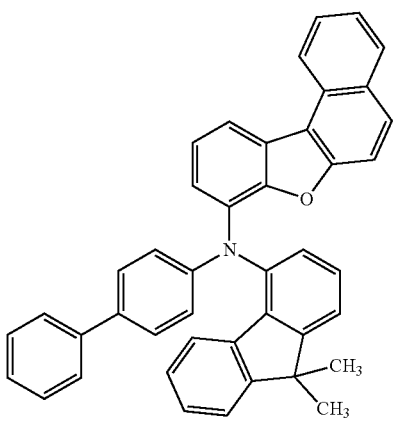

(5-33)
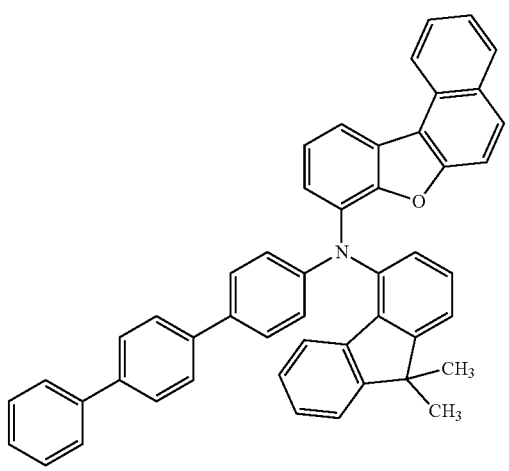
(5-34)
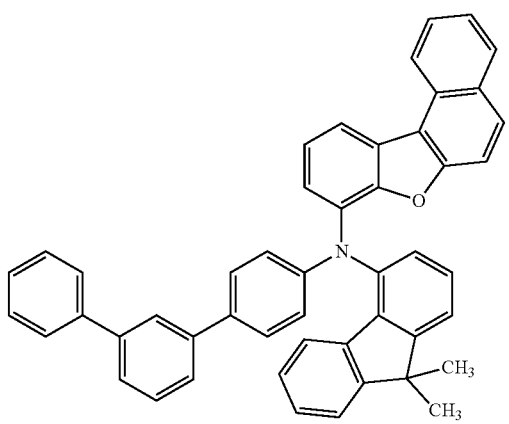
(5-35)
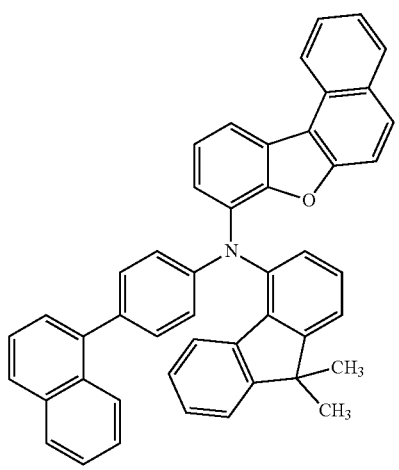
(5-36)
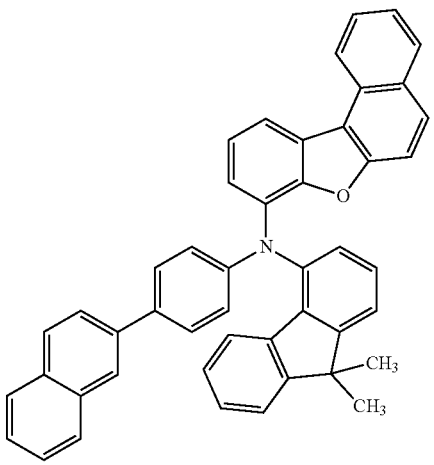
(5-37)
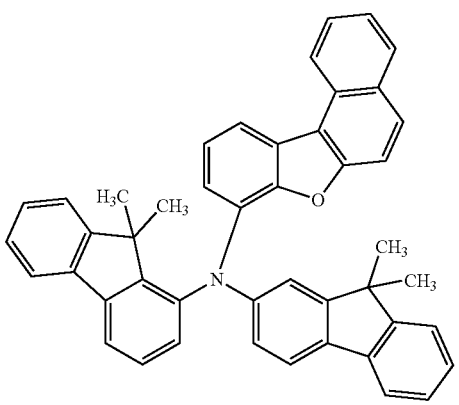
(5-38)
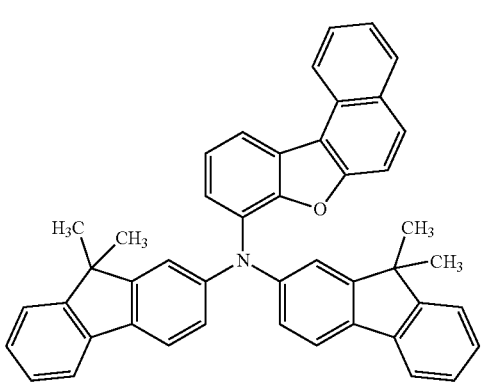

[Chemical Formulae 27]
(5-39)
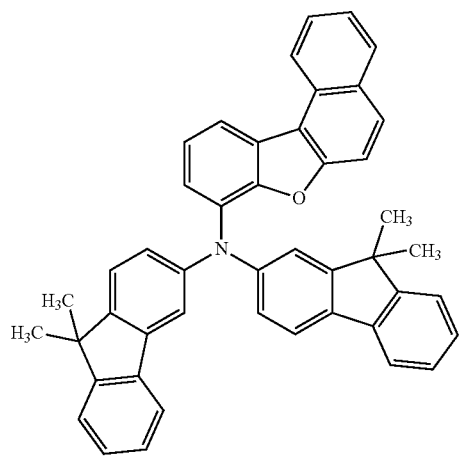
(5-40)
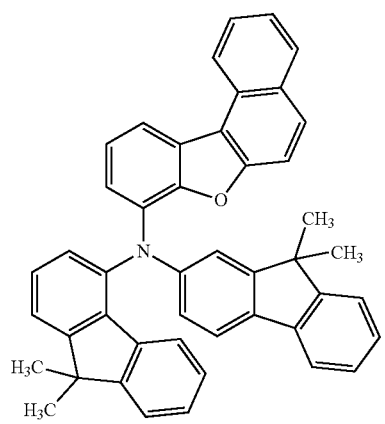
(5-41)
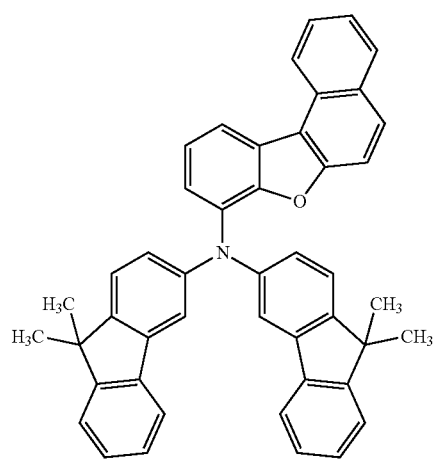
(5-42)
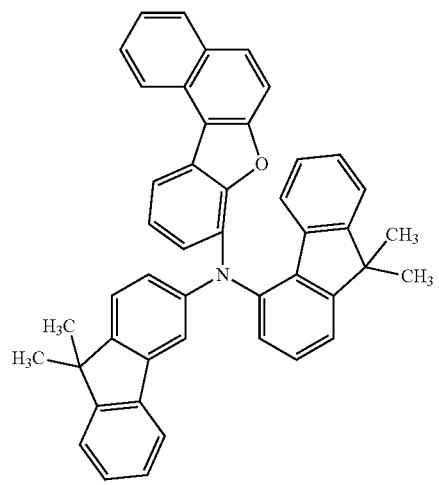
(5-43)
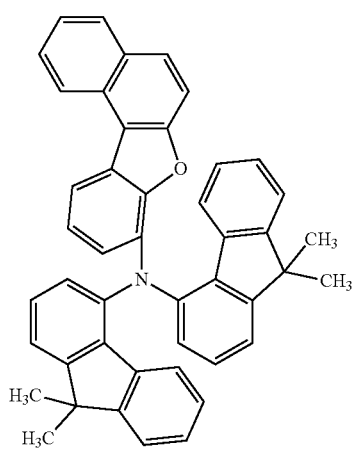
(5-44)
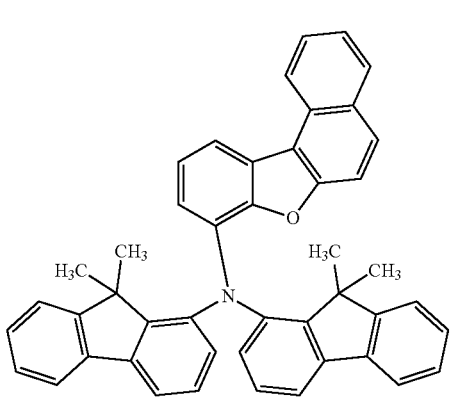

(5-45)
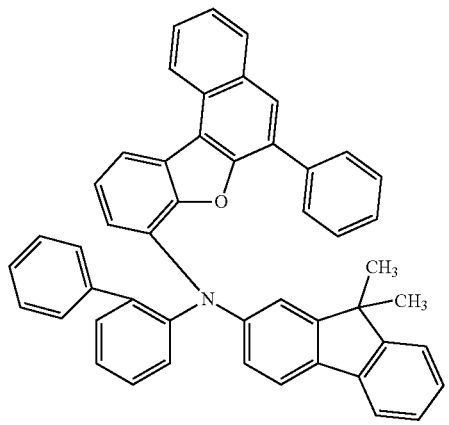
(5-46)
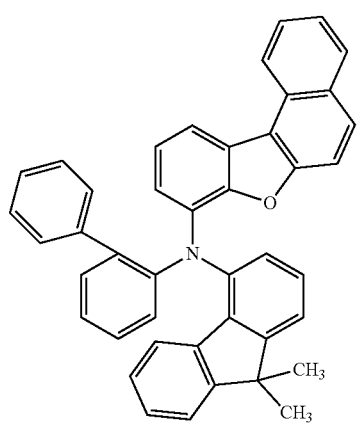
(5-47)
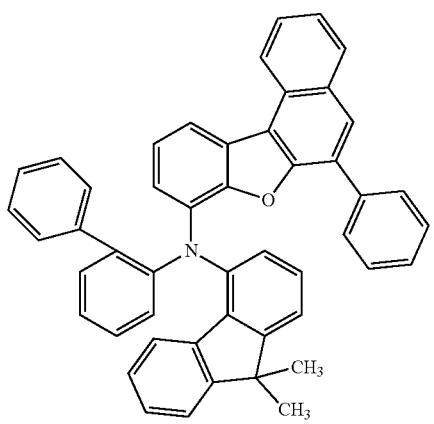
(5-48)
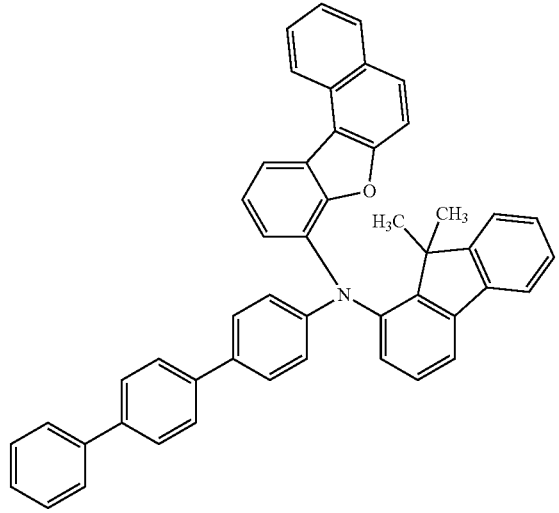
(5-49)
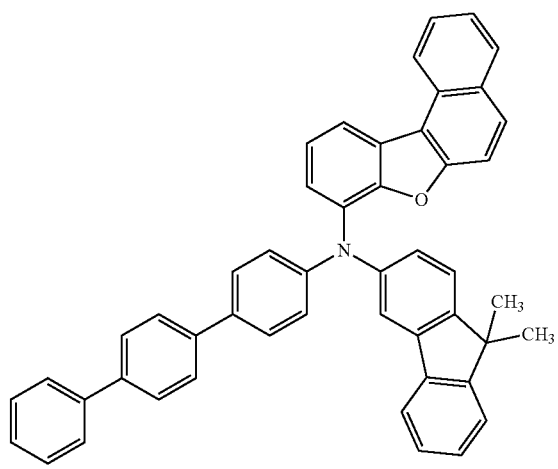
(5-50)
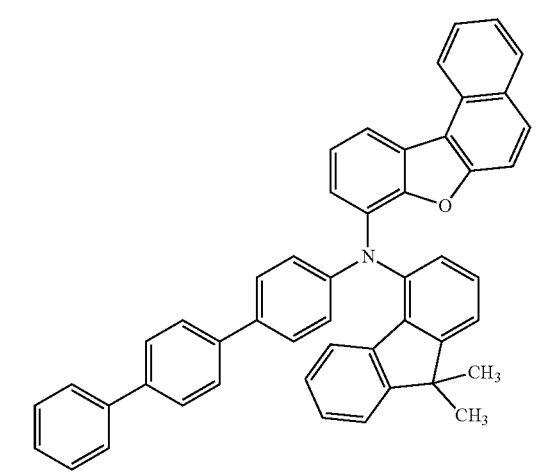

[Chemical Formulae 28]
(5-51)
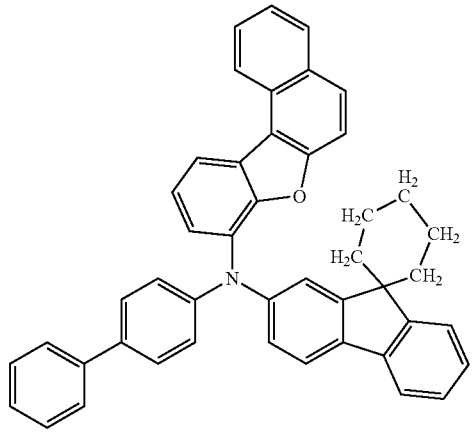
(5-52)
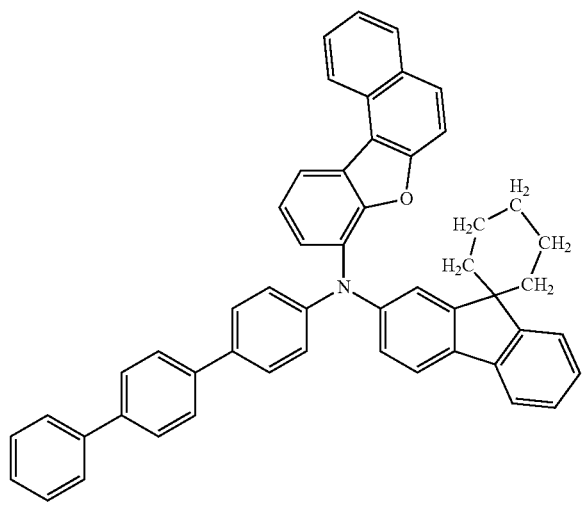
(5-53)
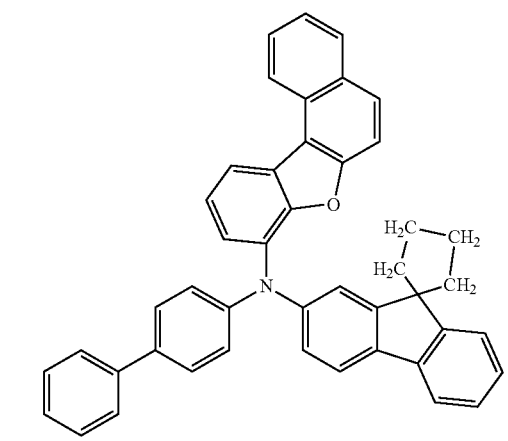
(5-54)
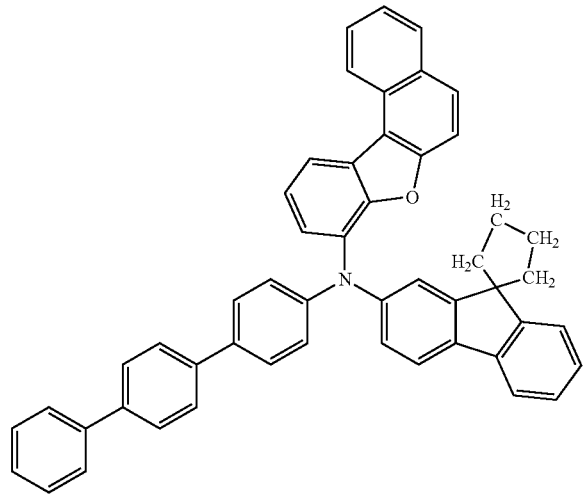
(5-55)
(5-56)
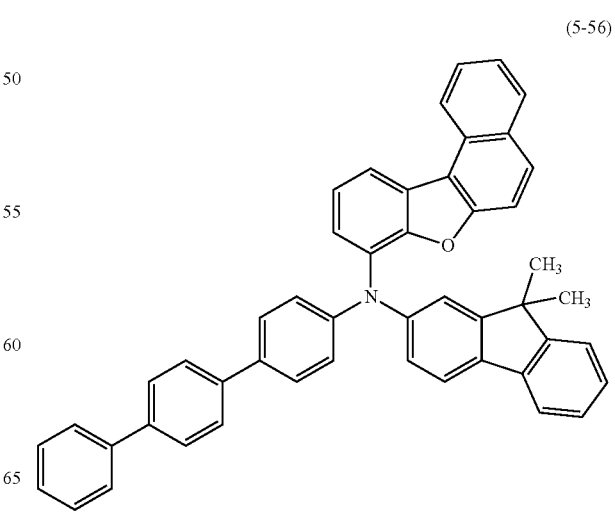

-continued
(5-57)
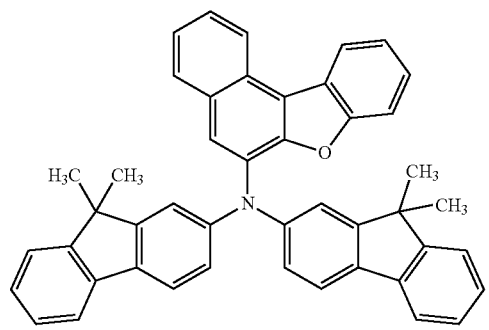
(5-58)
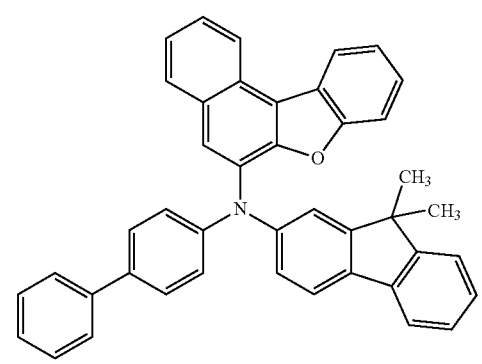
(5-59)
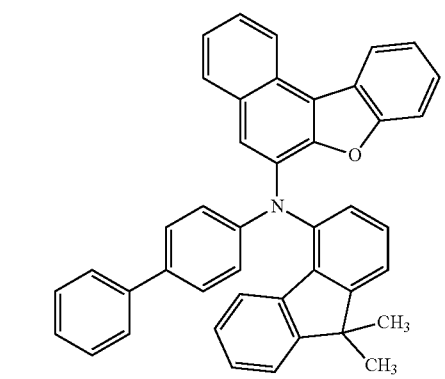
(5-60)
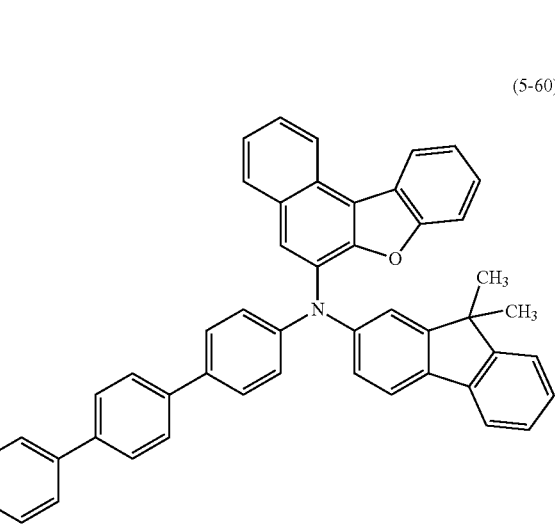
-continued
(5-61)
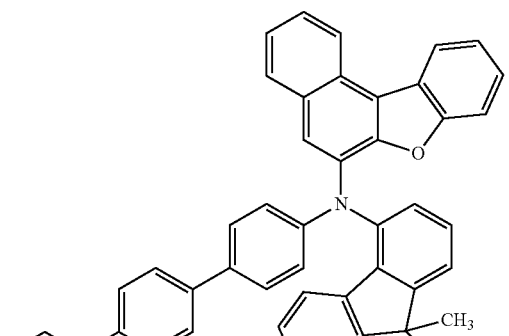
(5-62)
[Chemical Formulae 29]
(5-63)
(5-64)
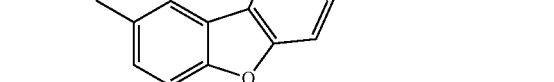

(5-65)
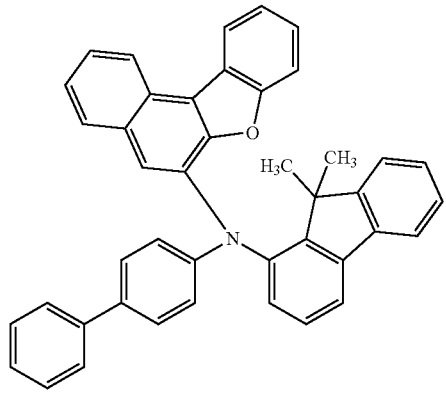
(5-68)
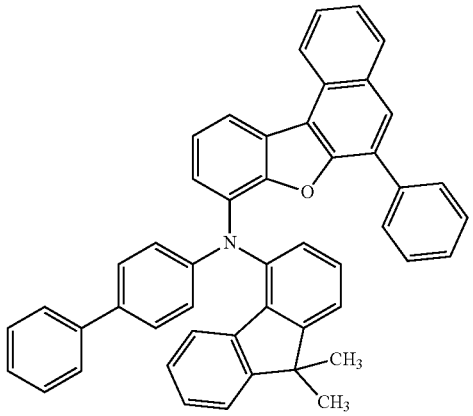
(5-66)
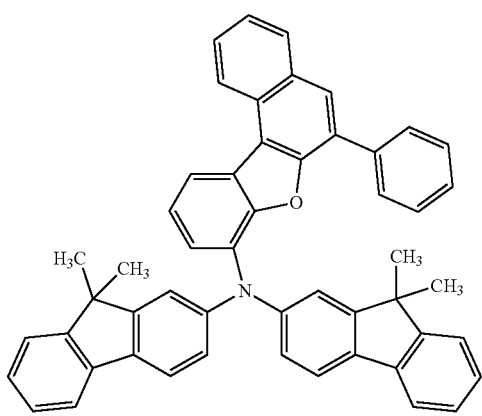
(5-69)
(5-67)
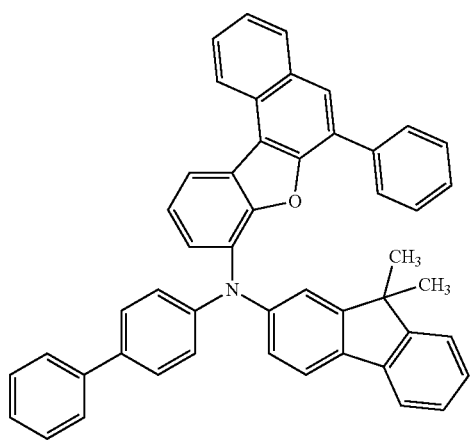
(5-70)
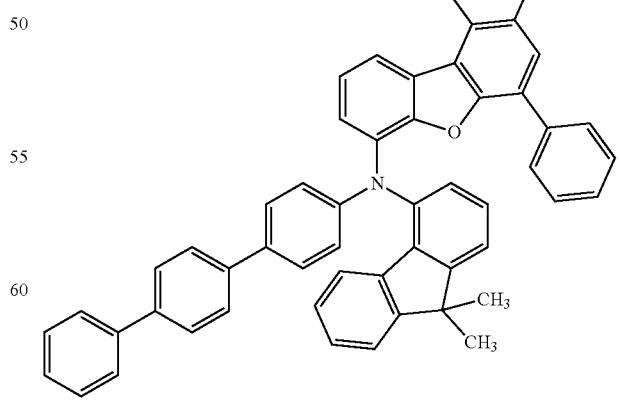

(5-71)
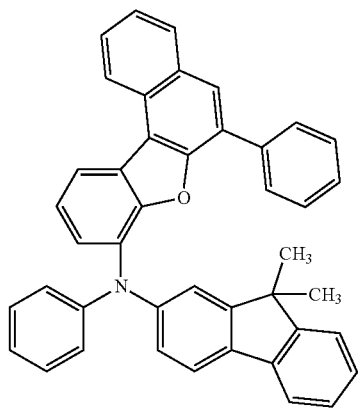
(5-72)
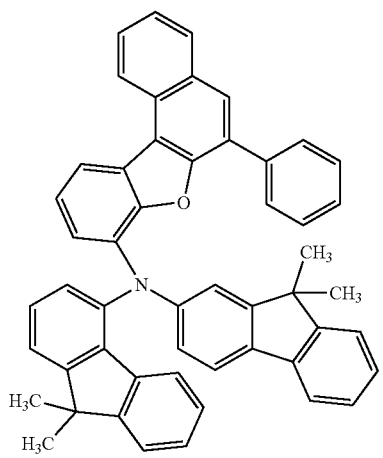
(5-73)
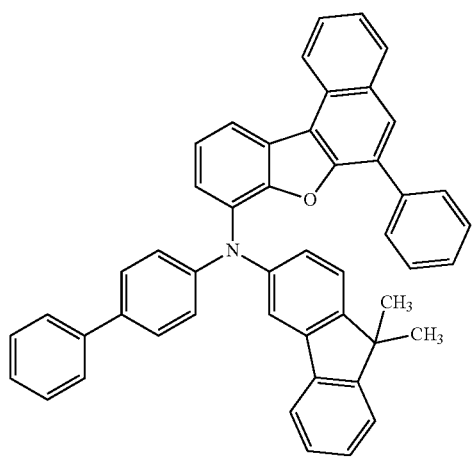
(5-74)
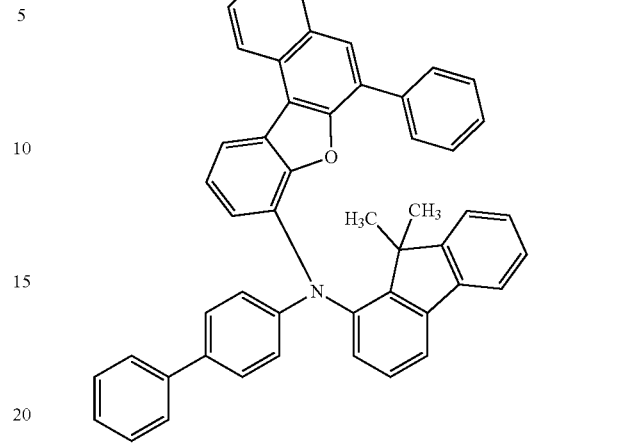
[Chemical Formulae 30]
(5-75)
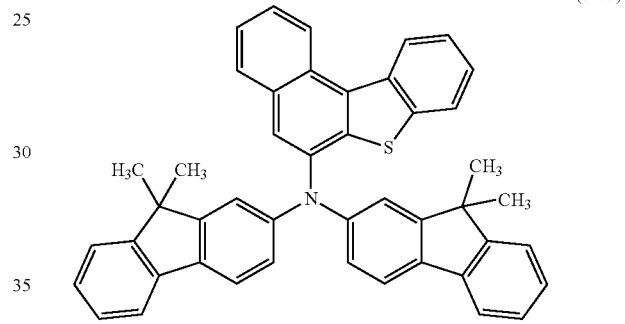
(5-76)
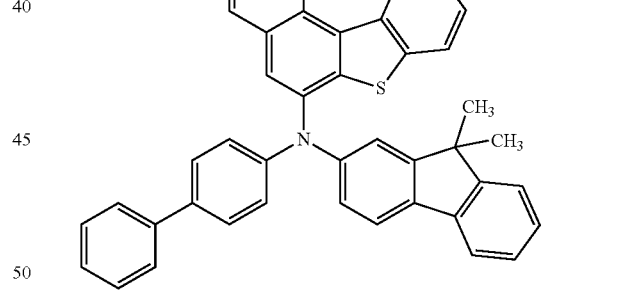
(5-77)
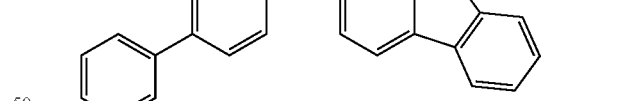

-continued
(5-78)
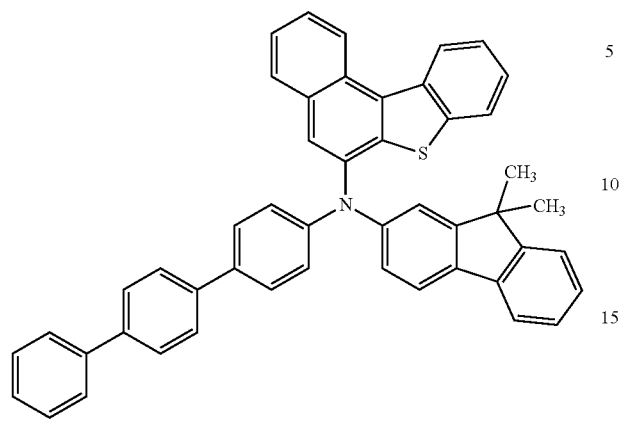
(5-79)
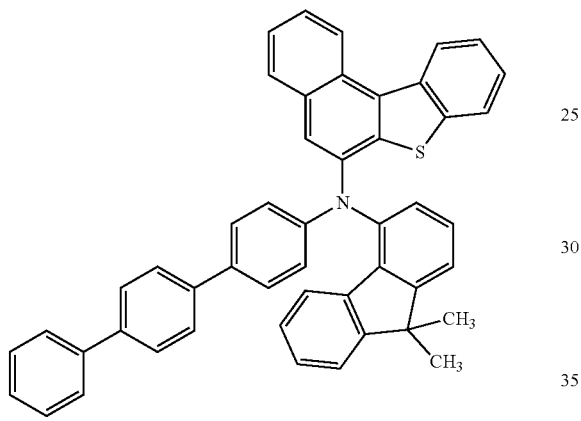
(5-80)
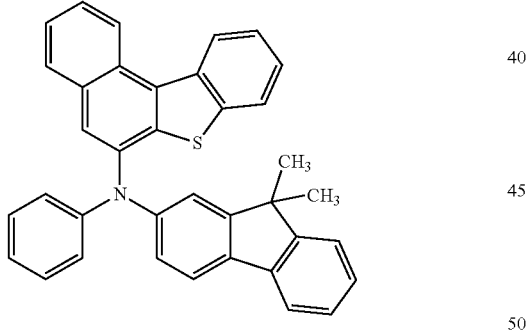
(5-81)
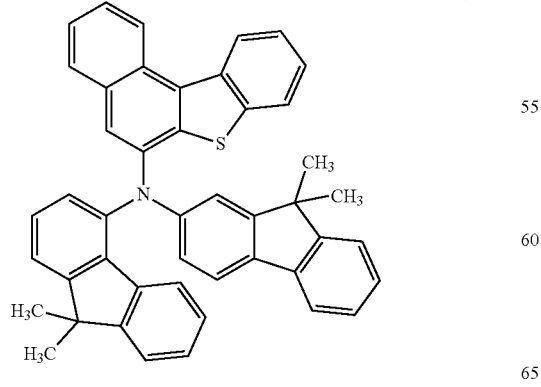
-continued
(5-82)
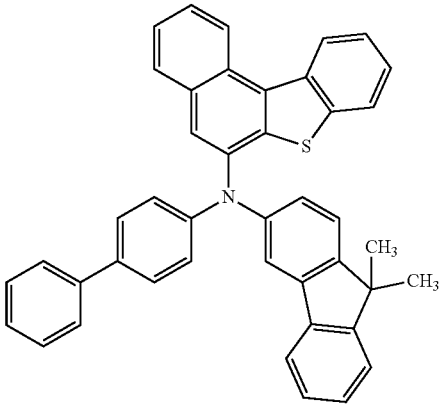
(5-83)
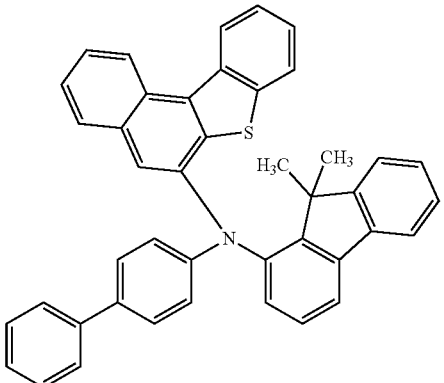
(5-84)
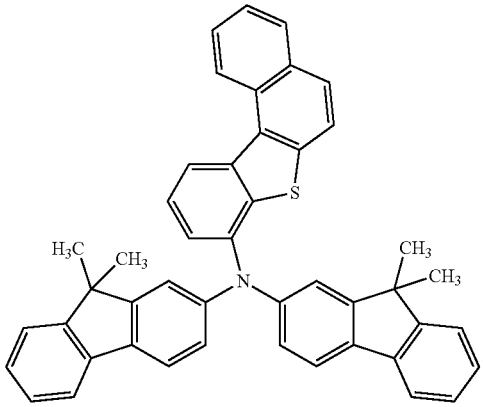
(5-85)
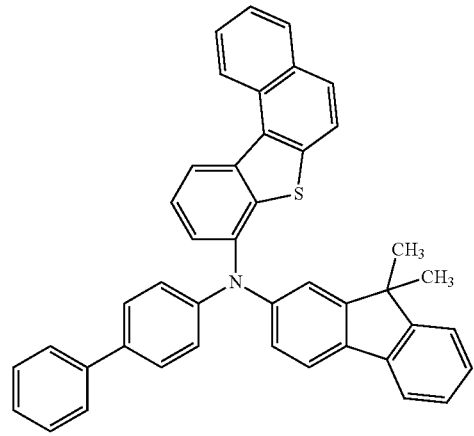

(5-86)
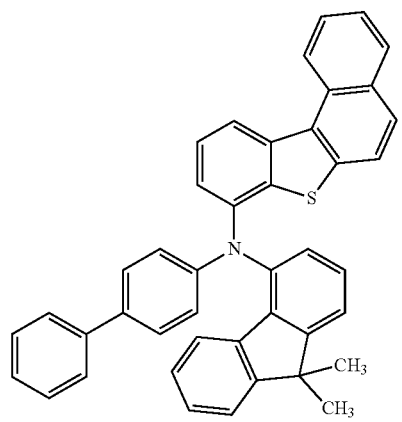
[Chemical Formulae 31]
(5-87)
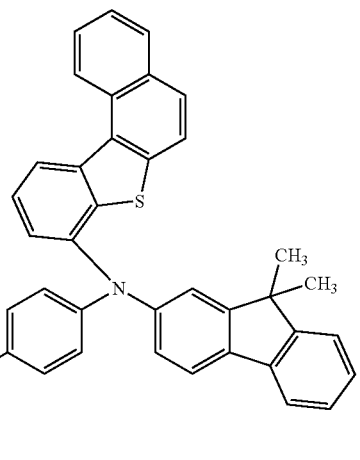
(5-88)
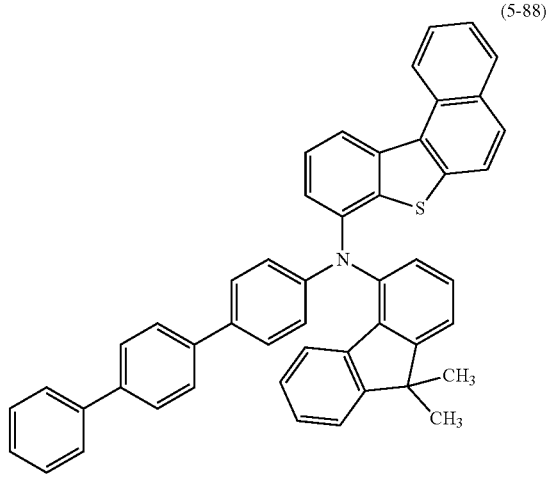
(5-89)
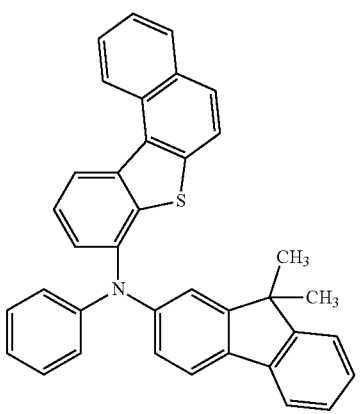
(5-90)
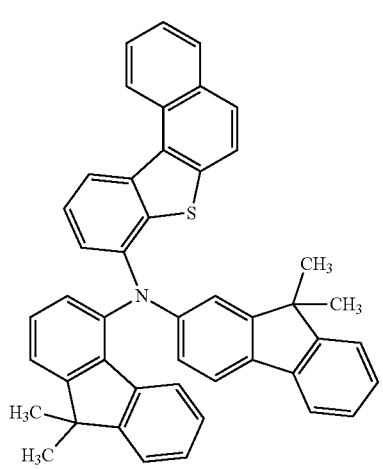
(5-91)
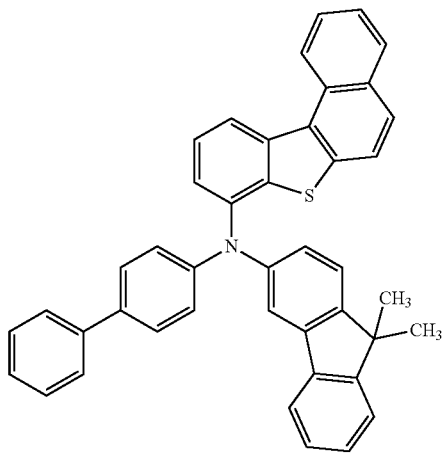

-continued
(5-92)
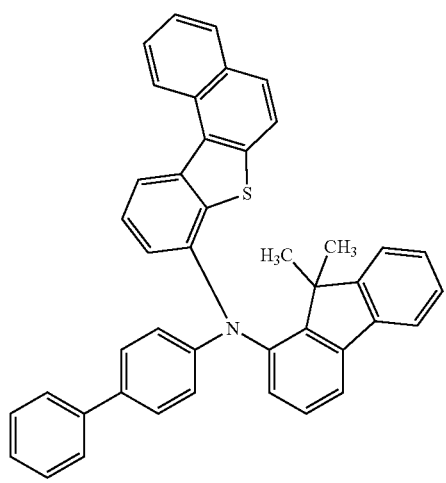
(5-93)
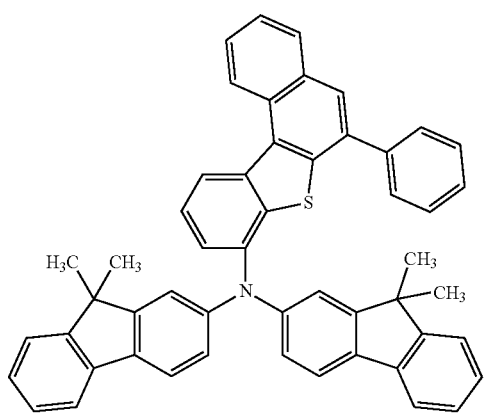
(5-94)
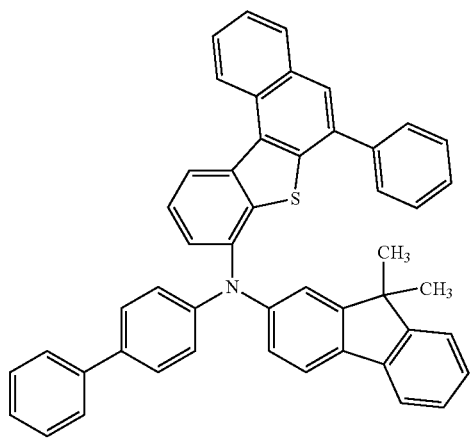
-continued
(5-95)
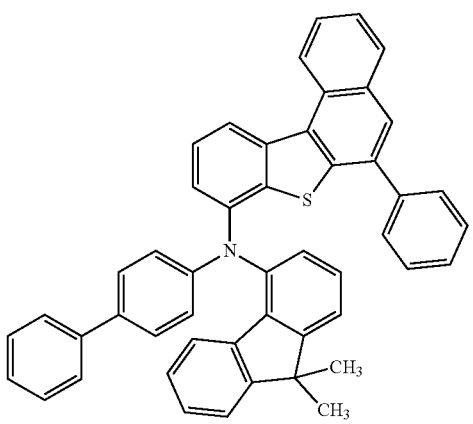
[Chemical Formulae 32]
(5-96)
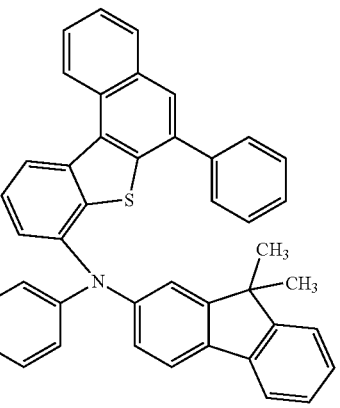
(5-97)
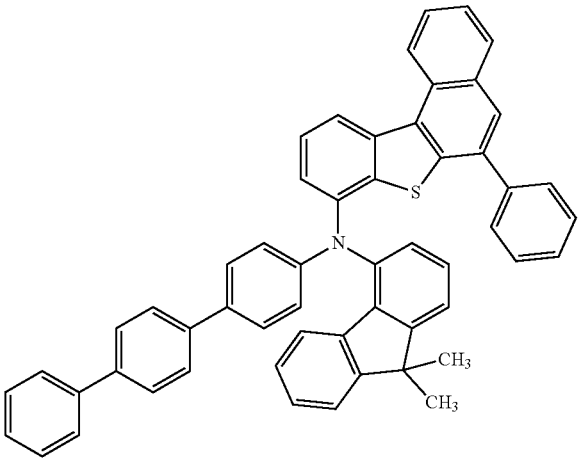

(5-98)
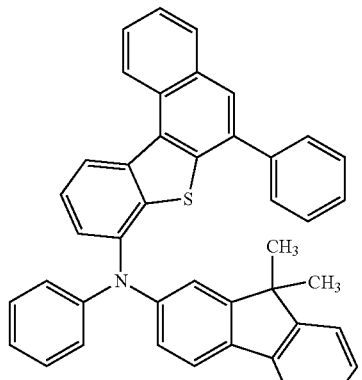
(5-99)
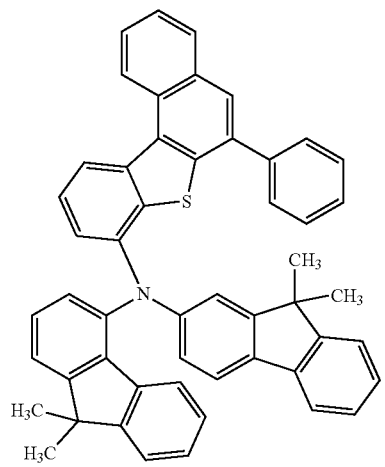
(5-100)
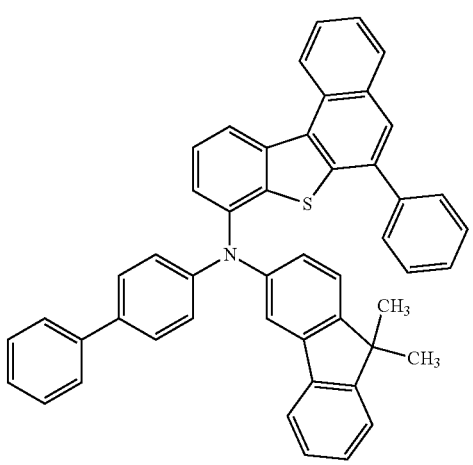
(5-101)
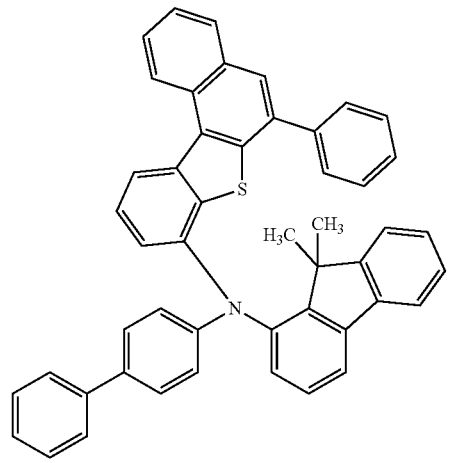
(5-102)
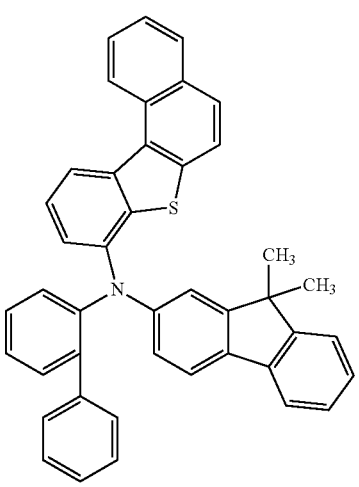
(5-103)
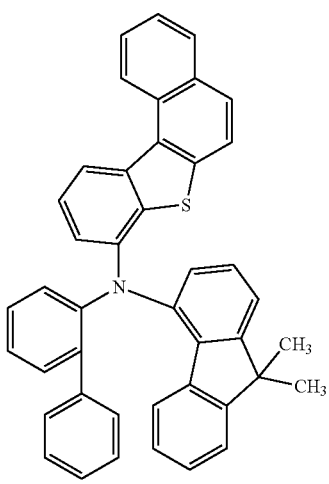

(5-104)

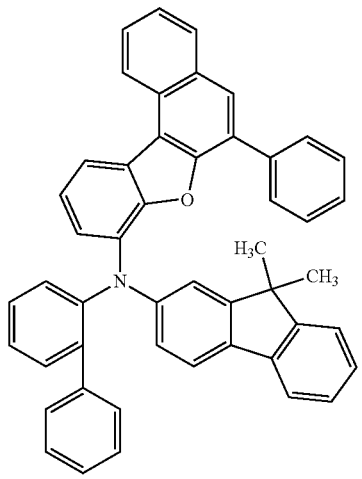

(5-105)

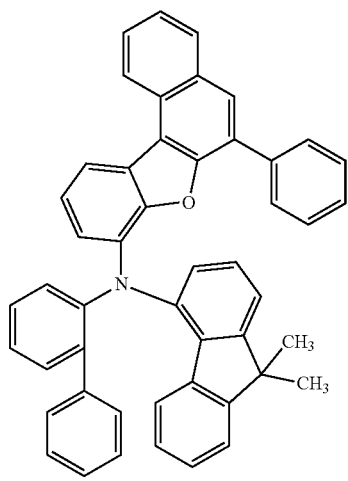

(5-106)

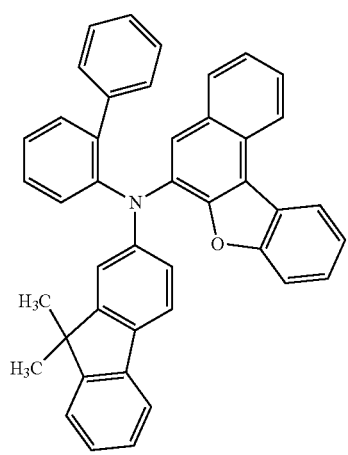

(5-107)

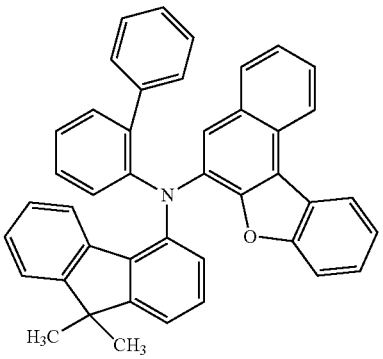

Next, a method for synthesizing the organic compound described above will be described using an organic compound represented by General Formula (G1-1a) below as an example. General Formula (G1-1a) shows a molecular structure in which A in General Formula (G1) above represents General Formula (g1) and the molecular structure of (g1) is fluoren-2-amine.

[Chemical Formula 33]

(G1-1a)

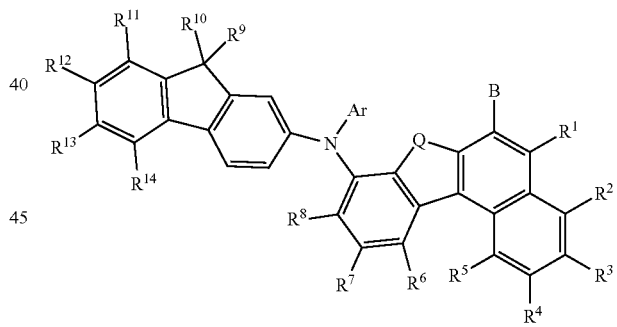

The organic compound represented by General Formula (G1-1a) can be synthesized as shown in Synthesis Schemes (a-1) and (a-2) below.

First, according to Reaction Formula (a-1), an arylamine compound (Compound 1) is coupled with a fluorene compound (Compound 2), whereby a fluorenylamine compound (Compound 3) can be obtained. Next, according to Reaction Formula (a-2), the fluorenylamine compound (Compound 3) is coupled with a benzonaphthofuran compound (Compound 4), whereby a target benzonaphthofuranylamine compound (G1-1a) can be obtained. Synthesis Schemes (a-1) and (a-2) are shown below.

[Chemical Formulae 34]

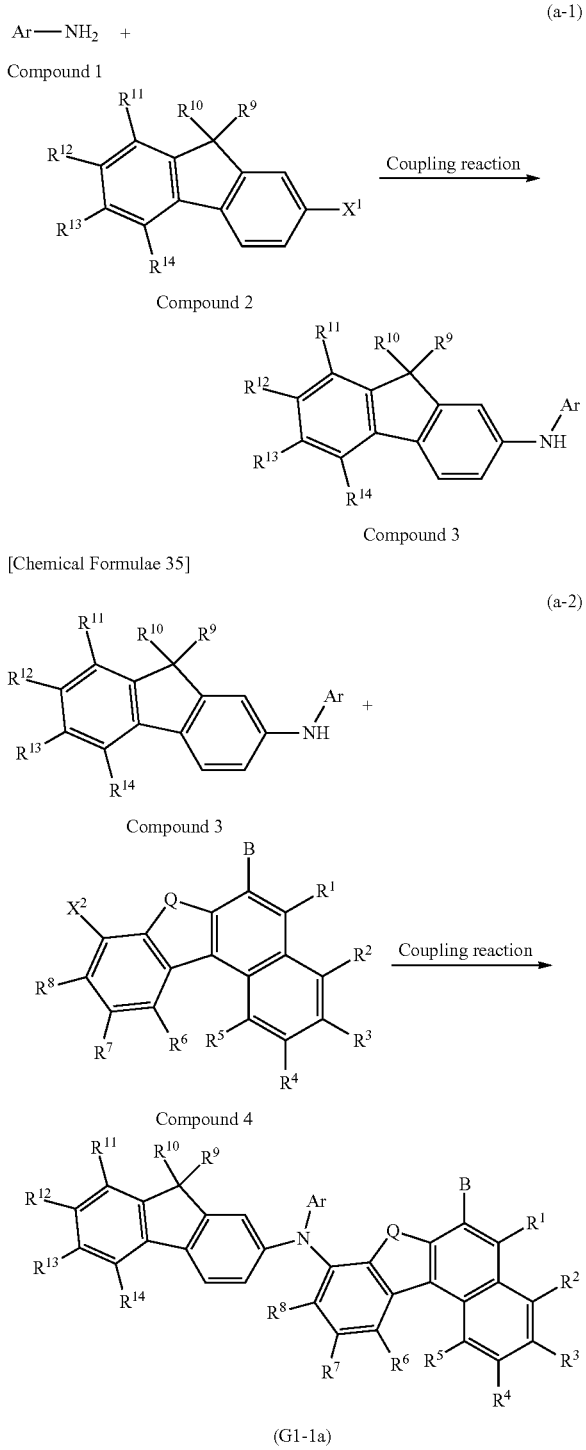

[Chemical Formulae 35]

In Synthesis Schemes (a-1) and (a-2), Q represents an oxygen atom or a sulfur atom. In addition, B, $R^1$ to $R^8$, and $R^{11}$ to $R^{14}$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group, and Ar represents a substituted or unsubstituted aryl group having 6 to 13 carbon atoms.

In Synthesis Schemes (a-1) and (a-2), $X^1$ and $X^2$ each independently represent chlorine, bromine, iodine, or a triflate group.

In the case where the Buchwald-Hartwig reaction is performed using a palladium catalyst in Synthesis Schemes (a-1) and (a-2), a palladium compound such as bis(dibenzylideneacetone)palladium(0), palladium(II) acetate, [1,1'-bis(diphenylphosphino)ferrocene]palladium(II) dichloride, tetrakis(triphenylphosphine)palladium(0), or allylpalladium (II) chloride (dimer) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP) can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. Reagents that can be used in the reaction are not limited to the above-described reagents. Alternatively, a compound in which an organotin group is bonded to an amino group can be used instead of Compound 1 or Compound 3.

Alternatively, in Synthesis Schemes (a-1) and (a-2), the Ullmann reaction using copper or a copper compound can be performed. Copper or a copper compound can be used in the reaction. As the base to be used, an inorganic base such as potassium carbonate can be given. As the solvent that can be used in the reaction, 1,3-dimethyl-3,4,5,6-tetrahydro-2(1H) pyrimidinone (DMPU), toluene, xylene, benzene, and the like can be given. In the Ullmann reaction, when the reaction temperature is 100° C. or higher, a target substance can be obtained in a shorter time in a higher yield; therefore, it is preferable to use DMPU or xylene having a high boiling point. A reaction temperature of 150° C. or higher is further preferred, and accordingly, DMPU is further preferably used. Reagents that can be used in the reaction are not limited to the above-described reagents.

Note that Compound 3 can also be synthesized by coupling an aryl compound (Compound 5) with a fluorenylamine compound (Compound 6) as in Synthesis Scheme (a-3) below.

[Chemical Formulae 36]

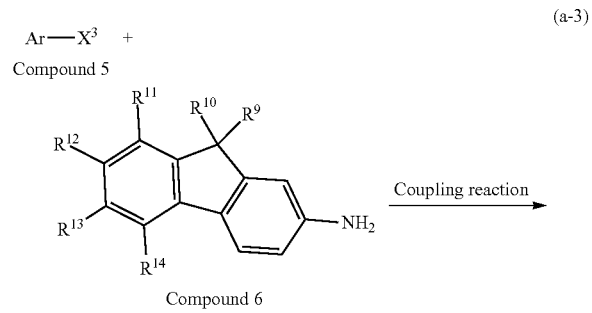

-continued

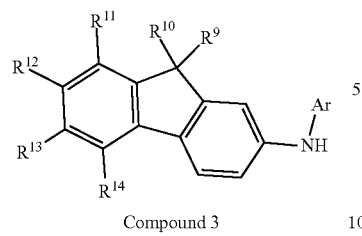

Compound 3

In Synthesis Scheme (a-3), $R^{11}$ to $R^{14}$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group, and Ar represents a substituted or unsubstituted aryl group having 6 to 13 carbon atoms.

In Synthesis Scheme (a-3), $X^3$ independently represents chlorine, bromine, iodine, or a triflate group. The same reaction conditions as those in Synthesis Schemes (a-1) and (a-2) can be used in Synthesis Scheme (a-3).

The organic compound represented by General Formula (G1-1a) above can be synthesized as shown in Synthesis Schemes (b-1) and (b-2) below.

First, according to Reaction Formula (b-1), an arylamine compound (Compound 1) is coupled with a benzonaphthofuran compound (Compound 4), whereby a benzonaphthofuranylamine compound (Compound 7) can be obtained. Next, according to Reaction Formula (b-2), the benzonaphthofuranylamine compound (Compound 7) is coupled with a fluorene compound (Compound 2), whereby a target benzonaphthofuranylamine compound (G1-1a) can be obtained. Synthesis Schemes (b-1) and (b-2) are shown below.

[Chemical Formulae 37]

(b-1)

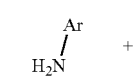

Compound 1

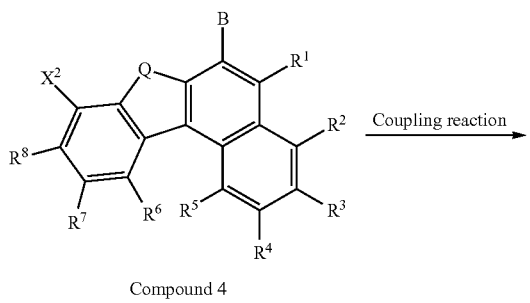

Compound 4

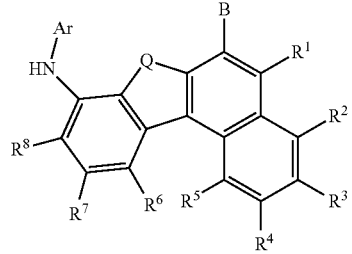

Compound 7

[Chemical Formulae 38]

(b-2)

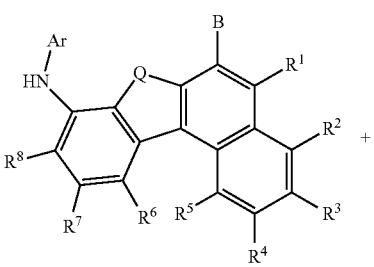

Compound 7

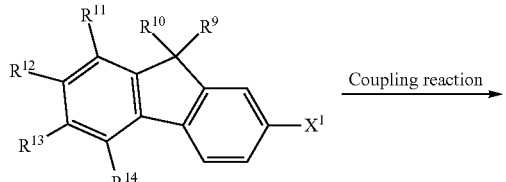

Compound 2

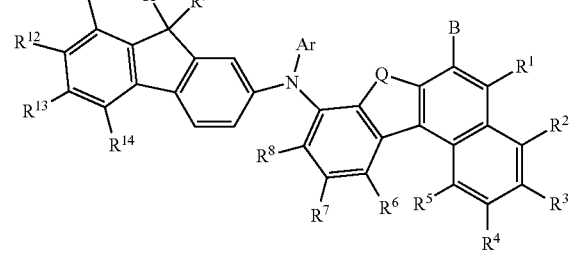

(G1-1a)

In Synthesis Schemes (b-1) and (b-2), Q represents an oxygen atom or a sulfur atom. In addition, B, $R^1$ to $R^8$, and $R^{11}$ to $R^{14}$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group, and Ar represents a substituted or unsubstituted aryl group having 6 to 13 carbon atoms.

In Synthesis Schemes (b-1) and (b-2), $X^1$ and $X^2$ each independently represent chlorine, bromine, iodine, or a triflate group.

In the case where the Buchwald-Hartwig reaction using a palladium catalyst or the Ullmann reaction using copper or a copper compound is performed in Synthesis Schemes (b-1) and (b-2), the same reaction conditions as those in Synthesis Schemes (a-1) and (a-2) can be used.

Note that Compound 7 can also be synthesized by coupling an aryl compound (Compound 5) with a benzonaphthofuranylamine compound (Compound 6) as in Synthesis Scheme (b-3) below.

[Chemical Formulae 39]

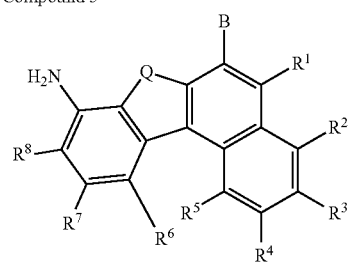

In Synthesis Scheme (b-3), Q represents an oxygen atom or a sulfur atom. In addition, B and $R^1$ to $R^8$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, Ar represents a substituted or unsubstituted aryl group having 6 to 13 carbon atoms.

In Synthesis Scheme (b-3), $X^3$ independently represents chlorine, bromine, iodine, or a triflate group. The same reaction conditions as those in Synthesis Schemes (a-1) and (a-2) can be used in Synthesis Scheme (b-3).

The organic compound represented by General Formula (G1-1a) above can be synthesized as shown in Synthesis Schemes (c-1) and (c-2) below.

First, according to Reaction Formula (c-1), a fluorenylamine compound (Compound 6) is coupled with a benzonaphthofuran compound (Compound 4), whereby a benzonaphthofuranylamine compound (Compound 8) can be obtained. Next, according to Reaction Formula (c-2), the benzonaphthofuranylamine compound (Compound 8) is coupled with an aryl compound (Compound 5), whereby a target benzonaphthofuranylamine compound (G1-1a) can be obtained. Synthesis Schemes (c-1) and (c-2) are shown below.

[Chemical Formulae 40]

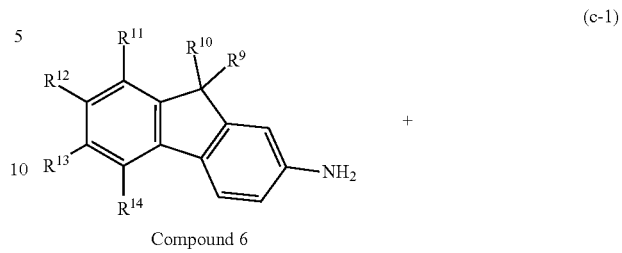

[Chemical Formulae 41]

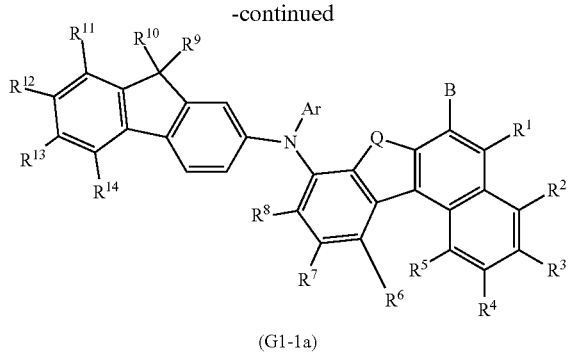

(G1-1a)

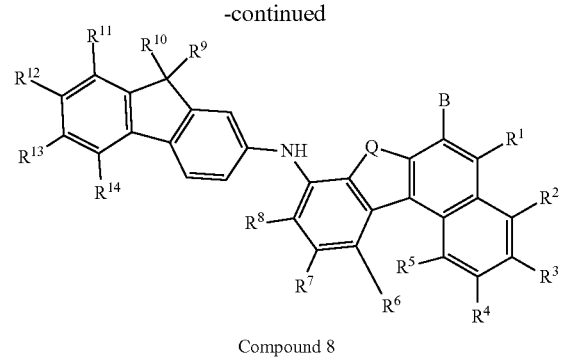

Compound 8

In Synthesis Schemes (c-1) and (c-2), Q represents an oxygen atom or a sulfur atom. In addition, B, $R^1$ to $R^8$, and $R^{11}$ to $R^{14}$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group, and Ar represents a substituted or unsubstituted aryl group having 6 to 13 carbon atoms.

In Synthesis Schemes (c-1) and (c-2), $X^2$ and $X^3$ each independently represent chlorine, bromine, iodine, or a triflate group.

In the case where the Buchwald-Hartwig reaction using a palladium catalyst or the Ullmann reaction using copper or a copper compound is performed in Synthesis Schemes (c-1) and (c-2), the same reaction conditions as those in Synthesis Schemes (a-1) and (a-2) can be used.

Note that Compound 8 can also be synthesized by Synthesis Scheme (c-3) below.

[Chemical Formulae 42]

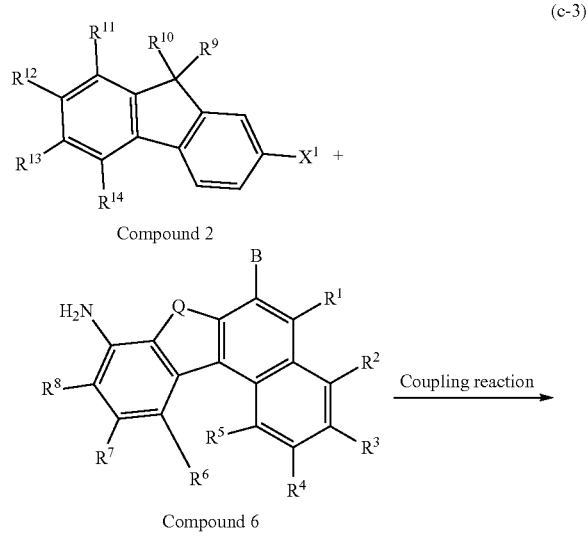

(c-3)

In Synthesis Scheme (c-3), Q represents an oxygen atom or a sulfur atom. In addition, B, $R^1$ to $R^8$, and $R^{11}$ to $R^{14}$ each represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms. In addition, $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group.

In Synthesis Scheme (c-3), $X^1$ independently represents chlorine, bromine, iodine, or a triflate group. The same reaction conditions as those in Synthesis Schemes (a-1) and (a-2) can be used in Synthesis Scheme (c-3).

The method for synthesizing the organic compound represented by General Formula (G1-1a) is not limited to Synthesis Schemes (a-1) and (a-3), Synthesis Schemes (b-1) and (b-3), and Synthesis Schemes (c-1) and (c-3) above.

The above is the description of the synthesis method for General Formula (G1-1a) in which A in General Formula (G1) represents General Formula (g1) and the molecular structure of (g1) is fluoren-2-amine. A compound in which A in General Formula (G1) represents General Formula (g1), and the molecular structure of (g1) is fluoren-1-amine, the molecular structure of (g1) is fluoren-3-amine, or the molecular structure of (g1) is fluoren-4-amine can also be synthesized by positioning a substituent of a fluorene compound at the 1-position, 3-position, or 4-position in Synthesis Schemes (a-1) and (a-3), Synthesis Schemes (b-1) and (b-3), and Synthesis Schemes (c-1) and (c-3).

In the case where B in General Formula (G1) represents General Formula (g1), a benzonaphthofuran-6-amine compound of the present invention can be obtained by using a compound including a substituent at the 6-position of benzonaphthofuran as a raw material.

Embodiment 2

In this embodiment, a light-emitting device of one embodiment of the present invention is described.

FIG. 1A is a diagram illustrating a light-emitting device of one embodiment of the present invention. The light-emitting device of one embodiment of the present invention includes a first electrode 101, a second electrode 102, and an EL layer 103. The EL layer 103 includes the organic compound described in Embodiment 1.

The EL layer 103 includes a light-emitting layer 113, and the light-emitting layer 113 contains a light-emitting material. A hole-injection layer 111 and a hole-transport layer 112 are provided between the light-emitting layer 113 and the first electrode 101. The organic compound described in Embodiment 1 has a high carrier-transport property, specifically, a high hole-transport property, and thus is preferably used for the hole-injection layer 111 and the hole-transport layer 112.

The light-emitting layer 113 may have a structure containing the organic compound described in Embodiment 1 and an electron-transport material in addition to the light-emitting material. In that case, the organic compound described in Embodiment 1 and the electron-transport material may be configured to form an exciplex. Formation of the exciplex having an appropriate emission wavelength allows efficient energy transfer to the light-emitting material, achieving a light-emitting device with high efficiency and a long lifetime.

Note that although FIG. 1A illustrates an electron-transport layer 114 and an electron-injection layer 115 in the EL layer 103 in addition to the light-emitting layer 113, the hole-injection layer 111, and the hole-transport layer 112, the structure of the light-emitting device is not limited thereto. Any of these layers may be omitted or a layer having another function may be included.

Next, examples of specific structures and materials of the aforementioned light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using a metal, an alloy, or a conductive compound having a high work function (specifically, 4.0 eV or more), a mixture thereof, or the like. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide (IWZO), and the like can be given. These conductive metal oxide films are usually formed by a sputtering method but may also be formed by application of a sol-gel method or the like. An example of the formation method is a method in which indium oxide-zinc oxide is formed by a sputtering method using a target in which 1 to 20 wt % zinc oxide is added to indium oxide. Indium oxide containing tungsten oxide and zinc oxide (IWZO) can also be formed by a sputtering method using a target containing 0.5 to 5 wt % tungsten oxide and 0.1 to 1 wt % zinc oxide with respect to indium oxide. Alternatively, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like can be given. Graphene can also be used. Note that when a composite material described later is used for a layer that is in contact with the first electrode 101 in the EL layer 103, an electrode material can be selected regardless of its work function.

Figure 1B:
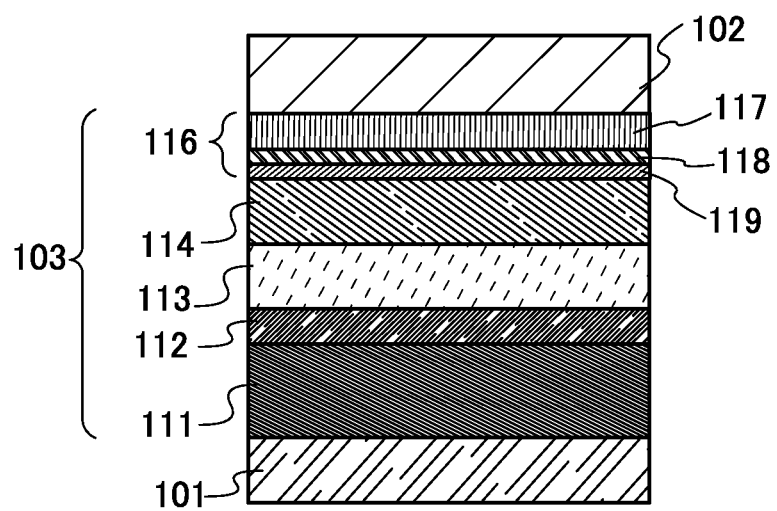

Although the EL layer 103 preferably has a stacked-layer structure, there is no particular limitation on the stacked-layer structure, and various layer structures such as a hole-injection layer, a hole-transport layer, a light-emitting layer, an electron-transport layer, an electron-injection layer, a carrier-blocking layer, an exciton-blocking layer, and a charge-generation layer can be employed. In this embodiment, two kinds of structures are described: the structure including the electron-transport layer 114 and the electron-injection layer 115 in addition to the hole-injection layer 111, the hole-transport layer 112, and the light-emitting layer 113 as illustrated in FIG. 1A; and the structure including the electron-transport layer 114 and a charge-generation layer 116 in addition to the hole-injection layer 111, the hole-transport layer 112, and the light-emitting layer 113 as illustrated in FIG. 1B. Materials forming the layers are specifically described below.

The hole-injection layer 111 contains a substance having an acceptor property. Either an organic compound or an inorganic compound can be used as the substance having an acceptor property.

As the substance having an acceptor property, a compound having an electron-withdrawing group (a halogen group or a cyano group) can be used; 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), 2-(7-dicyanomethylene-1,3,4,5,6,8,9,10-octafluoro-7H-pyren-2-ylidene)malononitrile, and the like can be given. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a halogen group such as a fluoro group, or a cyano group) has a very high electron-accepting property and thus is preferable. Specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) or copper phthalocyanine (CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), or a high molecule such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains the above-described acceptor substance can be used for the hole-injection layer 111. By using a composite material in which a material having a hole-transport property contains an acceptor substance, a material used to form an electrode can be selected regardless of its work function. In other words, besides a material having a high work function, a material having a low work function can also be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of 1×10⁻⁶ cm²/Vs or higher. Organic compounds which can be used as the material having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: Poly-TPD).

The material having a hole-transport property used for the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that has a naphthalene ring, or an aromatic monoamine in which a 9-fluorenyl group is bonded to nitrogen of the amine through an arylene group may be used. Note that these second organic compounds are preferably substances having an N,N-bis(4-biphenyl)amino group because a light-emitting device with a long lifetime can be manufactured. Specific examples of the above second organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4''-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4''-diphenyltriphenylamine (abbreviation: BBAPNB), 4-[4-(2-naphthyl)phenyl]-4',4''-diphenyltriphenylamine (abbreviation: BBAβNBi), 4,4'-diphenyl-4''-(6;1'-binaphthyl-2-yl)triphenylamine (abbreviation: BBAαNβNB), 4,4'-diphenyl-4''-(7;1'-binaphthyl-2-yl)triphenylamine (abbreviation: BBAαNβNB-03), 4,4'-diphenyl-4''-(7-phenyl)naphthyl-2-yltriphenylamine (abbreviation: BBAPβNB-03), 4,4'-diphenyl-4''-(6;2'-binaphthyl-2-yl)triphenylamine (abbreviation: BBA(βN2)B), 4,4'-diphenyl-4''-(7;2'-binaphthyl-2-yl)triphenylamine (abbreviation: BBA(βN2)B-03), 4,4'-diphenyl-4''-(4;2'-binaphthyl-1-yl)triphenylamine (abbreviation: BBAβNαNB), 4,4'-diphenyl-4''-(5;2'-binaphthyl-1-yl)triphenylamine (abbreviation: BBAβNαNB-02), 4-(4-biphenylyl)-4'-(2-naphthyl)-4''-phenyltriphenylamine (abbreviation: TPBiAβNB), 4-(3-biphenylyl)-4'-[4-(2-naphthyl)phenyl]-4''-phenyltriphenylamine (abbreviation: mTPBiAβNBi), 4-(4-biphenylyl)-4'-[4-(2-naphthyl)phenyl]-4''-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4''-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-diphenyl-4'-(2-naphthyl)-4''-{9-(4-biphenylyl)carbazole)}triphenylamine (abbreviation: YGTBiβNB), N-[4-(9-phenyl-9H-carbazol-3-yl)phenyl]-N-[4-(1-naphthyl)phenyl]-9,9'-spirobi(9H-fluoren)-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi(9H-fluoren)-4-amine (abbreviation: oFBiSF), N-(4-biphenyl)-N-(dibenzofuran-4-yl)-9,9-dimethyl-9H-fluoren-2-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H- fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Note that it is further preferable that the material having a hole-transport property used for the composite material have a relatively deep HOMO level greater than or equal to −5.7 eV and less than or equal to −5.4 eV. The relatively deep HOMO level of the material having a hole-transport property used for the composite material makes it easy to inject holes into the hole-transport layer 112 and to obtain a light-emitting device with a long lifetime.

The organic compound described in Embodiment 1 can be suitably used as the material having a hole-transport property used for the composite material.

Note that mixing the above composite material with a fluoride of an alkali metal or an alkaline earth metal (the proportion of fluorine atoms in the layer is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, whereby a light-emitting device having a low driving voltage can be obtained. The organic compound having an acceptor property is an easy-to-use material because evaporation is easy and its film can be easily formed.

The hole-transport layer 112 contains a material having a hole-transport property. The material having a hole-transport property preferably has a hole mobility of $1 \times 10^{-6}$ cm$^2$/Vs or more. As the material having a hole-transport property, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferable because these have favorable reliability, have high hole-transport properties, and contribute to a reduction in driving voltage. Note that any of the substances given as examples of the material having a hole-transport property that is used for the composite material for the hole-injection layer 111 can also be suitably used as the material included in the hole-transport layer 112. The organic compound described in Embodiment 1 can be highly suitably used as the material included in the hole-transport layer 112 because of its high hole-transport property. Furthermore, since the organic compound described in Embodiment 1 has a high hole-transport property, even when the hole-transport layer 112 is formed to have a large thickness of 100 nm or more, a light-emitting device with a small increase in driving voltage and favorable device characteristics can be provided. The large thickness of the hole-transport layer 112 facilitates appropriate formation of a microcavity structure because it allows the optical length between electrodes to be adjusted easily.

The light-emitting layer 113 contains a light-emitting substance and a host material. The light-emitting layer 113 may additionally contain other materials. Furthermore, the light-emitting layer 113 may be a stack of two layers with different compositions.

The light-emitting substance may be fluorescent substances, phosphorescent substances, substances exhibiting thermally activated delayed fluorescence (TADF), or other light-emitting substances.

Examples of a material that can be used as a fluorescent substance in the light-emitting layer 113 include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N''-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N''-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N''-triphenyl-1,4-phenylenediamine (abbreviation: 2DPAPA), N-[9,10-bis(1,1'-biphenyl-2-yl)-2-anthryl]-N$_N$,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N''-tetrakis(4-methylphenyl)tetracene-5,11-diamine (abbreviation: p-mPhTD), 7,14-diphenyl-N,N,N',N''-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-(pyrene-1,6-diyl)bis[(6,N-diphenylbenzo[b]naphtho[1,2-d]furan)-8-amine](abbreviation:1,6BnfAPrn-03), 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02), and 3,10-bis[N-(dibenzofuran-3-yl)-N-phenylamino]naphtho[2,3-b; 6,7-b']bisbenzofuran (abbreviation: 3,10FrA2Nbf(IV)-02). In particular, a condensed aromatic diamine compound typified by a pyrenediamine compound such as 1,6FLPAPrn, 1,6mMemFLPAPrn, and 1,6BnfAPrn-03 is preferable because of its high hole-trapping property, high emission efficiency, and high reliability. Fluorescent substances other than those can also be used.

In the case where a phosphorescent substance is used as a light-emitting substance in the light-emitting layer 113, examples of a material that can be used include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-j]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIracac). These are compounds exhibiting blue phosphorescent light, and are compounds having an emission wavelength peak at 440 nm to 520 nm.

Examples also include an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium (III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), or (acetylacetonato)bis(4,6-diphenylpyrimidinato)iridium(III) (abbreviation: [Ir(dppm)$_2$(acac)]), an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) or (acetylacetonato)bis(5-isopropyl-3-methyl-2-phenylpyrazinato)iridium(III) (abbreviation: [Ir(mppr-iPr)$_2$(acac)]), an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), [2-d3-methyl-(2-pyridinyl-κN)benzofuro[2,3-b]pyridine-κC]bis[2-(5-d3-methyl-2-pyridyl-κN2)phenyl-x]iridium(III) (abbreviation: [Ir(5mppy-d3)$_2$(mbfpypy-d3)]), or [2-d3-methyl-(2-pyridinyl-κN)benzofuro[2,3-b]pyridine-κC]bis[2-(2-pyridinyl-κN)phenyl-κC]iridium(III) (abbreviation: [Ir(ppy)$_2$(mbfpypy-d3)]), and a rare earth metal complex such as tris(acetylacetonato)(monophenanthroline)terbium(III) (abbreviation: [Tb(acac)$_3$(Phen)]). These are compounds that mainly exhibit green phosphorescent light, and have an emission wavelength peak at 500 nm to 600 nm. Note that an organometallic iridium complex having a pyrimidine skeleton is particularly preferable because of its distinctively high reliability and emission efficiency.

Examples also include an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), or bis[4,6-di(naphthalen-1-yl)pyrimidinato](dipivaloylmethanato)iridium(III) (abbreviation: [Ir(d1npm)$_2$(dpm)]), an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]), an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$)iridium(III) acetylacetonate (abbreviation: [Ir(piq)$_2$(acac)]), a platinum complex such as 2,3,7,8,12,13,17,18-octaethyl-21H,23H-porphyrin platinum(II) (abbreviation: PtOEP), and a rare earth metal complex such as tris(1,3-diphenyl-1,3-propanedionato)(monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]). These are compounds exhibiting red phosphorescent light, and have an emission peak at 600 nm to 700 nm. Furthermore, from the organometallic iridium complex having a pyrazine skeleton, red light emission with favorable chromaticity can be obtained.

Besides the above-described phosphorescent compounds, other known phosphorescent substances may be selected and used.

As the TADF material, a fullerene, a derivative thereof, an acridine, a derivative thereof, an eosin derivative, or the like can be used. Other examples include a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)), which are represented by the following structural formulae.

[Chemical Formulae 43]

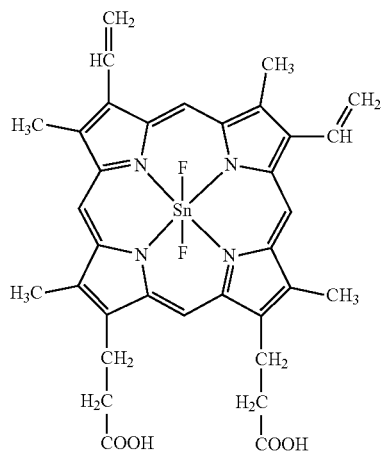

$SnF_2$(Proto IX)

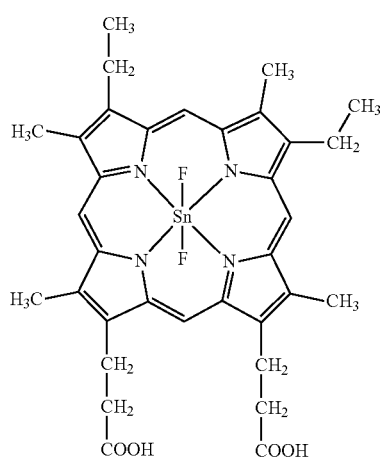

$SnF_2$(Meso IX)

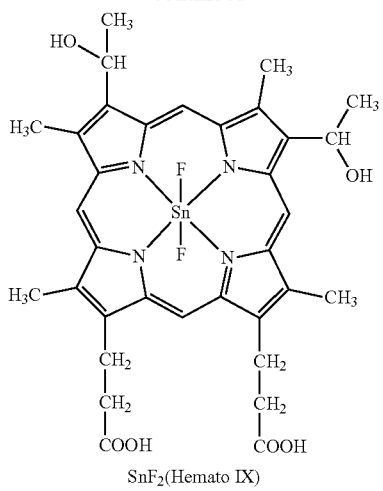

$SnF_2$(Hemato IX)

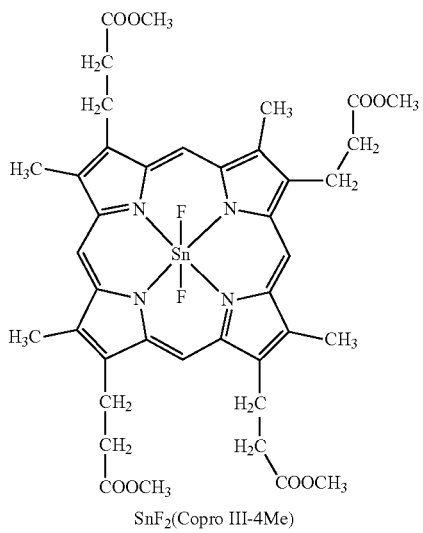

$SnF_2$(Copro III-4Me)

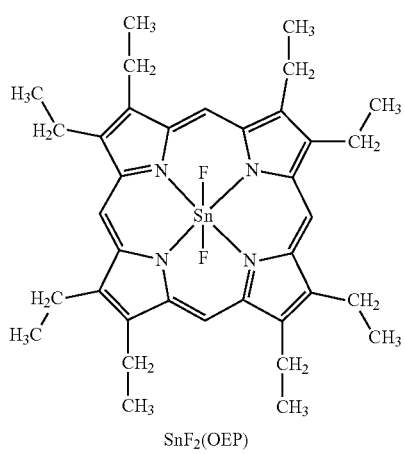

$SnF_2$(OEP)

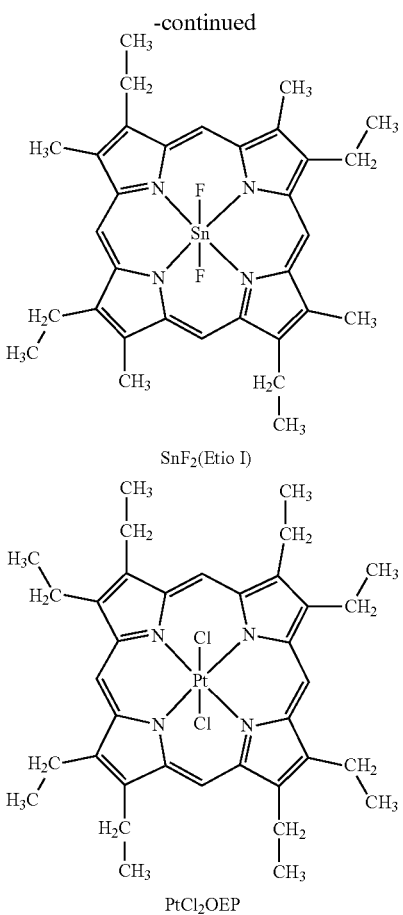

SnF₂(Etio I)

PtCl₂OEP

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. These heterocyclic compounds are preferable because of having both a high electron-transport property and a high hole-transport property owing to the π-electron rich heteroaromatic ring and the π-electron deficient heteroaromatic ring. Among skeletons having a π-electron deficient heteroaromatic ring, a pyridine skeleton, a diazine skeleton (a pyrimidine skeleton, a pyrazine skeleton, and a pyridazine skeleton), and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor property and reliability. Among skeletons having a π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the S1 level and the T1 level becomes small, and thus thermally activated delayed fluorescence can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formulae 44]

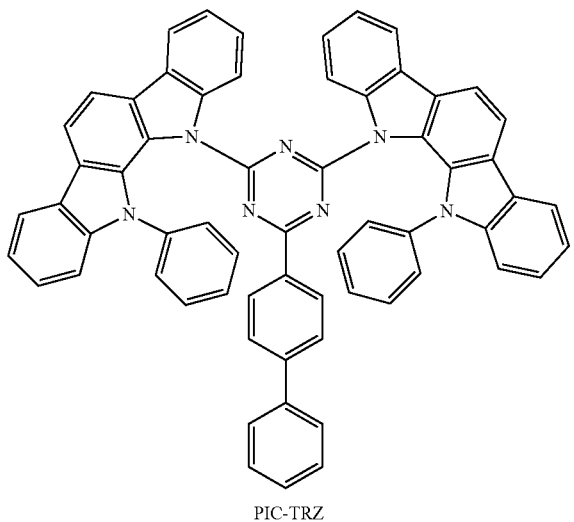

PIC-TRZ

-continued

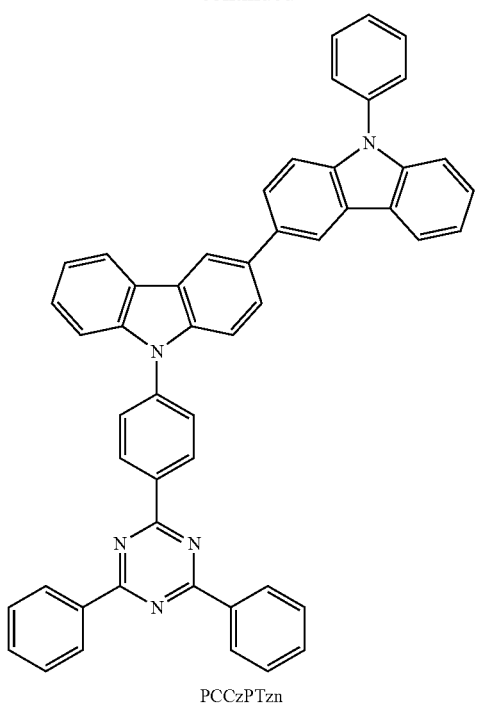

PCCzPTzn

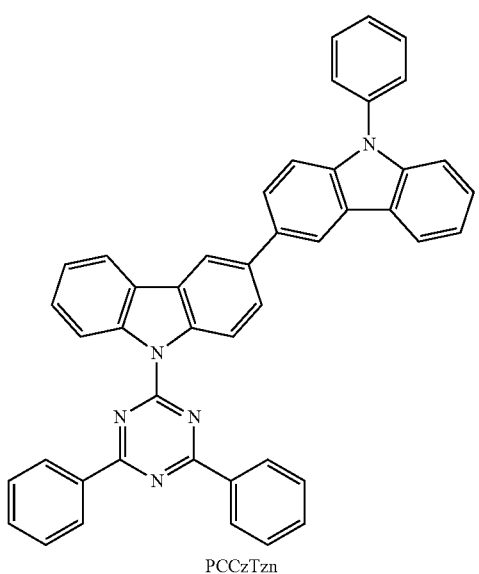

PCCzTzn

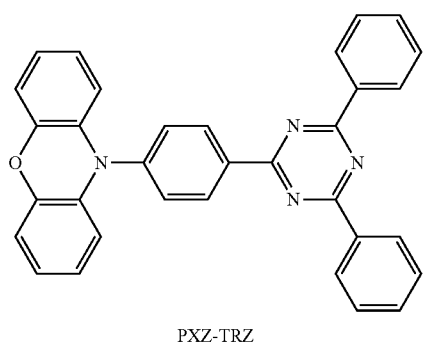

PXZ-TRZ

-continued

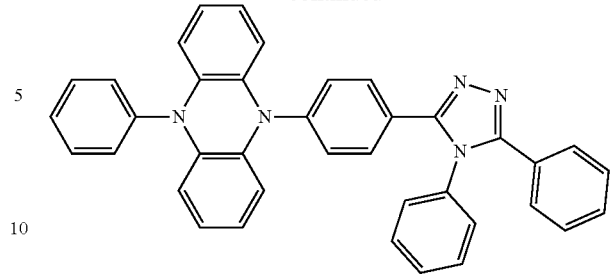

PPZ-3TPT

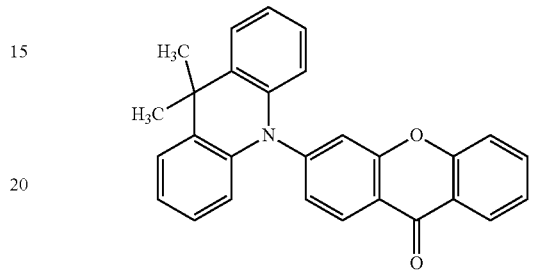

ACRXTN

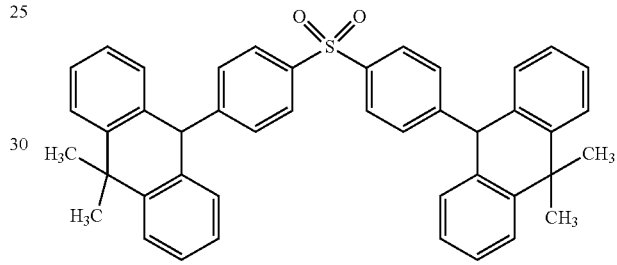

DMAC-DPS

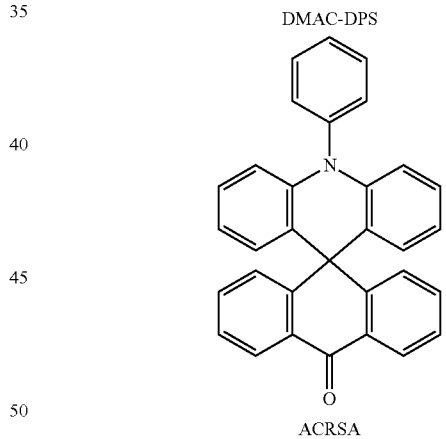

ACRSA

Note that the TADF material is a material that has a small difference between the S1 level and the T1 level and has a function of converting triplet excitation energy into singlet excitation energy by reverse intersystem crossing. Thus, it is possible to upconvert triplet excitation energy into singlet excitation energy (reverse intersystem crossing) using a little thermal energy and to efficiently generate a singlet excited state. In addition, the triplet excitation energy can be converted into light emission.

An exciplex whose excited state is formed by two kinds of substances has an extremely small difference between the S1 level and the T1 level and has a function of a TADF material that can convert triplet excitation energy into singlet excitation energy.

Note that a phosphorescent spectrum observed at low temperatures (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between S1 and T1 of the TADF material is preferably less than or equal to 0.3 eV, further preferably less than or equal to 0.2 eV.

When the TADF material is used as a light-emitting substance, the S1 level of the host material is preferably higher than the S1 level of the TADF material. In addition, the T1 level of the host material is preferably higher than the T1 level of the TADF material.

As the host material in the light-emitting layer, various carrier-transport materials such as a material having an electron-transport property, a material having a hole-transport property, and the TADF material can be used.

The material having a hole-transport property is preferably an organic compound having an amine skeleton or a π-electron rich heteroaromatic ring skeleton. Examples include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4'-(9-phenyl-9H-carbazol-3-yl)triphenylamine (abbreviation: PCBBiiBP), 4-(1-naphthyl)-4'-(9-phenyl-9H-carbazol-3-yl)-triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above, the compound having an aromatic amine skeleton and the compound having a carbazole skeleton are preferable because these have favorable reliability, have high hole-transport properties, and contribute to a reduction in driving voltage. The organic compounds described in Embodiment 1 can also be used.

As the material having an electron-transport property, for example, a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato] zinc(II) (abbreviation: ZnBTZ); or an organic compound having a π-electron deficient heteroaromatic ring skeleton is preferable. Examples of the organic compound having a π-electron deficient heteroaromatic ring skeleton include a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), or 4,8-bis[3-(dibenzothiophen-4-yl)phenyl]benzo[h]quinazoline (abbreviation: 4,8mDBtP2Bqn), and a heterocyclic compound having a pyridine skeleton, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

As the TADF material that can be used as the host material, the above-mentioned materials given as TADF materials can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. At this time, the TADF material functions as an energy donor, and the light-emitting substance functions as an energy acceptor.

This is very effective in the case where the light-emitting substance is a fluorescent substance. In that case, the S1 level of the TADF material is preferably higher than the S1 level of the fluorescent substance in order to achieve high emission efficiency. Furthermore, the T1 level of the TADF material is preferably higher than the S1 level of the fluorescent substance. Therefore, the T1 level of the TADF material is preferably higher than the T1 level of the fluorescent substance.

It is also preferable to use a TADF material that exhibits light emission overlapping with the wavelength of a lowest-energy-side absorption band of the fluorescent substance. This enables smooth transfer of excitation energy from the TADF material to the fluorescent substance and accordingly enables efficient light emission, which is preferable.

In order that singlet excitation energy is efficiently generated from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton that causes light emission) of the fluorescent substance. As the protective group, a substituent having no π bond and saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituent having no π bond has a poor carrier-transport property; thus, the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferable because of its high fluorescence quantum yield.

In the case where a fluorescent substance is used as the light-emitting substance, a material having an anthracene skeleton is suitable for the host material. The use of a substance having an anthracene skeleton as a host material for a fluorescent substance makes it possible to achieve a light-emitting layer with favorable emission efficiency and durability. As the substance having an anthracene skeleton that is used as the host material, a substance having a diphenylanthracene skeleton, in particular, a substance having a 9,10-diphenylanthracene skeleton, is preferable because of its chemical stability. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material having a dibenzocarbazole skeleton is preferable because its HOMO level is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzofluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: α,N-βNPAnth). In particular, CzPA, cgDBCzPA, 2mBnfPPA, and PCzPA are preferably selected because they exhibit favorable characteristics.

Note that a host material may be a material of a mixture of a plurality of kinds of substances; in the case of using a mixed host material, it is preferable to mix a material having an electron-transport property with a material having a hole-transport property. When the material having an electron-transport property is mixed with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1. Note that the organic compounds described in Embodiment 1 can be suitably used as the material having an electron-transport property in the mixed host material.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed by these mixed materials. A combination is preferably selected so as to form an exciplex that exhibits light emission overlapping with the wavelength of a lowest-energy-side absorption band of a light-emitting substance, because energy can be transferred smoothly and light emission can be efficiently obtained. The use of the structure is preferable because the driving voltage is also be reduced.

Note that at least one of the materials forming an exciplex may be a phosphorescent substance. In this case, triplet excitation energy can be efficiently converted into singlet excitation energy by reverse intersystem crossing.

A combination of a material having an electron-transport property and a material having a hole-transport property whose HOMO level is higher than or equal to the HOMO level of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

Note that the formation of an exciplex can be confirmed by a phenomenon in which the emission spectrum of the mixed film in which the material having a hole-transport property and the material having an electron-transport property are mixed is shifted to the longer wavelength side than the emission spectrum of each of the materials (or has another peak on the longer wavelength side), observed by comparison of the emission spectrum of the material having a hole-transport property, the emission spectrum of the material having an electron-transport property, and the emission spectrum of the mixed film of these materials, for example. Alternatively, the formation of an exciplex can be confirmed by a difference in transient response, such as a phenomenon in which the transient photoluminescence (PL) lifetime of the mixed film has longer lifetime components or has a larger proportion of delayed components than that of each of the materials, observed by comparison of the transient PL of the material having a hole-transport property, the transient PL of the material having an electron-transport property, and the transient PL of the mixed film of these materials. The transient PL can be rephrased as transient electroluminescence (EL). That is, the formation of an exciplex can also be confirmed by a difference in transient response observed by comparison of the transient EL of the material having a hole-transport property, the transient EL of the material having an electron-transport property, and the transient EL of the mixed film of these materials.

The electron-transport layer 114 is a layer containing a substance having an electron-transport property. As the substance having an electron-transport property, it is possible to use any of the above-listed substances having electron-transport properties that can be used as the host material.

The electron mobility of the electron-transport layer 114 in the case where the square root of the electric field strength [V/cm] is 600 is preferably higher than or equal to $1 \times 10^{-7}$ cm$^2$/Vs and lower than or equal to $5 \times 10^{-5}$ cm$^2$/Vs. Lowering the electron-transport property of the electron-transport layer 114 enables control of the amount of electrons injected into the light-emitting layer and can prevent the light-emitting layer from having excess electrons. The electron-transport layer preferably includes a material having an electron-transport property and an alkali metal, an alkaline earth metal, a compound thereof, or a complex thereof. It is particularly preferable that this structure be employed when the hole-injection layer is formed using a composite material that includes a material having a hole-transport property with a relatively deep HOMO level of −5.7 eV or higher and −5.4 eV or lower, in which case a long lifetime can be achieved. Here, the material having an electron-transport property preferably has a HOMO level of higher than or equal to −6.0 eV. The material having an electron-transport property is preferably an organic compound having an anthracene skeleton and is further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal itself, the alkaline earth metal itself, the compound thereof, and the complex thereof have an 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) thereof or the like can also be used. There is preferably a difference in the concentration (including 0) of the alkali metal itself, the alkaline earth metal itself, the compound thereof, or the complex thereof in the electron-transport layer in the thickness direction.

As the electron-injection layer 115, a layer containing an alkali metal, an alkaline earth metal, or a compound thereof, such as lithium fluoride (LiF), cesium fluoride (CsF), calcium fluoride (CaF$_2$), or 8-hydroxyquinolinato-lithium (abbreviation: Liq), may be provided between the electron-transport layer 114 and the second electrode 102. An electrode or a layer that is formed using a substance having an electron-transport property and that includes an alkali metal, an alkaline earth metal, or a compound thereof can be used as the electron-injection layer 115. Examples of the electrode include a substance in which electrons are added at high concentration to a mixed oxide of calcium and aluminum.

Note that as the electron-injection layer 115, it is possible to use a layer that contains a substance having an electron-transport property (preferably an organic compound having a bipyridine skeleton) and contains a fluoride of the alkali metal or the alkaline earth metal at a concentration higher than or equal to that at which the electron-injection layer 115 becomes in a microcrystalline state (50 wt % or higher). Since the layer has a low refractive index, a light-emitting device having more favorable external quantum efficiency can be provided.

Instead of the electron-injection layer 115, the charge-generation layer 116 may be provided (FIG. 1B). The charge-generation layer 116 refers to a layer capable of injecting holes into a layer in contact therewith on the cathode side and injecting electrons into a layer in contact therewith on the anode side when supplied with a potential. The charge-generation layer 116 includes at least a P-type layer 117. The P-type layer 117 is preferably formed using the composite materials given above as the material that can form the hole-injection layer 111. The P-type layer 117 may be formed by stacking a film containing the above acceptor material as a material included in the composite material and a film containing the above hole-transport material. When a potential is applied to the P-type layer 117, electrons are injected into the electron-transport layer 114 and holes are injected into the second electrode 102 that is a cathode; thus, the light-emitting device operates. Since the organic compound of one embodiment of the present invention has a low refractive index, using the organic compound for the P-type layer 117 enables the light-emitting device to have high external quantum efficiency.

Note that one or both of an electron-relay layer 118 and an electron-injection buffer layer 119 are preferably provided in the charge-generation layer 116 in addition to the P-type layer 117.

The electron-relay layer 118 contains at least a substance having an electron-transport property and has a function of preventing an interaction between the electron-injection buffer layer 119 and the P-type layer 117 to transfer electrons smoothly. The LUMO level of the substance having an electron-transport property contained in the electron-relay layer 118 is preferably between the LUMO level of an acceptor substance in the P-type layer 117 and the LUMO level of a substance contained in a layer of the electron-transport layer 114 in contact with the charge-generation layer 116. A specific energy level of the LUMO level of the substance having an electron-transport property used for the electron-relay layer 118 may be higher than or equal to −5.0 eV, preferably higher than or equal to −5.0 eV and lower than or equal to −3.0 eV Note that as the substance having an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed so as to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). Note that as the substance having an electron-transport property, a material similar to the above-described material forming the electron-transport layer 114 can be used for the formation.

As a substance forming the second electrode 102, a metal, an alloy, an electrically conductive compound, or a mixture thereof having a low work function (specifically, 3.8 eV or less) or the like can be used. As specific examples of such a cathode material, elements belonging to Group 1 or Group 2 of the periodic table, such as alkali metals, e.g., lithium (Li) and cesium (Cs)), magnesium (Mg), calcium (Ca), and strontium (Sr), alloys containing these (MgAg and AlLi), rare earth metals such as europium (Eu) and ytterbium (Yb), alloys containing these rare earth metals, and the like can be given. However, when the electron-injection layer is provided between the second electrode 102 and the electron-transport layer, as the second electrode 102, a variety of conductive materials such as Al, Ag, ITO, or indium oxide-tin oxide containing silicon or silicon oxide can be used regardless of their work functions.

Films of these conductive materials can be formed by a dry process such as a vacuum evaporation method or a sputtering method, an inkjet method, a spin coating method, or the like. Alternatively, the films may be formed by a wet process using a sol-gel method or a wet process using a paste of a metal material.

Various methods can be used as a method for forming the EL layer 103 regardless of whether it is a dry process or a wet process. For example, a vacuum evaporation method, a gravure printing method, an offset printing method, a screen printing method, an ink-jet method, a spin coating method, or the like may be used.

Different deposition methods may be used to form the electrodes or the layers described above.

The structure of the layers provided between the first electrode 101 and the second electrode 102 is not limited to the above structure. However, a structure is preferable in which a light-emitting region where holes and electrons recombine is provided at a position away from the first electrode 101 and the second electrode 102 so as to prevent quenching caused by the proximity of the light-emitting region and a metal used for electrodes and carrier-injection layers.

Furthermore, in order to inhibit energy transfer from an exciton generated in the light-emitting layer, it is preferable to form the hole-transport layer and the electron-transport layer that are in contact with the light-emitting layer 113, particularly a carrier-transport layer closer to the recombination region in the light-emitting layer 113, using the light-emitting material of the light-emitting layer or a substance having a wider band gap than the light-emitting material included in the light-emitting layer.

Next, an embodiment of a light-emitting device with a structure where a plurality of light-emitting units are stacked (also referred to as a stacked-type element or a tandem element) will be described with reference to FIG. 1C. This light-emitting device is a light-emitting device including a plurality of light-emitting units between an anode and a cathode. One light-emitting unit has substantially the same structure as that of the EL layer 103, which is illustrated in FIG. 1A. In other words, the light-emitting device illustrated in FIG. 1C can be called a light-emitting device including a plurality of light-emitting units, and the light-emitting device illustrated in FIG. 1A or FIG. 1B can be called a light-emitting device including one light-emitting unit.

Figure 1C:
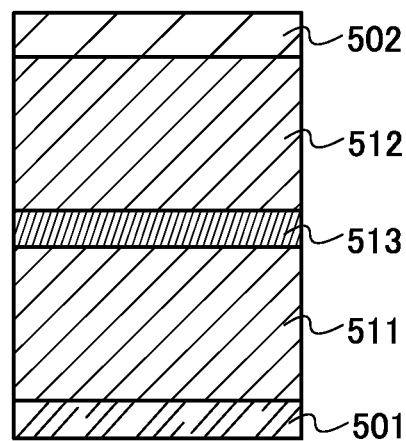

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 in FIG. 1A, and the same substance as what is given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied to the anode 501 and the cathode 502. That is, in FIG. 1C, any layer can be used as the charge-generation layer 513 as long as the layer injects electrons into the first light-emitting unit 511 and injects holes into the second light-emitting unit 512 in the case where a voltage is applied such that the potential of the anode is higher than the potential of the cathode.

The charge-generation layer 513 is preferably formed with a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. Note that in the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the electron-injection buffer layer 119 is provided in the charge-generation layer 513, the electron-injection buffer layer 119 serves as an electron-injection layer in the light-emitting unit on the anode side; therefore, an electron-injection layer is not necessarily formed in the light-emitting unit on the anode side.

The light-emitting device having two light-emitting units is described with reference to FIG. 1C; however, the same can also be applied to a light-emitting device in which three or more light-emitting units are stacked. With a plurality of light-emitting units partitioned by the charge-generation layer 513 between a pair of electrodes as in the light-emitting device according to this embodiment, it is possible to provide a long-life element that can emit light with high luminance at a low current density. Moreover, a light-emitting apparatus that can be driven at a low voltage and has low power consumption can be achieved.

Furthermore, when emission colors of the light-emitting units are different, light emission of a desired color can be obtained from the light-emitting device as a whole. For example, in a light-emitting device having two light-emitting units, emission colors of red and green are obtained in the first light-emitting unit and an emission color of blue is obtained in the second light-emitting unit, whereby a light-emitting device that emits white light as the whole light-emitting device can be obtained.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. Those may include a low molecular material, a middle molecular material (including an oligomer and a dendrimer), or a high molecular material.

Embodiment 3

In this embodiment, a light-emitting apparatus using the light-emitting device described in Embodiment 2 will be described.

In this embodiment, a light-emitting apparatus fabricated using the light-emitting device described in Embodiment 2 will be described with reference to FIG. 2. Note that FIG. 2A is a top view illustrating the light-emitting apparatus, and FIG. 2B is a cross-sectional view taken along A-B and C-D in FIG. 2A. This light-emitting apparatus includes a driver circuit portion (source line driver circuit) 601, a pixel portion 602, and a driver circuit portion (gate line driver circuit) 603, which are for controlling light emission of a light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2B. The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, an acrylic resin, or the like.

There is no particular limitation on the structure of transistors used in pixels and driver circuits. For example, an inverted staggered transistor or a staggered transistor may be used. Furthermore, top-gate transistors or bottom-gate transistors may be used. There is no particular limitation on a semiconductor material used for the transistors, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material for the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic device with significantly reduced power consumption can be achieved.

For stable characteristics of the transistor or the like, a base film is preferably provided. The base film can be formed to be a single-layer or a stacked-layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where a positive photosensitive acrylic resin is used as a material for the insulator 614, only the upper end portion of the insulator 614 preferably has a curved surface with a curvature radius (0.2 µm to 3 µm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stacked layer of titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 wt % to 20 wt %, indium tin oxide containing silicon, or zinc oxide (ZnO)).

Note that a light-emitting device is formed with the first electrode 613, the EL layer 616, and the second electrode 617. The light-emitting device is the light-emitting device described in Embodiment 2. A plurality of light-emitting devices are formed in the pixel portion, and the light-emitting apparatus of this embodiment may include both the light-emitting device described in Embodiment 2 and a light-emitting device having a different structure.

The sealing substrate 604 and the element substrate 610 are attached to each other using the sealant 605, so that a structure is employed in which a light-emitting device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not illustrated in FIG. 2, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely to transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, or the like; a material containing aluminum nitride, hafnium nitride, silicon nitride, tantalum nitride, titanium nitride, niobium nitride, molybdenum nitride, zirconium nitride, gallium nitride, or the like; or a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

By an ALD method, a uniform protective film with few defects can be formed even on a surface with a complex uneven shape or upper, side, and lower surfaces of a touch panel.

As described above, the light-emitting apparatus fabricated using the light-emitting device described in Embodiment 2 can be obtained.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has high emission efficiency, the light-emitting apparatus with low power consumption can be obtained.

FIG. 3 illustrates examples of a light-emitting apparatus in which full color display is achieved by formation of a light-emitting device exhibiting white light emission and provision of coloring layers (color filters) and the like. FIG. 3A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 3A, a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed by pixels of the four colors.

FIG. 3B shows an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
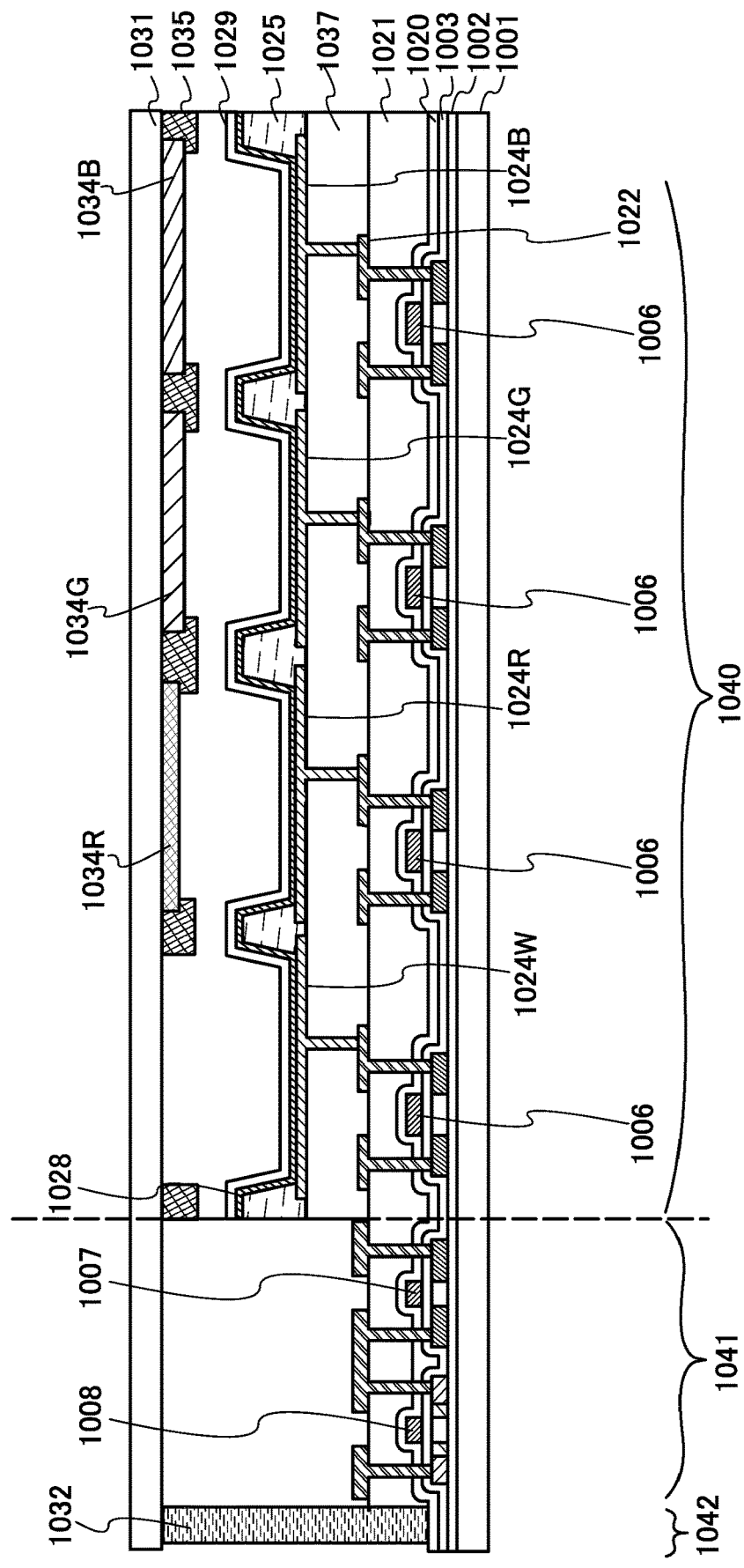
FIG. 4 is a conceptual diagram of an active matrix light-emitting apparatus.

The above-described light-emitting apparatus is a light-emitting apparatus having a structure in which light is extracted to the substrate 1001 side where the FETs are formed (a bottom-emission type), but may be a light-emitting apparatus having a structure in which light emission is extracted to the sealing substrate 1031 side (a top-emission type). FIG. 4 shows a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting devices are each an anode here, but may each be a cathode. Furthermore, in the case of the top-emission light-emitting apparatus illustrated in FIG. 4, the first electrodes are preferably reflective electrodes. The structure of the EL layer 1028 is such a structure as that of the EL layer 103 described in Embodiment 2, and an element structure with which white light emission can be obtained.

In the case of such a top-emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission-type light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1 \times 10^{-2}$ Ωcm or lower. In addition, the semi-transmissive and semi-reflective electrode is a film having a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer; for example, in combination with the structure of the above-described tandem light-emitting device, a plurality of EL layers each including a single or a plurality of light-emitting layer(s) may be provided in one light-emitting device with a charge-generation layer interposed between the EL layers.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because a microcavity structure suitable for wavelengths of the corresponding color is employed in each subpixel, in addition to the effect of an improvement in luminance owing to yellow light emission.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has high emission efficiency, the light-emitting apparatus with low power consumption can be obtained.

Figure 5A:
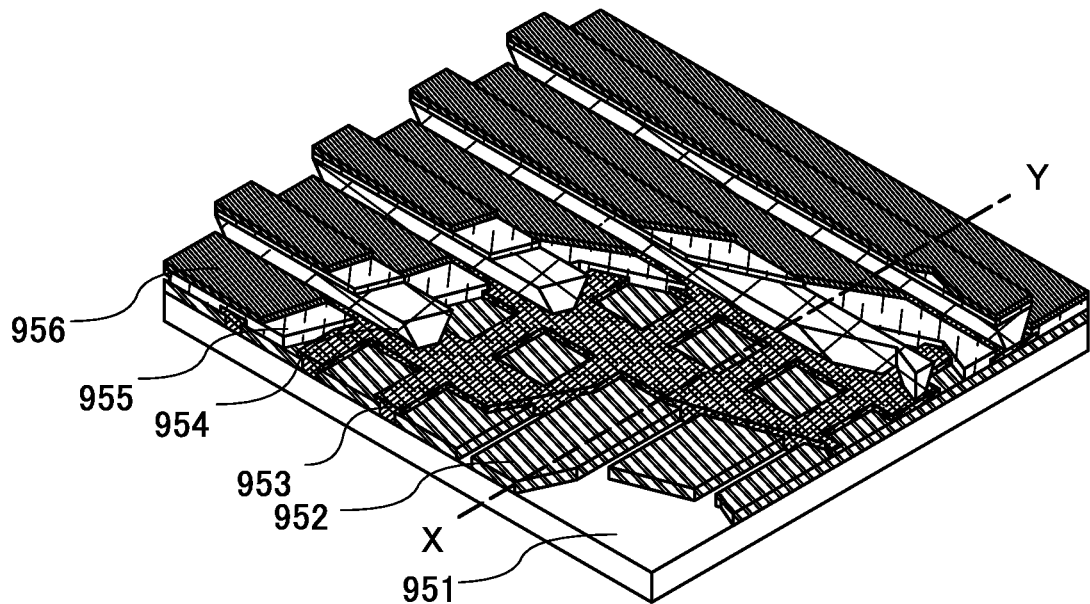
FIG. 5A and FIG. 5B are conceptual diagrams of a passive matrix light-emitting apparatus.
Figure 5B:
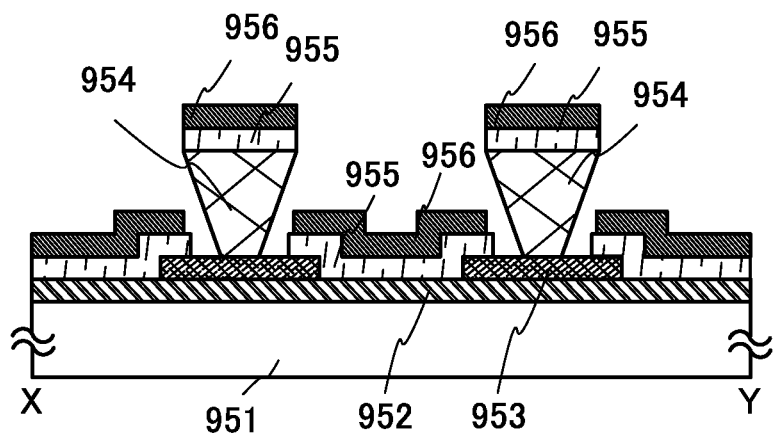

The active matrix light-emitting apparatus is described above, whereas a passive matrix light-emitting apparatus is described below. FIG. 5 illustrates a passive matrix light-emitting apparatus fabricated using the present invention. Note that FIG. 5A is a perspective view illustrating the light-emitting apparatus, and FIG. 5B is a cross-sectional view taken along X-Y in FIG. 5A. In FIG. 5, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting device due to static charge or the like can be prevented. The passive-matrix light-emitting apparatus also uses the light-emitting device described in Embodiment 2; thus, the light-emitting apparatus can have favorable reliability or low power consumption.

Since many minute light-emitting devices arranged in a matrix can each be controlled in the light-emitting apparatus described above, the light-emitting apparatus can be suitably used as a display device for displaying images.

This embodiment can be freely combined with any of the other embodiments.

Embodiment 4

Figure 6A:
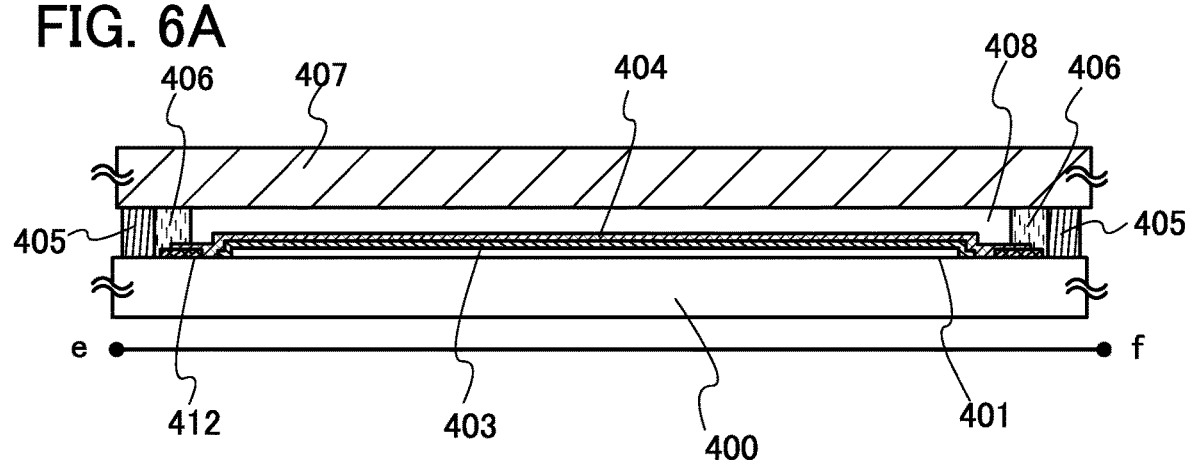
FIG. 6A and FIG. 6B are diagrams illustrating a lighting device.
Figure 6B:
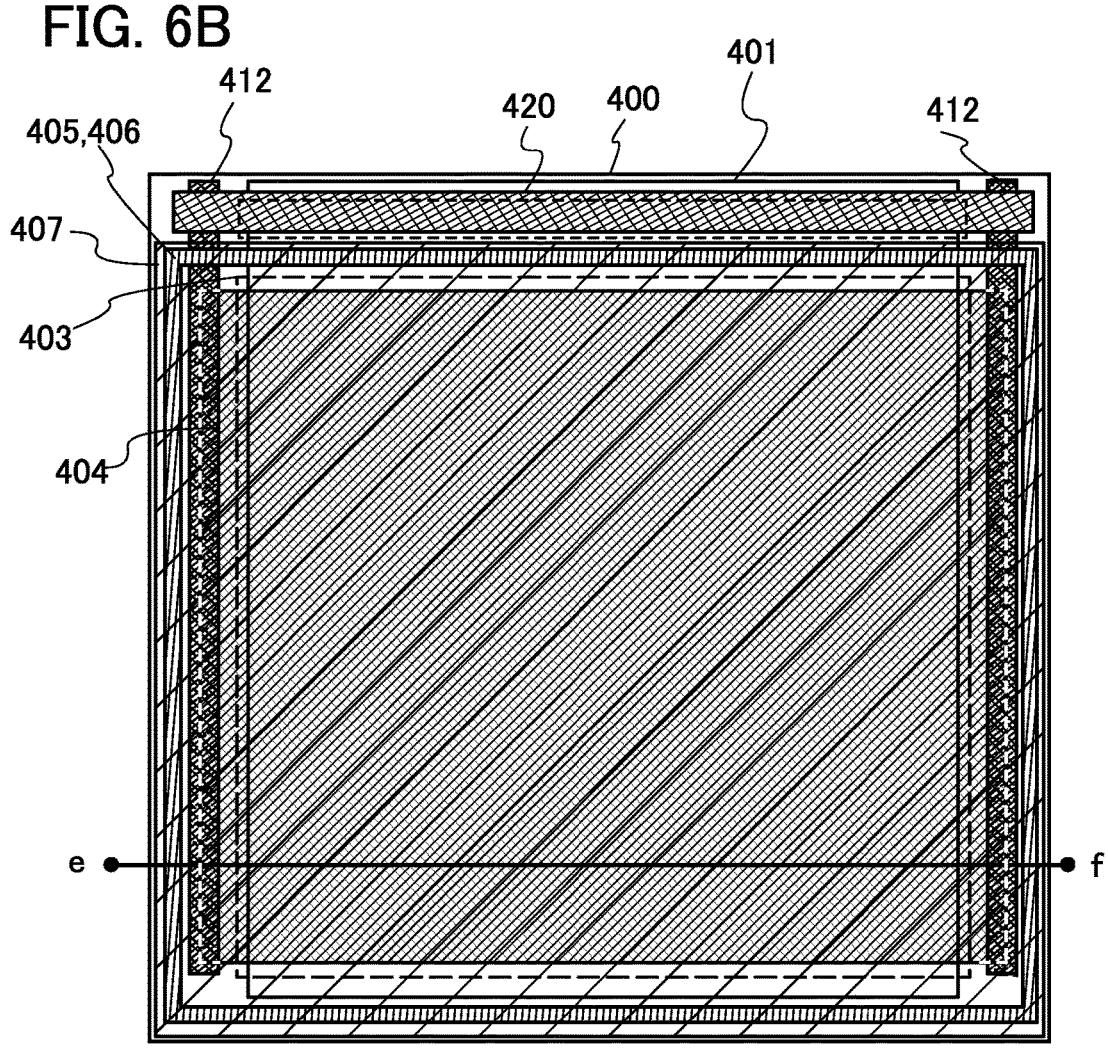

In this embodiment, an example in which the light-emitting device described in Embodiment 2 is used for a lighting device will be described with reference to FIG. 6. FIG. 6B is a top view of the lighting device, and FIG. 6A is a cross-sectional view taken along e-f in FIG. 6B.

In the lighting device in this embodiment, a first electrode 401 is formed over a substrate 400 which is a support and has a light-transmitting property. The first electrode 401 corresponds to the first electrode 101 in Embodiment 2. In the case where light emission is extracted from the first electrode 401 side, the first electrode 401 is formed with a material having a light-transmitting property.

A pad 412 for supplying a voltage to a second electrode 404 is formed over the substrate 400.

An EL layer 403 is formed over the first electrode 401. The EL layer 403 has a structure corresponding to the structure of the EL layer 103 in Embodiment 2, or the structure in which the light-emitting units 511 and 512 are combined with the charge-generation layer 513. Note that for these structures, the corresponding description can be referred to.

The second electrode 404 is formed to cover the EL layer 403. The second electrode 404 corresponds to the second electrode 102 in Embodiment 2. In the case where light-emission is extracted from the first electrode 401 side, the second electrode 404 is formed with a material having high reflectivity. The second electrode 404 is supplied with a voltage when connected to the pad 412.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, whereby the lighting device is completed. It is possible to use only either the sealant 405 or 406. In addition, the inner sealant 406 can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting device described in Embodiment 2 as an EL device; thus, the light-emitting apparatus can have low power consumption.

Embodiment 5

In this embodiment, examples of electronic devices each partly including the light-emitting device described in Embodiment 2 are described. The light-emitting device described in Embodiment 2 is a light-emitting device with high emission efficiency and low power consumption. As a result, the electronic devices described in this embodiment can be electronic devices each including a light-emitting portion with low power consumption.

Examples of electronic devices to which the light-emitting device is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of these electronic devices are shown below.

FIG. 7A shows an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in Embodiment 2 are arranged in a matrix in the display portion 7103.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7B1 is a computer which includes a main body 7201, a housing 7202, a display portion 7203, a keyboard 7204, an external connection port 7205, a pointing device 7206, and the like. Note that this computer is fabricated using the light-emitting devices described in Embodiment 2 arranged in a matrix in the display portion 7203. The computer in FIG. 7B1 may be such a mode as illustrated in FIG. 7B2. The computer in FIG. 7B2 is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

FIG. 7C shows an example of a portable terminal. A mobile phone includes operation buttons 7403, an external connection port 7404, a speaker 7405, a microphone 7406, and the like in addition to a display portion 7402 incorporated in a housing 7401. Note that a mobile phone 7400 includes the display portion 7402 which is fabricated by arranging the light-emitting devices described in Embodiment 2 in a matrix.

The portable terminal illustrated in FIG. 7C may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on the screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Figure 8A:
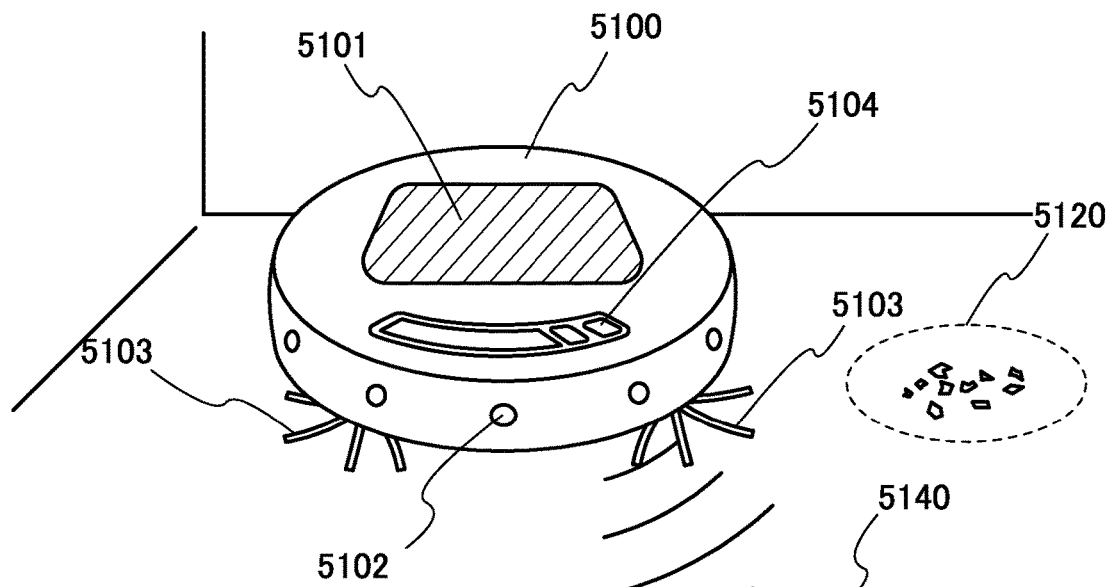
FIG. 8A, FIG. 8B, and FIG. 8C are diagrams illustrating electronic devices.

FIG. 8A is a schematic view showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device such as a smartphone.

The light-emitting apparatus of one embodiment of the present invention can be used for the display 5101.

Figure 8B:
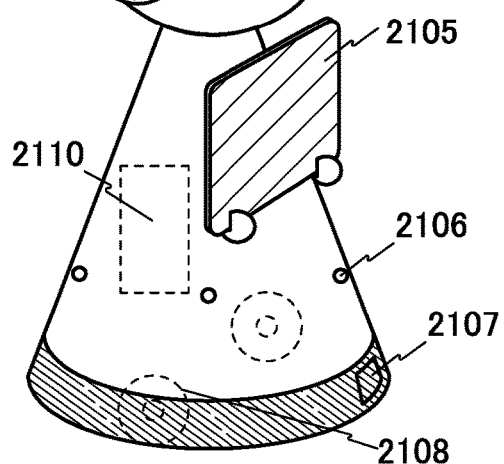

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
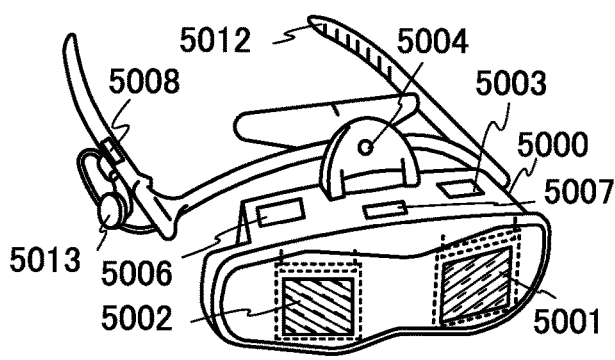

FIG. 8C shows an example of a goggle-type display. The goggle-type display includes, for example, a housing 5000, a display portion 5001, a speaker 5003, an LED lamp 5004, operation keys 5005 (including a power switch or an operation switch), a connection terminal 5006, a sensor 5007 (a sensor having a function of measuring force, displacement, position, speed, acceleration, angular velocity, rotational frequency, distance, light, liquid, magnetism, temperature, a chemical substance, sound, time, hardness, an electric field, current, voltage, power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
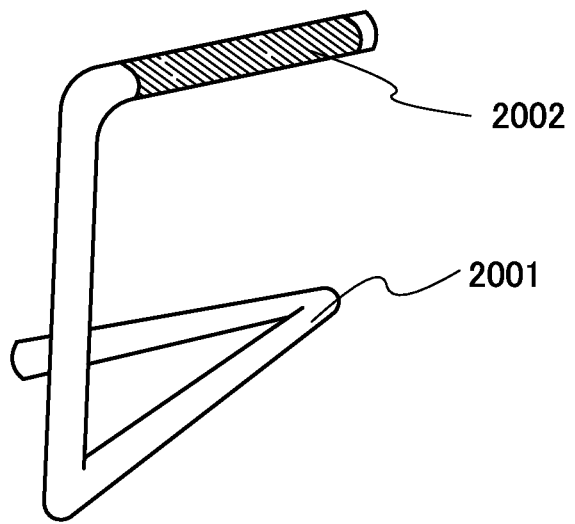
FIG. 9 is a diagram illustrating a lighting device.

FIG. 9 shows an example in which the light-emitting device described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
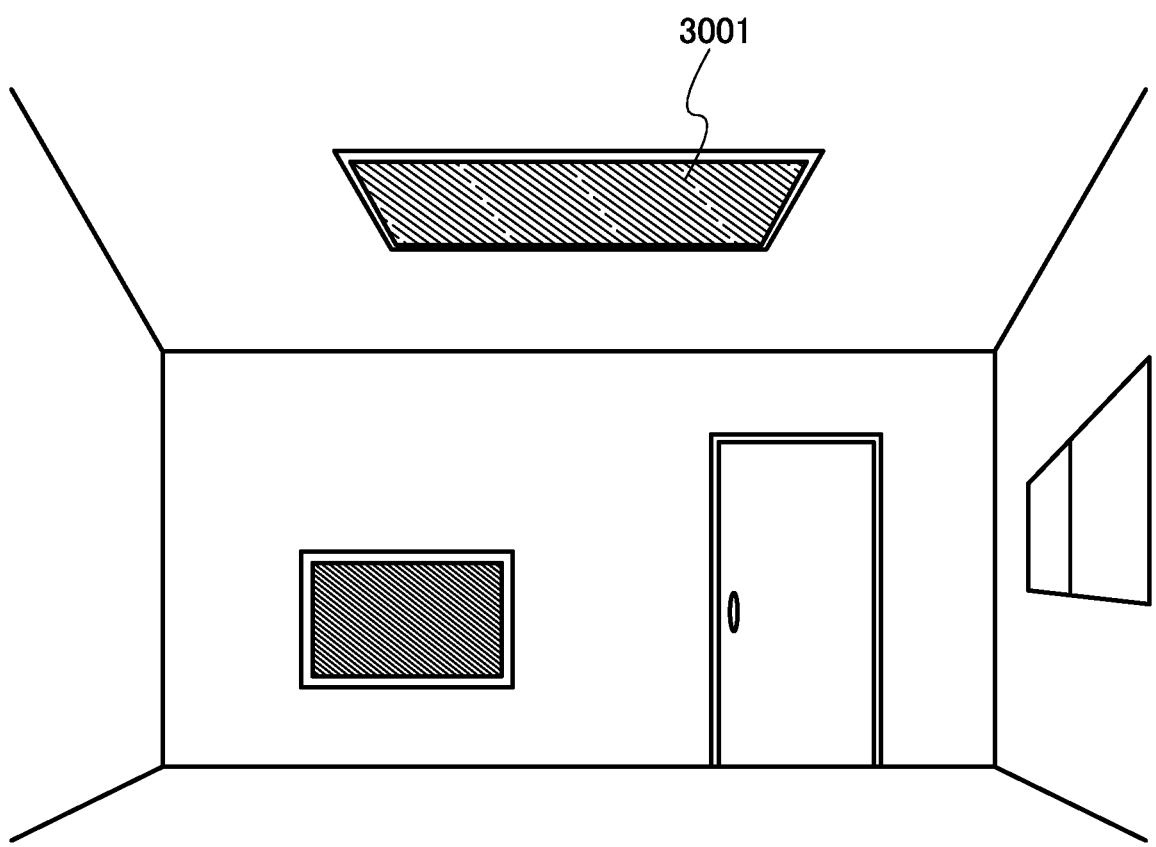
FIG. 10 is a diagram illustrating a lighting device.

FIG. 10 shows an example in which the light-emitting device described in Embodiment 2 is used for an indoor lighting device 3001. Since the light-emitting device described in Embodiment 2 is a light-emitting device with high emission efficiency, the lighting device can have low power consumption. Furthermore, the light-emitting device described in Embodiment 2 can have a larger area, and thus can be used for a large-area lighting device. Furthermore, the light-emitting device described in Embodiment 2 is thin, and thus can be used for a lighting device having a reduced thickness.

Figure 11:
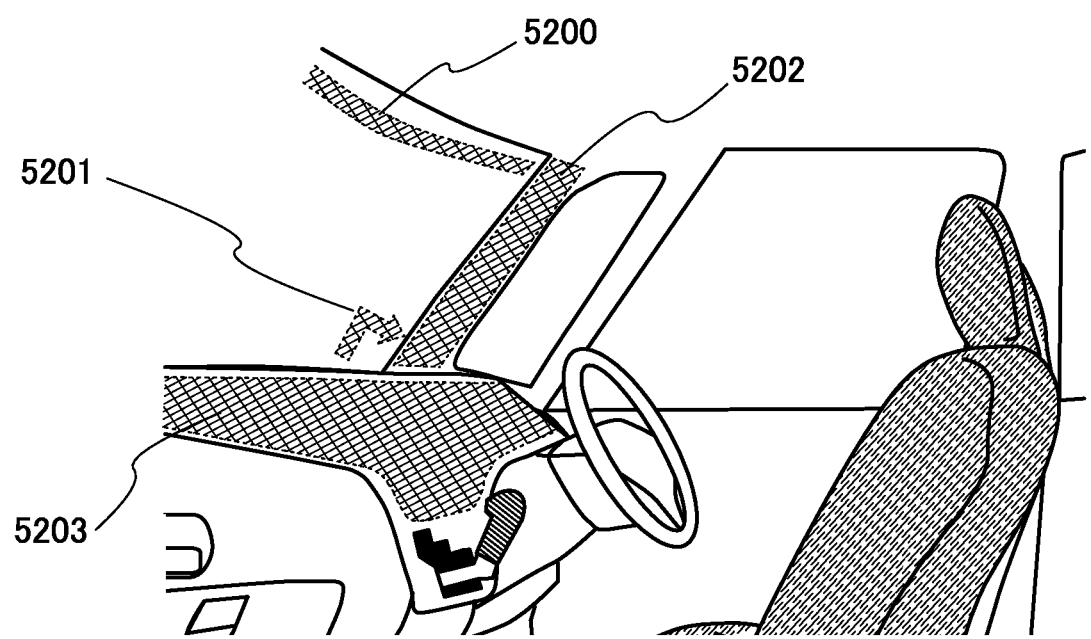
FIG. 11 is a diagram illustrating in-vehicle display devices and lighting devices.

The light-emitting device described in Embodiment 2 can also be incorporated in an automobile windshield or an automobile dashboard. FIG. 11 illustrates one mode in which the light-emitting device described in Embodiment 2 is used for a windshield and a dashboard of an automobile. A display region 5200 to a display region 5203 are each display provided using the light-emitting device described in Embodiment 2.

The display region 5200 and the display region 5201 are display devices provided in the automobile windshield, in which the light-emitting devices described in Embodiment 2 are incorporated. When the light-emitting devices described in Embodiment 2 are fabricated using electrodes having light-transmitting properties as a first electrode and a second electrode, what is called see-through display devices, through which the opposite side can be seen, can be obtained. See-through display can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting devices described in Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be provided on the display region 5200 to the display region 5202. The display region 5200 to the display region 5203 can also be used as lighting devices.

Figure 12A:
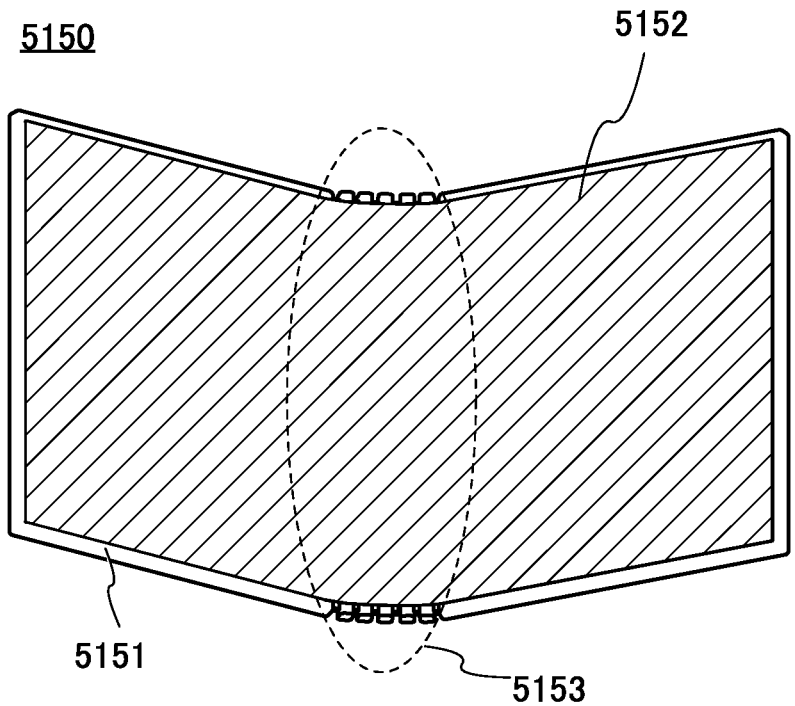
FIG. 12A and FIG. 12B are diagrams illustrating an electronic device.
Figure 12B:
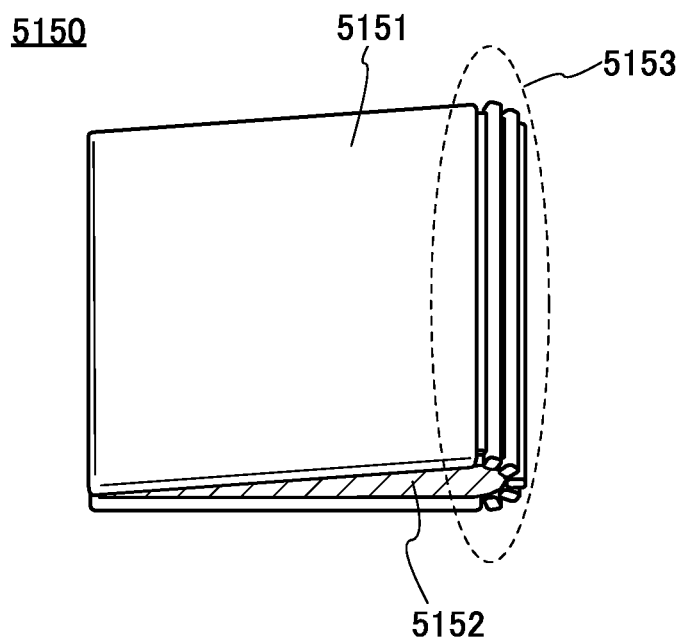

FIG. 12A and FIG. 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) including a touch sensor (an input device). The light-emitting apparatus of one embodiment of the present invention can be used for the display region 5152.

Figure 13A:
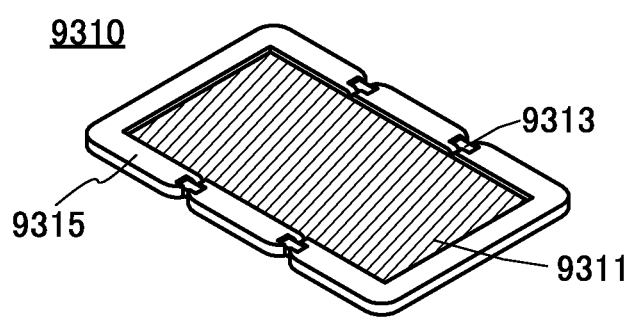
FIG. 13A, FIG. 13B, and FIG. 13C are diagrams illustrating an electronic device.
Figure 13B:
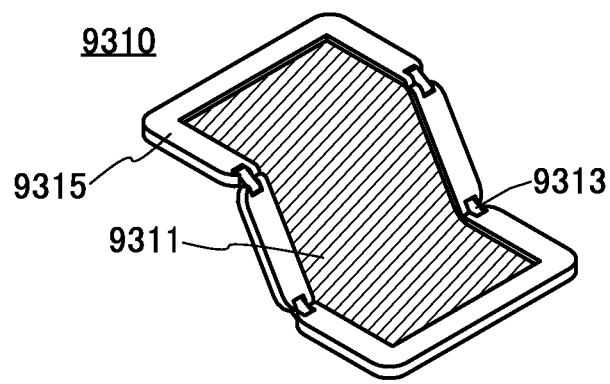
Figure 13C:
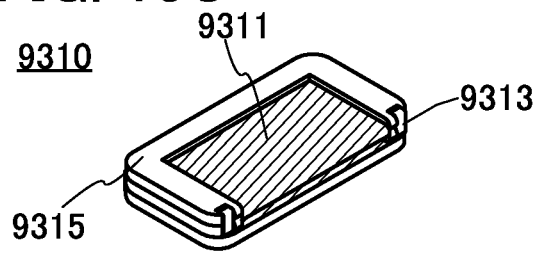

FIG. 13A to FIG. 13C illustrate a foldable portable information terminal 9310. FIG. 13A illustrates the portable information terminal 9310 that is opened. FIG. 13B illustrates the portable information terminal 9310 that is in the state of being changed from one of an opened state and a folded state to the other. FIG. 13C illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting apparatus of one embodiment of the present invention can be used for the display panel 9311.

Note that the structures described in this embodiment can be combined with the structures described in any of Embodiment 1 to Embodiment 4 as appropriate.

As described above, the application range of the light-emitting apparatus including the light-emitting device described in Embodiment 2 is wide so that this light-emitting apparatus can be applied to electronic devices in a variety of fields. With the use of the light-emitting device described in Embodiment 2, an electronic device with low power consumption can be obtained.

Example 1

Synthesis Example 1

In this synthesis example, a method for synthesizing N-(1,1'-biphenyl-2-yl)-N-(9,9-dimethyl-9H-fluoren-2-yl)benzo[b]naphtho[1,2-d]furan-6-amine (abbreviation: oFBiBnf(6)), which is represented by Structural Formula (5-106) in Embodiment 1, will be described. The structural formula of oFBiBnf(6) is shown below.

[Chemical Formula 45]

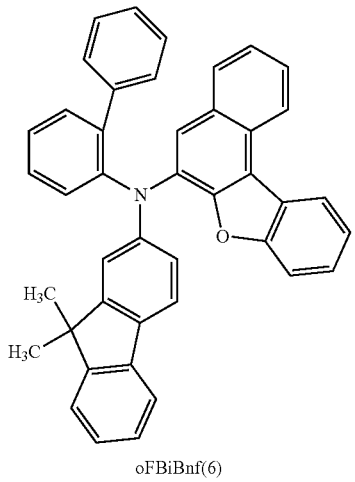

oFBiBnf(6)

Step 1: Synthesis of N-(1,1'-biphenyl-2-yl)benzo[b]naphtho[1,2-d]furan-6-amine

Into a 200 mL three-neck flask equipped with a reflux pipe, 5.2 g (15 mmol) of 6-iodobenzo[b]naphtho[1,2-d]furan, 2.5 g (15 mmol) of 2-biphenylamine, and 0.12 g (0.30 mmol) of 2-dicyclohexylphosphino-2',6'-dimethoxybiphenyl were put, and the air in the flask was replaced with nitrogen. Into the flask, 2.9 g (30 mmol) of sodium tert-butoxide and 110 mL of xylene were added, and degassing under reduced pressure and replacement with nitrogen were performed three times. Into the flask, 86 mg (0.15 mmol) of bis(bis(dibenzylideneacetone)palladium)(0) was added, and stirring was performed at 110° C. for 3 hours. After the stirring, an insoluble matter was removed from the mixture obtained by suction filtration. Water was added to the obtained filtrate, and an aqueous layer was subjected to extraction with toluene. The obtained organic layer was washed twice with water and washed with a saturated saline solution, and dried with anhydrous magnesium sulfate. The obtained mixture was gravity-filtered to remove the anhydrous magnesium sulfate. The obtained filtrate was concentrated to give 5.5 g of a target brown solid in a yield of 95%. The synthesis scheme of Step 1 is shown below.

[Chemical Formulae 46]

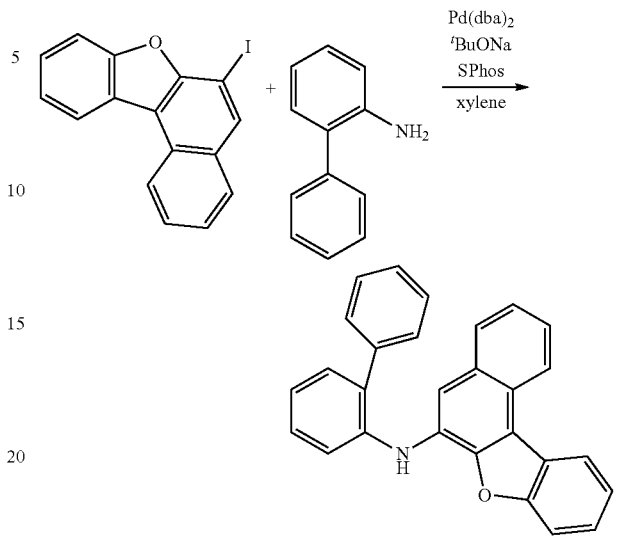

Analysis results by nuclear magnetic resonance spectroscopy ($^1$H-NMR) of the brown solid obtained in Step 1 above are shown below. These indicate that N-(1,1'-biphenyl-2-yl)benzo[b]naphtho[1,2-d]furan-6-amine was obtained in Step 1.

$^1$H NMR (dichloromethane-d2, 300 MHz): δ=8.52 (d, J=7.8 Hz, 1H), 7.91 (d, J=8.7 Hz, 1H), 7.84 (d, J=8.4 Hz, 1H), 7.68-7.32 (m, 14H), 7.19 (t, J=4.2 Hz, 1H), 6.39 (s, 1H)

<Step 2: Synthesis of N-(1,1'-biphenyl-2-yl)-N-(9,9-dimethyl-9H-fluoren-2-yl)benzo[b]naphtho[1,2-d]furan-6-amine (abbreviation: oFBiBnf(6))>

Into a 200 mL three-neck flask equipped with a reflux pipe, 2.0 g (5.2 mmol) of N-(1,1'-biphenyl-2-yl)benzo[b]naphtho[1,2-d]furan-6-amine, which was obtained in Step 1, and 1.4 g (5.2 mmol) of 2-bromo-9,9-dimethylfluorene were put, and the air in the flask was replaced with nitrogen. Into the flask, 1.0 g (10 mmol) of sodium tert-butoxide, 0.30 mL of tri-tert-butylphosphine (a 10 wt % hexane solution), and 50 mL of xylene were added, and degassing under reduced pressure and replacement with nitrogen were performed three times. Into the flask, 30 mg (0.51 mmol) of bis(bis(dibenzylideneacetone)palladium)(0) was added, and stirring was performed at 90° C. for 6 hours. After the stirring, water was added to the reactant, and an aqueous layer was subjected to extraction with toluene. The obtained organic layer was washed twice with water and subsequently washed with a saturated saline solution, and dried with anhydrous magnesium sulfate. The obtained mixture was gravity-filtered to remove the anhydrous magnesium sulfate. The obtained filtrate was concentrated to give 2.9 g of a yellow solid, which contains a target substance, in a yield of 96%.

By the train sublimation method, 2.4 g of the obtained yellow solid was sublimated and purified. In the sublimation purification, the solid was heated at 200° C. for 16 hours under a pressure of 3.6 Pa with a flow of argon at 15 mL/min. After the sublimation purification, 1.6 g of a target pale yellow solid was obtained at a collection rate of 66%. The synthesis scheme of Step 2 is shown below.

[Chemical Formulae 47]

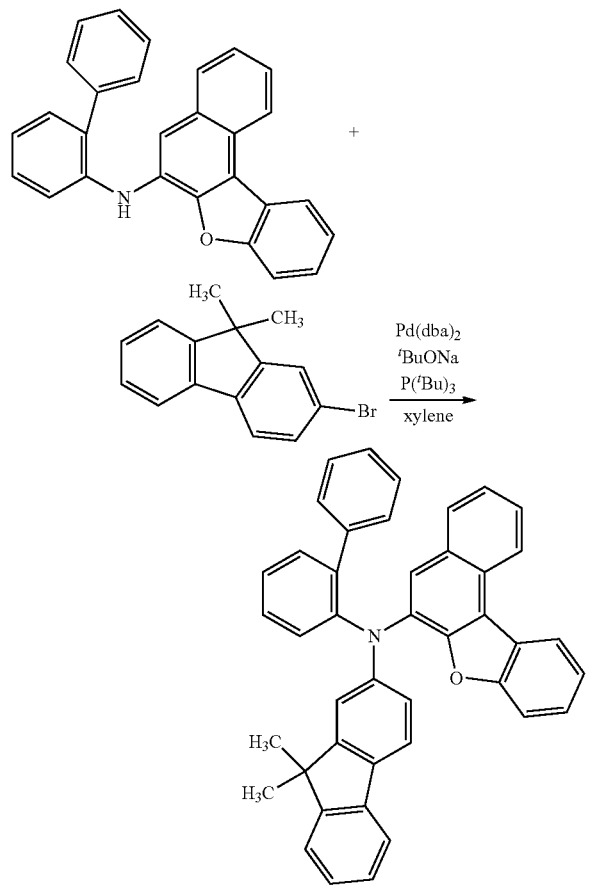

Figure 14A:
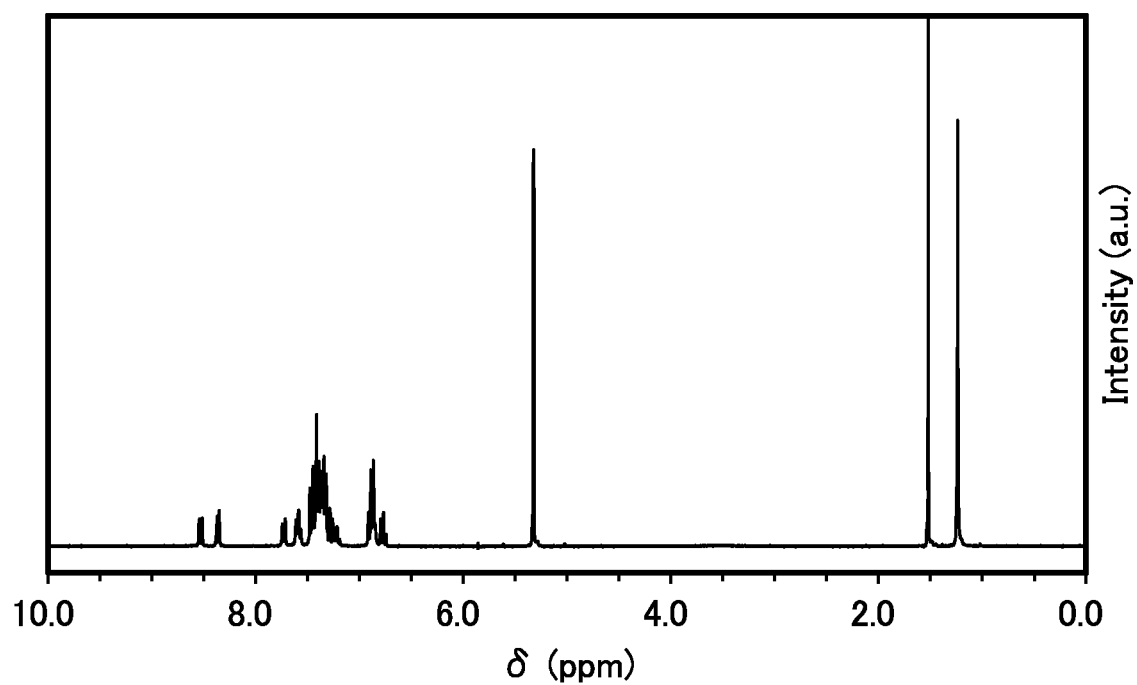
FIG. 14A and FIG. 14B are $^1$H NMR charts of oFBiBnf (6).
Figure 14B:
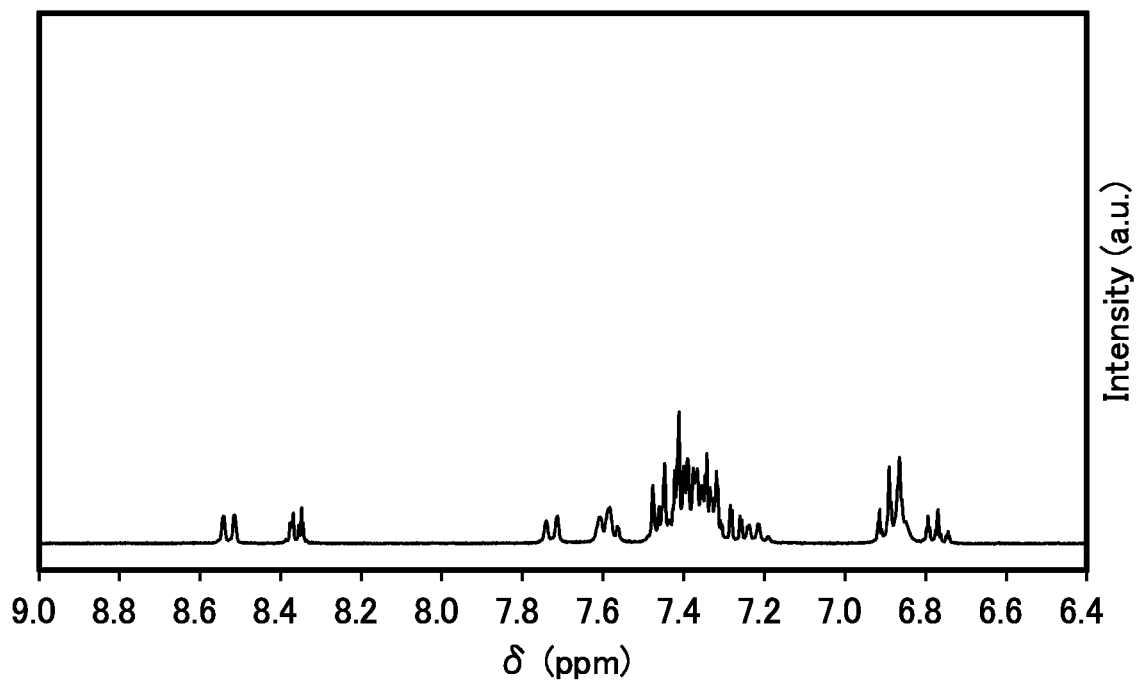

Given below are $^1$H-NMR numerical data of the obtained solid. FIG. 14A and FIG. 14B show $^1$H-NMR charts. These results indicate that oFBiBnf(6) was obtained in this synthesis example.

$^1$H NMR (dichloromethane-d2, 300 MHz): δ=8.53 (d, J=8.4 Hz, 1H), 8.38-8.34 (m, 1H), 7.73 (d, J=8.4 Hz, 1H), 7.58 (t, J=6.6 Hz, 2H), 7.48-7.20 (m, 15H), 6.91-6.85 (m, 4H), 6.77 (t, J=7.5 Hz, 1H), 1.24 (s, 6H)

Next, the ultraviolet-visible absorption spectra (hereinafter, simply referred to as "absorption spectra") and emission spectra of a toluene solution and a solid thin film of oFBiBnf(6) were measured. The solid thin film was formed over a quartz substrate by a vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$ [% T/(100–% R)]) obtained from a transmittance and a reflectance of the substrate and the thin film. Note that % T represents a transmittance and % R represents a reflectance. The emission spectrum was measured with a fluorescence spectrophotometer (FS920, manufactured by Hamamatsu Photonics K.K.).

Figure 15:
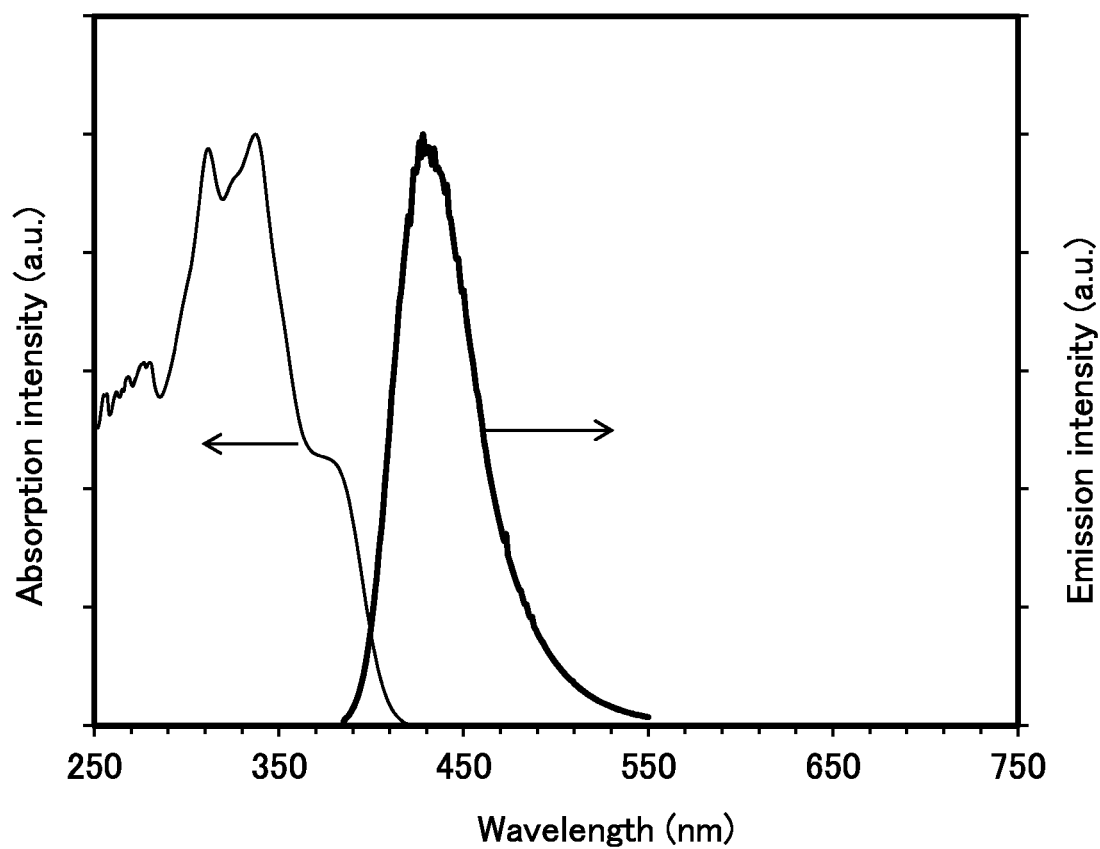
FIG. 15 shows an absorption spectrum and an emission spectrum of oFBiBnf(6) in a toluene solution.
Figure 16:
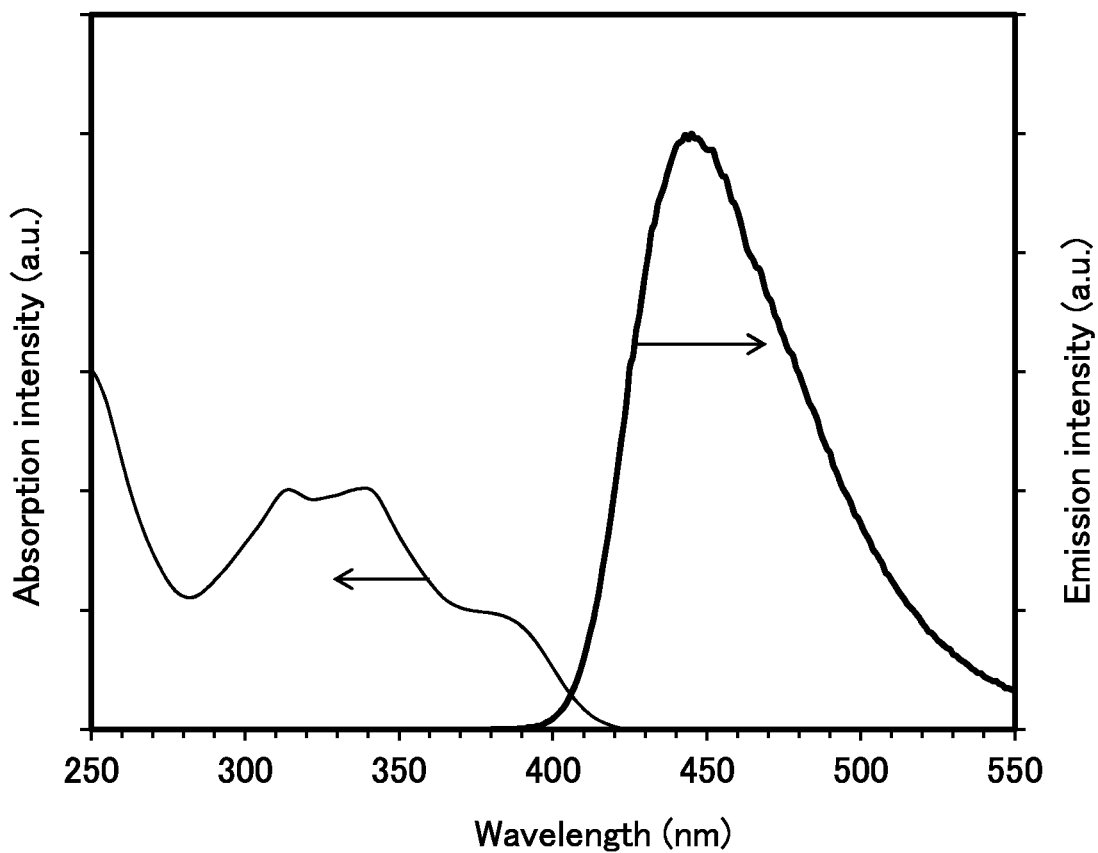
FIG. 16 shows an absorption spectrum and an emission spectrum of a thin film of oFBiBnf(6).

FIG. 15 shows the obtained measurement results of the absorption spectrum and the emission spectrum of the toluene solution. FIG. 16 shows the measurement results of the absorption spectrum and the emission spectrum of the solid thin film. From the results in FIG. 15, for the toluene solution of oFBiBnf(6), the absorption peaks including the shoulder peak were observed at around 382 nm, 337 nm, and 311 nm, and the emission wavelength peak was observed at 429 nm (excitation wavelength: 377 nm). From the results in FIG. 16, for the solid thin film of oFBiBnf(6), the absorption peaks including the shoulder peak were observed at around 385 nm, 339 nm, 315 nm, and 248 nm, and the emission wavelength peak was observed at around 445 nm (excitation wavelength: 370 nm).

The HOMO level and the LUMO level of oFBiBnf(6) were calculated on the basis of a cyclic voltammetry (CV) measurement. The calculation method is shown below.

An electrochemical analyzer (model number: ALS model 600A or 600C, manufactured by BAS Inc.) was used as a measurement apparatus. To prepare a solution for the CV measurement, dehydrated dimethylformamide (DMF) (manufactured by Sigma-Aldrich Inc., 99.8%, catalog No. 22705-6) was used as a solvent, tetra-n-butylammonium perchlorate (n-Bu$_4$NClO$_4$) (manufactured by Tokyo Chemical Industry Co., Ltd., catalog No. T0836) as a supporting electrolyte was dissolved at a concentration of 100 mmol/L, and the object to be measured was dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for non-aqueous solvent, manufactured by BAS Inc.) was used as a reference electrode. Note that the measurement was performed at room temperature (20 to 25° C.).

The scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, according to the measurement results of the oxidation potential Ea [V] of oFBiBnf(6), the HOMO level was found to be −5.49 eV. By contrast, according to the measurement results of the reduction potential Ec [V], the LUMO level was found to be −2.36 eV. In addition, the results of repetitive measurement of the oxidation-reduction wave showed that when the waveform of the first cycle was compared with that of the hundredth cycle, 92% of the peak intensity and 95% of the peak intensity were maintained in the Ea measurement and the Ec measurement, respectively, which confirmed that oFBiBnf(6) had extremely high resistance to oxidation and reduction.

Differential scanning calorimetry (DSC measurement) was performed on oFBiBnf(6) by PyrislDSC manufactured by PerkinElmer, Inc. The differential scanning calorimetry was performed in the following manner: the temperature was raised from −10° C. to 270° C. at a temperature rising rate of 40° C./min and held at the temperature for one minute, and then the temperature was decreased to −10° C. at a temperature decreasing rate of 100° C./min. This operation was performed twice in succession. It was revealed from the result of the second cycle of the DSC measurement that the glass transition point of oFBiBnf(6) was 119° C., that is, oFBiBnf(6) was a substance with extremely high heat resistance.

Then, thermogravimetry-differential thermal analysis of oFBiBnf(6) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 366° C., which shows that oFBiBnf(6) is a substance with favorable sublimability.

From the above results, it was found that the organic compound of one embodiment of the present invention has both high heat resistance and favorable sublimability, and can provide an organic optical device (a light-emitting device and a light-receiving device) with high heat resistance and increase the productivity of device manufacturing.

Example 2

Synthesis Example 2>>

In this synthesis example, a method for synthesizing N-(1,1'-biphenyl-2-yl)-N-(9,9-dimethyl-9H-fluoren-4-yl) benzo[b]naphtho[1,2-d]furan-6-amine (abbreviation: oFBi (4)Bnf(6)), which is represented by Structural Formula (5-107) in Embodiment 1, will be described. The structural formula of oFBi(4)Bnf(6) is shown below.

[Chemical Formula 48]

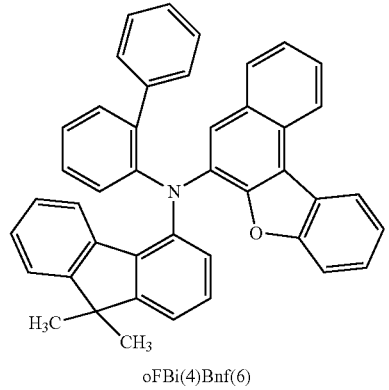

oFBi(4)Bnf(6)

Step 1: Synthesis of N-(1,1'-biphenyl-2-yl)benzo[b] naphtho[1,2-d]furan-6-amine

The synthesis was performed in a manner similar to that of Step 1 in Synthesis Example 1 of Example 1.

Step 2: Synthesis of N-(1,1'-biphenyl-2-yl)-N-(9,9-dimethyl-9H-fluoren-4-yl)benzo[b]naphtho[1,2-d] furan-6-amine (abbreviation: oFBi(4)Bnf(6))

Into a 200 mL three-neck flask equipped with a reflux pipe, 2.0 g (5.2 mmol) of N-(1,1'-biphenyl-2-yl)benzo[b] naphtho[1,2-d]furan-6-amine, which was obtained in Step 1, and 1.4 g (5.2 mmol) of 4-bromo-9-dimethylfluorene were put, and the air in the flask was replaced with nitrogen. Into the flask, 1.0 g (10 mmol) of sodium tert-butoxide, 0.30 mL of tri-tert-butylphosphine (a 10 wt % hexane solution), and 50 mL of xylene were added, and degassing under reduced pressure and replacement with nitrogen were performed three times. Into the flask, 30 mg (0.51 mmol) of bis(bis (dibenzylideneacetone)palladium)(0) was added, and stirring was performed at 80° C. for 16 hours. After the stirring, water was added to the reactant, and an aqueous layer was subjected to extraction with toluene. The obtained organic layer was washed twice with water and subsequently washed with a saturated saline solution, and dried with anhydrous magnesium sulfate. The obtained mixture was gravity-filtered to remove the anhydrous magnesium sulfate. The obtained filtrate was concentrated to give 2.9 g of a yellow solid, which contains a target substance. The yellow solid was purified by recrystallization (toluene/hexane) to give 1.4 g of a target white solid in a yield of 47%.

By the train sublimation method, 1.4 g of the obtained white solid was sublimated and purified. In the sublimation purification, the white solid was heated at 205° C. for 15 hours under a pressure of 3.6 Pa with a flow of argon at 15 mL/min. After the sublimation purification, 1.1 g of a target white solid was obtained at a collection rate of 78%. The synthesis scheme is shown below.

[Chemical Formulae 49]

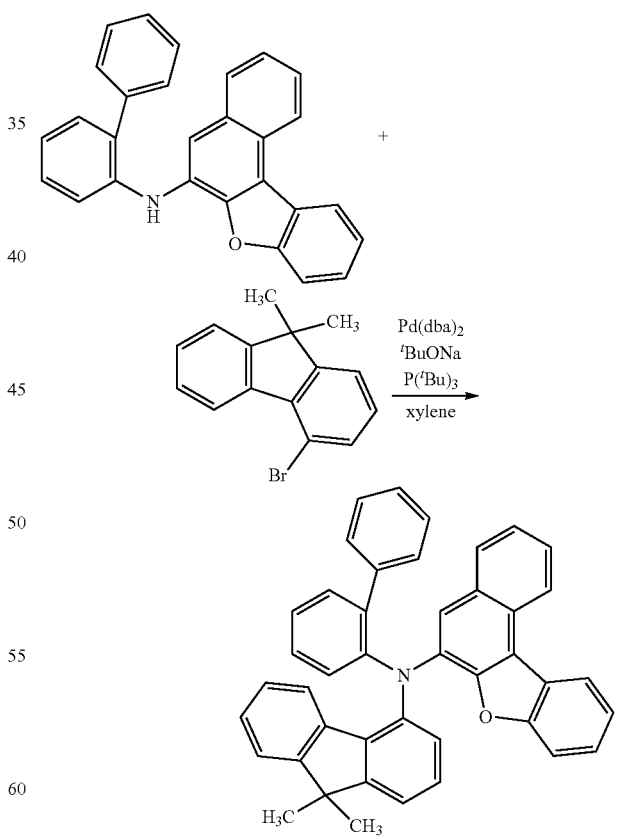

Figure 17A:
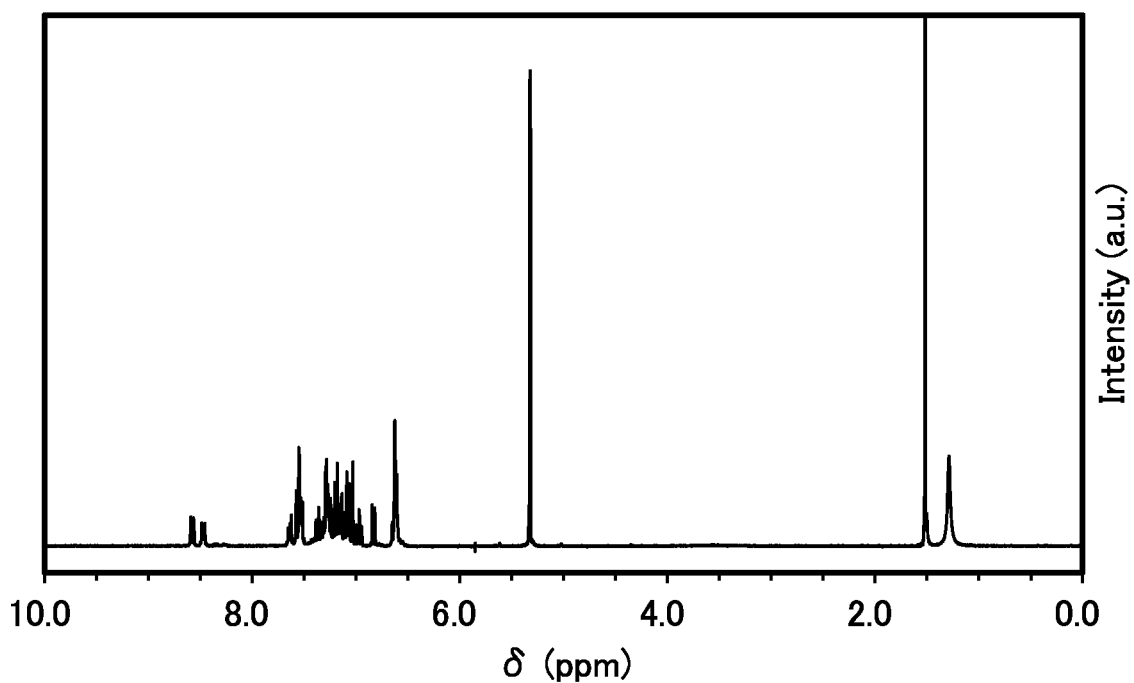
FIG. 17A and FIG. 17B are $^1$H NMR charts of oFBi(4)Bnf(6).
Figure 17B:
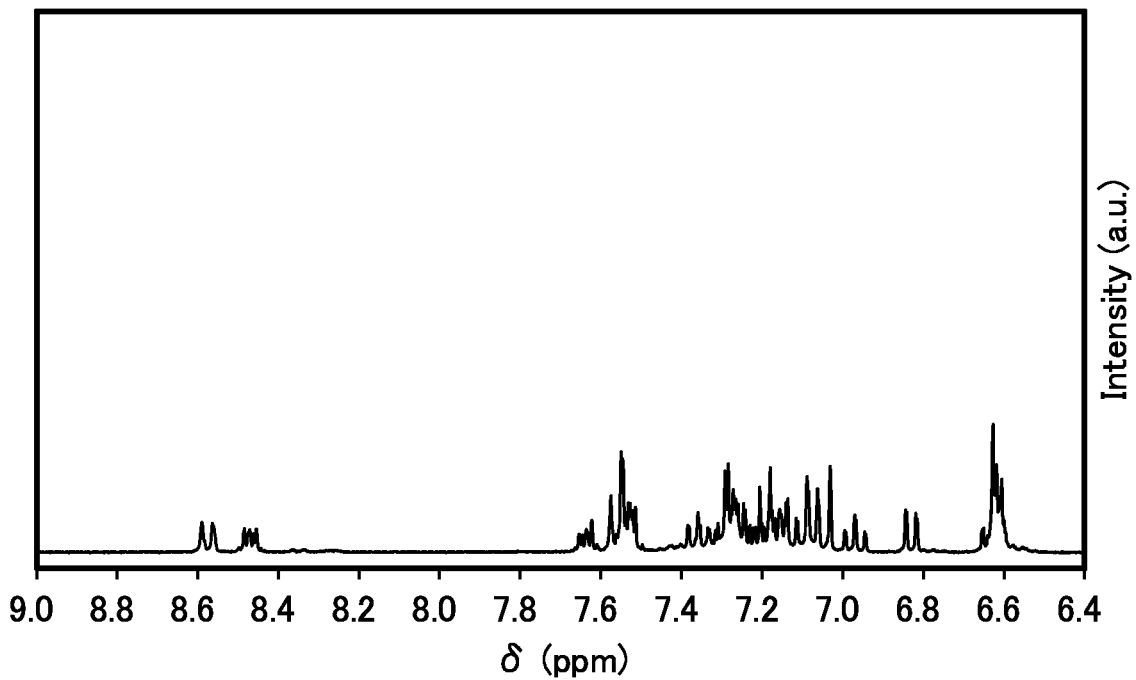

Given below are ¹H-NMR numerical data of the obtained solid. FIG. 17A and FIG. 17B show ¹H-NMR charts. These results indicate that oFBi(4)Bnf(6) was obtained in this synthesis example.

¹H NMR (dichloromethane-d2, 300 MHz): δ=8.57 (d, J=7.8 Hz, 1H), 8.50-8.44 (m, 1H), 7.66-7.50 (m, 5H), 7.42-7.03 (m, 12H), 6.97 (t, J=7.5 Hz, 1H), 6.83 (d, J=7.5 Hz, 1H), 6.65-6.55 (m, 4H), 1.29 (s, 6H)

Next, the ultraviolet-visible absorption spectra (hereinafter, simply referred to as "absorption spectra") and emission spectra of a toluene solution and a solid thin film of oFBi(4)Bnf(6) were measured. The measurement method and the measurement apparatus are the same as those in Example 1; therefore, repeated description will be omitted.

Figure 18:
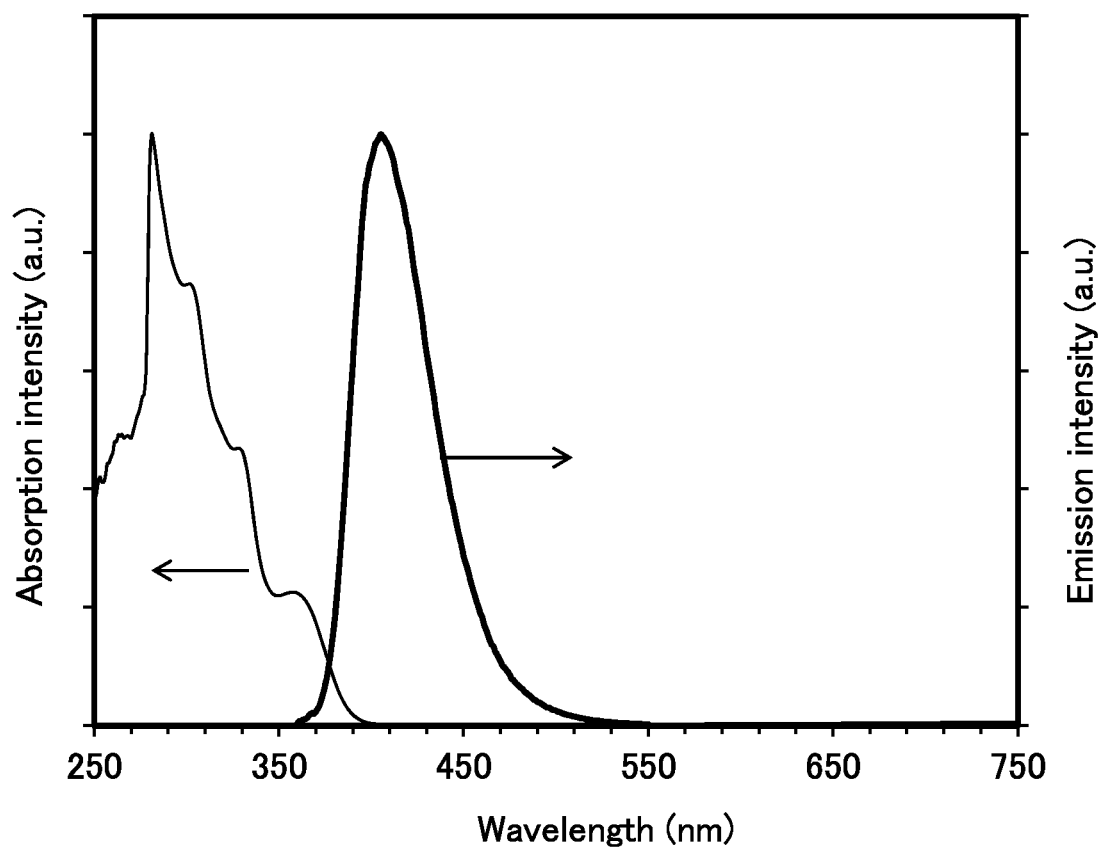
FIG. 18 shows an absorption spectrum and an emission spectrum of oFBi(4)Bnf(6) in a toluene solution.
Figure 19:
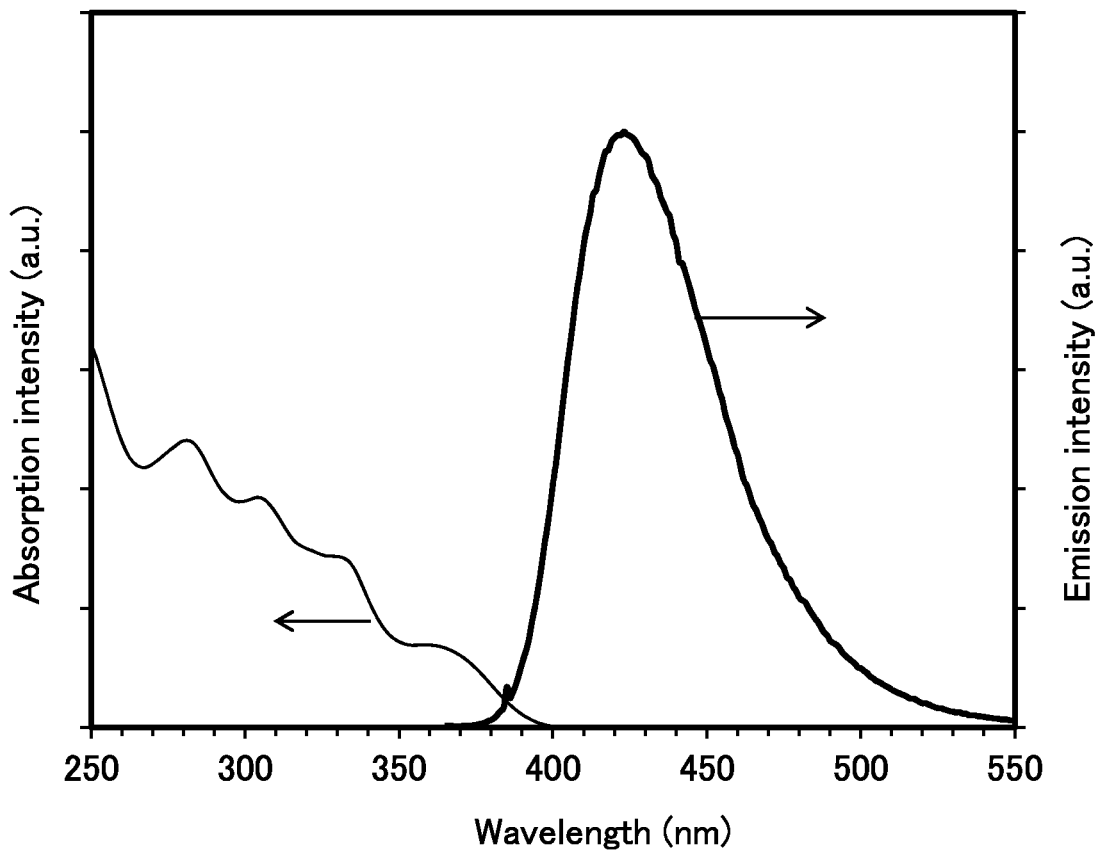
FIG. 19 shows an absorption spectrum and an emission spectrum of a thin film of oFBi(4)Bnf(6).

FIG. 18 shows the obtained measurement results of the absorption spectrum and the emission spectrum of the toluene solution. FIG. 19 shows the measurement results of the absorption spectrum and the emission spectrum of the solid thin film. From the results in FIG. 18, for the toluene solution of oFBi(4)Bnf(6), the absorption peaks including the shoulder peak were observed at around 357 nm, 328 nm, and 301 nm, and the emission wavelength peak was observed at 405 nm (excitation wavelength: 353 nm). From the results in FIG. 19, for the solid thin film of oFBi(4)Bnf(6), the absorption peaks including the shoulder peak were observed at around 360 nm, 332 nm, 304 nm, and 282 nm, and the emission wavelength peak was observed at around 423 nm (excitation wavelength: 360 nm).

The HOMO level and the LUMO level of oFBi(4)Bnf(6) were calculated on the basis of a cyclic voltammetry (CV) measurement. The calculation method, the measurement method, and the measurement apparatus are the same as those in Example 1; therefore, repeated description will be omitted.

As a result, the HOMO level and the LUMO level of oFBi(4)Bnf(6) were found to be −5.64 eV and −2.32 eV, respectively. In addition, in repetitive measurement of the oxidation-reduction wave, when the waveform of the first cycle was compared with that of the hundredth cycle, 79% of the peak intensity and 97% of the peak intensity were maintained in the Ea measurement and the Ec measurement, respectively, which confirmed that oFBi(4)Bnf(6) had extremely high resistance to oxidation and reduction.

Differential scanning calorimetry (DSC measurement) was performed on oFBi(4)Bnf(6) by PyrislDSC manufactured by PerkinElmer, Inc. The differential scanning calorimetry was performed in the following manner: the temperature was raised from −10° C. to 253° C. at a temperature rising rate of 40° C./min and held at the temperature for one minute, and then the temperature was decreased to −10° C. at a temperature decreasing rate of 100° C./min. This operation was performed twice in succession. It was revealed from the result of the second cycle of the DSC measurement that the glass transition point of oFBi(4)Bnf(6) was 114° C., that is, oFBi(4)Bnf(6) was a substance with extremely high heat resistance.

Then, thermogravimetry-differential thermal analysis of oFBi(4)Bnf(6) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 343° C., which shows that oFBi(4)Bnf(6) is a substance with favorable sublimability.

From the above results, it was found that the organic compound of one embodiment of the present invention has both high heat resistance and favorable sublimability, and can provide an organic optical device (a light-emitting device and a light-receiving device) with high heat resistance and increase the productivity of device manufacturing.

Example 3

Synthesis Example 3>>

In this synthesis example, a method for synthesizing N-(1,1'-biphenyl-4-yl)-N-(9,9-dimethyl-9H-fluoren-4-yl) benzo[b]naphtho[1,2-d]furan-6-amine (abbreviation: FBi(4) Bnf(6)), which is represented by Structural Formula (5-59) in Embodiment 1, will be described. The structural formula of FBi(4)Bnf(6) is shown below.

[Chemical Formula 50]

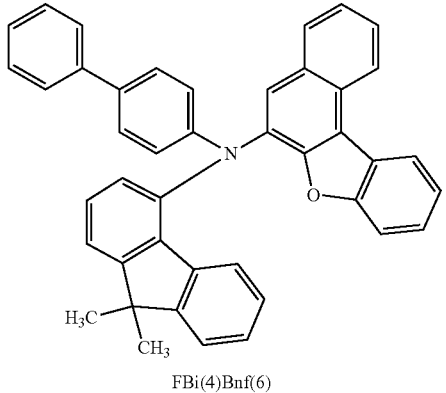

FBi(4)Bnf(6)

Step 1: Synthesis of N-(9,9-dimethyl-9H-fluoren-4-yl)t-butoxycarbonylamine

Into a 200 mL three-neck flask equipped with a reflux pipe, 5.4 g (20 mmol) of 4-bromo-9,9-dimethyl-9H-fluoren, 2.3 g (20 mmol) of tert-butyl carbamate, 0.23 g (0.40 mmol) of 4,5-bis(diphenylphosphino)-9,9-dimethylxanthene (abbreviation: Xantphos), and 13 g (40 mmol) of cesium carbonate were put, and the air in the flask was replaced with nitrogen. Into the flask, 100 mL of anhydrous 1,4-dioxane was added, and then the mixture was degassed under reduced pressure. A nitrogen stream was made to flow in the flask, the mixture was stirred at 60° C., 55 mg 0.20 mmol) of palladium(II) acetate was added, and then stirring was performed at 80° C. for 3 hours. After the stirring, the precipitate was removed by suction filtration, and then the mixture was washed three times with approximately 100 mL of water using a 500 mL separating funnel. An aqueous layer obtained by the washing was subjected to extraction three times with approximately 200 mL of toluene, and the obtained extracted solution and organic layer were combined and washed once with approximately 300 mL of a saturated saline solution. Anhydrous magnesium sulfate was added to the obtained organic layer, the mixture was left for one hour, and then gravity filtration was performed. The compound obtained by concentration of the obtained filtrate was purified by silica gel column chromatography (developing solvent: toluene:ethyl acetate=9:1) to give 5.5 g of a target white solid in a yield of 88%. The synthesis scheme of Step 1 is shown below.

[Chemical Formulae 51]

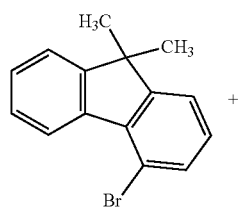

+

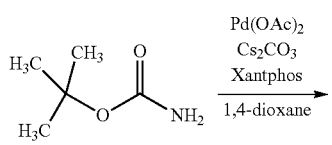

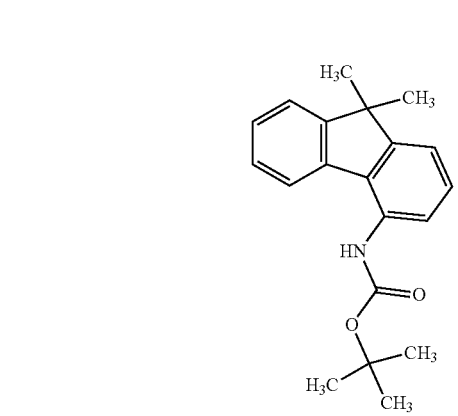

Step 2: Synthesis of
9,9-dimethyl-9H-fluoren-4-amine

Into a 1000 mL recovery flask, 5.5 g (18 mmol) of N-(9,9-dimethyl-9H-fluoren-4-yl)t-butoxycarbonylamine, which was obtained in Step 1, and 100 mL of dichloromethane were put, and a nitrogen stream was made to flow in the flask. Into the solution, 5.2 mL (8.1 g, 71 mmol) of trifluoroacetic acid was dropped from a dropping funnel for 5 minutes, and then stirring was performed at room temperature for approximately 16 hours. After the stirring, the recovery flask was cooled with ice, and then 100 mL of a potassium hydroxide solution (0.7 mmol) was added for neutralization. The obtained mixture was separated into an organic phase and an aqueous phase using a 500 mL separating funnel, and the organic phase was washed three times with approximately 100 mL of water. The water used for the washing was subjected to extraction three times with 200 mL of toluene, and the obtained extracted solution and organic phase were combined and washed with approximately 200 mL of a saturated saline solution. Anhydrous magnesium sulfate was added to the organic phase obtained after the washing, the mixture was left for one hour, gravity filtration was performed, and then the obtained filtrate was concentrated. The obtained compound was dried in a vacuum to give 3.2 g of a target white solid in a yield of 86%. The synthesis scheme of Step 2 is shown below.

[Chemical Formulae 52]

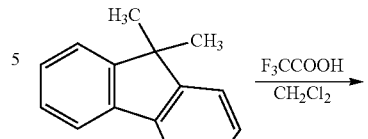

F₃CCOOH
———————
CH₂Cl₂

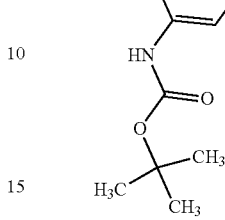

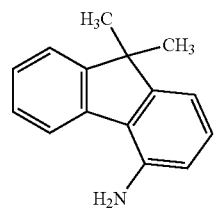

Step 3: Synthesis of N-(9,9-dimethyl-9H-fluoren-4-yl)benzo[b]naphtho[1,2-d]furan-6-amine Into a 200 mL three-neck flask equipped with a reflux pipe, 1.5 g (7.2 mmol) of 9,9-dimethyl-9H-fluoren-4-amine, which was obtained in Step 2, 2.5 g (7.2 mmol) of 6-iodobenzo[b]naphtho[1,2-d]furan, 0.18 g (0.4 mmol) of 2-dicyclohexylphosphino-2',6'-dimethoxybiphenyl(sphos), and 1.5 g (15 mmol) of t-butoxysodium were put, and the air in the flask was replaced with nitrogen. Into the flask, 40 mL of toluene was added, degassing under reduced pressure was performed, and then a nitrogen stream was made to flow in the flask. This mixture was stirred at 60° C., 0.11 g (0.20 mmol) of bis(bis(dibenzylideneacetone)palladium)(0) was put into the flask at the same temperature, and then stirring was performed at 80° C. for 3 hours. After the stirring, the obtained mixture was washed three times with approximately 100 mL of water using a 1 L separating funnel. The water used for the washing was subjected to extraction three times with approximately 100 mL of toluene, and the obtained extracted solution and organic phase were combined and washed with approximately 200 mL of a saturated saline solution. Anhydrous magnesium sulfate was added to the obtained organic phase, the mixture was left for one hour, and then the obtained filtrate was concentrated to give 3.5 g of a dark brown compound. The obtained compound was purified by silica gel column chromatography (developing solvent: hexane: toluene=2:1) to give 1.8 g of a target substance in a yield of 59%. The synthesis scheme of Step 3 is shown below.

[Chemical Formulae 53]

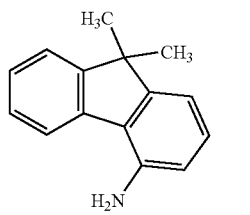 +

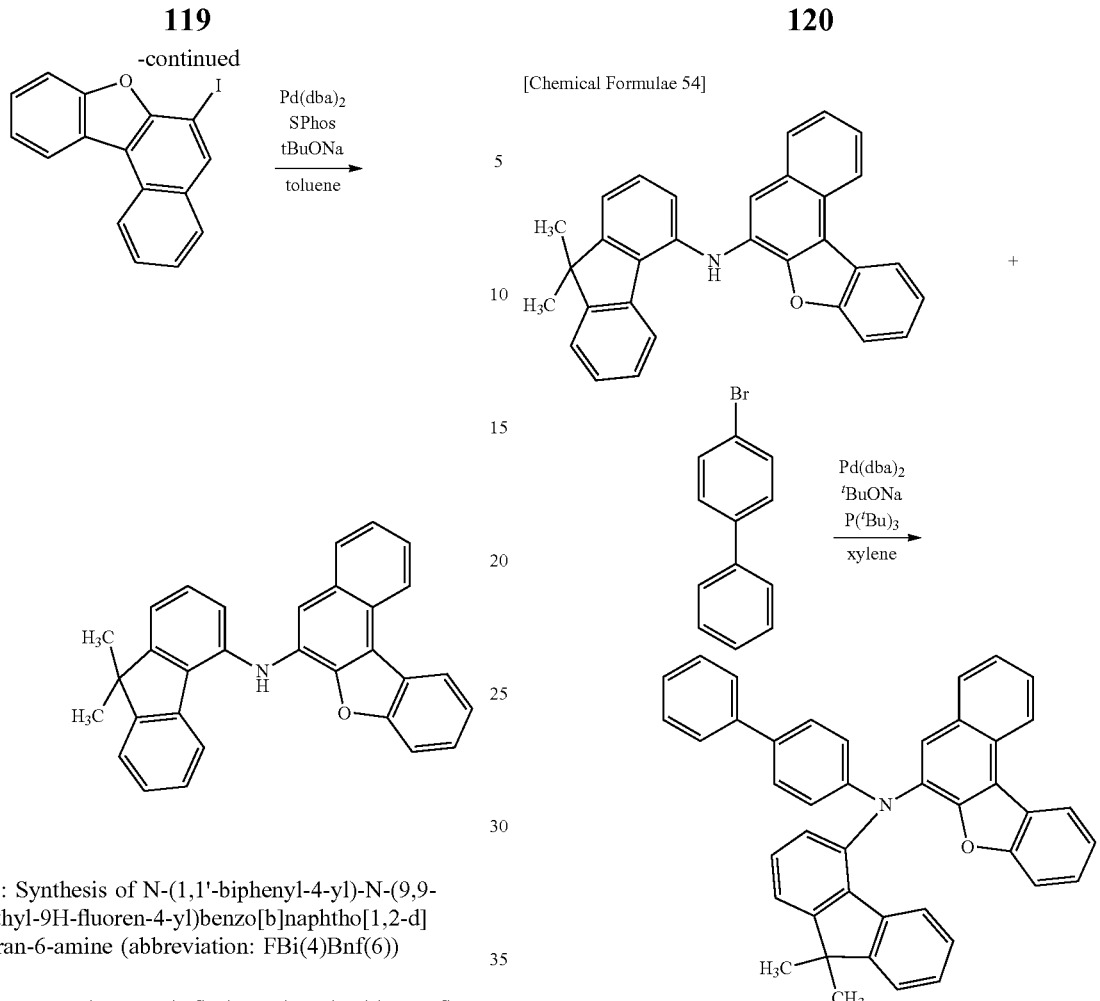

Step 4: Synthesis of N-(1,1'-biphenyl-4-yl)-N-(9,9-dimethyl-9H-fluoren-4-yl)benzo[b]naphtho[1,2-d]furan-6-amine (abbreviation: FBi(4)Bnf(6))

Into a 200 mL three-neck flask equipped with a reflux pipe, 1.8 g (4.1 mmol) of N-(9,9-dimethyl-9H-fluoren-4-yl)benzo[b]naphtho[1,2-d]furan-6-amine, which was obtained in Step 3, and 0.96 g (4.1 mmol) of 4-bromobiphenyl were put, and the air in the flask was replaced with nitrogen. Into the flask, 0.80 g (8.3 mmol) of sodium tert-butoxide, 0.30 mL of tri-tert-butylphosphine (a 10 wt % hexane solution), and 25 mL of xylene were added, and degassing under reduced pressure and replacement with nitrogen were performed three times. Into the flask, 24 mg (0.41 mmol) of bis(bis(dibenzylideneacetone)palladium)(0) was added, and stirring was performed at 80° C. for 4 hours. After the stirring, water was added to the reactant, and an aqueous layer was subjected to extraction with toluene. The obtained organic layer was washed twice with water and subsequently washed with a saturated saline solution, and dried with anhydrous magnesium sulfate. The obtained mixture was gravity-filtered to remove the anhydrous magnesium sulfate. The obtained filtrate was concentrated to give 3.4 g of a pale yellow solid. The obtained pale yellow solid was purified by high-performance liquid chromatography (HPLC) (mobile phase: chloroform) to give 2.2 g of a target white solid in a yield of 93%.

By the train sublimation method, 1.8 g of the obtained white solid was sublimated and purified. In the sublimation purification, the solid was heated at 230° C. for 16 hours under a pressure of 3.1 Pa with a flow of argon at 15 mL/min. After the sublimation purification, 1.2 g of a target white solid was obtained at a collection rate of 66%. The synthesis scheme of Step 4 is shown below.

Figure 20A:
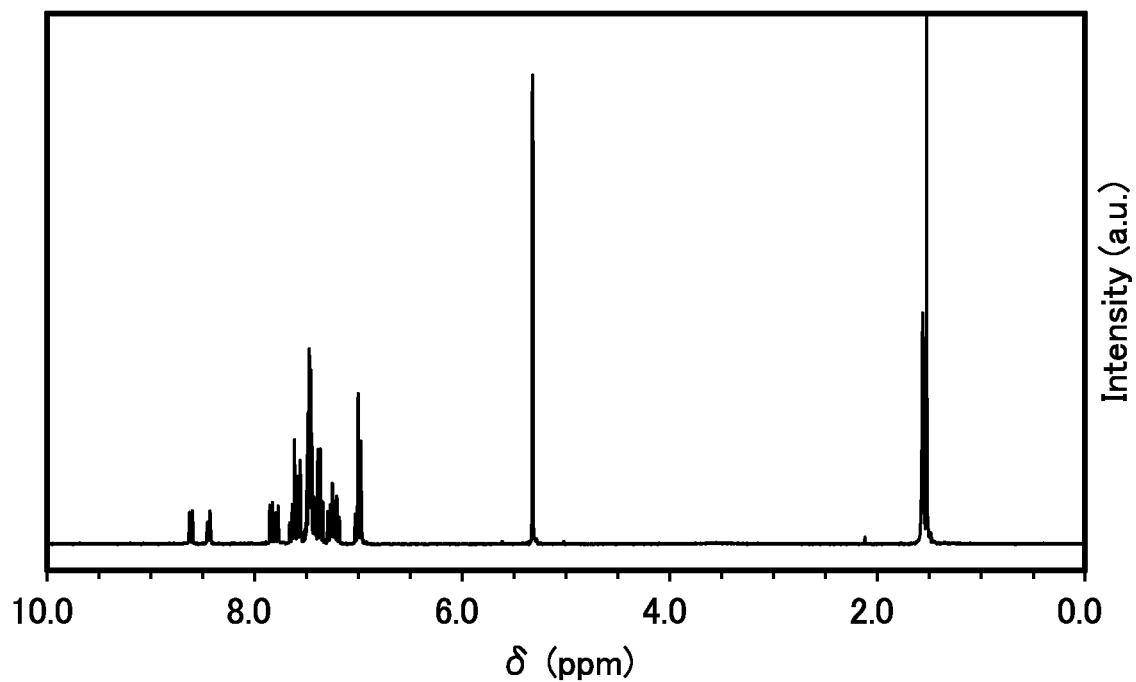
FIG. 20A and FIG. 20B are $^1$H NMR charts of FBi(4)Bnf(6).
Figure 20B:
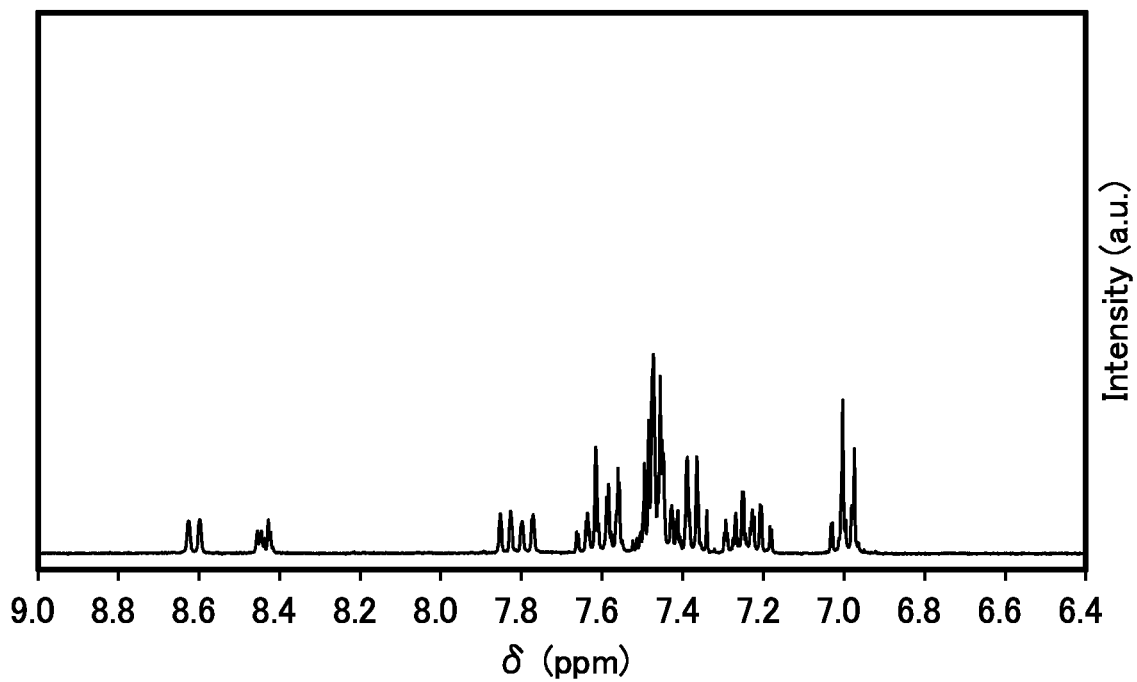

Given below are $^1$H-NMR numerical data of the obtained solid. FIG. 20A and FIG. 20B show $^1$H-NMR charts. These results indicate that FBi(4)Bnf(6) was obtained in this synthesis example.

$^1$H NMR (dichloromethane-d2, 300 MHz): δ=8.61 (d, J=8.4 Hz, 1H), 8.45-8.42 (m, 1H), 7.84 (d, J=7.8 Hz, 1H), 7.78 (d, J=8.1 Hz, 1H), 7.66-7.18 (m, 18H), 7.03-6.96 (m, 3H), 1.57 (s, 6H)

Next, the ultraviolet-visible absorption spectra (hereinafter, simply referred to as "absorption spectra") and emission spectra of a toluene solution and a solid thin film of FBi(4)Bnf(6) were measured. The measurement method and the measurement apparatus are the same as those in Example 1; therefore, repeated description will be omitted.

Figure 21:
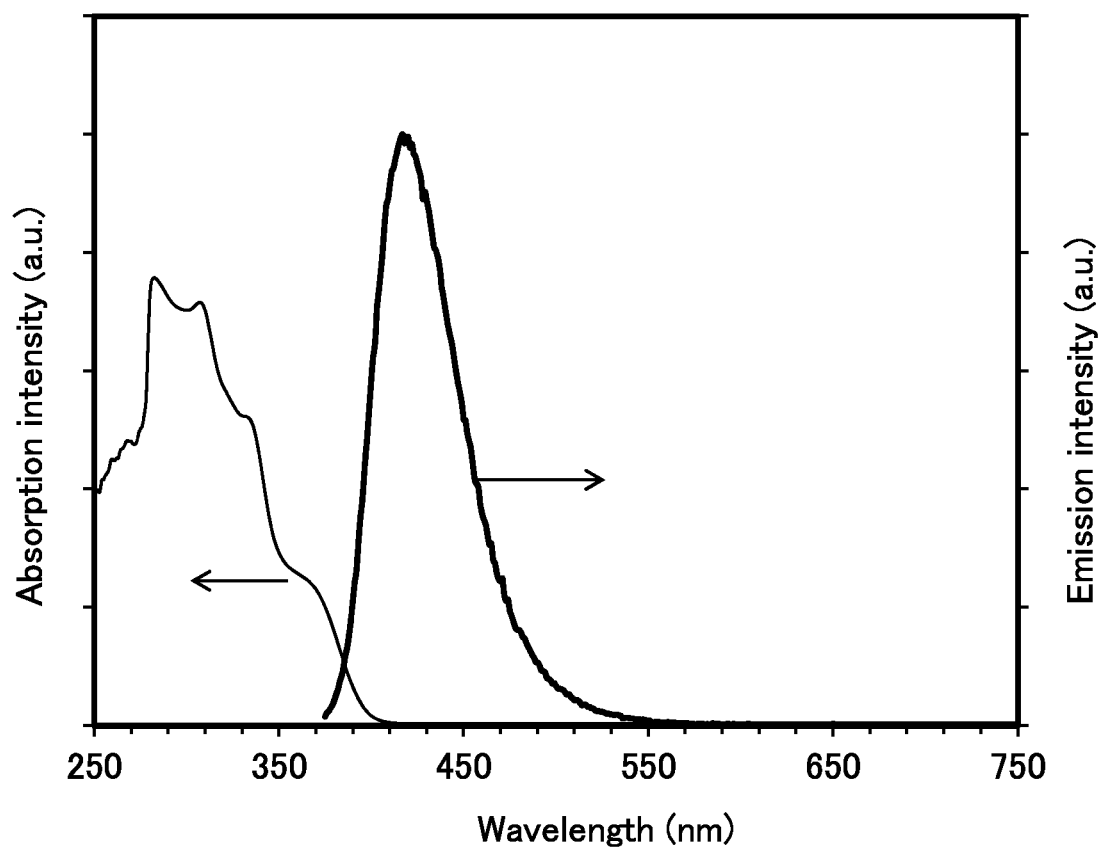
FIG. 21 shows an absorption spectrum and an emission spectrum of FBi(4)Bnf(6) in a toluene solution.
Figure 22:
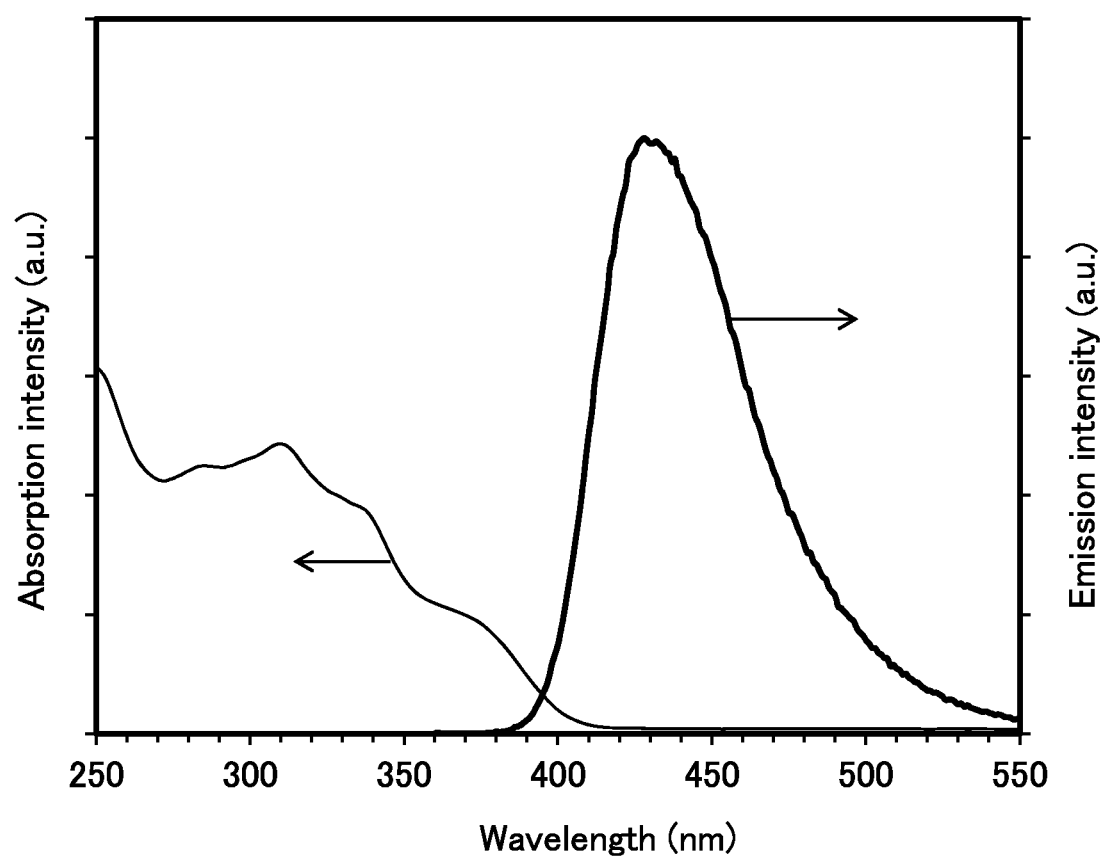
FIG. 22 shows an absorption spectrum and an emission spectrum of a thin film of FBi(4)Bnf(6).

FIG. 21 shows the obtained measurement results of the absorption spectrum and the emission spectrum of the toluene solution. FIG. 22 shows the measurement results of the absorption spectrum and the emission spectrum of the solid thin film. From the results in FIG. 21, for the toluene solution of FBi(4)Bnf(6), the absorption peaks including the shoulder peak were observed at around 371 nm, 336 nm, 307 nm, and 283 nm, and the emission wavelength peak was observed at 428 nm (excitation wavelength: 370 nm). From the results in FIG. 22, for the solid thin film of FBi(4)Bnf(6), the absorption peaks including the shoulder peak were observed at around 374 nm, 337 nm, 309 nm, and 285 nm, and the emission wavelength peak was observed at around 428 nm (excitation wavelength: 350 nm).

The HOMO level and the LUMO level of FBi(4)Bnf(6) were calculated on the basis of a cyclic voltammetry (CV) measurement. The calculation method is shown below. The calculation method, the measurement method, and the measurement apparatus are the same as those in Example 1; therefore, repeated description will be omitted.

As a result, the HOMO level and the LUMO level of FBi(4)Bnf(6) were found to be −5.64 eV and −2.40 eV, respectively. In addition, in repetitive measurement of the oxidation-reduction wave, when the waveform of the first cycle was compared with that of the hundredth cycle, 79% of the peak intensity and 93% of the peak intensity were maintained in the Ea measurement and the Ec measurement, respectively, which confirmed that FBi(4)Bnf(6) had high resistance to oxidation and reduction.

Differential scanning calorimetry (DSC measurement) was performed on FBi(4)Bnf(6) by Pyris1DSC manufactured by PerkinElmer, Inc. The differential scanning calorimetry was performed in the following manner: the temperature was raised from −10° C. to 280° C. at a temperature rising rate of 40° C./min and held at the temperature for one minute, and then the temperature was decreased to −10° C. at a temperature decreasing rate of 100° C./min. This operation was performed twice in succession. It was revealed from the result of the second cycle of the DSC measurement that the glass transition point of FBi(4)Bnf(6) was 134° C., that is, FBi(4)Bnf(6) was a substance with extremely high heat resistance.

Then, thermogravimetry-differential thermal analysis of FBi(4)Bnf(6) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 390° C., which shows that FBi(4)Bnf(6) is a substance with favorable sublimability.

From the above results, it was found that the organic compound of one embodiment of the present invention has both high heat resistance and favorable sublimability, and can provide an organic optical device (a light-emitting device and a light-receiving device) with high heat resistance and increase the productivity of device manufacturing.

Example 4

Synthesis Example 4>>

In this synthesis example, a method for synthesizing N-(1,1'-biphenyl-4-yl)-N-(9,9-dimethyl-9H-fluoren-2-yl)benzo[b]naphtho[1,2-d]furan-6-amine (abbreviation: FBiBnf(6)), which is represented by Structural Formula (5-58) in Embodiment 1, will be described. The structural formula of FBiBnf(6) is shown below.

[Chemical Formula 55]

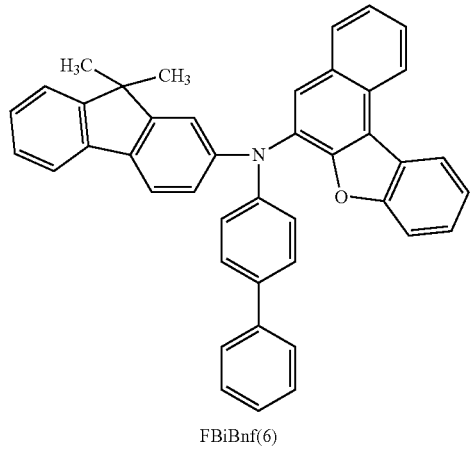

FBiBnf(6)

Step 1: Synthesis of N-(9,9-dimethyl-9H-fluoren-2-yl)benzo[b]naphtho[1,2-d]furan-6-amine Into a 200 mL three-neck flask equipped with a reflux pipe, 2.1 g (10 mmol) of 9,9-dimethyl-9H-fluoren-2-amine, 3.4 g (10 mmol) of 6-iodobenzo[b]naphtho[1,2-d]furan, 0.84 mg (0.2 mmol) of 2-dicyclohexylphosphino-2',6'-dimethoxybiphenyl(sphos), and 2.0 g (20 mmol) of t-butoxysodium were put, and the air in the flask was replaced with nitrogen. Into the flask, 50 mL of toluene was added, degassing under reduced pressure was performed, and then a nitrogen stream was made to flow in the flask. This mixture was stirred at 60° C., 60 mg (0.11 mmol) of bis(bis(dibenzylideneacetone)palladium)(0) was put into the flask at the same temperature, and then stirring was performed at 80° C. for 7 hours. After the stirring, 600 mL of toluene was added to the obtained mixture, and stirring was performed at 100° C. while heating was performed. At the same temperature, the mixture was filtered through alumina, Florisil (Wako Pure Chemical Industries, Ltd., Catalog No. 066-05265), and Celite (Wako Pure Chemical Industries, Ltd., Catalog No. 537-02305). A solid obtained by concentration of the obtained filtrate was recrystallized with 300 mL of ethanol to give 2.5 g of a target white solid in a yield of 58%. The synthesis scheme of Step 1 is shown below.

[Chemical Formulae 56]

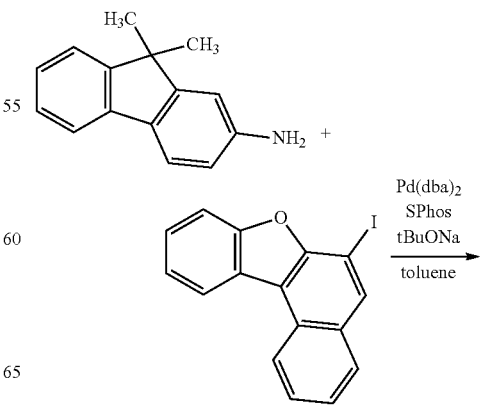

-continued

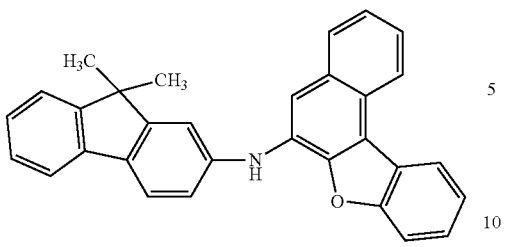

Step 2: Synthesis of N-(1,1'-biphenyl-4-yl)-N-(9,9-dimethyl-9H-fluoren-2-yl)-benzo[b]naphtho[1,2-d]furan-6-amine (abbreviation: FBiBnf(6))

Into a 200 mL three-neck flask equipped with a reflux pipe, 1.1 g (2.5 mmol) of N-(9,9-dimethyl-9H-fluoren-2-yl) benzo[b]naphtho[1,2-d]furan-6-amine, which was obtained in Step 1, 0.58 g (2.5 mmol) of 4-bromobiphenyl, 0.86 mg (0.2 mmol) of 2-di-tert-butylphosphino-2',4',6'-triisopropyl-biphenyl(tBuxphos), and 0.52 g (5.0 mmol) of t-butoxysodium were put, and the air in the flask was replaced with nitrogen. Into the flask, 25 mL of xylene was added, degassing under reduced pressure was performed, and then a nitrogen stream was made to flow in the flask. This mixture was stirred at 80° C., 62 mg (0.11 mmol) of bis(bis(dibenzylideneacetone)palladium)(0) was put into the flask at the same temperature, and then stirring was performed at 110° C. for 5 hours. After the stirring, 600 mL of toluene was added to the obtained mixture, and stirring was performed at 100° C. while heating was performed. At the same temperature, the mixture was filtered through alumina, Florisil (Wako Pure Chemical Industries, Ltd., Catalog No. 066-05265), and Celite (Wako Pure Chemical Industries, Ltd., Catalog No. 537-02305). A solid obtained by concentration of the obtained filtrate was purified by silica gel column chromatography (developing solvent: hexane: toluene=1:1) and then purified by high-performance liquid chromatography (developing solvent: chloroform) to give 0.96 g of a target pale yellow solid in a yield of 66%.

By the train sublimation method, 0.96 g of the obtained pale yellow solid was sublimated and purified. In the sublimation purification, the pale yellow solid was heated at 270° C. for 16 hours under a pressure of 2.5 Pa with a flow of argon at 15 mL/min. After the sublimation purification, 0.80 g of a target white solid was obtained at a collection rate of 84%. The synthesis scheme of Step 2 is shown below.

[Chemical Formulae 57]

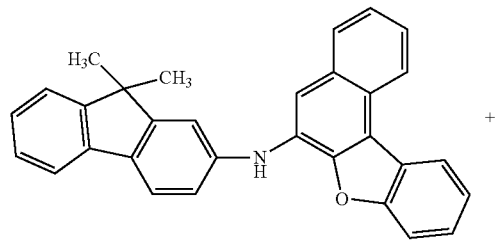

+

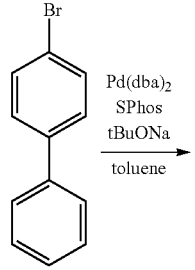

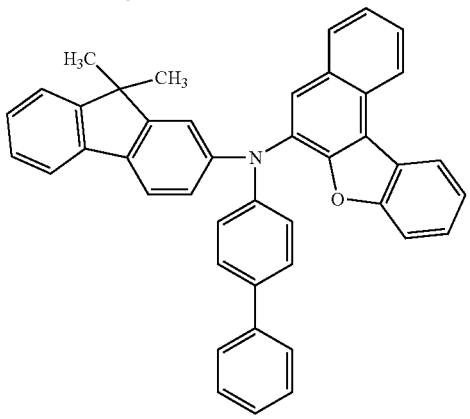

Figure 23A:
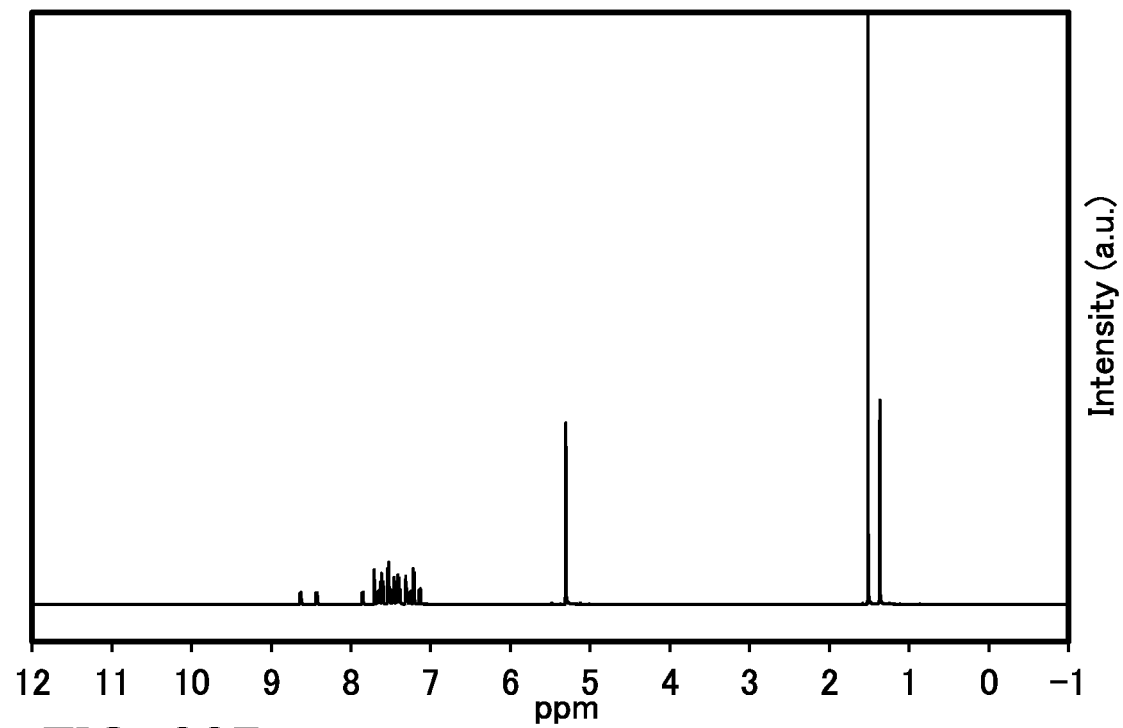
FIG. 23A and FIG. 23B are $^1$H NMR charts of FBiBnf(6).
Figure 23B:
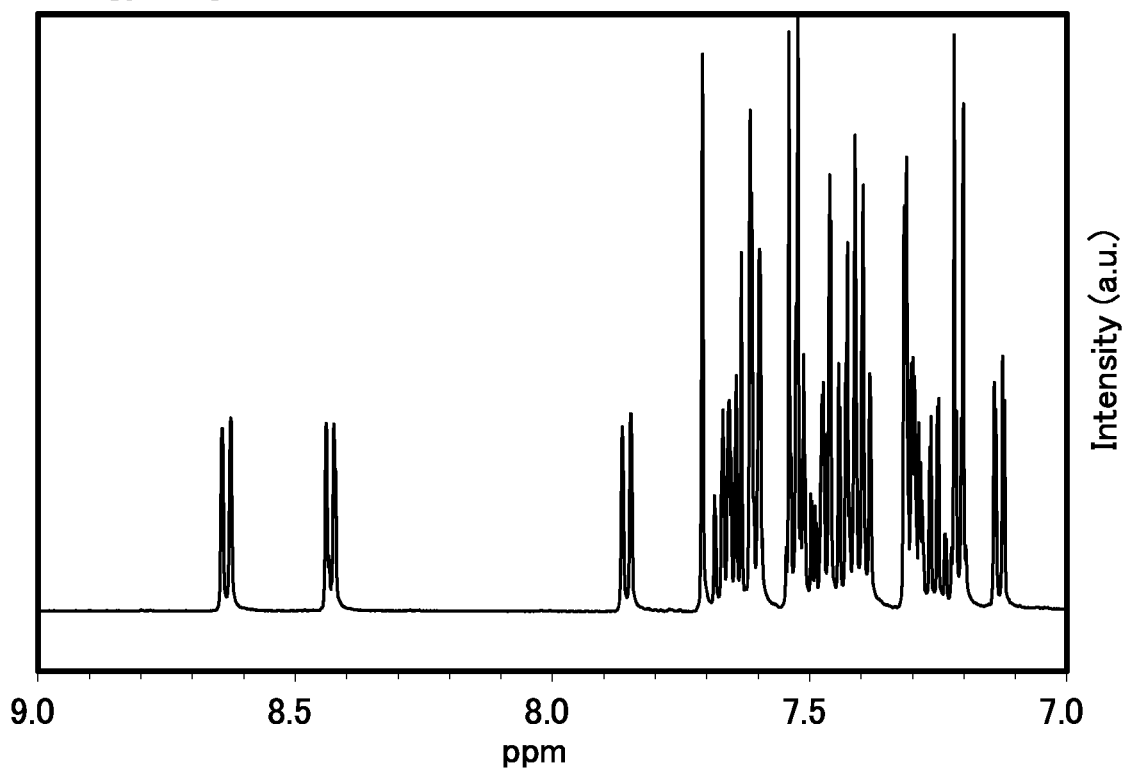

Given below are $^1$H-NMR numerical data of the obtained solid. FIG. 23A and FIG. 23B show $^1$H-NMR charts. These results indicate that FBiBnf(6) was obtained in this synthesis example.

$^1$H NMR (dichloromethane-d2, 300 MHz): δ=8.63 (d, J=8.0 Hz, 1H), 8.43 (dd, J1=6.8 Hz, J2=1.5 Hz, 1H), 7.86 (d, J=8.0 Hz, 1H), 7.71 (s, 1H), 7.69-7.59 (m, 5H), 7.53 (d, J=8.5 Hz, 2H), 7.52-7.38 (m, 7H), 7.32-7.24 (m, 4H), 7.21 (d, J=9.0 Hz, 2H), 7.13 (dd, J1=8.3 Hz, J2=1.5 Hz, 1H) 1.37 (s, 6H)

Next, the ultraviolet-visible absorption spectra (hereinafter, simply referred to as "absorption spectra") and emission spectra of a toluene solution and a solid thin film of FBiBnf(6) were measured. The measurement method and the measurement apparatus are the same as those in Example 1; therefore, repeated description will be omitted.

Figure 24:
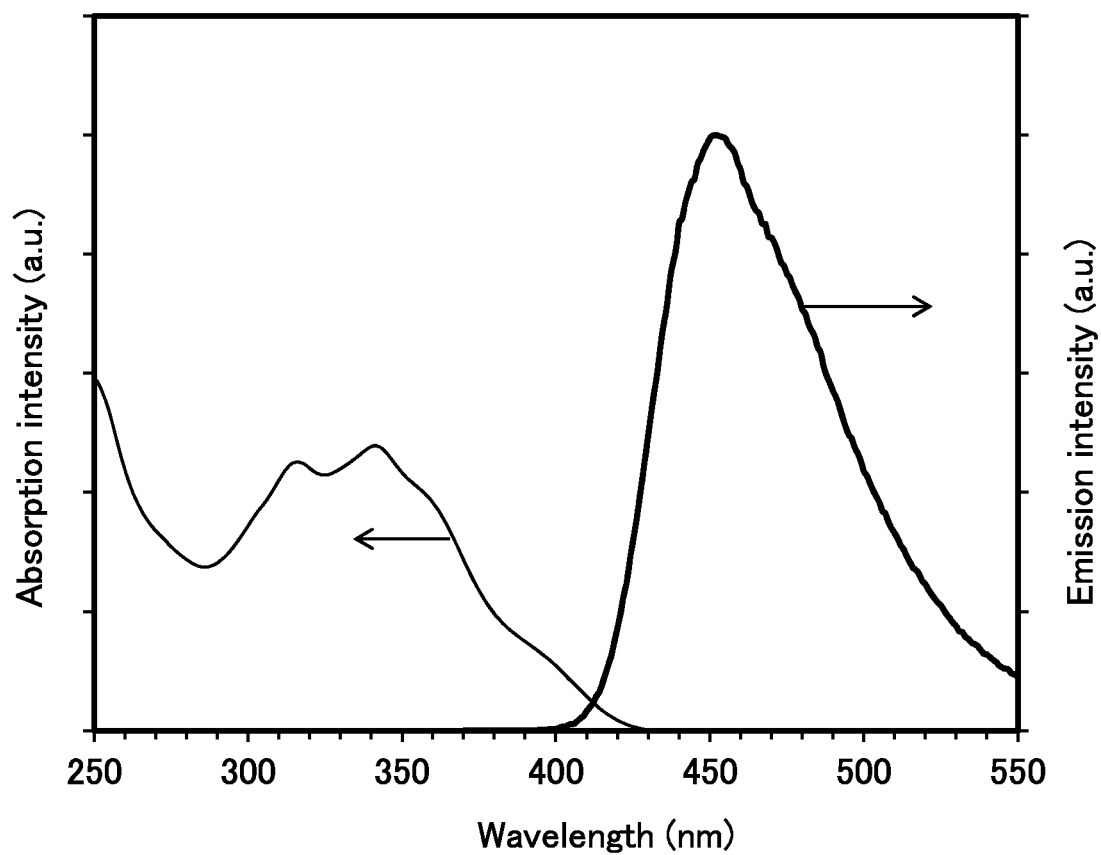
FIG. 24 shows an absorption spectrum and an emission spectrum of FBiBnf(6) in a toluene solution.
Figure 25:
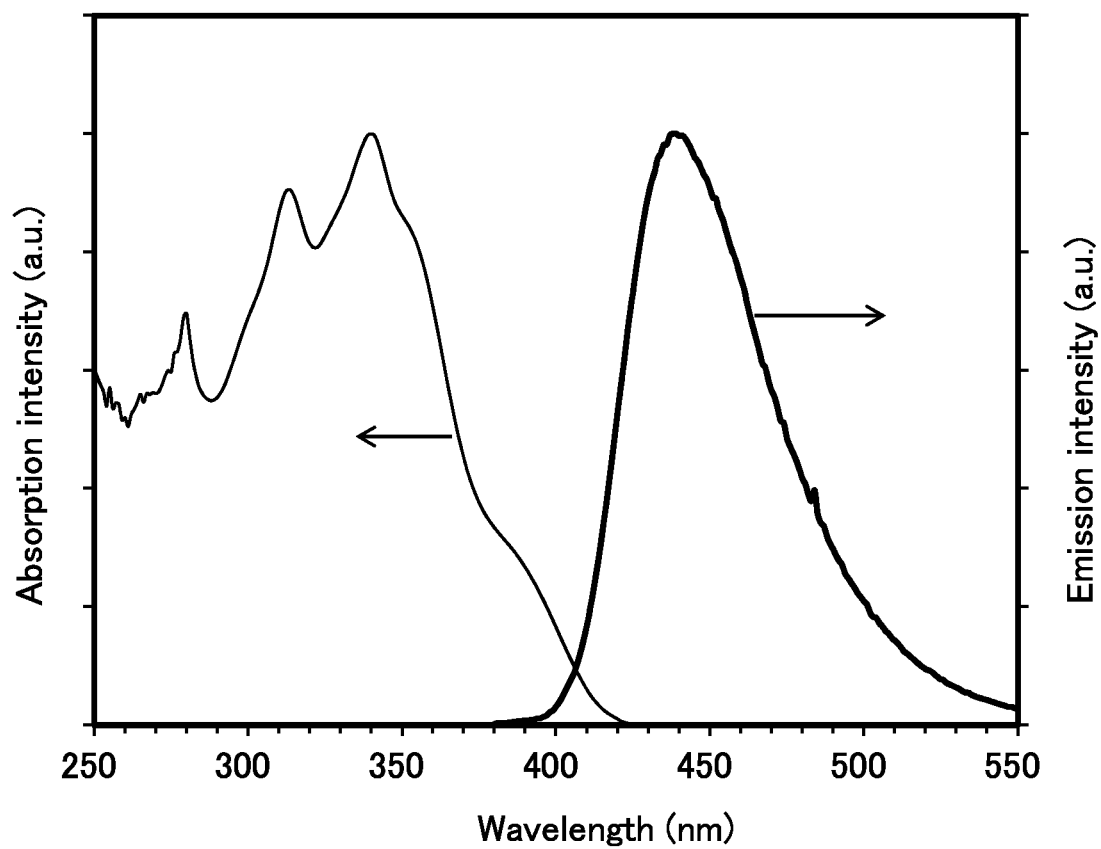
FIG. 25 shows an absorption spectrum and an emission spectrum of a thin film of FBiBnf(6).

FIG. 24 shows the obtained measurement results of the absorption spectrum and the emission spectrum of the toluene solution. FIG. 25 shows the measurement results of the absorption spectrum and the emission spectrum of the solid thin film. From the results in FIG. 24, for the toluene solution of FBiBnf(6), the absorption peaks including the shoulder peak were observed at around 389 nm, 352 nm, 340 nm, and 313 nm, and the emission wavelength peak was observed at 438 nm (excitation wavelength: 360 nm). From the results in FIG. 25, for the solid thin film of FBiBnf(6), the absorption peaks including the shoulder peak were observed at around 396 nm, 358 nm, 341 nm, and 316 nm, and the emission wavelength peak was observed at around 452 nm (excitation wavelength: 365 nm).

The HOMO level and the LUMO level of FBiBnf(6) were calculated on the basis of a cyclic voltammetry (CV) measurement. The calculation method is shown below. The calculation method, the measurement method, and the measurement apparatus are the same as those in Example 1; therefore, repeated description will be omitted.

As a result, the HOMO level and the LUMO level of FBiBnf(6) were found to be −5.48 eV and −2.41 eV, respectively. In addition, in repetitive measurement of the oxidation-reduction wave, when the waveform of the first cycle was compared with that of the hundredth cycle, 87% of the peak intensity and 97% of the peak intensity were maintained in the Ea measurement and the Ec measurement, respectively, which confirmed that FBiBnf(6) had extremely high resistance to oxidation and reduction.

Differential scanning calorimetry (DSC measurement) was performed on FBiBnf(6) by PyrislDSC manufactured by PerkinElmer, Inc. The differential scanning calorimetry was performed in the following manner: the temperature was raised from −10° C. to 300° C. at a temperature rising rate of 40° C./min and held at the temperature for one minute, and then the temperature was decreased to −10° C. at a temperature decreasing rate of 100° C./min. This operation was performed twice in succession. It was revealed from the result of the second cycle of the DSC measurement that the glass transition point of FBiBnf(6) was 128° C., that is, FBiBnf(6) was a substance with extremely high heat resistance.

Then, thermogravimetry-differential thermal analysis of FBiBnf(6) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 352° C., which shows that FBiBnf(6) is a substance with favorable sublimability.

From the above results, it was found that the organic compound of one embodiment of the present invention has both high heat resistance and favorable sublimability, and can provide an organic optical device (a light-emitting device and a light-receiving device) with high heat resistance and increase the productivity of device manufacturing.

Example 5

In this example, the light-emitting device of one embodiment of the present invention described in the embodiment will be described. The structural formulae of organic compounds used in this example are shown below.

[Chemical Formulae 58]

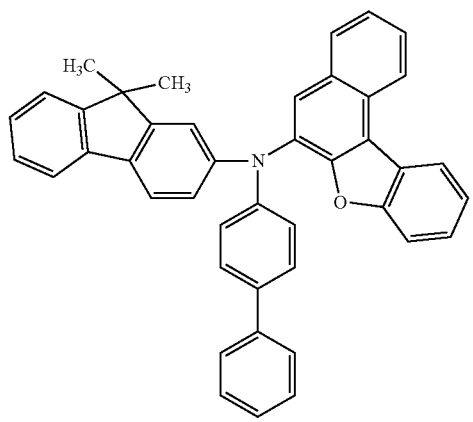

FBiBnf(6)

(i)

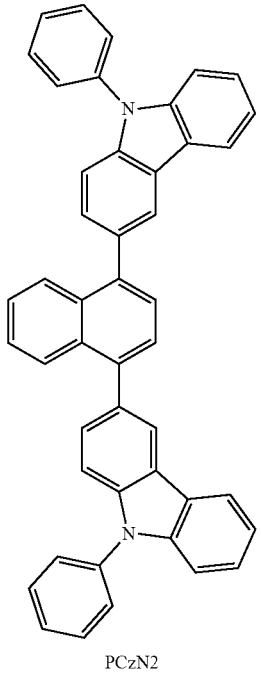

PCzN2

(ii)

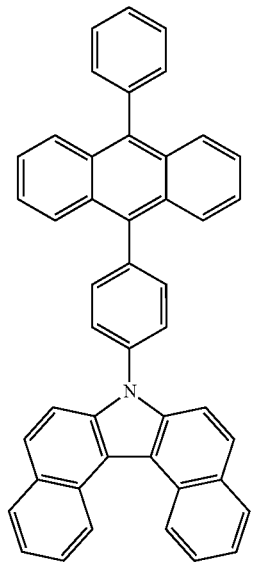

cgDBCzPA (iii)

-continued (iv)

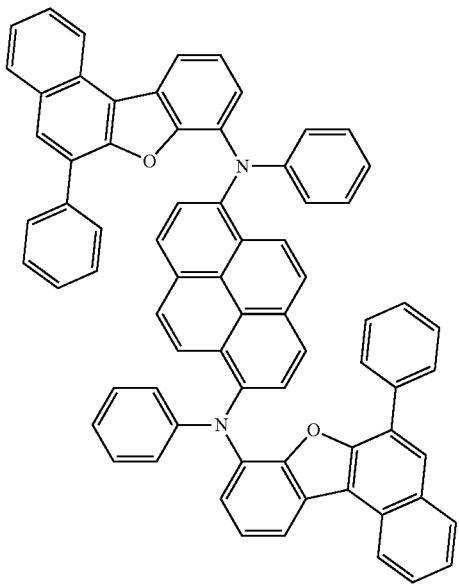

1,6BnfAPrn-03

(v)

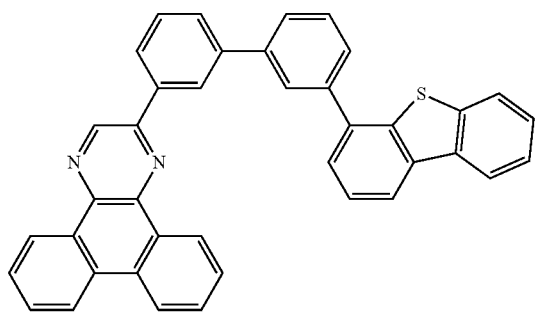

2mDBTBPDBq-II (vi)

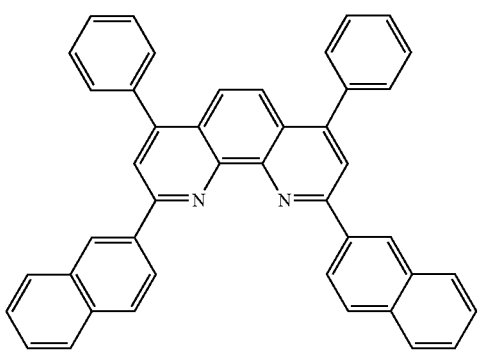

NBPhen

-continued (vii)

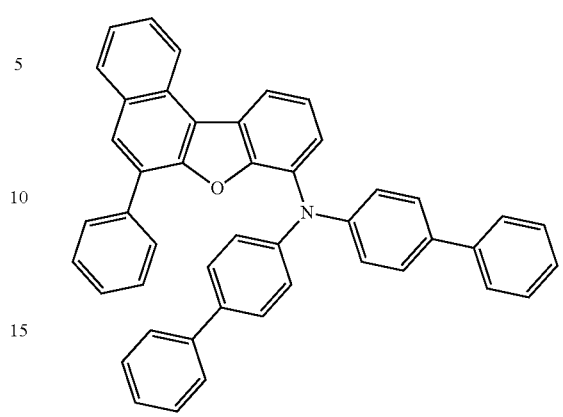

BBABnf (Method for Fabricating Light-Emitting Device 1)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-4-yl)-N-(9,9-dimethyl-9H-fluoren-2-yl)benzo[b]naphtho[1,2-d]furan-6-amine (abbreviation: FBiBnf(6)) represented by Structural Formula (i) above and ALD-MP001Q (manufactured by Analysis Atelier Corporation, material serial No. 1S20180314) were co-evaporated over the first electrode 101 to have a weight ratio of 1:0.1 (=FBiBnf(6): ALD-MP001Q) to a thickness of 10 nm by an evaporation method using resistance heating, whereby the hole-injection layer 111 was formed.

Subsequently, over the hole-injection layer 111, FBiBnf (6) was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Subsequently, 7-[4-(10-phenyl-9-anthryl)phenyl]-7H-dibenzo[c,g]carbazole (abbreviation: cgDBCzPA) represented by Structural Formula (iii) above and N,N'-(pyrene-1,6-diyl)bis[(6,N-diphenylbenzo[b]naphtho[1,2-d]furan)-8-amine] (abbreviation: 1,6BnfAPrn-03) represented by Structural Formula (iv) above were co-evaporated to a thickness of 25 nm at a weight ratio of 1:0.03 (=cgDBCzPA: 1,6BnfAPrn-03), whereby the light-emitting layer 113 was formed.

After that, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (v) above was formed to a thickness of 15 nm, and then, 2,9-di(2-naphthyl)-4,7-diphenyl-1,10-phenanthroline (abbreviation: NBPhen) represented by Structural Formula (vi) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 1 of this example was fabricated.

(Method for Fabricating Comparative Light-Emitting Device 1)

A comparative light-emitting device 1 was fabricated in a manner similar to that of the light-emitting device 1 except that N,N-bis(4-biphenyl)-6-phenylbenzo[b]naphtho[1,2-d]furan-8-amine (abbreviation: BBABnf) represented by Structural Formula (vii) above was used instead of FBiBnf(6) in the light-emitting device 1.

(Method for Fabricating Light-Emitting Device 2)

A light-emitting device 2 was fabricated in a manner similar to that of the light-emitting device 1 except that the thickness of FBiBnf(6) in the hole-transport layer of the light-emitting device 1 was changed from 20 nm to 120 nm.

(Method for Fabricating Comparative Light-Emitting Device 2)

A comparative light-emitting device 2 was fabricated in a manner similar to that of the light-emitting device 2 except that BBABnf was used instead of FBiBnf(6) in the light-emitting device 2.

The element structures of the light-emitting devices are listed in the following tables.

TABLE 1

| | hole-injection layer 10 nm | hole-transport layer 1 20 nm | hole-transport layer 2 10 nm | light-emitting layer 25 nm | electron-transport layer 1 15 nm | electron-transport layer 2 10 nm |
|---|---|---|---|---|---|---|
| light-emitting device 1 | FBiBnf(6): ALD-MP001Q (1:0.1) | FBiBnf(6) | PCzN2 | cgDBCzPA: 1,6BnfAPrn-03 (1:0.03) | 2mDBTBPDBq-II | NBPhen |
| comparative light-emitting device 1 | BBABnf: ALD-MP001Q (1:0.1) | BBABnf | | | | |

TABLE 2

| | hole-injection layer 10 nm | hole-transport layer 1 120 nm | hole-transport layer 2 10 nm | light-emitting layer 25 nm | electron-transport layer 1 15 nm | electron-transport layer 2 10 nm |
|---|---|---|---|---|---|---|
| light-emitting device 2 | FBiBnf(6): ALD-MP001Q (1:0.1) | FBiBnf(6) | PCzN2 | cgDBCzPA: 1,6BnfAPrn-03 (10.03) | 2mDBTBPDBq-II | NBPhen |
| comparative light-emitting device 2 | BBABnf: ALD-MP001Q (1:0.1) | BBABnf | | | | |

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 26:
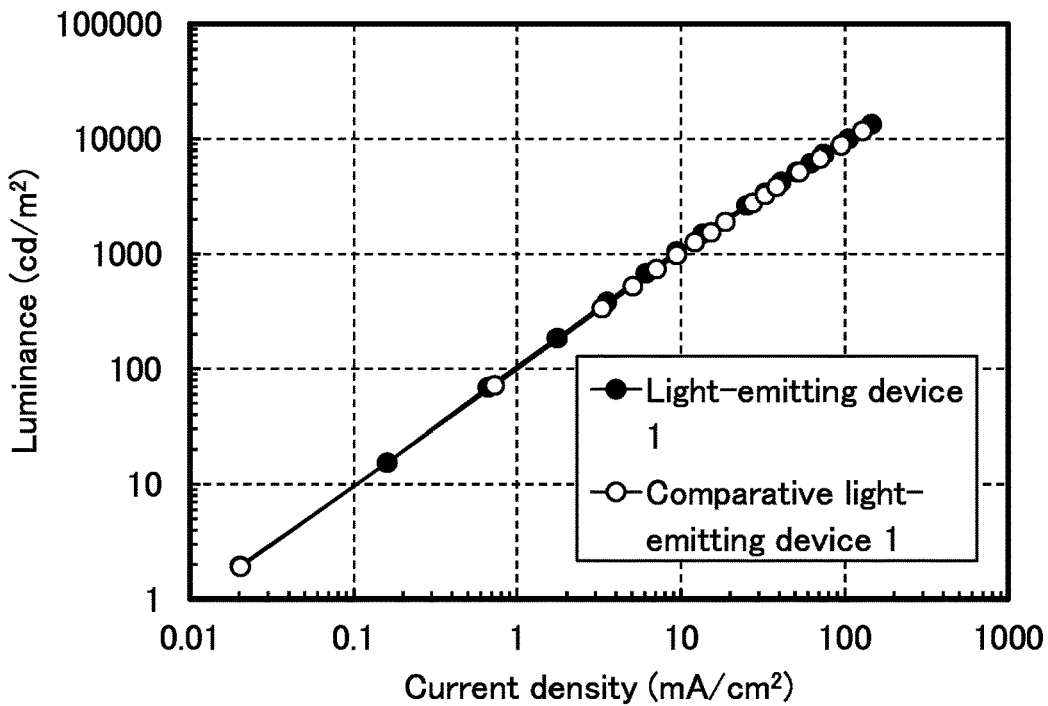
FIG. 26 shows luminance-current density characteristics of a light-emitting device 1 and a comparative light-emitting device 1.
Figure 27:
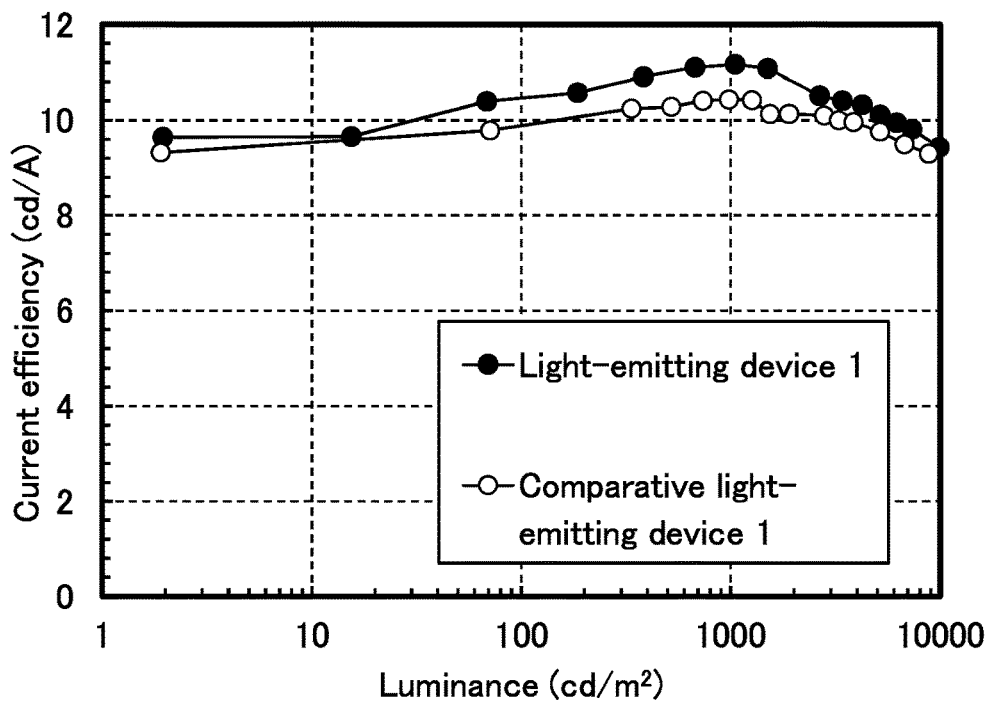
FIG. 27 shows current efficiency-luminance characteristics of the light-emitting device 1 and the comparative light-emitting device 1.
Figure 28:
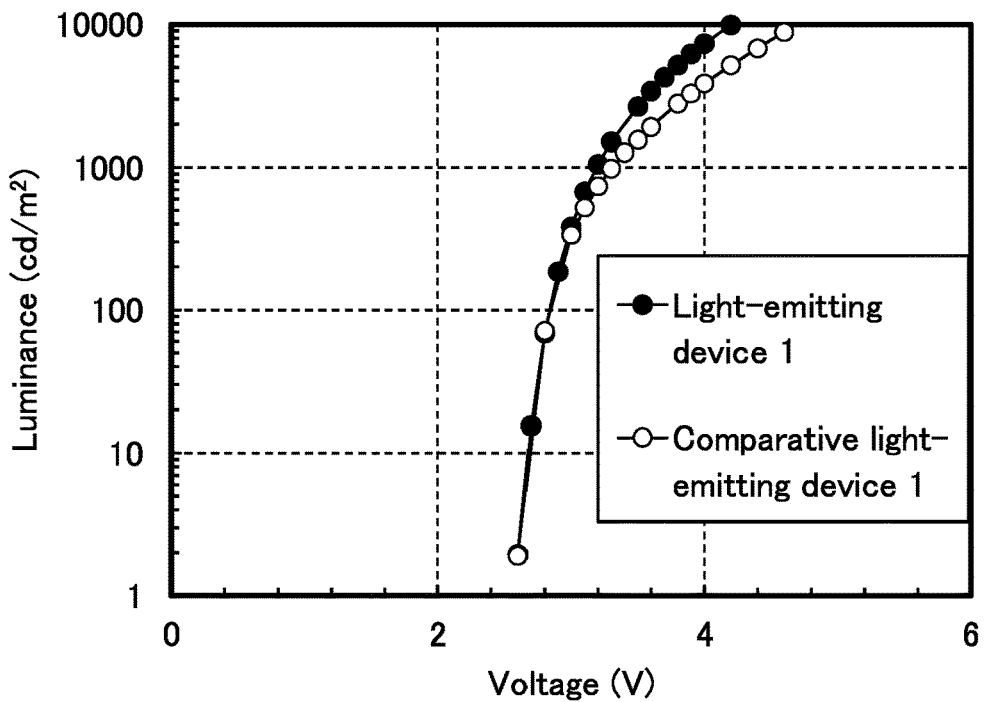
FIG. 28 shows luminance-voltage characteristics of the light-emitting device 1 and the comparative light-emitting device 1.
Figure 29:
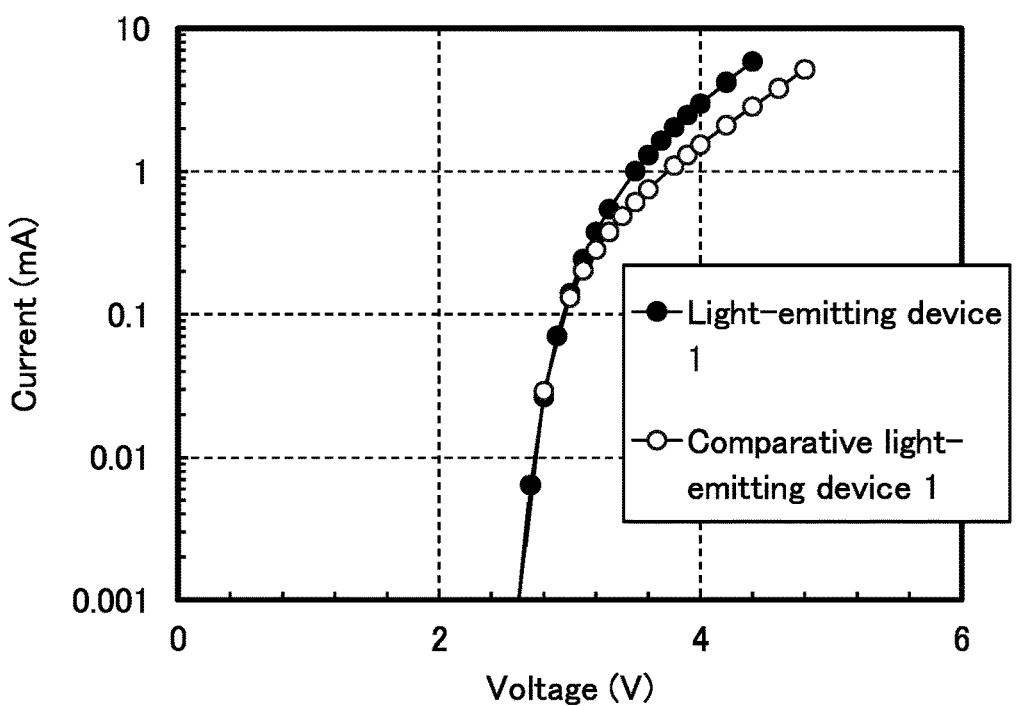
FIG. 29 shows current-voltage characteristics of the light-emitting device 1 and the comparative light-emitting device 1.
Figure 30:
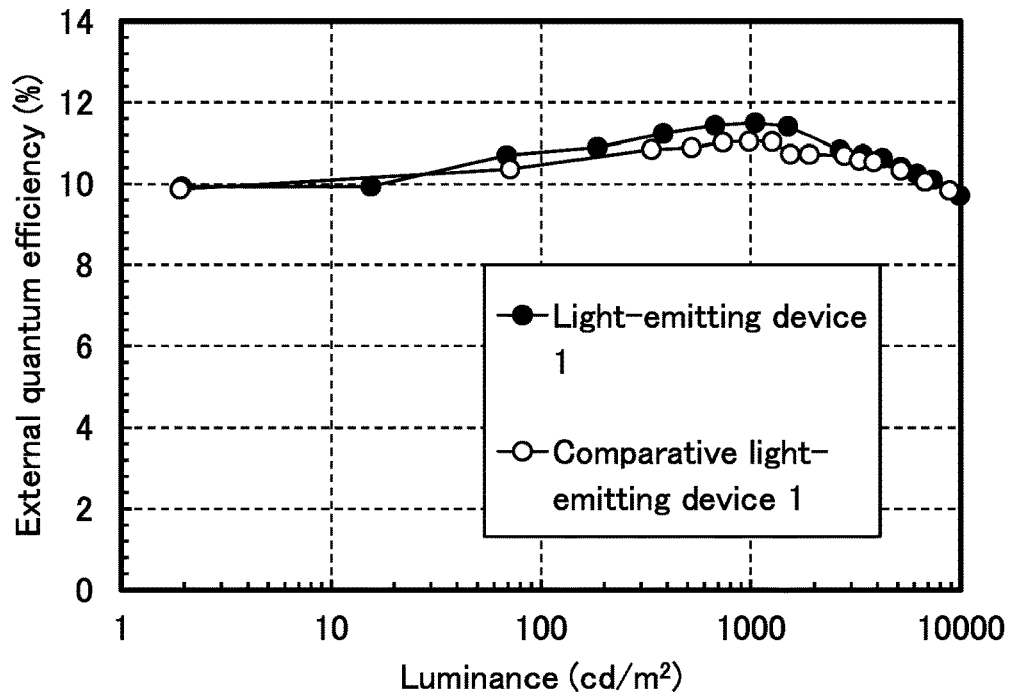
FIG. 30 shows external quantum efficiency-luminance characteristics of the light-emitting device 1 and the comparative light-emitting device 1.
Figure 31:
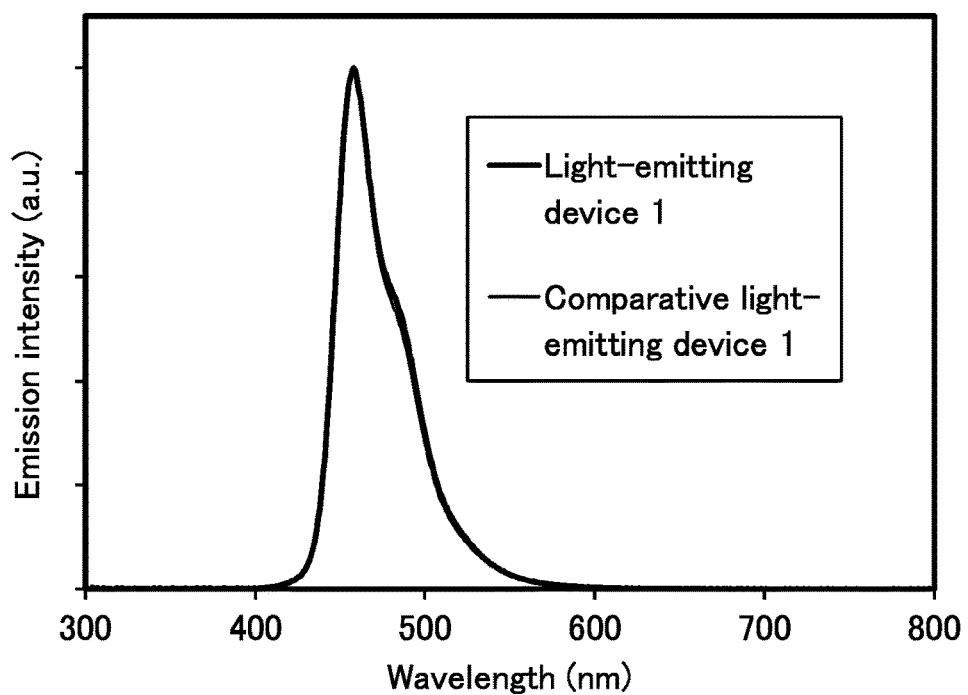
FIG. 31 shows emission spectra of the light-emitting device 1 and the comparative light-emitting device 1.
Figure 32:
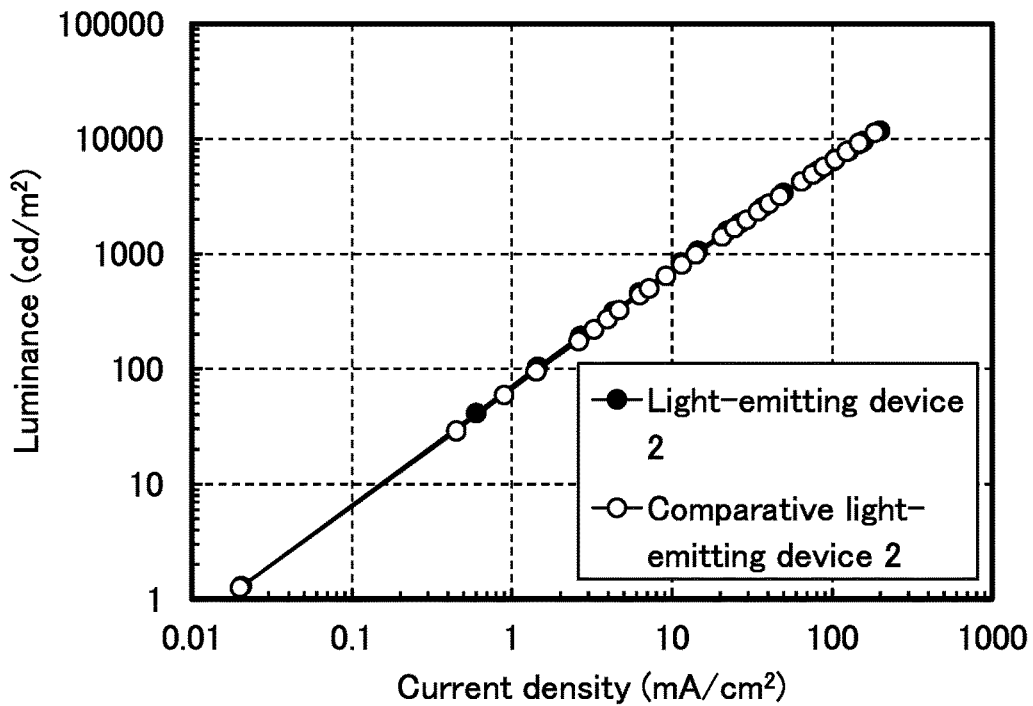
FIG. 32 shows luminance-current density characteristics of a light-emitting device 2 and a comparative light-emitting device 2.
Figure 33:
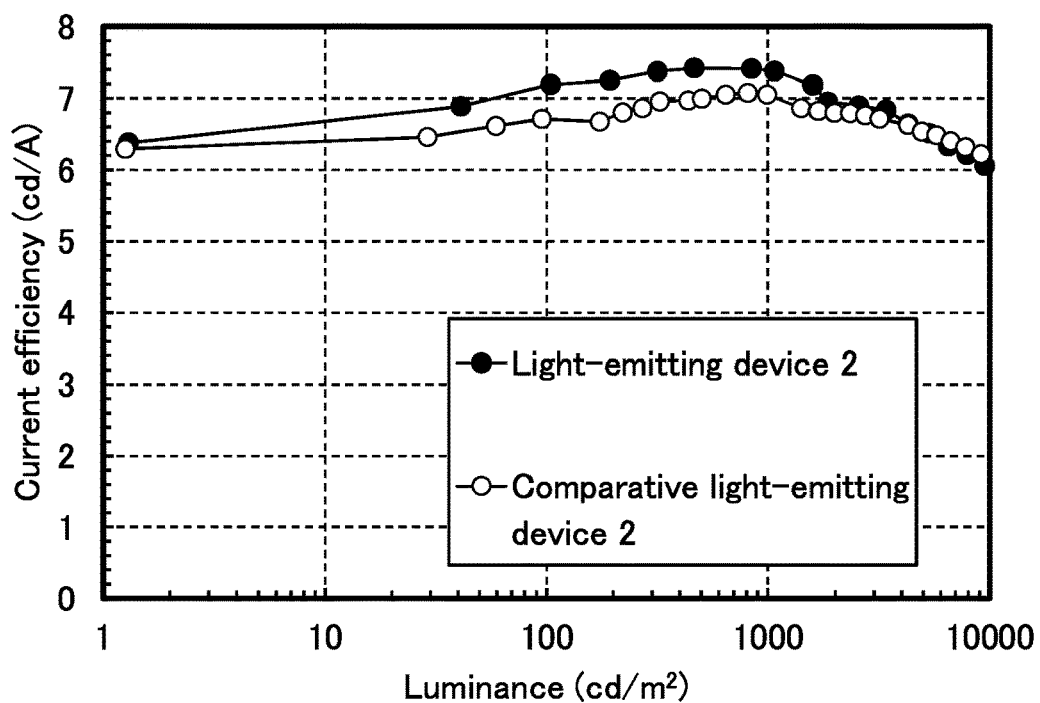
FIG. 33 shows current efficiency-luminance characteristics of the light-emitting device 2 and the comparative light-emitting device 2.
Figure 34:
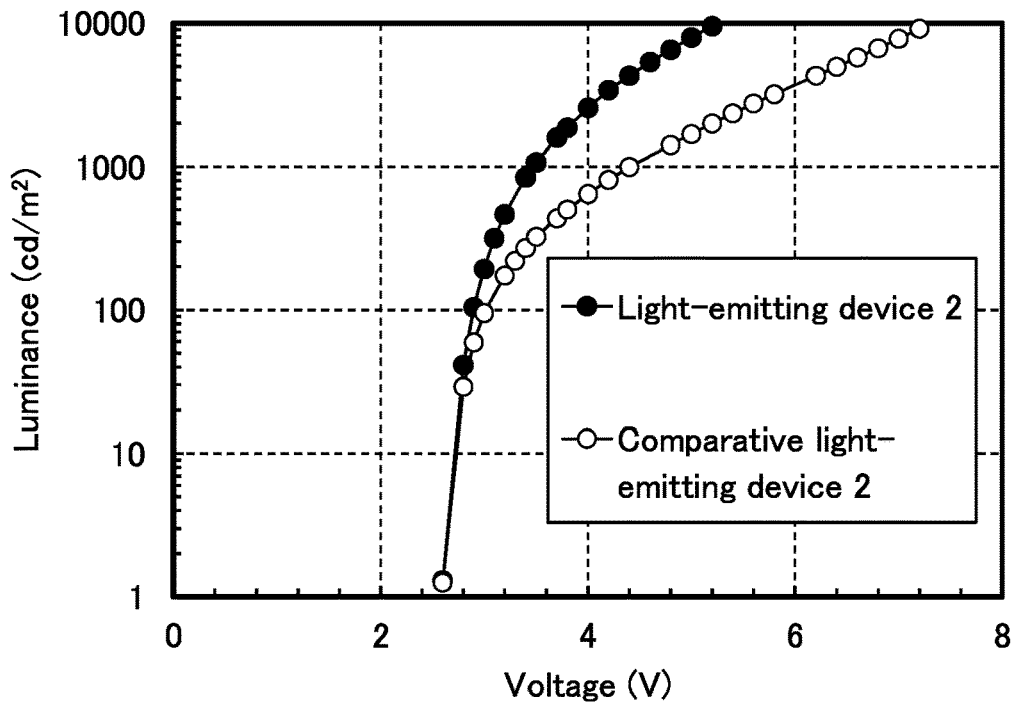
FIG. 34 shows luminance-voltage characteristics of the light-emitting device 2 and the comparative light-emitting device 2.
Figure 35:
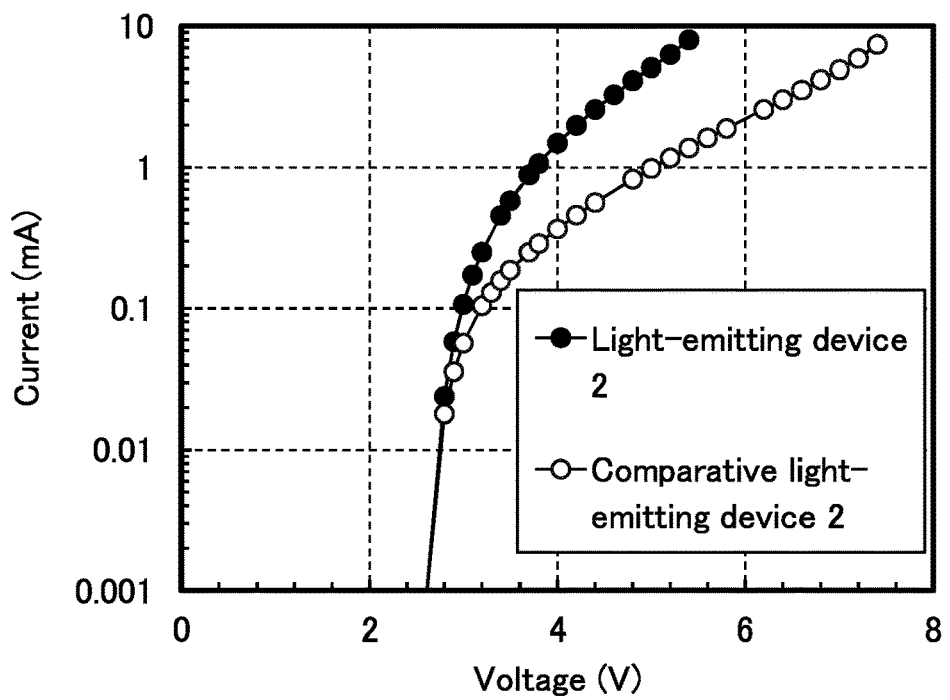
FIG. 35 shows current-voltage characteristics of the light-emitting device 2 and the comparative light-emitting device 2.
Figure 36:
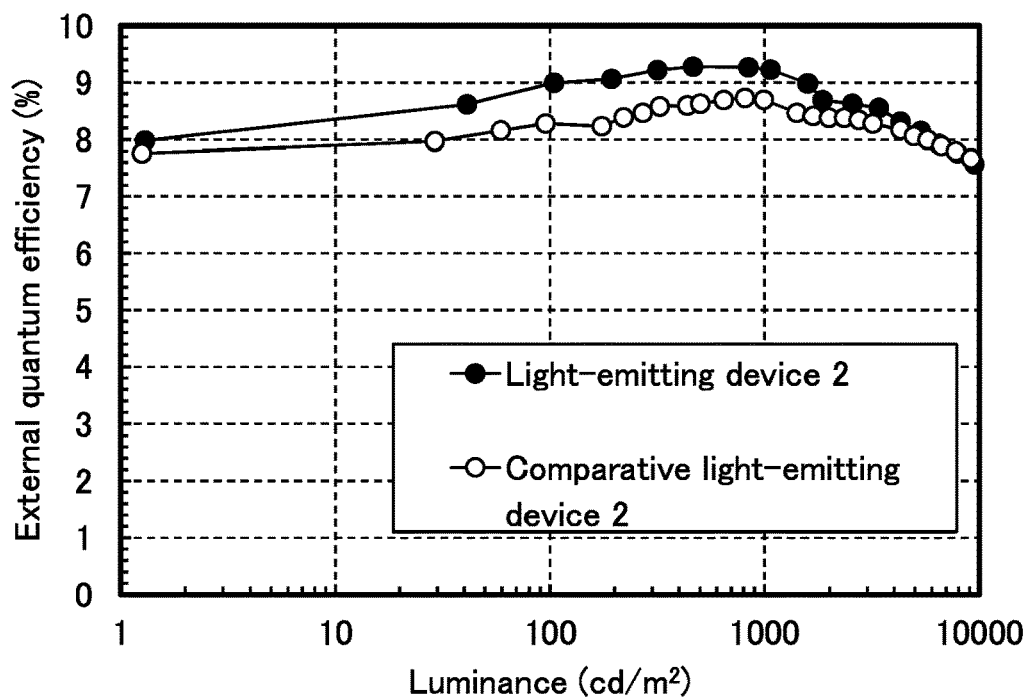
FIG. 36 shows external quantum efficiency-luminance characteristics of the light-emitting device 2 and the comparative light-emitting device 2.
Figure 37:
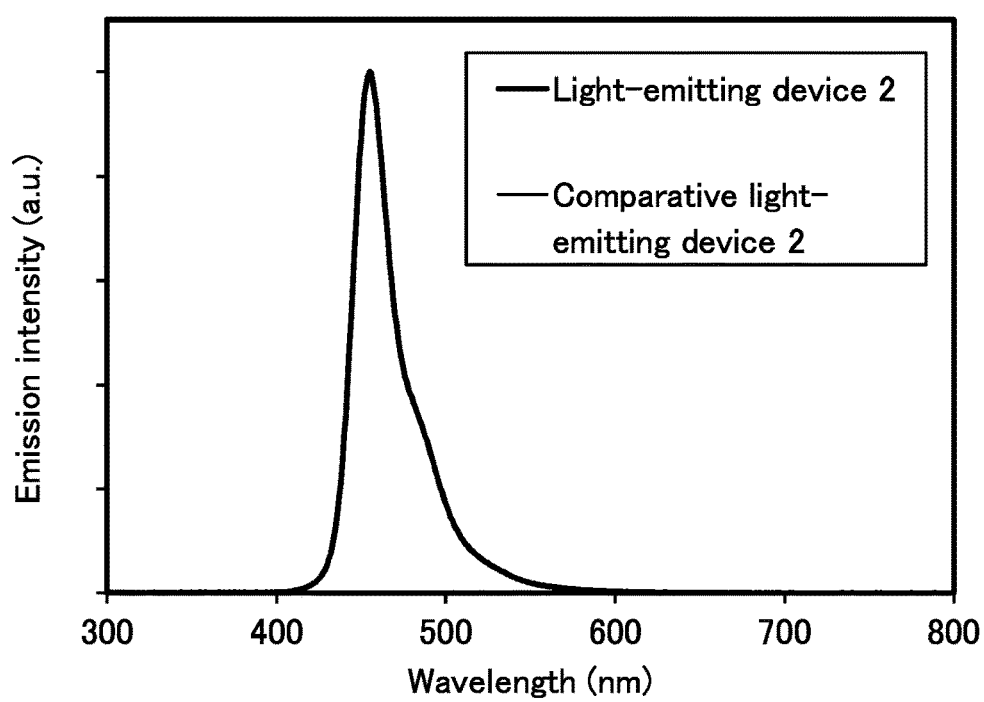
FIG. 37 shows emission spectra of the light-emitting device 2 and the comparative light-emitting device 2.

FIG. 26 shows the luminance-current density characteristics of the light-emitting device 1 and the comparative light-emitting device 1; FIG. 27, the current efficiency-luminance characteristics; FIG. 28, the luminance-voltage characteristics; FIG. 29, the current-voltage characteristics; FIG. 30, the external quantum efficiency-luminance characteristics; and FIG. 31, the emission spectra. FIG. 32 shows the luminance-current density characteristics of the light-emitting device 2 and the comparative light-emitting device 2; FIG. 33, the current efficiency-luminance characteristics; FIG. 34, the luminance-voltage characteristics; FIG. 35, the current-voltage characteristics; FIG. 36, the external quantum efficiency-luminance characteristics; and FIG. 37, the emission spectra. Main characteristics of the light-emitting devices at approximately 1000 cd/m² are listed below.

TABLE 3

| | voltage (V) | current (mA) | current density (mA/cm²) | chromaticity x | chromaticity y | current efficiency (cd/A) | external quantum efficiency (%) |
|---|---|---|---|---|---|---|---|
| light-emitting device 1 | 3.2 | 0.38 | 9.4 | 0.14 | 0.12 | 11.2 | 11.5 |
| comparative light-emitting device 1 | 3.3 | 0.38 | 9.4 | 0.14 | 0.12 | 10.4 | 11.0 |

TABLE 4

| | voltage (V) | current (mA) | current density (mA/cm²) | chromaticity x | chromaticity y | current efficiency (cd/A) | external quantum efficiency (%) |
|---|---|---|---|---|---|---|---|
| light-emitting device 2 | 3.5 | 0.58 | 14.5 | 0.14 | 0.09 | 7.4 | 9.2 |
| comparative light-emitting device 2 | 4.4 | 0.56 | 14.1 | 0.14 | 0.09 | 7.1 | 8.7 |

It was found from FIG. 26 to FIG. 31 that the light-emitting device 1 of one embodiment of the present invention is an EL device with high emission efficiency. It is also found that although the light-emitting device 2 and the comparative light-emitting device 2 are each an element in which FBiBnf(6) or BBABnf in the hole-transport layer is a thick film with a thickness of 120 nm, the light-emitting device 2 of one embodiment of the present invention is an element in which an increase in voltage is small even with the large thickness. This indicates that FBiBnf(6), which is the organic compound of one embodiment of the present invention, is an organic compound having a high carrier-transport property, specifically, a high hole-transport property.

Figure 38:
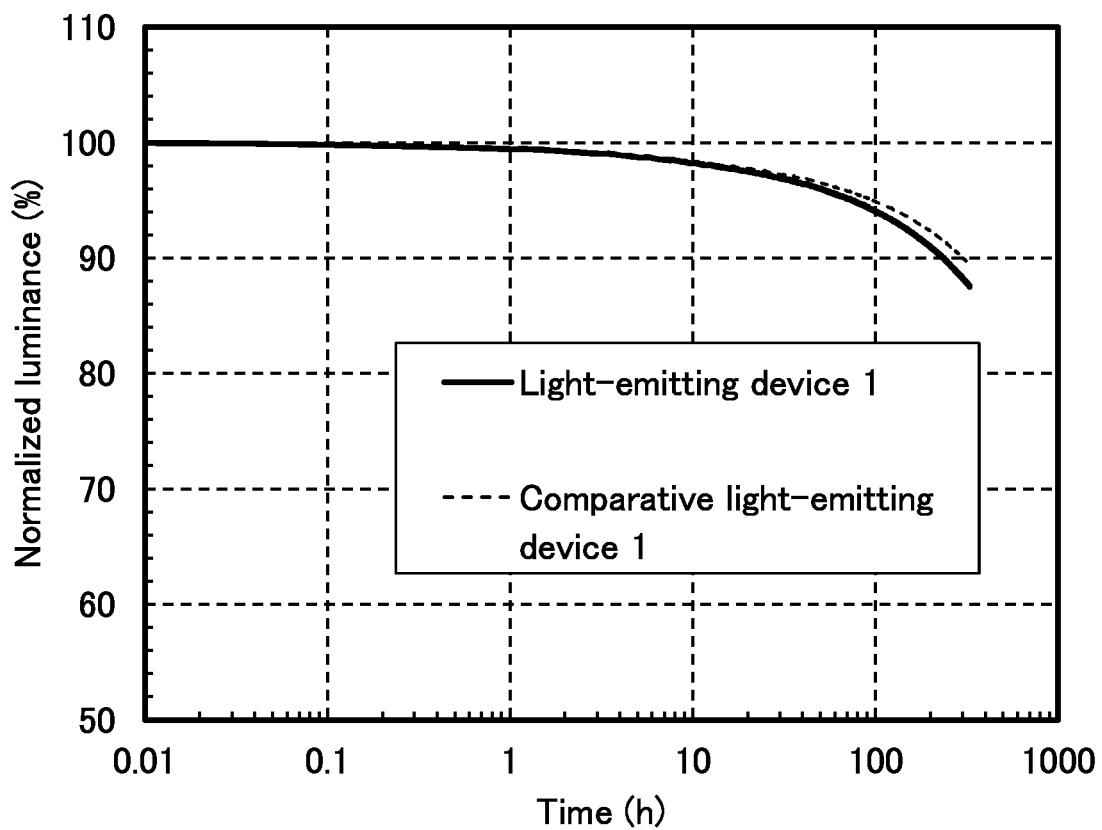
FIG. 38 shows normalized luminance-temporal change characteristics of the light-emitting device 1 and the comparative light-emitting device 1.
Figure 39:
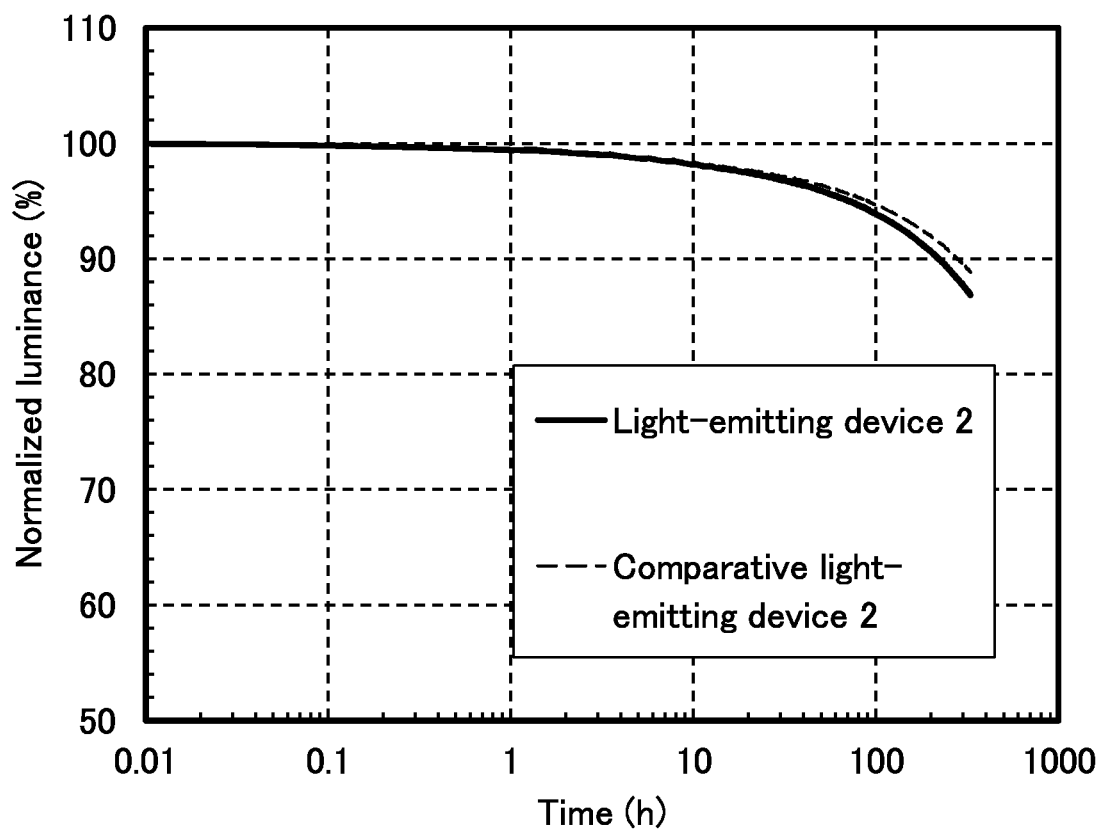
FIG. 39 shows normalized luminance-temporal change characteristics of the light-emitting device 2 and the comparative light-emitting device 2.

FIG. 38 and FIG. 39 are graphs showing a change in luminance over driving time at a current density of 50 mA/cm². As shown in FIG. 38 and FIG. 39, the light-emitting device 1 and the light-emitting device 2, which are the light-emitting devices of embodiments of the present invention, were found to be light-emitting devices with a long lifetime like the comparative light-emitting device 1 and the comparative light-emitting device 2.

Example 6

In this example, the light-emitting device of one embodiment of the present invention described in the embodiment will be described. The structural formulae of organic compounds used in this example are shown below.

[Chemical Formulae 59]

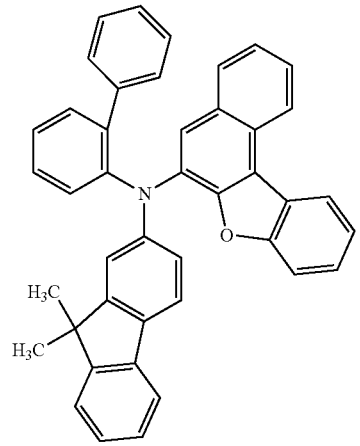

(viii)

oFBiBnf(6)

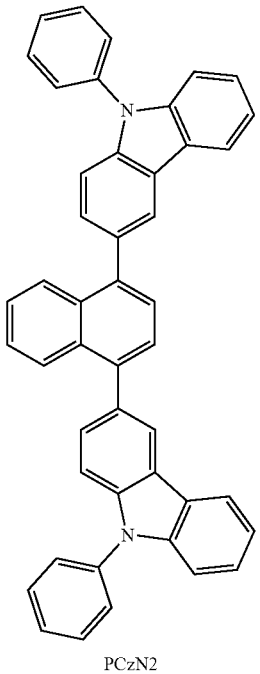

(ii)

PCzN2

(iii)

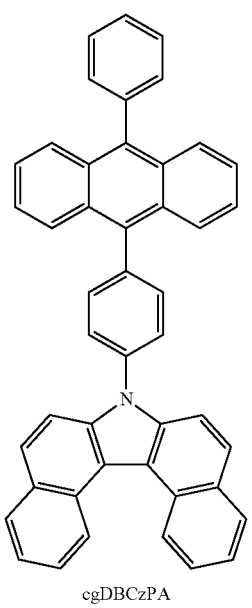

cgDBCzPA (iv)

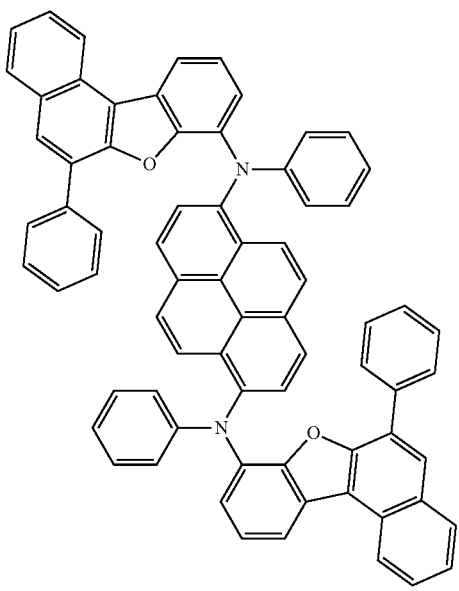

1,6BnfAPrn-03

(v)

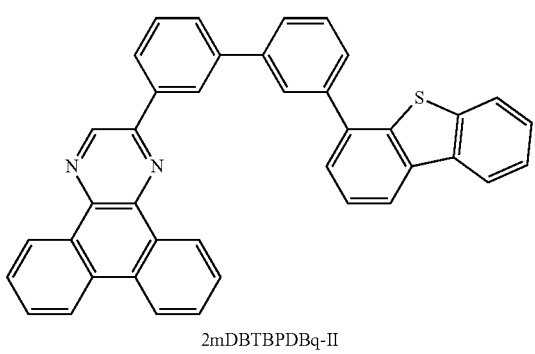

2mDBTBPDBq-II

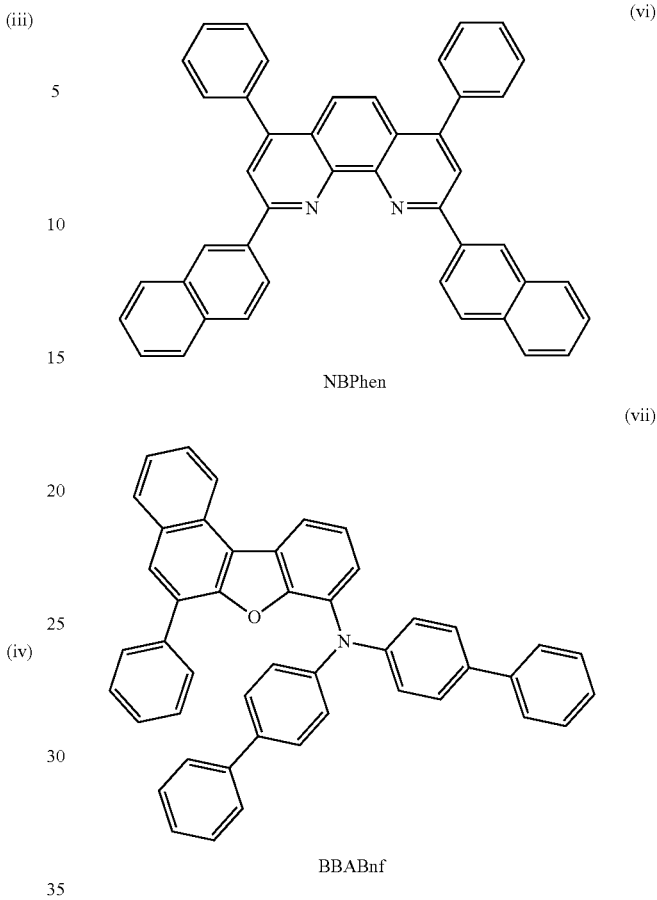

NBPhen

BBABnf (Method for Fabricating Light-Emitting Device 3)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately 10-4 Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-2-yl)-N-(9,9-dimethyl-9H-fluoren-2-yl)benzo[b]naphtho[1,2-d]furan-6-amine (abbreviation: oFBiBnf(6)) represented by Structural Formula (viii) above and ALD-MP001Q (manufactured by Analysis Atelier Corporation, material serial No. 1S20180314) were co-evaporated over the first electrode 101 to have a weight ratio of 1:0.1 (=oFBiBnf(6): ALD-MP001Q) to a thickness of 10 nm by an evaporation method using resistance heating, whereby the hole-injection layer 111 was formed.

Subsequently, over the hole-injection layer 111, oFBiBnf (6) was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Subsequently, 7-[4-(10-phenyl-9-anthryl)phenyl]-7H-dibenzo[c,g]carbazole (abbreviation: cgDBCzPA) represented by Structural Formula (iii) above and N,N'-(pyrene-1,6-diyl)bis[(6,N-diphenylbenzo[b]naphtho[1,2-d]furan)-8-amine] (abbreviation: 1,6BnfAPrn-03) represented by Structural Formula (iv) above were co-evaporated to a thickness of 25 nm at a weight ratio of 1:0.03 (=cgDBCzPA: 1,6BnfAPrn-03), whereby the light-emitting layer 113 was formed.

After that, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (v) above was formed to a thickness of 15 nm, and then, 2,9-di(2-naphthyl)-4,7-diphenyl-1,10-phenanthroline (abbreviation: NBPhen) represented by Structural Formula (vi) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 3 of this example was fabricated.

(Method for Fabricating Comparative Light-Emitting Device 3)

A comparative light-emitting device 3 was fabricated in a manner similar to that of the light-emitting device 3 except that N,N-bis(4-biphenyl)-6-phenylbenzo[b]naphtho[1,2-d]furan-8-amine (abbreviation: BBABnf) represented by Structural Formula (vii) above was used instead of oFBiBnf(6) in the light-emitting device 3.

(Method for fabricating light-emitting device 4) A light-emitting device 4 was fabricated in a manner similar to that of the light-emitting device 3 except that the thickness of oFBiBnf(6) in the hole-transport layer of light-emitting device 3 was changed from 20 nm to 120 nm.

(Method for Fabricating Comparative Light-Emitting Device 4)

A comparative light-emitting device 4 was fabricated in a manner similar to that of the light-emitting device 4 except that BBABnf was used instead of oFBiBnf(6) in the light-emitting device 4.

The element structures of the light-emitting devices are listed in the following tables.

TABLE 5

| | hole-injection layer 10 nm | hole-transport layer 1 20 nm | hole-transport layer 2 10 nm | light-emitting layer 25 nm | electron-transport layer 1 15 nm | electron-transport layer 2 10 nm |
|---|---|---|---|---|---|---|
| light-emitting device 3 | oFBiBnf(6): ALD-MP001Q (1:0.1) | oFBiBnf(6) | PCzN2 | cgDBCzPA: 1,6BnAPrn-03 (1:0.03) | 2mDBTBPDBq-II | NBPhen |
| comparative light-emitting device 3 | BBABnf: ALD-MP001Q (1:0.1) | BBABnf | | | | |

TABLE 6

| | hole-injection layer 10 nm | hole-transport layer 1 120 nm | hole-transport layer 2 10 nm | light-emitting layer 25 nm | electron-transport layer 1 15 nm | electron-transport layer 2 10 nm |
|---|---|---|---|---|---|---|
| light-emitting device 4 | oFBiBnf(6): ALD-MP001Q (1:0.1) | oFBiBnf(6) | PCzN2 | cgDBCzPA: 1,6BnfAPrn-03 (1:0.03) | 2mDBTBPDBq-II | NBPhen |
| comparative light-emitting device 4 | BBABnf: ALD-MP001Q (1:0.1) | BBABnf | | | | |

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 40:
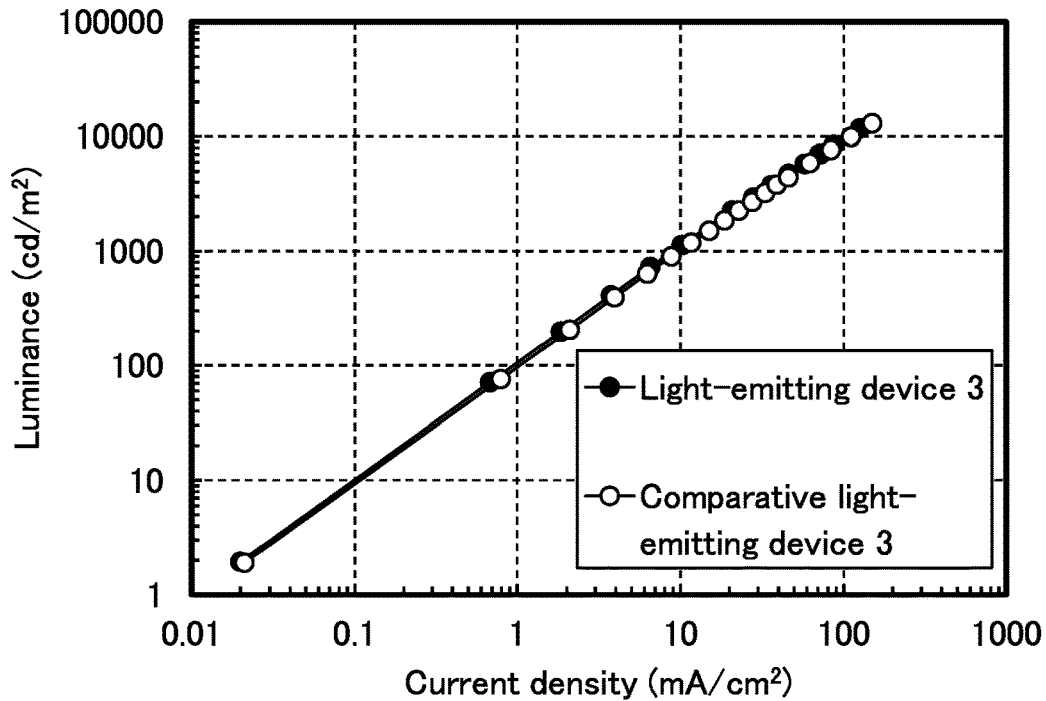
FIG. 40 shows luminance-current density characteristics of a light-emitting device 3 and a comparative light-emitting device 3.
Figure 41:
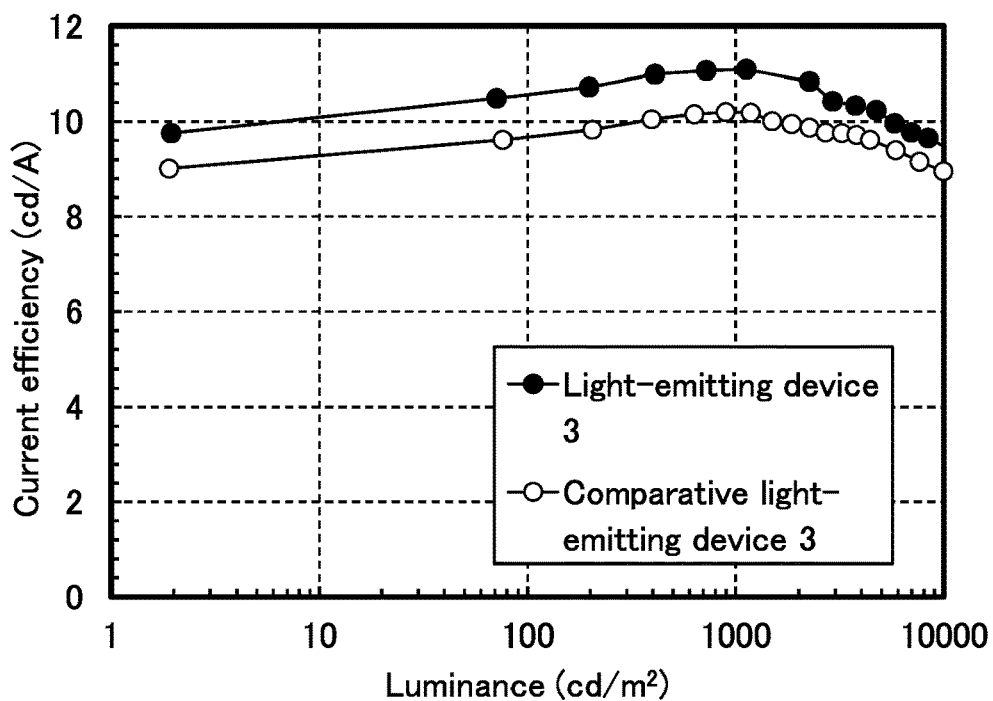
FIG. 41 shows current efficiency-luminance characteristics of the light-emitting device 3 and the comparative light-emitting device 3.
Figure 42:
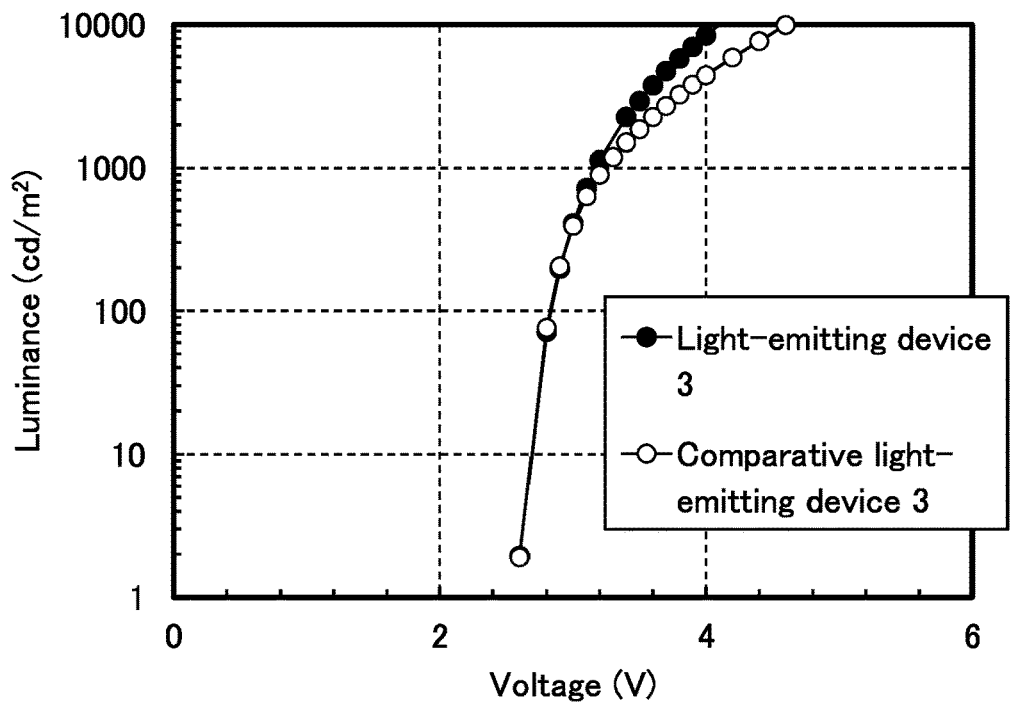
FIG. 42 shows luminance-voltage characteristics of the light-emitting device 3 and the comparative light-emitting device 3.
Figure 43:
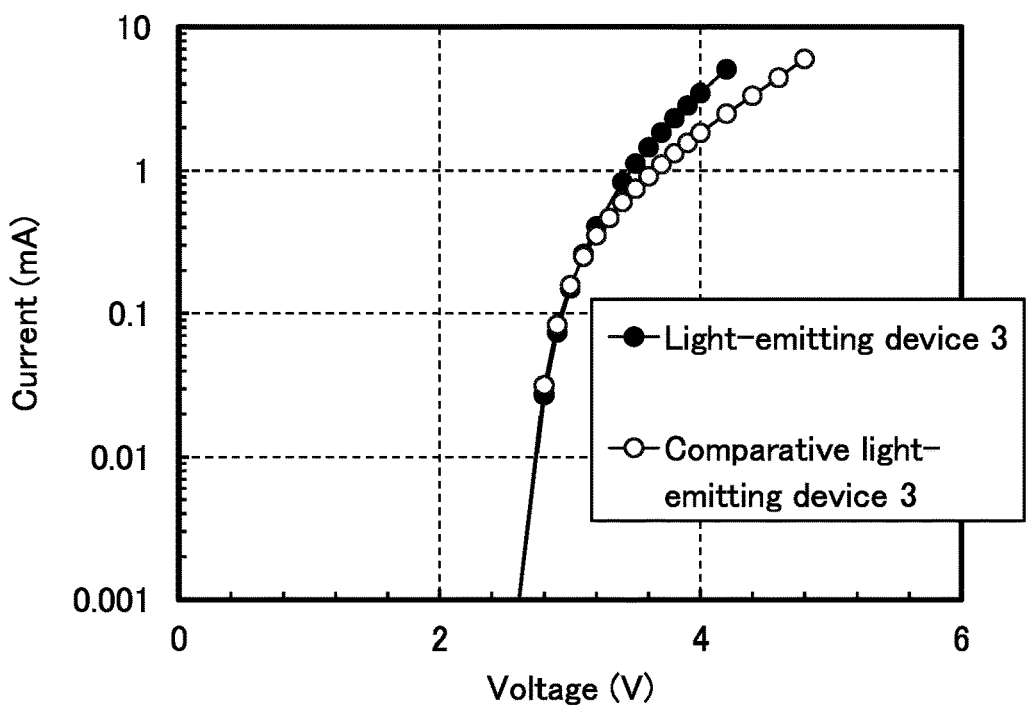
FIG. 43 shows current-voltage characteristics of the light-emitting device 3 and the comparative light-emitting device 3.
Figure 44:
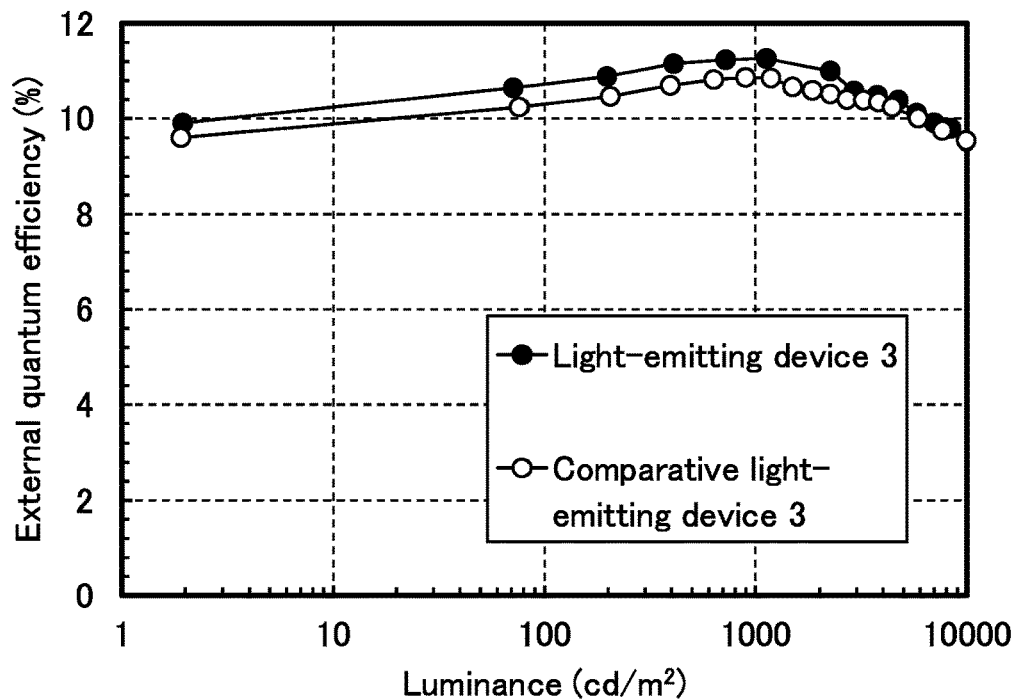
FIG. 44 shows external quantum efficiency-luminance characteristics of the light-emitting device 3 and the comparative light-emitting device 3.
Figure 45:
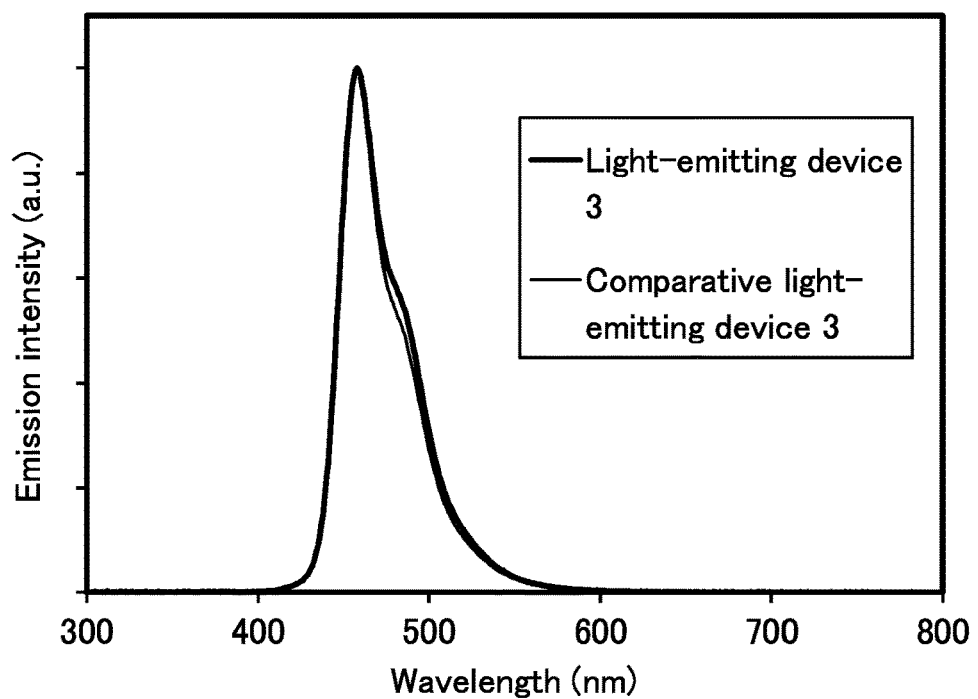
FIG. 45 shows emission spectra of the light-emitting device 3 and the comparative light-emitting device 3.
Figure 46:
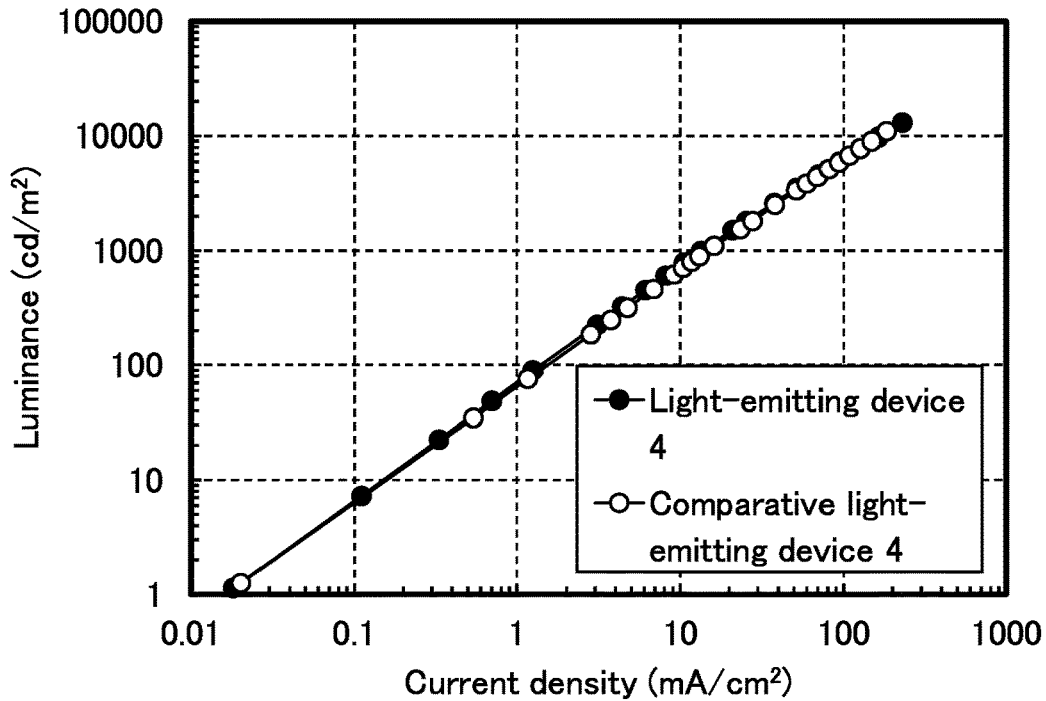
FIG. 46 shows luminance-current density characteristics of a light-emitting device 4 and a comparative light-emitting device 4.
Figure 47:
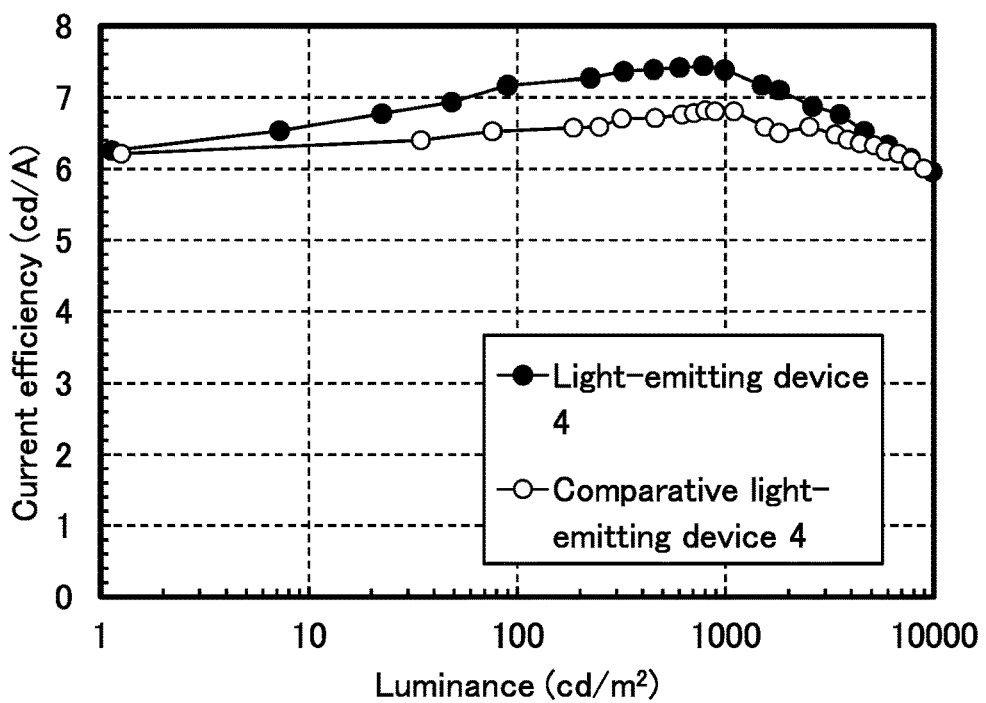
FIG. 47 shows current efficiency-luminance characteristics of the light-emitting device 4 and the comparative light-emitting device 4.
Figure 48:
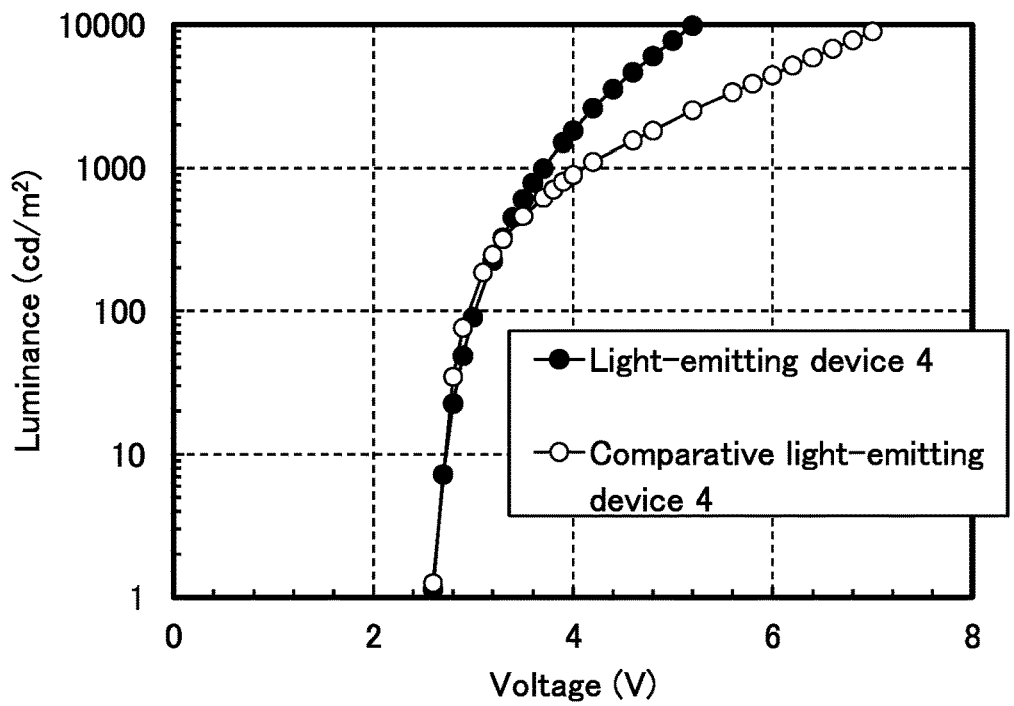
FIG. 48 shows luminance-voltage characteristics of the light-emitting device 4 and the comparative light-emitting device 4.
Figure 49:
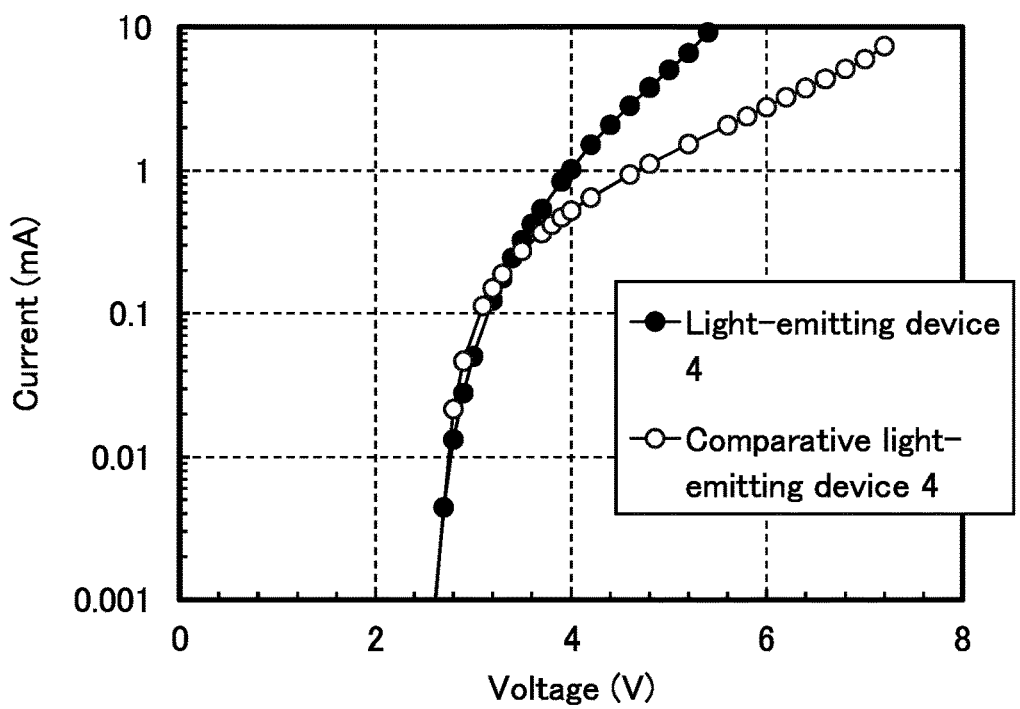
FIG. 49 shows current-voltage characteristics of the light-emitting device 4 and the comparative light-emitting device 4.
Figure 50:
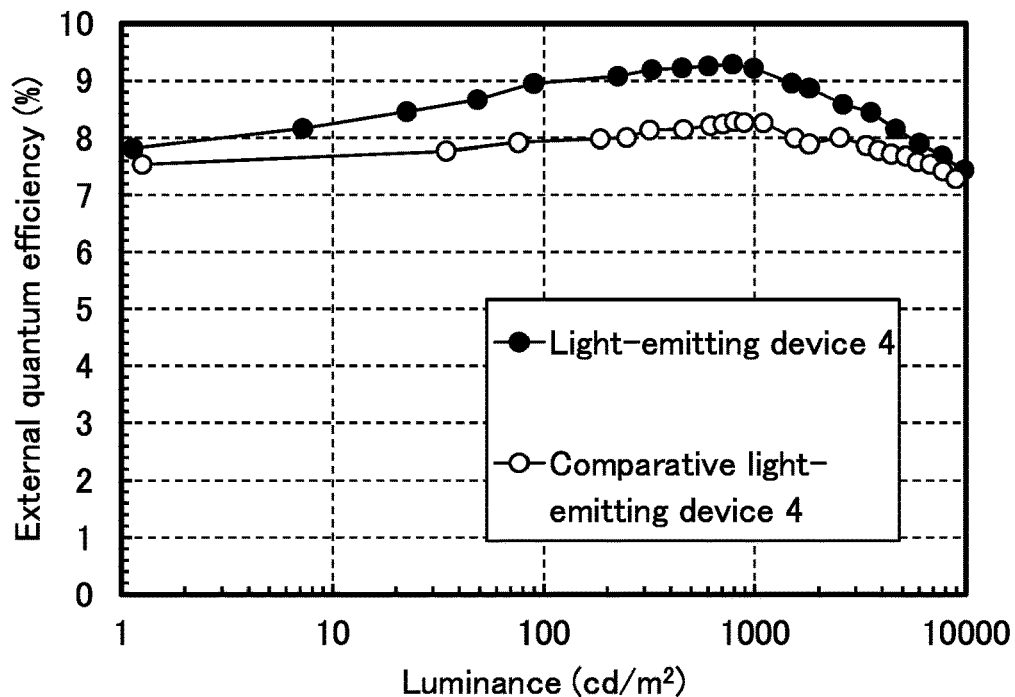
FIG. 50 shows external quantum efficiency-luminance characteristics of the light-emitting device 4 and the comparative light-emitting device 4.
Figure 51:
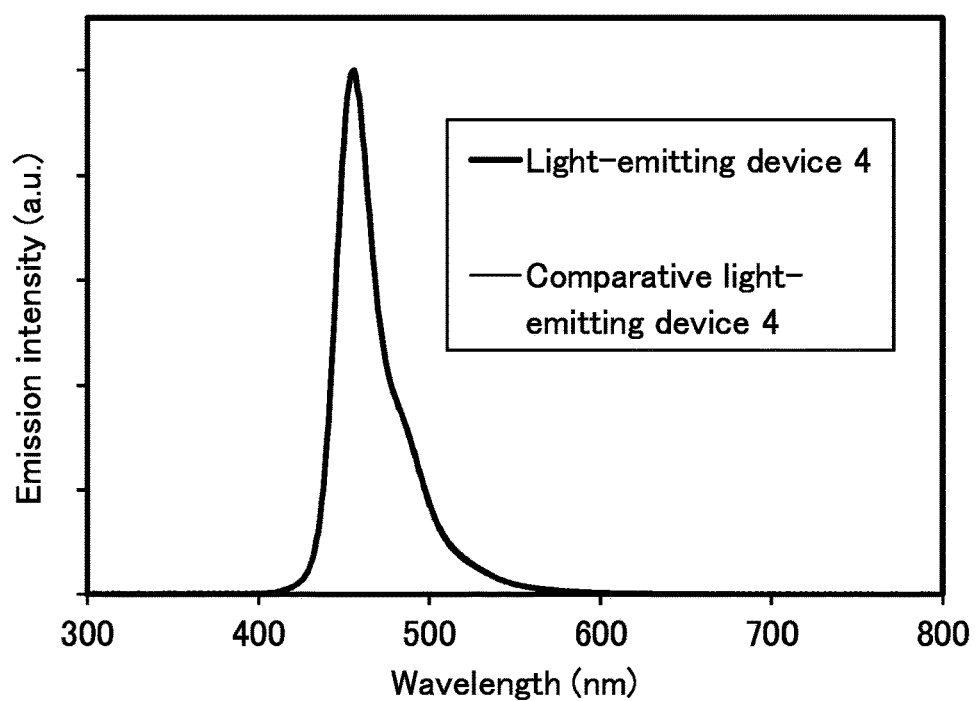
FIG. 51 shows emission spectra of the light-emitting device 4 and the comparative light-emitting device 4.

FIG. 40 shows the luminance-current density characteristics of the light-emitting device 3 and the comparative light-emitting device 3; FIG. 41, the current efficiency-luminance characteristics; FIG. 42, the luminance-voltage characteristics; FIG. 43, the current-voltage characteristics; FIG. 44, the external quantum efficiency-luminance characteristics; and FIG. 45, the emission spectra. FIG. 46 shows the luminance-current density characteristics of the light-emitting device 4 and the comparative light-emitting device 4; FIG. 47, the current efficiency-luminance characteristics; FIG. 48, the luminance-voltage characteristics; FIG. 49, the current-voltage characteristics; FIG. 50, the external quantum efficiency-luminance characteristics; and FIG. 51, the emission spectra. Main characteristics of the light-emitting devices at approximately 1000 cd/m$^2$ are listed below.

TABLE 7

| | voltage (V) | current (mA) | current density (mA/cm$^2$) | chromaticity x | chromaticity y | current efficiency (cd/A) | external quantum efficiency (%) |
|---|---|---|---|---|---|---|---|
| light-emitting device 3 | 3.2 | 0.41 | 10.2 | 0.14 | 0.12 | 11.1 | 11.3 |
| comparative light-emitting device 3 | 3.2 | 0.35 | 8.8 | 0.14 | 0.11 | 10.2 | 10.9 |

TABLE 8

| | voltage (V) | current (mA) | current density (mA/cm$^2$) | chromaticity x | chromaticity y | current efficiency (cd/A) | external quantum efficiency (%) |
|---|---|---|---|---|---|---|---|
| light-emitting device 4 | 3.7 | 0.54 | 13.4 | 0.14 | 0.09 | 7.4 | 9.2 |
| comparative light-emitting device 4 | 4.2 | 0.65 | 16.2 | 0.14 | 0.09 | 6.8 | 8.3 |

It was found from FIG. 40 to FIG. 45 that the light-emitting device 3 of one embodiment of the present invention is an EL device with high emission efficiency. FIG. 48 and FIG. 49 show that although the light-emitting device 4 and the comparative light-emitting device 4 are each an element in which oFBiBnf(6) or BBABnf in the hole-transport layer is a thick film with a thickness of 120 nm, the light-emitting device 4 of one embodiment of the present invention is an element in which an increase in voltage is small even with the large thickness. This indicates that oFBiBnf(6), which is the organic compound of one embodiment of the present invention, is an organic compound having a high carrier-transport property, specifically, a high hole-transport property.

Figure 52:
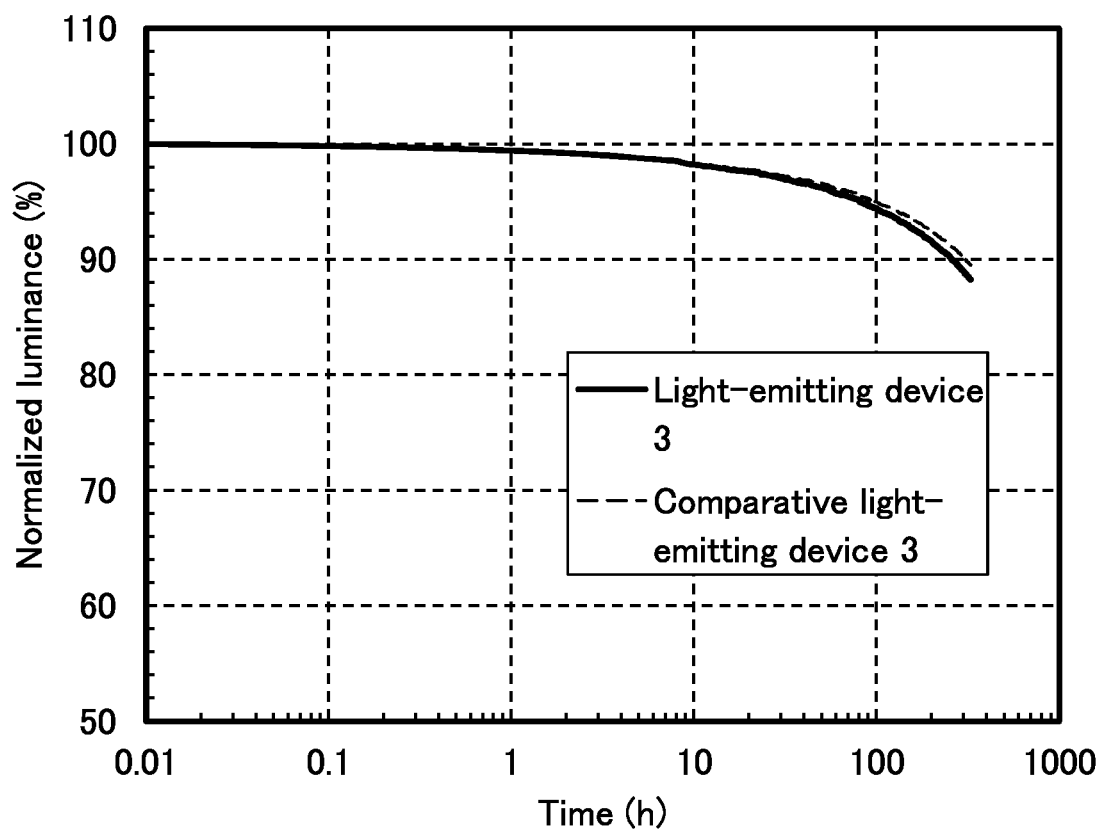
FIG. 52 shows normalized luminance-temporal change characteristics of the light-emitting device 3 and the comparative light-emitting device 3.
Figure 53:
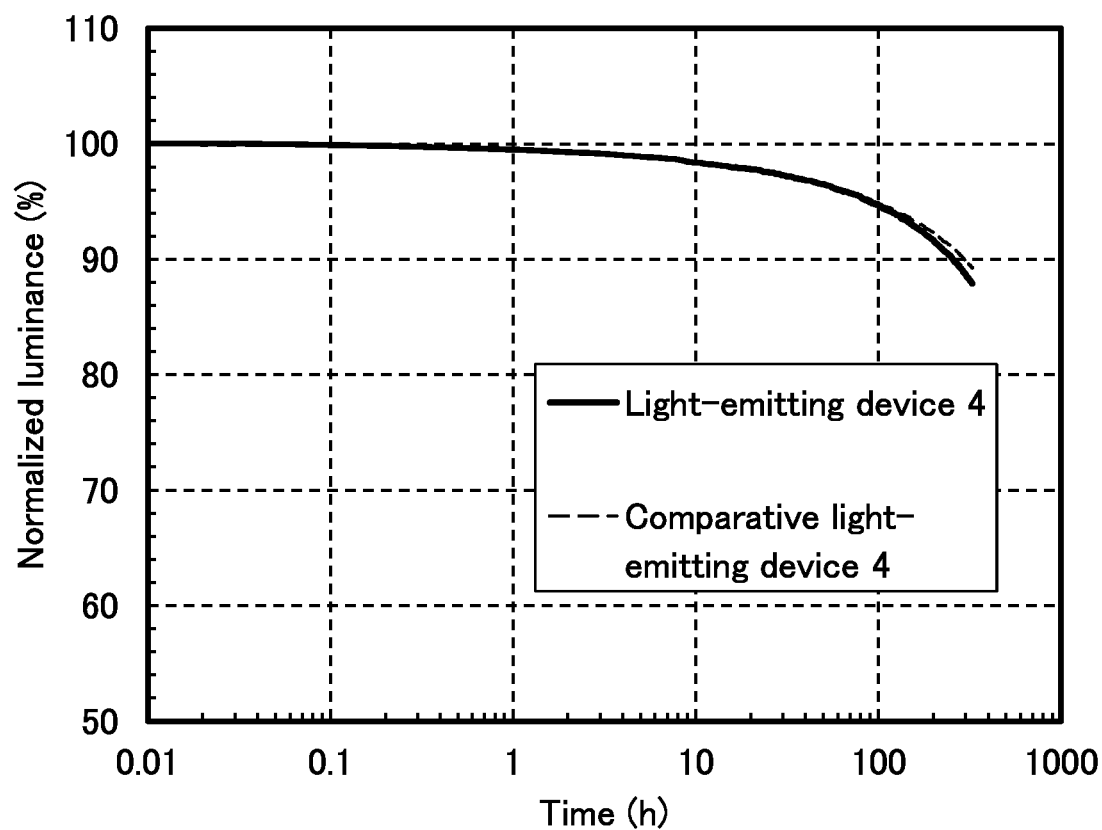
FIG. 53 shows normalized luminance-temporal change characteristics of the light-emitting device 4 and the comparative light-emitting device 4.

FIG. 52 and FIG. 53 are graphs showing a change in luminance over driving time at a current density of 50 mA/cm$^2$. As shown in FIG. 52 and FIG. 53, the light-emitting device 3 and the light-emitting device 4, which are the light-emitting devices of embodiments of the present invention, were found to be light-emitting devices with a long lifetime like the comparative light-emitting device 3 and the comparative light-emitting device 4.

Example 7

In this example, the light-emitting device of one embodiment of the present invention described in the embodiment will be described. The structural formulae of organic compounds used in this example are shown below.

[Chemical Formulae 60]

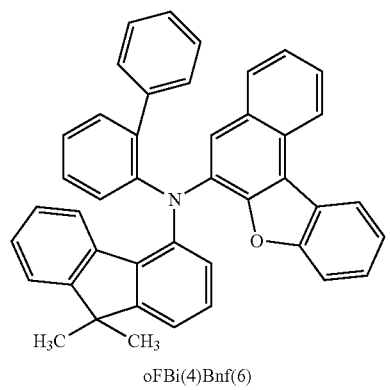

(ix)

oFBi(4)Bnf(6)

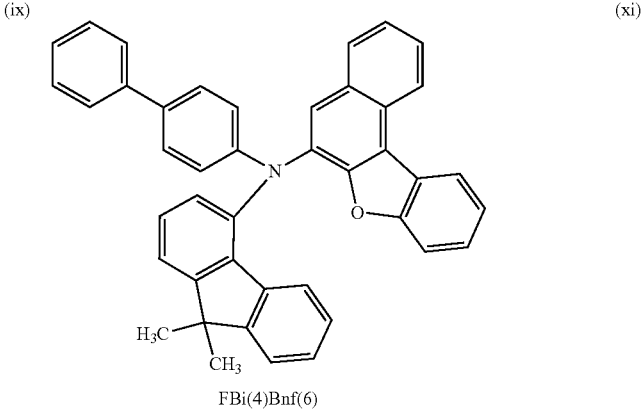

(xi)

FBi(4)Bnf(6)

-continued
(ii)
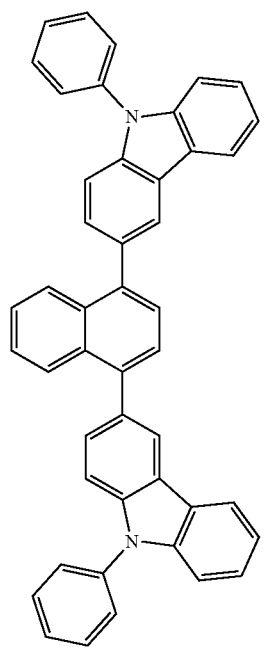
PCzN2
(iii)
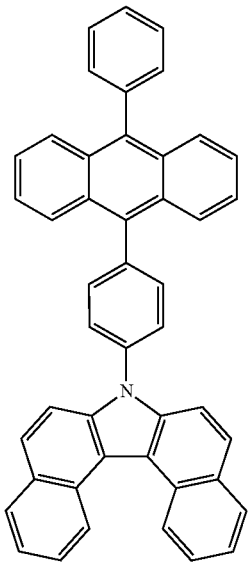
cgDBCzPA
(x)
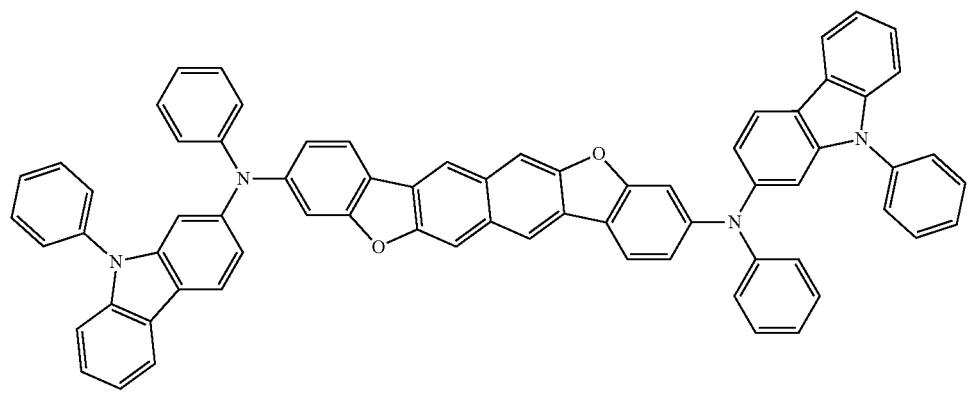
3,10PCA2Nbf(IV)-02
(v)
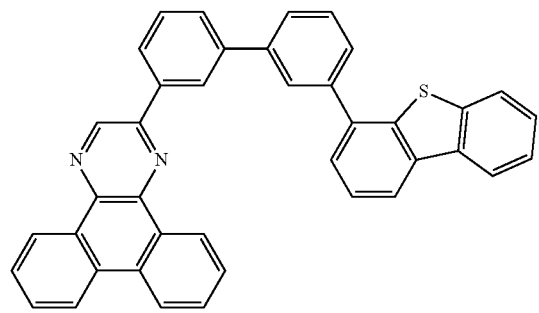
2mDBTBPDBq-II
(vi)
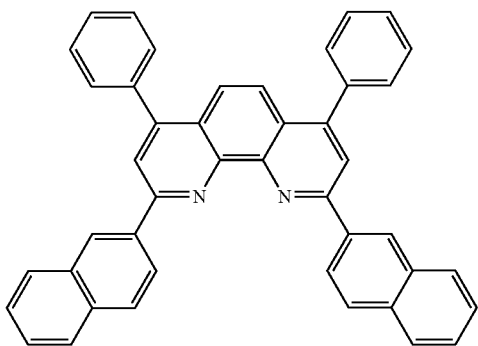
NBPhen (Method for Fabricating Light-Emitting Device 5)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-2-yl)-N-(9,9-dimethyl-9H-fluoren-4-yl)benzo[b]naphtho[1,2-d]furan-6-amine (abbreviation: oFBi(4)Bnf(6)) represented by Structural Formula (ix) above and ALD-MP001Q (manufactured by Analysis Atelier Corporation, material serial No. 1S20180314) were co-evaporated over the first electrode 101 to have a weight ratio of 1:0.1 (=oFBi(4)Bnf(6): ALD-MP001Q) to a thickness of 10 nm by an evaporation method using resistance heating, whereby the hole-injection layer 111 was formed.

Subsequently, over the hole-injection layer 111, oFBi(4)Bnf(6) was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Subsequently, 7-[4-(10-phenyl-9-anthryl)phenyl]-7H-dibenzo[c,g]carbazole (abbreviation: cgDBCzPA) represented by Structural Formula (iii) above and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (x) above were co-evaporated to a thickness of 25 nm at a weight ratio of 1:0.015 (=cgDBCzPA: 3,10PCA2Nbf(IV)-02), whereby the light-emitting layer 113 was formed.

After that, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (v) above was formed to a thickness of 15 nm, and then, 2,9-di(2-naphthyl)-4,7-diphenyl-1,10-phenanthroline (abbreviation: NBPhen) represented by Structural Formula (vi) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 5 of this example was fabricated.

(Method for Fabricating Light-Emitting Device 6)

A light-emitting device 6 was fabricated in a manner similar to that of the light-emitting device 5 except that N-(1,1'-biphenyl-4-yl)-N-(9,9-dimethyl-9H-fluoren-4-yl) benzo[b]naphtho[1,2-d]furan-6-amine (abbreviation: FBi(4)Bnf(6)) represented by Structural Formula (xi) above was used instead of oFBi(4)Bnf(6) in the light-emitting device 5.

The element structures of the light-emitting devices are listed in the following tables.

TABLE 9

|  | hole-injection layer 10 nm | hole-transport layer 1 20 nm | hole-transport layer 2 10 nm | light-emitting layer 25 nm | electron-transport layer hole-injection layer 15 nm | electron-transport layer 1 10 nm |
| --- | --- | --- | --- | --- | --- | --- |
| light-emitting device 5 | oFBi(4)Bnf(6): ALD-MP001Q (1:0.1) | oFBi(4)Bnl(6) | PCzN2 | cgDBCzPA: 3,10PCA2Nbl(IV)-02 (1:0.015) | 2mDBTBPDBq-II | NBPhen |
| light-emitting device 6 | FBi(4)Bnf(6): ALD-MP001Q (1:0.1) | FBi(4)Bnf(6) |  |  |  |  |

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 54:
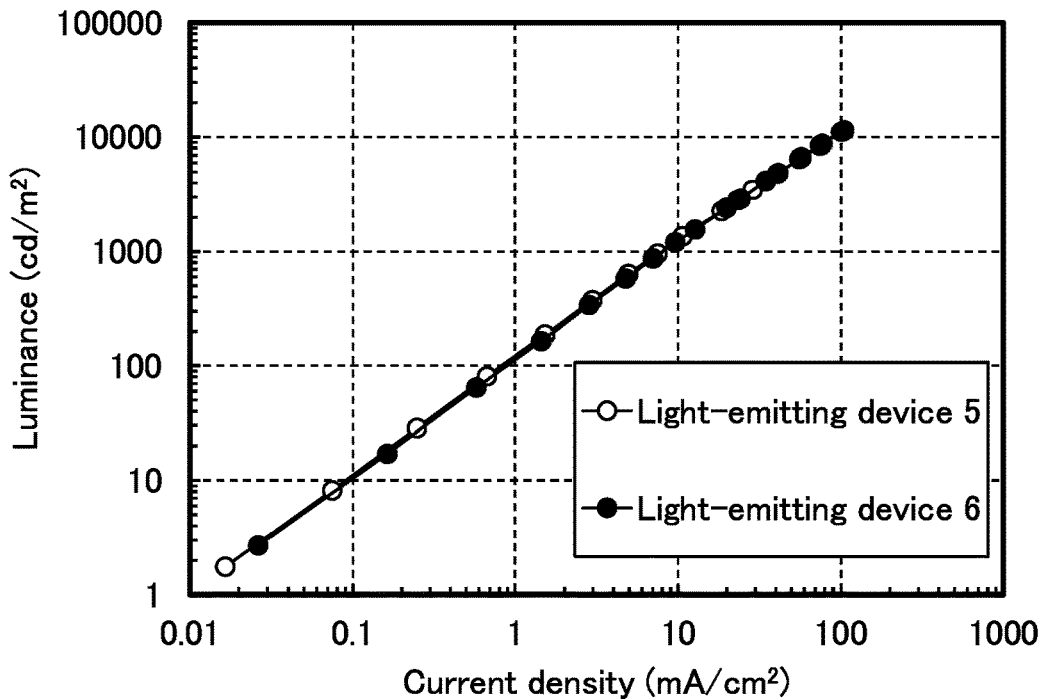
FIG. 54 shows luminance-current density characteristics of a light-emitting device 5 and a light-emitting device 6.
Figure 55:
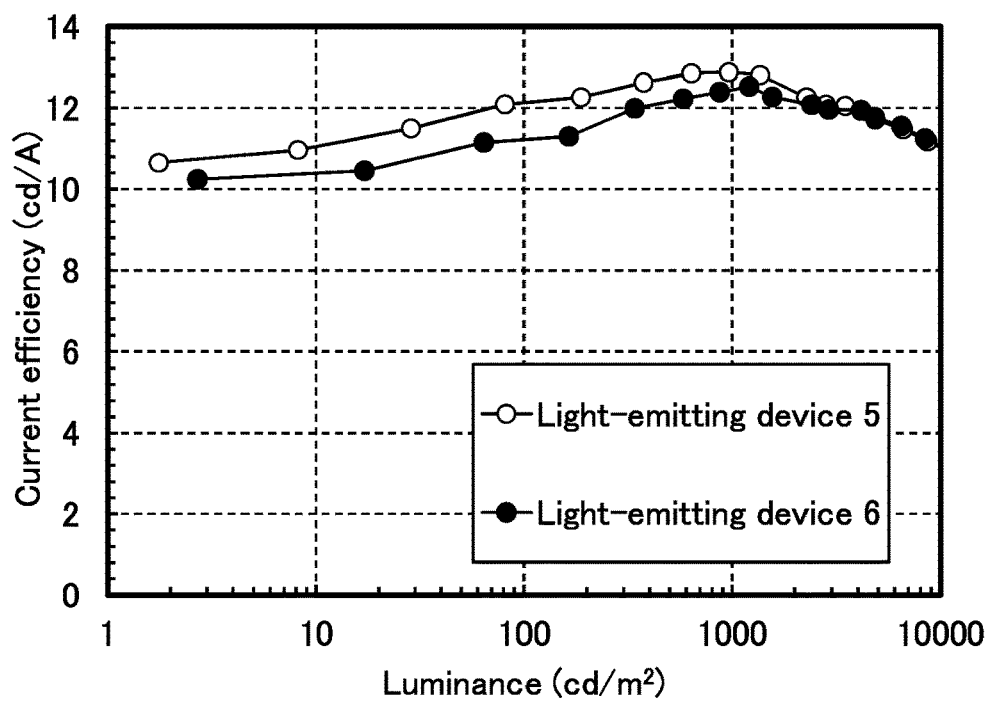
FIG. 55 shows current efficiency-luminance characteristics of the light-emitting device 5 and the light-emitting device 6.
Figure 56:
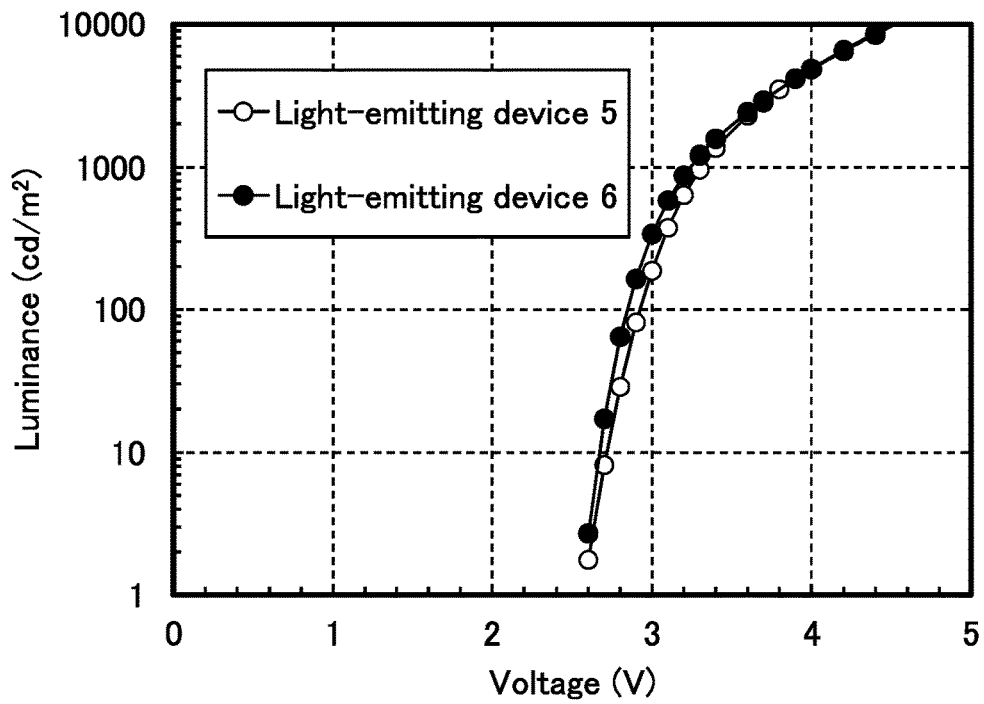
FIG. 56 shows luminance-voltage characteristics of the light-emitting device 5 and the light-emitting device 6.
Figure 57:
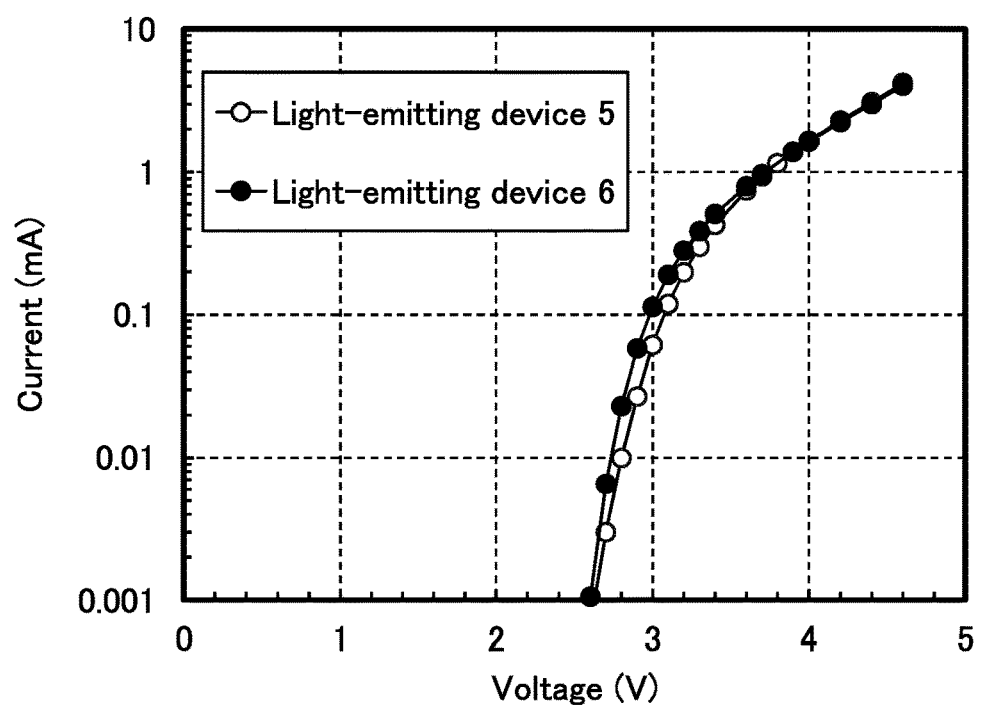
FIG. 57 shows current-voltage characteristics of the light-emitting device 5 and the comparative light-emitting device 6.
Figure 58:
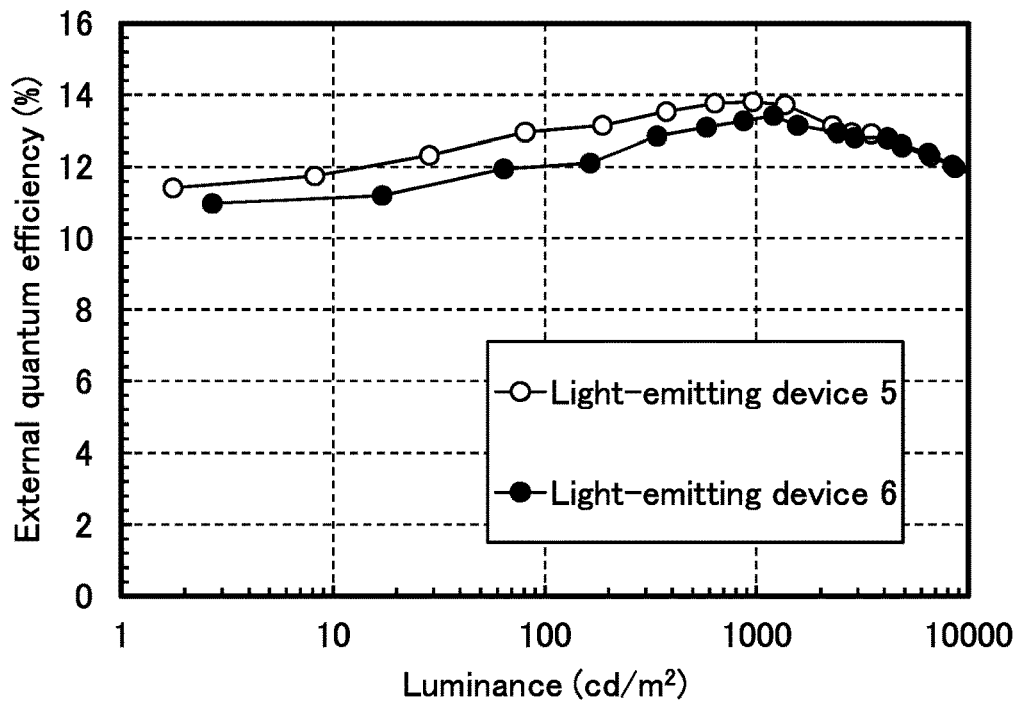
FIG. 58 shows external quantum efficiency-luminance characteristics of the light-emitting device 5 and the light-emitting device 6.
Figure 59:
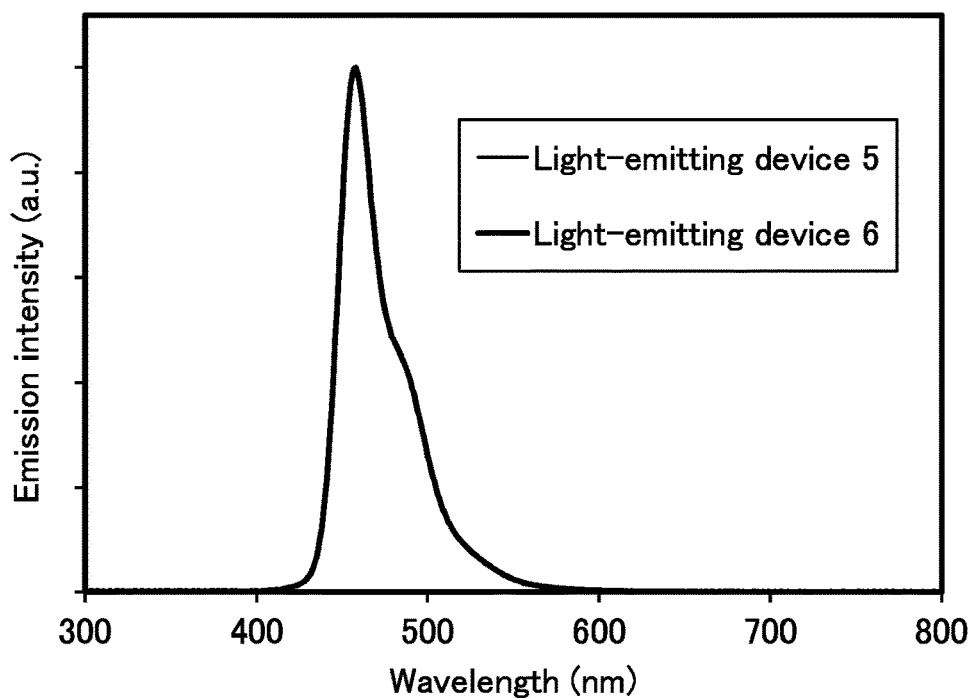
FIG. 59 shows emission spectra of the light-emitting device 5 and the light-emitting device 6.

FIG. 54 shows the luminance-current density characteristics of the light-emitting device 5 and the comparative light-emitting device 6; FIG. 55, the current efficiency-luminance characteristics; FIG. 56, the luminance-voltage characteristics; FIG. 57, the current-voltage characteristics; FIG. 58, the external quantum efficiency-luminance characteristics; and FIG. 59, the emission spectra. Main characteristics of the light-emitting devices at approximately 1000 cd/m² are listed below.

TABLE 10

|  | voltage (V) | current (mA) | current density (mA/cm²) | chromaticity x | chromaticity y | current efficiency (cd/A) | external quantum efficiency (%) |
| --- | --- | --- | --- | --- | --- | --- | --- |
| light-emitting device 5 | 3.3 | 0.30 | 7.5 | 0.14 | 0.11 | 12.9 | 13.8 |
| light-emitting device 6 | 3.2 | 0.28 | 7.0 | 0.14 | 0.11 | 12.4 | 13.3 |

It was found from FIG. 54 to FIG. 59 that the light-emitting device 5 and the light-emitting device 6 of embodiments of the present invention are EL devices with high emission efficiency.

Example 8

Synthesis Example 5

In this synthesis example, a method for synthesizing N-(1,1'-biphenyl-4-yl)-N-(9,9-dimethyl-9H-fluoren-2-yl) benzo[b]naphtho[1,2-d]furan-8-amine (abbreviation: FBiBnf(8)), which is represented by Structural Formula (5-55) in Embodiment 1, will be described. The structural formula of FBiBnf(8) is shown below.

[Chemical Formula 61]

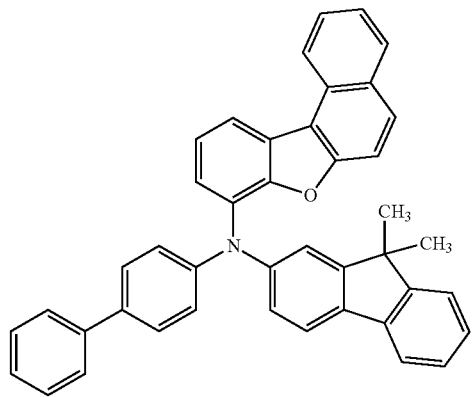

FBiBnf(8)

Step 1: Synthesis of FBiBnf(8)

Into a 500 mL three-neck flask equipped with a reflux pipe, 1.6 g (6.3 mmol) of 8-chloro-benzo[b]naphtho[1,2-d] furan, 2.3 g (6.3 mmol) of 2-(4-biphenylyl)amino-9,9-dimethylfluoren, 1.2 g (13 mol) of sodium tert-butoxide, 44 mg (0.13 mmol) of di-tert-butyl(1-methyl-2,2-diphenylcyclopropyl)phosphine (commonly known name: cBRIDP (regR)), and 30 mL of xylene were put, and the air in the flask was replaced with nitrogen. Into the flask, 36 mg (63 μmol) of bis(bis(dibenzylideneacetone)palladium)(0) was added, and the mixture was heated at 160° C. for 6 hours.

Toluene and water were added to the obtained mixture, and the mixture was separated into an organic layer and an aqueous layer. The obtained organic layer was washed twice with water and subsequently washed with a saturated saline solution. The organic layer was dried with magnesium sulfate. The obtained mixture was gravity-filtered to remove the magnesium sulfate. The obtained filtrate was concentrated and dried to give 4.3 g of a blackish-brown solid. The obtained solid was purified by silica gel chromatography (hexane: toluene=3:1) to give 2.2 g of a white solid in a yield of 60%. The synthesis scheme of Step 1 is shown below.

[Chemical Formulae 62]

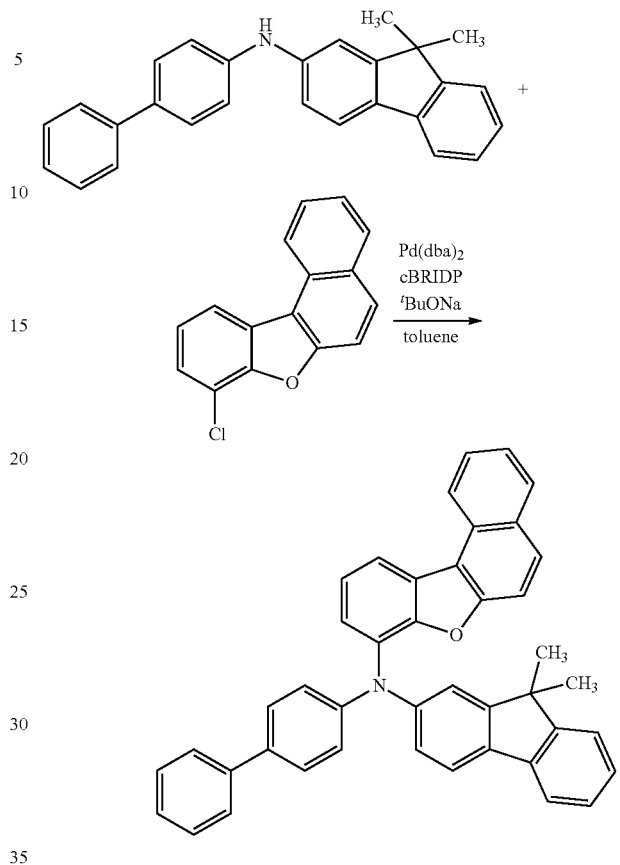

By the train sublimation method, 2.0 g of the obtained white solid was sublimated and purified. In the sublimation purification, the solid was heated at 260° C. for 16 hours under a pressure of 5.6 Pa with a flow of argon at 10 mL/min. After the sublimation purification, 1.6 g of a target white solid was obtained at a collection rate of 80%.

Figure 60A:
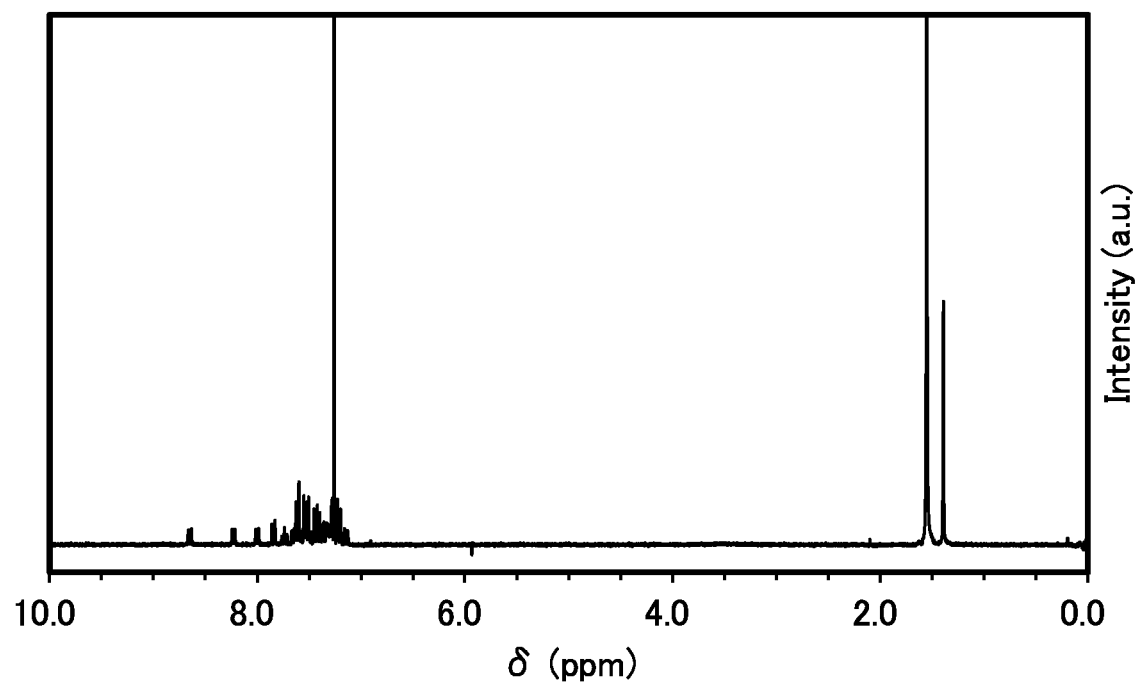
FIG. 60A and FIG. 60B are $^1$H NMR charts of FBiBnf(8).
Figure 60B:
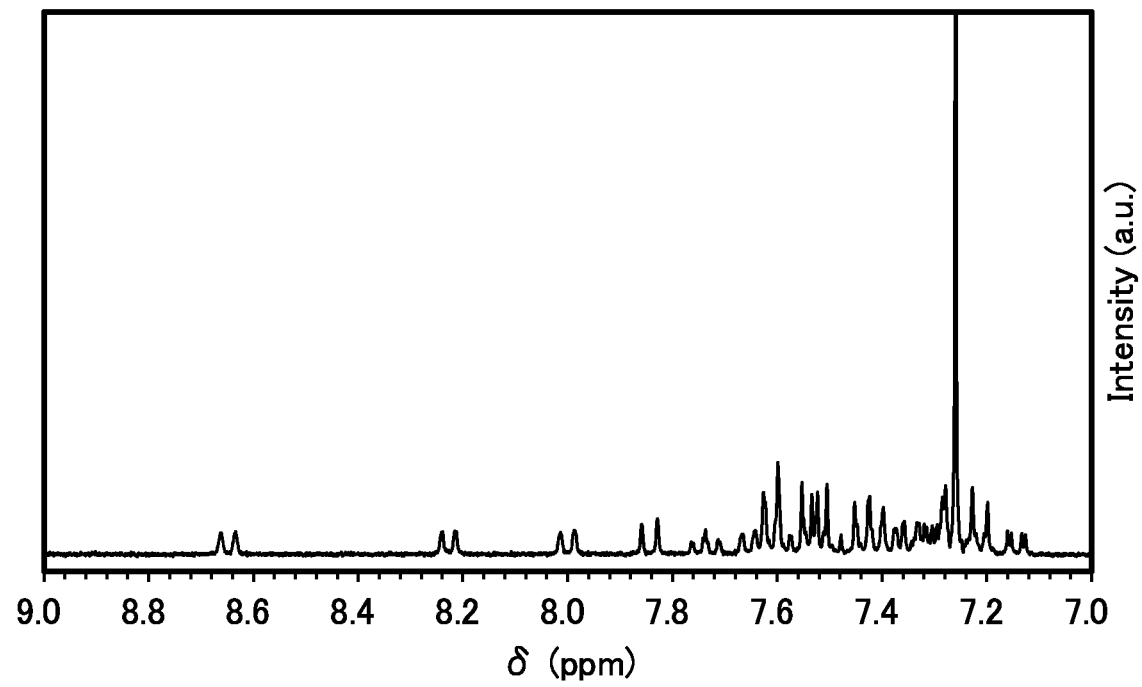

Given below are $^1$H-NMR numerical data of the obtained solid. FIG. 60 shows $^1$H-NMR charts. Note that FIG. 60B is a graph where the range from 7.0 ppm to 9.0 ppm in FIG. 60A is enlarged. This indicates that FBiBnf(8) was obtained.

$^1$H NMR (chloroform-d, 300 MHz): δ=8.65 (d, J=8.7 Hz, 1H), 8.23 (d, J=6.9 Hz, 1H), 8.00 (d, J=8.1 Hz, 1H), 7.84 (d, J=9.3 Hz, 1H), 7.74 (t, J=8.4 Hz, 1H), 7.65 (d, J=6.9 Hz, 1H), 7.63-7.28 (m, 16H), 7.21 (d, J=8.7 Hz, 2H), 7.14 (dd, J=4.2, 2.1 Hz, 1H), 1.39 (s, 6H)

Next, the ultraviolet-visible absorption spectra (hereinafter, simply referred to as "absorption spectra") and emission spectra of a toluene solution and a solid thin film of FBiBnf(8) were measured. The solid thin film was formed over a quartz substrate by a vacuum evaporation method.

For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$ [% T/(100–% R)]) obtained from a transmittance and a reflectance of the substrate and the thin film. Note that % T represents a transmittance and % R represents a reflectance.

The emission spectrum was measured with a fluorescence spectrophotometer (FP-8600, manufactured by JASCO Corporation).

Figure 61:
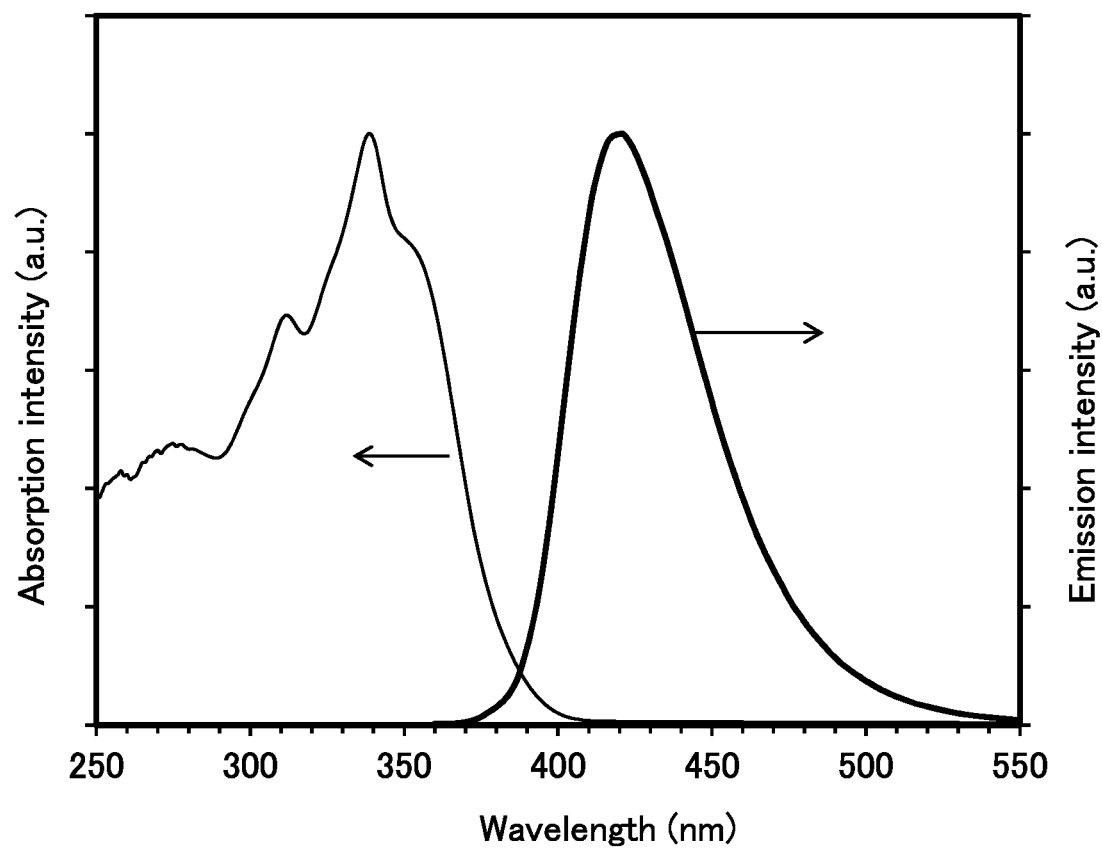
FIG. 61 shows an absorption spectrum and an emission spectrum of FBiBnf(8) in a toluene solution.
Figure 62:
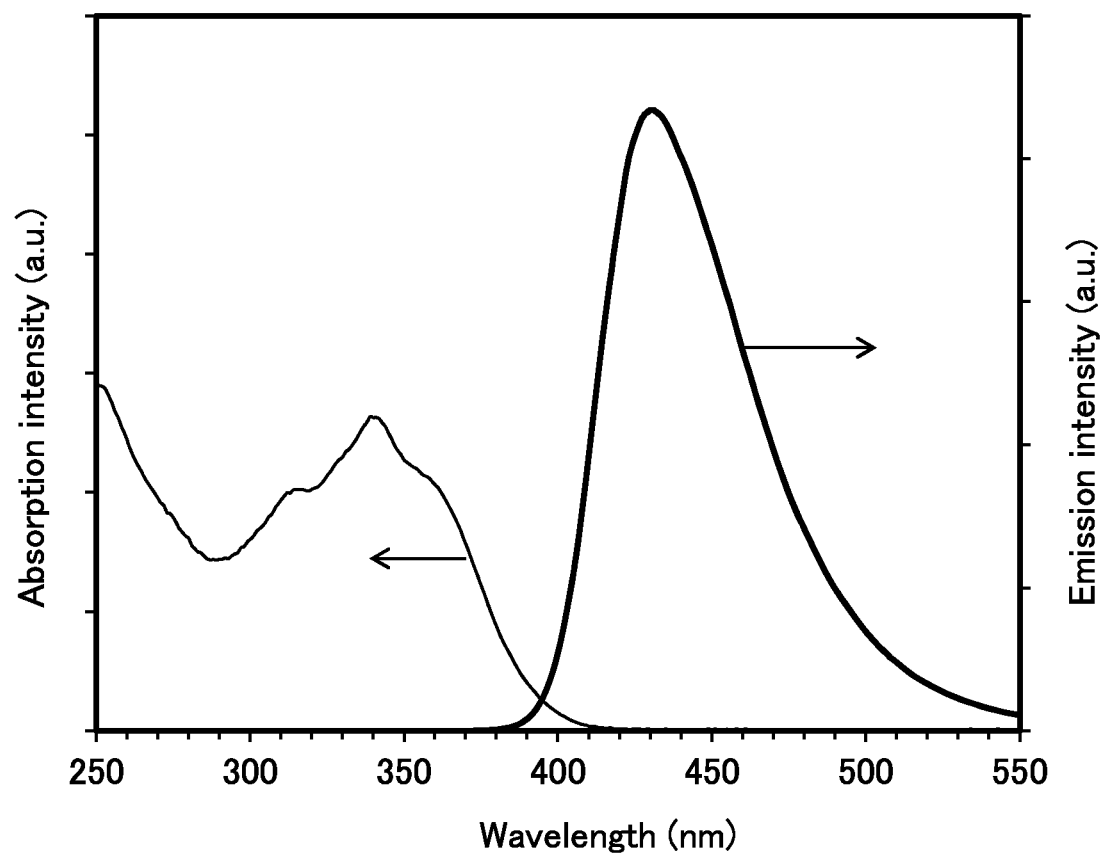
FIG. 62 shows an absorption spectrum and an emission spectrum of a thin film of FBiBnf(8).

FIG. 61 shows the obtained measurement results of the absorption spectrum and the emission spectrum of the toluene solution. The horizontal axis represents wavelength and the vertical axes represent absorption intensity and emission intensity. FIG. 62 shows the measurement results of the absorption spectrum and the emission spectrum of the solid thin film. The horizontal axis represents wavelength and the vertical axes represent absorption intensity and emission intensity. From the results in FIG. 61, for the toluene solution of FBiBnf(8), the absorption peaks were observed at around 357 nm and 339 nm, and the emission wavelength peak was observed at around 421 nm (excitation wavelength: 350 nm). From the results in FIG. 62, for the solid thin film of FBiBnf(8), the absorption peaks were observed at around 360 nm, 341 nm, 315 nm, and 250 nm, and the emission wavelength peak was observed at around 431 nm (excitation wavelength: 340 nm).

The HOMO level and the LUMO level of FBiBnf(8) were calculated on the basis of a cyclic voltammetry (CV) measurement. The calculation method, the measurement method, and the measurement apparatus are the same as those in Example 1; therefore, repeated description will be omitted.

As a result, in the measurement of the oxidation potential Ea [V] of FBiBnf(8), the HOMO level was found to be −5.48 eV. Meanwhile, in the measurement of the reduction potential Ec [V], the LUMO level was found to be −2.37 eV. In addition, in repetitive measurement of the oxidation-reduction wave, when the waveform of the first cycle was compared with that of the hundredth cycle, 85% of the peak intensity and 94% of the peak intensity were maintained in the Ea measurement and the Ec measurement, respectively, which confirmed that FBiBnf(8) had extremely high resistance to oxidation and reduction.

Differential scanning calorimetry (DSC measurement) was performed on FBiBnf(8) by DSC8231-SL manufactured by Rigaku Corporation. The differential scanning calorimetry was performed in the following manner: the temperature was raised from 0° C. to 290° C. at a temperature rising rate of 10° C./min and held at the temperature for one minute, and then the temperature was decreased to 0° C. at a temperature decreasing rate of 10° C./min. This operation was performed three times in succession. It was revealed from the result of the second cycle of the DSC measurement that the glass transition point of FBiBnf(8) was 118° C., that is, FBiBnf(8) was a substance with extremely high heat resistance.

Then, thermogravimetry-differential thermal analysis of FBiBnf(8) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 422° C., which shows that FBiBnf(8) is a substance with favorable sublimability.

Example 9

Synthesis Example 6>>

In this synthesis example, a method for synthesizing N-(1,1′-biphenyl-2-yl)-N-(9,9-dimethyl-9H-fluoren-2-yl) benzo[b]naphtho[1,2-d]furan-8-amine (abbreviation: oFBiBnf(8)), which is represented by Structural Formula (5-3) in Embodiment 1, will be described. The structural formula of oFBiBnf(8) is shown below.

[Chemical Formula 63]

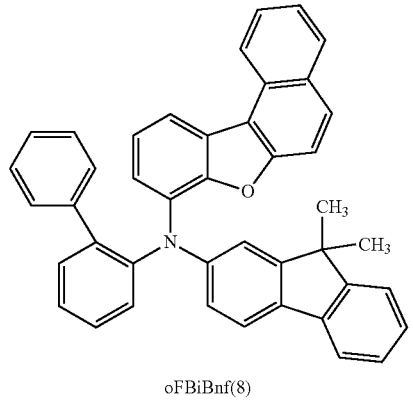

oFBiBnf(8)

Step 1: Synthesis N-(1,1′-biphenyl-2-yl)-N-(9,9-dimethyl-9H-fluoren-2-yl)benzo[b]naphtho[1,2-d]furan-8-amine (abbreviation: oFBiBnf(8))

Into a 500 mL three-neck flask equipped with a reflux pipe, 1.6 g (6.3 mmol) of 8-chloro-benzo[b]naphtho[1,2-d]furan, 2.3 g (6.3 mmol) of 2-(2-biphenylyl)amino-9,9-dimethylfluoren, 1.2 g (13 mol) of sodium tert-butoxide, 44 mg (0.13 mmol) of di-tert-butyl(1-methyl-2,2-diphenylcyclopropyl)phosphine (commonly known name: cBRIDP (regR)), and 30 mL of xylene were put, and the air in the flask was replaced with nitrogen. Into the flask, 36 mg (63 μmol) of bis(bis(dibenzylideneacetone)palladium)(0) was added, and the mixture was heated at 160° C. for 12 hours.

Toluene and water were added to the obtained mixture, and the mixture was separated into an organic layer and an aqueous layer. The obtained organic layer was washed twice with water and subsequently washed with a saturated saline solution. The organic layer was dried with magnesium sulfate. The obtained mixture was gravity-filtered to remove the magnesium sulfate. The obtained filtrate was concentrated and dried to give 4.1 g of a blackish-brown solid. The obtained solid was purified by silica gel chromatography (hexane: toluene=4:1) to give 1.2 g of a white solid in a yield of 33%. The synthesis scheme of this synthesis example is shown below.

[Chemical Formulae 64]

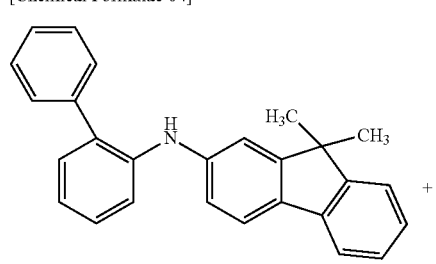

-continued

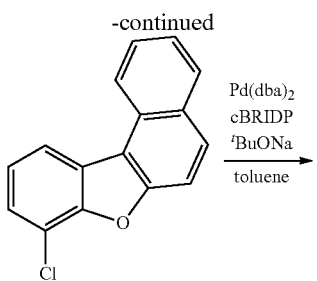

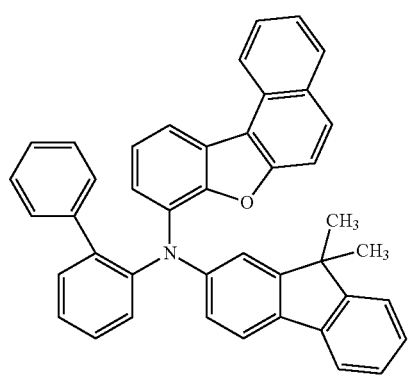

By the train sublimation method, 1.2 g of the obtained white solid was sublimated and purified. In the sublimation purification, the solid was heated at 225° C. for 16 hours under a pressure of 4.0 Pa with a flow of argon at 15 mL/min. After the sublimation purification, 1.1 g of a target white solid was obtained at a collection rate of 92%.

Figure 63A:
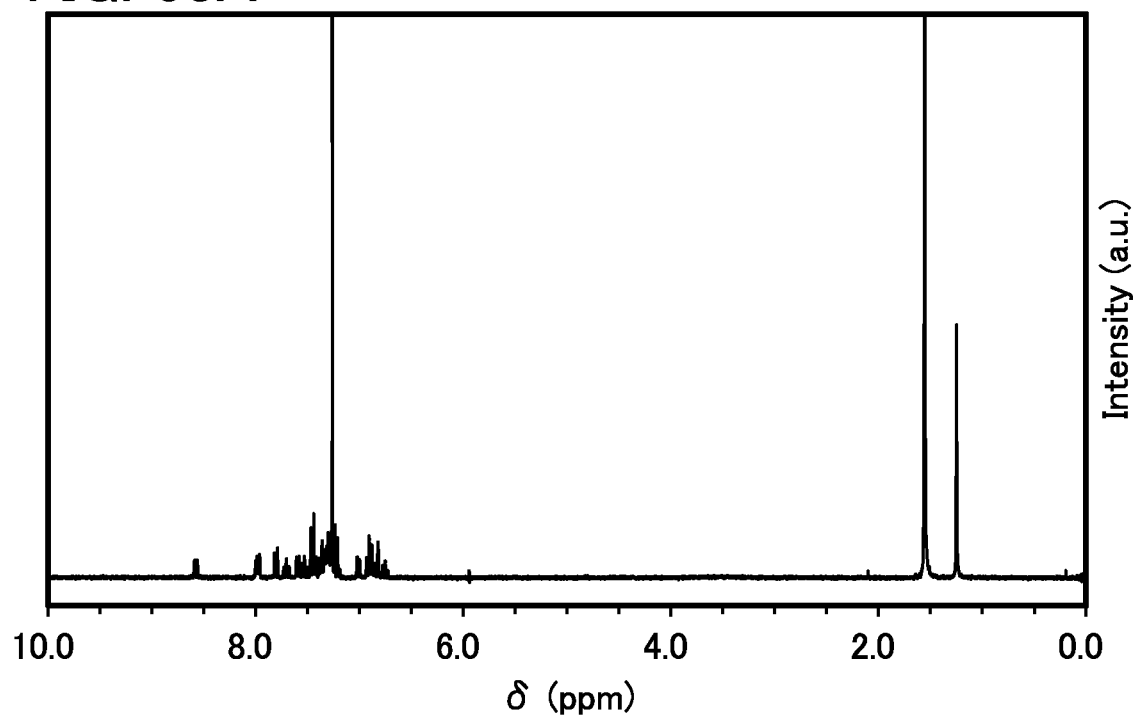
FIG. 63A and FIG. 63B are $^1$H NMR charts of oFBiBnf(8).
Figure 63B:
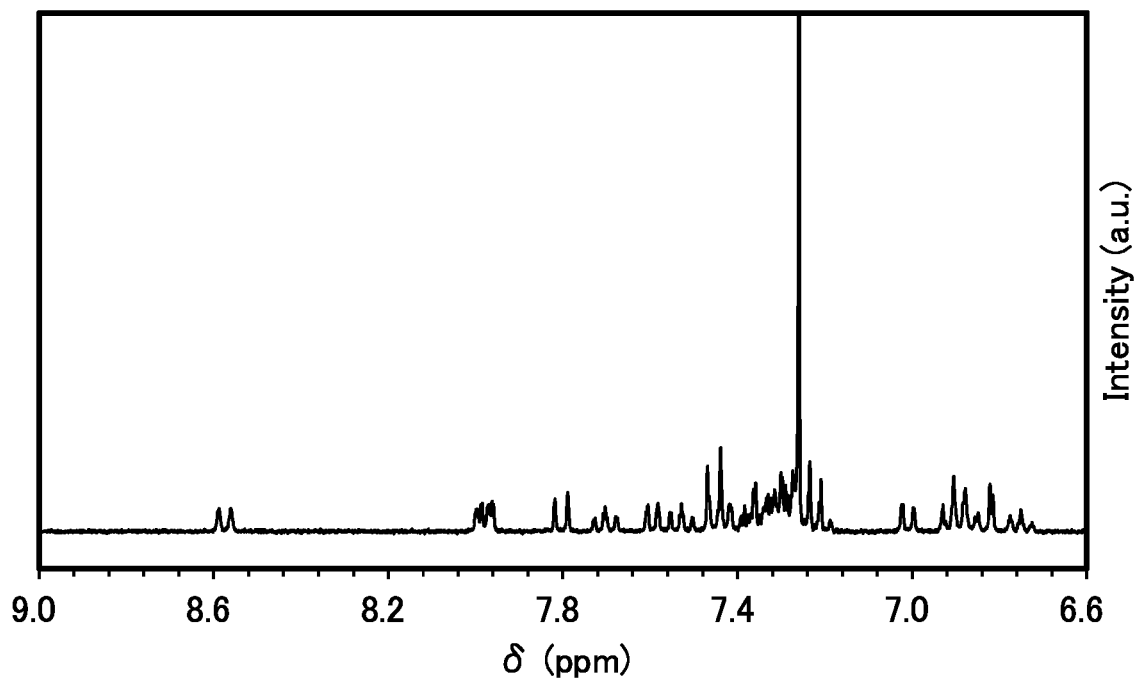

Given below are $^1$H-NMR numerical data of the obtained solid. FIG. 63 shows $^1$H-NMR charts. Note that FIG. 63B is a graph where the range from 6.6 ppm to 9.0 ppm in FIG. 63A is enlarged. This indicates that oFBiBnf(8) was obtained.

$^1$H NMR (chloroform-d, 300 MHz): δ=8.57 (d, J=7.8 Hz, 1H), 8.00-7.96 (m, 2H), 7.80 (d, J=8.7 Hz, 1H), 7.70 (t, J=6.6 Hz, 1H), 7.59 (d, J=6.6 Hz, 1H), 7.53 (t, J=7.5 Hz, 1H), 7.49-7.18 (m, 12H), 7.01 (d, J=7.2 Hz, 1H), 6.94-6.79 (m, 4H), 6.75 (t, J=7.2 Hz, 1H), 1.25 (s, 6H)

Next, the ultraviolet-visible absorption spectra (hereinafter, simply referred to as "absorption spectra") and emission spectra of a toluene solution and a solid thin film of oFBiBnf(8) were measured. The measurement method and the measurement apparatus are the same as those in Example 7; therefore, repeated description will be omitted.

Figure 64:
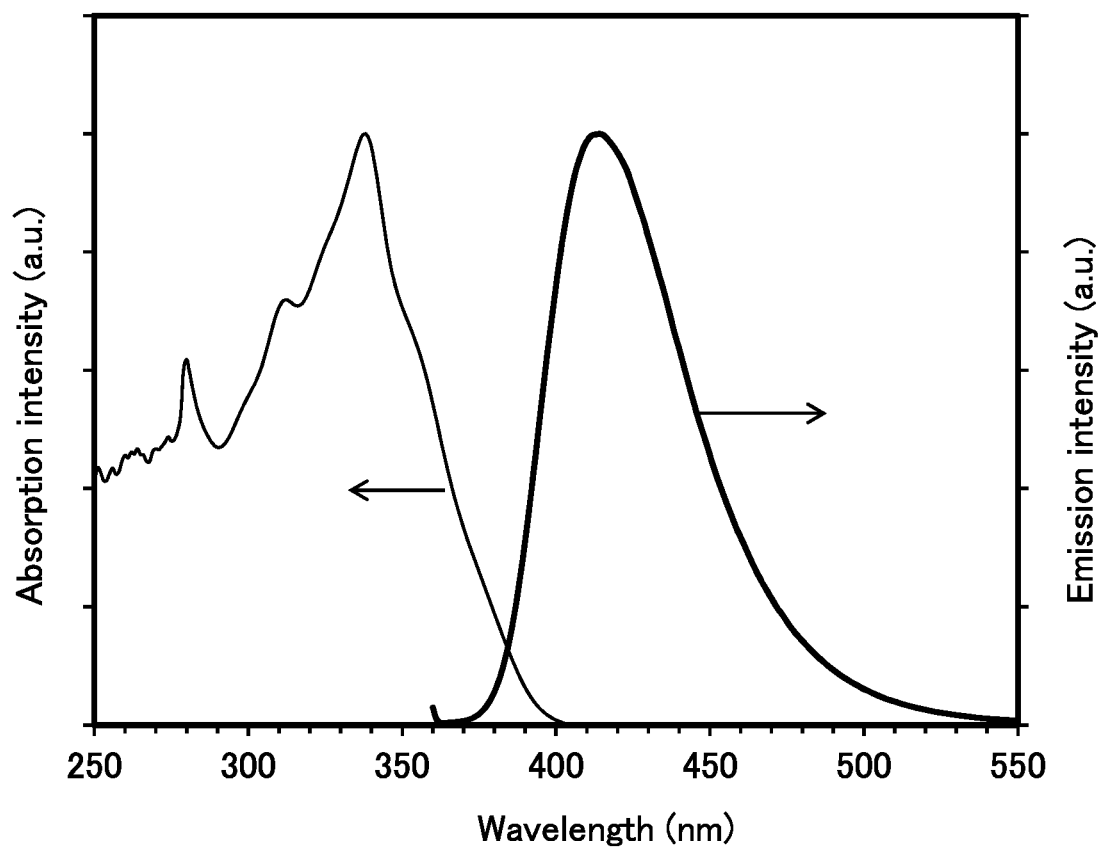
FIG. 64 shows an absorption spectrum and an emission spectrum of oFBiBnf(8) in a toluene solution.
Figure 65:
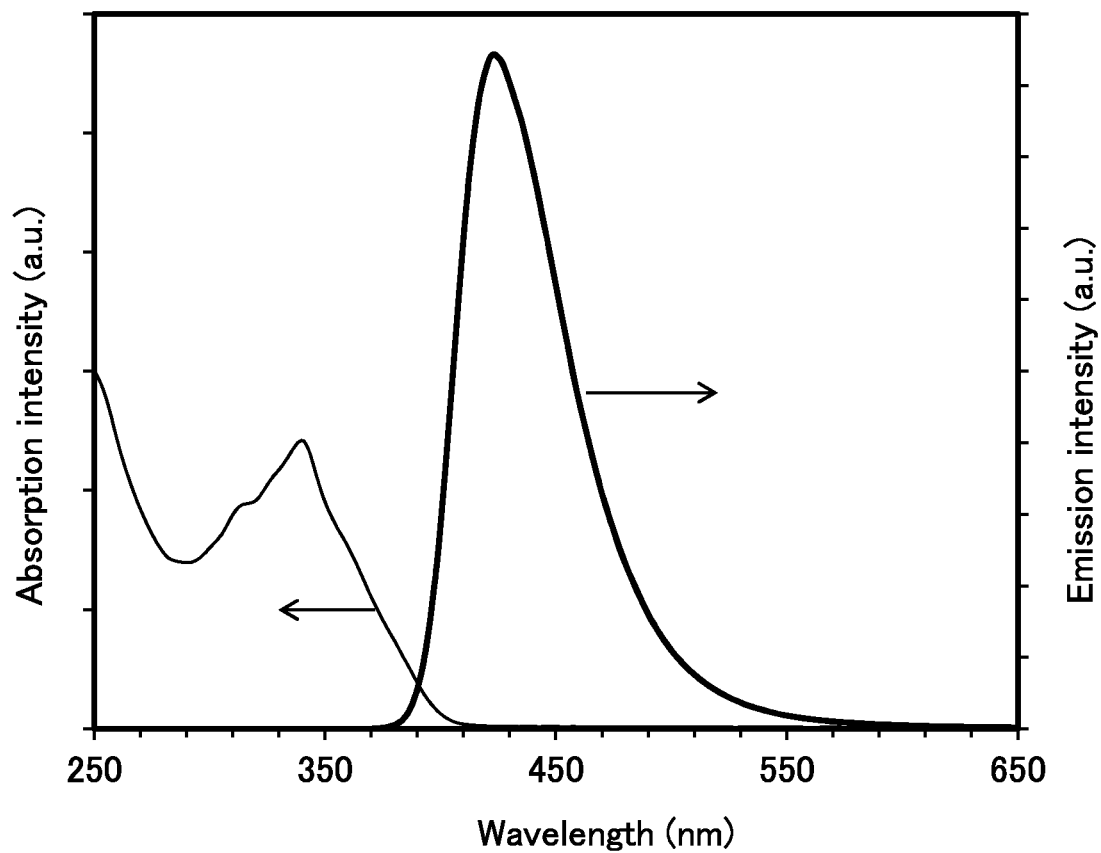
FIG. 65 shows an absorption spectrum and an emission spectrum of a thin film of oFBiBnf(8).

FIG. 64 shows the obtained measurement results of the absorption spectrum and the emission spectrum of the toluene solution. The horizontal axis represents wavelength and the vertical axes represent absorption intensity and emission intensity. FIG. 65 shows the measurement results of the absorption spectrum and the emission spectrum of the solid thin film. The horizontal axis represents wavelength and the vertical axes represent absorption intensity and emission intensity.

From the results in FIG. 64, for the toluene solution of oFBiBnf(8), the absorption peaks were observed at around 377 nm, 357 nm, and 339 nm, and the emission wavelength peak was observed at around 414 nm (excitation wavelength: 335 nm).

From the results in FIG. 65, for the solid thin film of oFBiBnf(8), the absorption peaks were observed at around 390 nm, 385 nm, 360 nm, and 340 nm, and the emission wavelength peak was observed at around 423 nm (excitation wavelength: 340 nm).

The HOMO level and the LUMO level of oFBiBnf(8) were calculated on the basis of a cyclic voltammetry (CV) measurement. The measurement method and the measurement apparatus are the same as those in Example 1; therefore, repeated description will be omitted.

As a result, in the measurement of the oxidation potential Ea [V] of oFBiBnf(8), the HOMO level was found to be −5.48 eV. Meanwhile, in the measurement of the reduction potential Ec [V], the LUMO level was found to be −2.34 eV. In addition, in repetitive measurement of the oxidation-reduction wave, when the waveform of the first cycle was compared with that of the hundredth cycle, 92% of the peak intensity and 94% of the peak intensity were maintained in the Ea measurement and the Ec measurement, respectively, which confirmed that oFBiBnf(8) had extremely high resistance to oxidation and reduction.

Differential scanning calorimetry (DSC measurement) was performed on oFBiBnf(8) by DSC8231-SL manufactured by Rigaku Corporation. The differential scanning calorimetry was performed in the following manner: the temperature was raised from 0° C. to 220° C. at a temperature rising rate of 10° C./min and held at the temperature for one minute, and then the temperature was decreased to 0° C. at a temperature decreasing rate of 10° C./min. This operation was performed three times in succession. It was revealed from the result of the second cycle of the DSC measurement that the glass transition point of oFBiBnf(8) was 114° C., that is, oFBiBnf(8) was a substance with extremely high heat resistance.

Then, thermogravimetry-differential thermal analysis of oFBiBnf(8) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 364° C., which shows that oFBiBnf(8) is a substance with favorable sublimability.

Example 10

Synthesis Example 7>>

In this synthesis example, a method for synthesizing N-(1,1'-biphenyl-4-yl)-N-(9,9-dimethyl-9H-fluoren-4-yl) benzo[b]naphtho[1,2-d]furan-8-amine (abbreviation: FBi(4) Bnf(8)), which is represented by Structural Formula (5-32) in Embodiment 1, will be described. The structural formula of FBi(4)Bnf(8) is shown below.

[Chemical Formula 65]

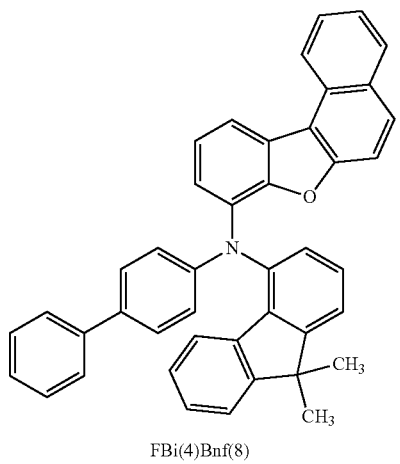

FBi(4)Bnf(8)

Step 1: Synthesis of FBi(4)Bnf(8)

Into a 500 mL three-neck flask equipped with a reflux pipe, 1.5 g (5.8 mmol) of 8-chloro-benzo[b]naphtho[1,2-d]furan, 2.0 g (5.8 mmol) of 4-(4-biphenylyl)amino-9,9-dimethylfluoren, 1.1 g (12 mol) of sodium tert-butoxide, 60 mg (0.15 mmol) of 2-dicyclohexylphosphino-2',6'-dimethoxybiphenyl(commonly known name: Sphos), and 30 mL of xylene were put, and the air in the flask was replaced with nitrogen. Into the flask, 33 mg (58 μmol) of bis(bis(dibenzylideneacetone)palladium)(0) was added, and the mixture was heated at 160° C. for 7 hours.

Toluene and water were added to the obtained mixture, and the mixture was separated into an organic layer and an aqueous layer. The obtained organic layer was washed twice with water and subsequently washed with a saturated saline solution. The organic layer was dried with magnesium sulfate. The obtained mixture was gravity-filtered to remove the magnesium sulfate. The obtained filtrate was concentrated and dried to give 3.6 g of a blackish-brown solid. By high-performance liquid chromatography, 3.6 g of the blackish-brown solid was purified (used solvent: chloroform). The obtained fraction solution was concentrated, and the obtained solid was washed with hexane. The obtained solid was dried to give 1.7 g of a white solid in a yield of 51%. The synthesis scheme of this synthesis example is shown below.

[Chemical Formulae 66]

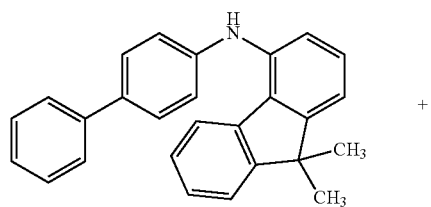

+

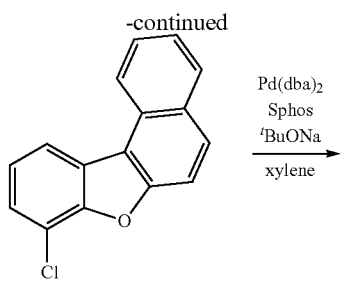

$\xrightarrow{\text{Pd(dba)}_2, \text{Sphos}, {}^t\text{BuONa}, \text{xylene}}$

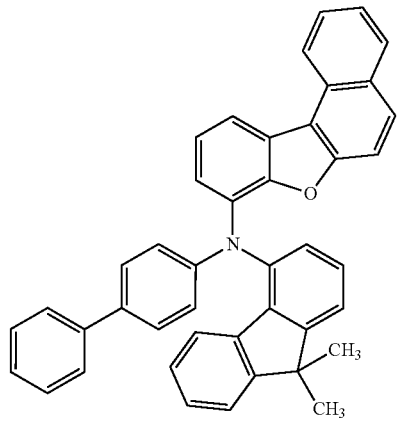

By the train sublimation method, 1.7 g of the obtained white solid was sublimated and purified. In the sublimation purification, the solid was heated at 245° C. for 19 hours under a pressure of 3.8 Pa with a flow of argon at 15 mL/min. After the sublimation purification, 1.4 g of a target white solid was obtained at a collection rate of 82%.

Figure 66A:
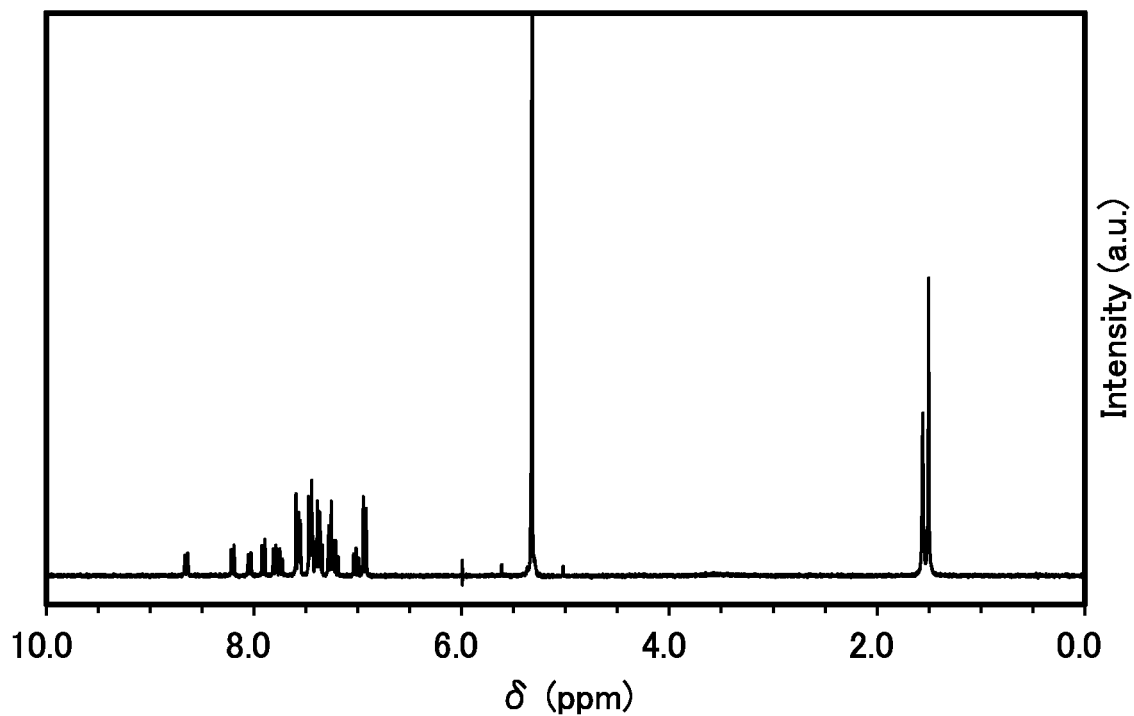
FIG. 66A and FIG. 66B are $^1$H NMR charts of FBi(4)Bnf(8).
Figure 66B:
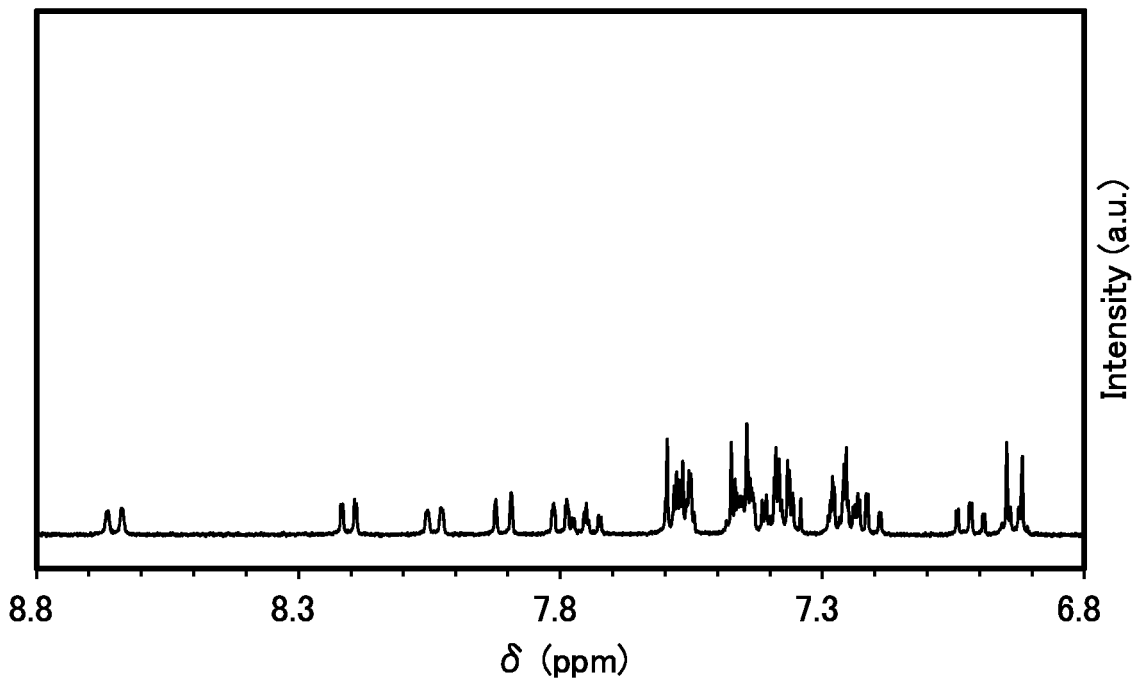

Given below are $^1$H-NMR numerical data of the obtained solid. FIG. 66 shows $^1$H-NMR charts. Note that FIG. 66B is a graph where the range from 6.8 ppm to 8.8 ppm in FIG. 66A is enlarged. This indicates that FBi(4)Bnf(8) was obtained.

$^1$H NMR (dichloromethane-d2, 300 MHz): δ=8.64 (d, J=8.1 Hz, 1H), 8.20 (dd, J=3.9, 1.2 Hz, 1H), 8.04 (d, J=7.5 Hz, 1H), 7.91 (d, J=8.7 Hz, 1H), 7.80 (d, J=7.5 Hz, 1H), 7.75 (t, J=6.9 Hz, 1H), 7.63-7.52 (m, 4H), 7.50-7.32 (m, 8H), 7.31-7.16 (m, 4H), 7.02 (t, J=7.5 Hz, 1H), 6.93 (d, J=9.0 Hz, 2H), 1.50 (s, 6H)

Next, the ultraviolet-visible absorption spectra (hereinafter, simply referred to as "absorption spectra") and emission spectra of a toluene solution and a solid thin film of FBi(4)Bnf(8) were measured. The measurement method and the measurement apparatus are the same as those in Example 7; therefore, repeated description will be omitted.

Figure 67:
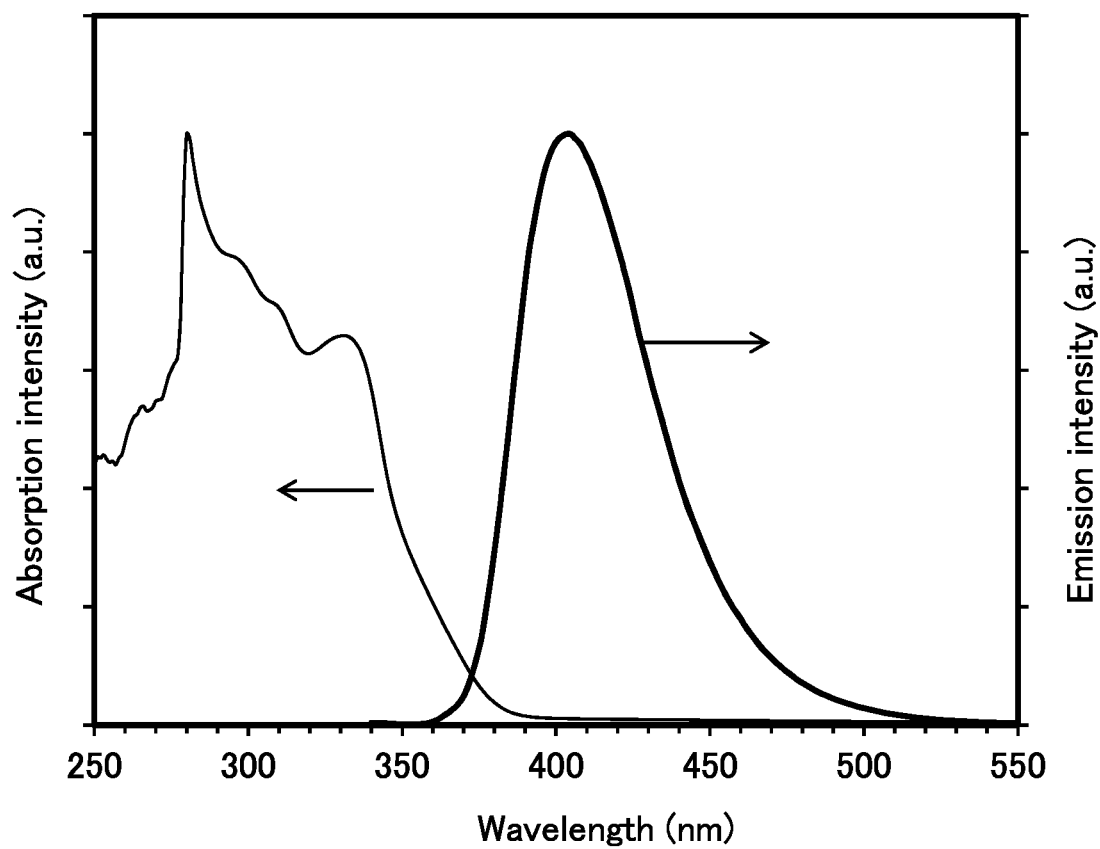
FIG. 67 shows an absorption spectrum and an emission spectrum of FBi(4)Bnf(8) in a toluene solution.
Figure 68:
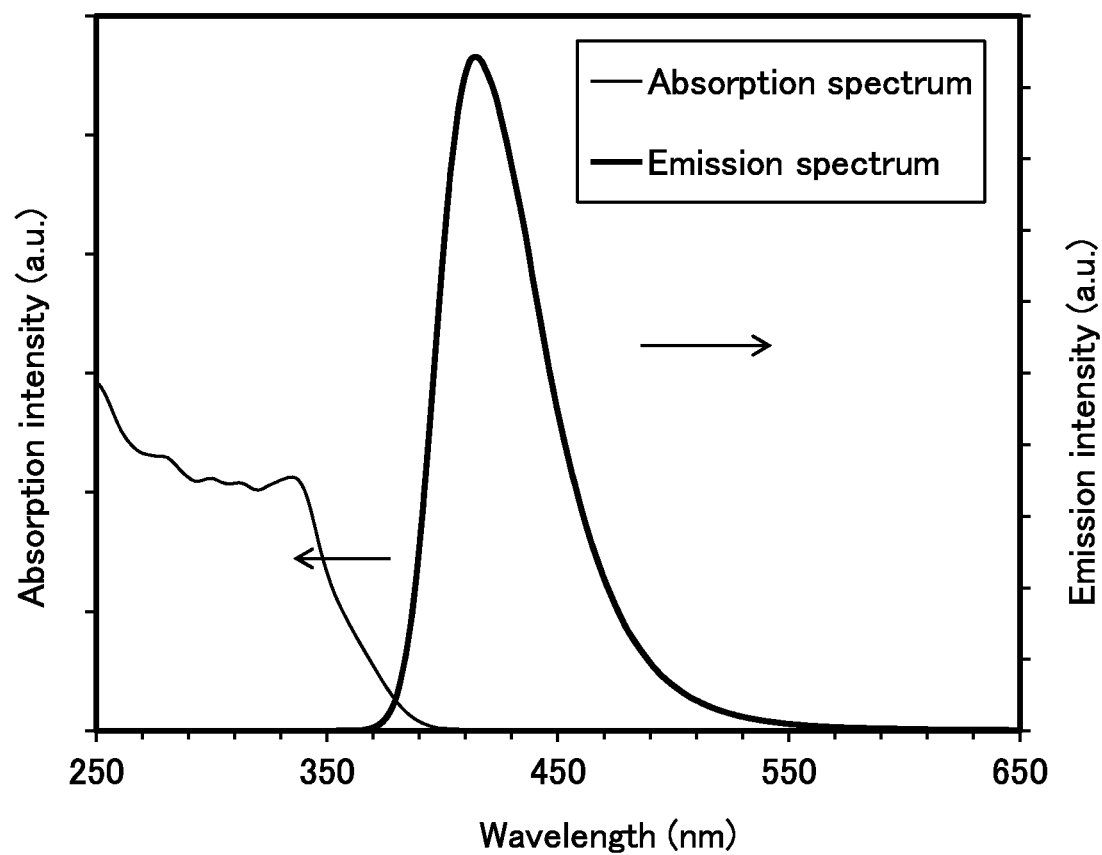
FIG. 68 shows an absorption spectrum and an emission spectrum of a thin film of FBi(4)Bnf(8).

FIG. 67 shows the obtained measurement results of the absorption spectrum and the emission spectrum of the toluene solution. The horizontal axis represents wavelength and the vertical axes represent absorption intensity and emission intensity. FIG. 68 shows the measurement results of the absorption spectrum and the emission spectrum of the solid thin film. The horizontal axis represents wavelength and the vertical axes represent absorption intensity and emission intensity.

From the results in FIG. 67, for the toluene solution of FBi(4)Bnf(8), the absorption peaks were observed at around 331 nm, 310 nm, and 298 nm, and the emission wavelength peak was observed at around 404 nm (excitation wavelength: 330 nm).

From the results in FIG. 68, for the solid thin film of FBi(4)Bnf(8), the absorption peaks were observed at around 370 nm, 335 nm, 316 nm, and 302 nm, and the emission wavelength peak was observed at around 414 nm (excitation wavelength: 335 nm).

The HOMO level and the LUMO level of FBi(4)Bnf(8) were calculated on the basis of a cyclic voltammetry (CV) measurement. The calculation method, the measurement method, and the measurement apparatus are the same as those in Example 1; therefore, repeated description will be omitted.

As a result, in the measurement of the oxidation potential Ea [V] of FBi(4)Bnf(8), the HOMO level was found to be −5.58 eV. Meanwhile, in the measurement of the reduction potential Ec [V], the LUMO level was found to be −2.37 eV. In addition, in repetitive measurement of the oxidation-reduction wave, when the waveform of the first cycle was compared with that of the hundredth cycle, 80% of the peak intensity and 95% of the peak intensity were maintained in the Ea measurement and the Ec measurement, respectively, which confirmed that FBi(4)Bnf(8) had extremely high resistance to oxidation and reduction.

Differential scanning calorimetry (DSC measurement) was performed on FBi(4)Bnf(8) by DSC8231-SL manufactured by Rigaku Corporation. The differential scanning calorimetry was performed in the following manner: the temperature was raised from 0° C. to 290° C. at a temperature rising rate of 10° C./min and held at the temperature for one minute, and then the temperature was decreased to 0° C. at a temperature decreasing rate of 10° C./min. This operation was performed three times in succession. It was revealed from the result of the second cycle of the DSC measurement that the glass transition point of FBi(4)Bnf(8) was 118° C., that is, FBi(4)Bnf(8) was a substance with extremely high heat resistance.

Then, thermogravimetry-differential thermal analysis of FBi(4)Bnf(8) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 394° C., which shows that FBi(4)Bnf(8) is a substance with favorable sublimability.

Example 11

Synthesis Example 8>>

In this synthesis example, a method for synthesizing N-(1,1'-biphenyl-2-yl)-N-(9,9-dimethyl-9H-fluoren-4-yl) benzo[b]naphtho[1,2-d]furan-8-amine (abbreviation: oFBi (4)Bnf(8)), which is represented by Structural Formula (5-46) in the embodiment, will be described. The structural formula of oFBi(4)Bnf(8) is shown below.

[Chemical Formula 67]

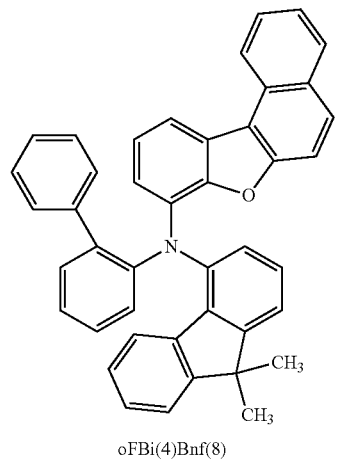

oFBi(4)Bnf(8)

Step 1: Synthesis of oFBi(4)Bnf(8)

Into a 500 mL three-neck flask equipped with a reflux pipe, 1.6 g (6.3 mmol) of 8-chloro-benzo[b]naphtho[1,2-d] furan, 2.3 g (6.3 mmol) of 4-(2-biphenylyl)amino-9,9-dimethylfluoren, 1.2 g (13 mol) of sodium tert-butoxide, 44 mg (0.13 mmol) of di-tert-butyl(1-methyl-2,2-diphenylcyclopropyl)phosphine (commonly known name: cBRIDP (regR)), and 30 mL of xylene were put, and the air in the flask was replaced with nitrogen. Into the flask, 36 mg (63 μmol) of bis(bis(dibenzylideneacetone)palladium)(0) was added, and the mixture was heated at 160° C. for 10 hours.

Toluene and water were added to the obtained mixture, and the mixture was separated into an organic layer and an aqueous layer. The obtained organic layer was washed twice with water and subsequently washed with a saturated saline solution. The organic layer was dried with magnesium sulfate. The obtained mixture was gravity-filtered to remove the magnesium sulfate. The obtained filtrate was concentrated and dried to give 4.4 g of a blackish-brown solid. The obtained solid was purified by silica gel chromatography (hexane: toluene=3:1) to give 1.8 g of a white solid. By high-performance liquid chromatography, 1.8 g of the obtained solid was purified (used solvent: chloroform). The obtained fraction solution was concentrated, and the obtained solid was washed with hexane. The obtained solid was dried to give 1.1 g of a white solid in a yield of 30%. The LC/MS analysis results revealed that m/z of the obtained white solid was 578, and thus the solid was found to be a target substance. The synthesis scheme of this synthesis example is shown below.

[Chemical Formulae 68]

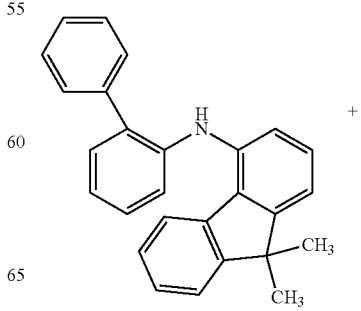

153
-continued

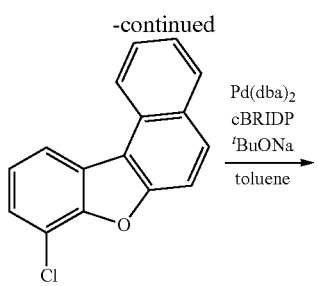

Pd(dba)₂
cBRIDP
ᵗBuONa
toluene
→

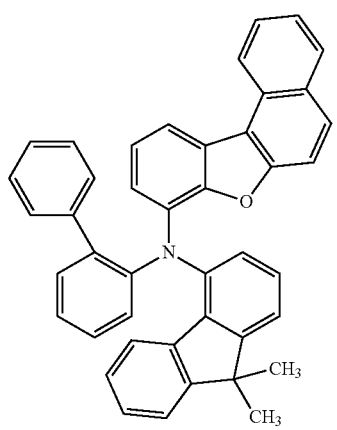

By the train sublimation method, 1.1 g of the obtained white solid was sublimated and purified. In the sublimation purification, the solid was heated at 220° C. for 16 hours under a pressure of 5.2 Pa with a flow of argon at 10 mL/min. After the sublimation purification, 0.78 g of a target white solid was obtained at a collection rate of 71%.

Next, the ultraviolet-visible absorption spectra (hereinafter, simply referred to as "absorption spectra") and emission spectra of a toluene solution and a solid thin film of oFBi(4)Bnf(8) were measured. The measurement method and the measurement apparatus are the same as those in Example 7; therefore, repeated description will be omitted.

Figure 69:
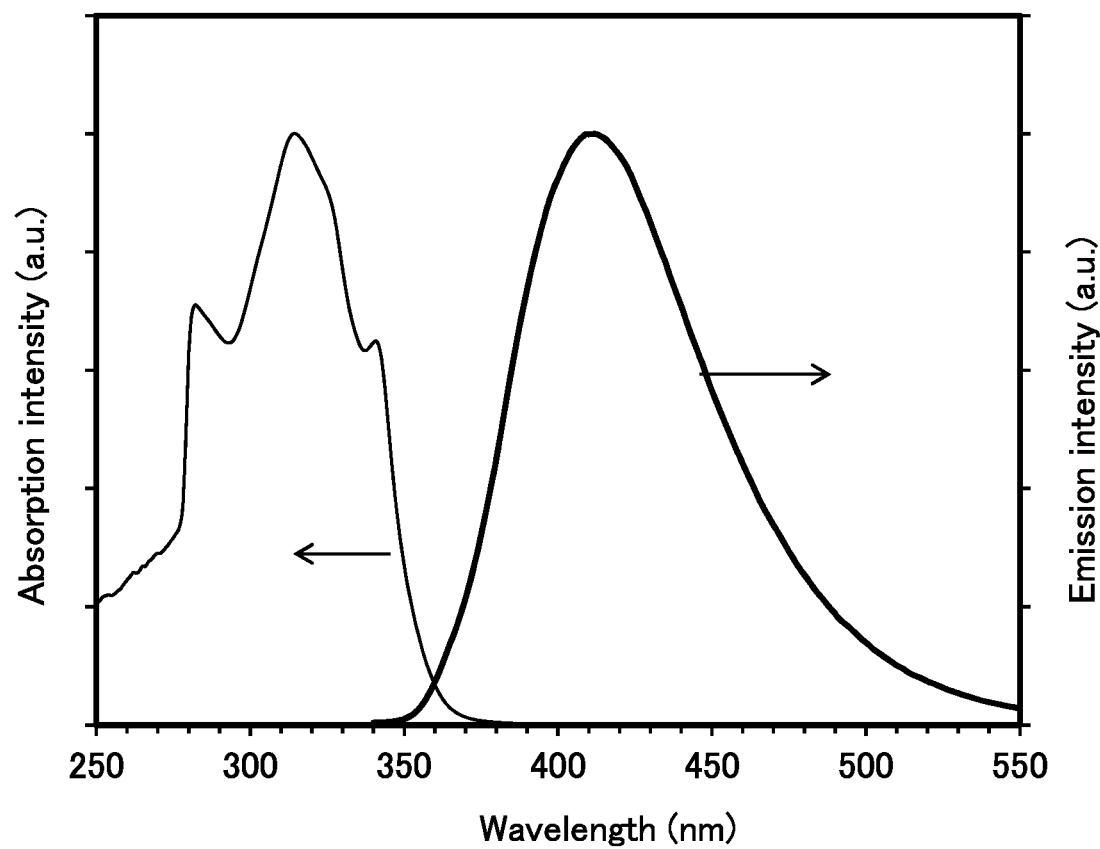
FIG. 69 shows an absorption spectrum and an emission spectrum of oFBi(4)Bnf(8) in a toluene solution.
Figure 70:
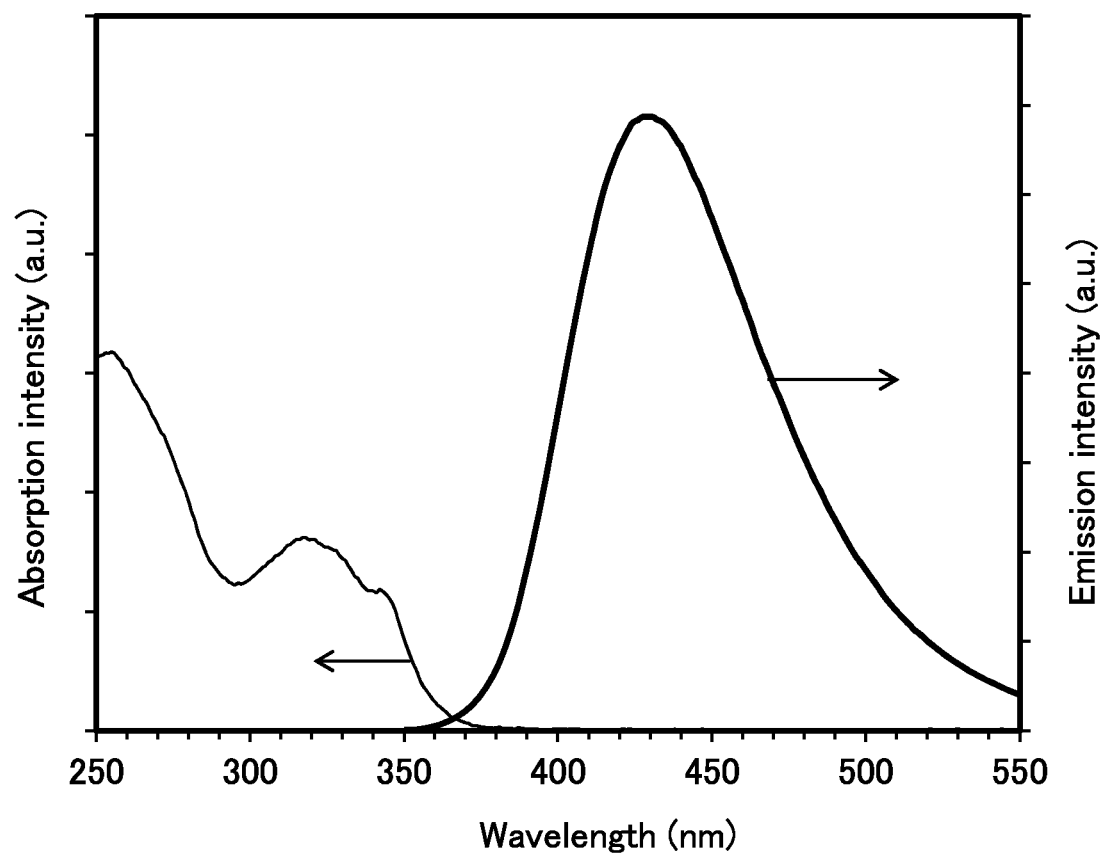
FIG. 70 shows an absorption spectrum and an emission spectrum of a thin film of oFBi(4)Bnf(8).

FIG. 69 shows the obtained measurement results of the absorption spectrum and the emission spectrum of the toluene solution. The horizontal axis represents wavelength and the vertical axes represent absorption intensity and emission intensity. FIG. 70 shows the measurement results of the absorption spectrum and the emission spectrum of the solid thin film. The horizontal axis represents wavelength and the vertical axes represent absorption intensity and emission intensity.

From the results in FIG. 69, for the toluene solution of oFBi(4)Bnf(8), the absorption peaks were observed at around 341 nm, 327 nm, and 314 nm, and the emission wavelength peak was observed at around 412 nm (excitation wavelength: 330 nm). From the results in FIG. 70, for the solid thin film of oFBi(4)Bnf(8), the absorption peaks were

154 observed at around 342 nm and 318 nm, and the emission wavelength peak was observed at around 428 nm (excitation wavelength: 340 nm).

The HOMO level and the LUMO level of oFBi(4)Bnf(8) were calculated on the basis of a cyclic voltammetry (CV) measurement. The calculation method, the measurement method, and the measurement apparatus are the same as those in Example 1; therefore, repeated description will be omitted.

As a result, in the measurement of the oxidation potential Ea [V] of oFBi(4)Bnf(8), the HOMO level was found to be −5.41 eV. Meanwhile, in the measurement of the reduction potential Ec [V], the LUMO level was found to be −2.35 eV. In addition, in repetitive measurement of the oxidation-reduction wave, when the waveform of the first cycle was compared with that of the hundredth cycle, 85% of the peak intensity and 88% of the peak intensity were maintained in the Ea measurement and the Ec measurement, respectively, which confirmed that oFBi(4)Bnf(8) had extremely high resistance to oxidation and reduction.

Differential scanning calorimetry (DSC measurement) was performed on oFBi(4)Bnf(8) by DSC8231-SL manufactured by Rigaku Corporation. The differential scanning calorimetry was performed in the following manner: the temperature was raised from 0° C. to 250° C. at a temperature rising rate of 10° C./min and held at the temperature for one minute, and then the temperature was decreased to 0° C. at a temperature decreasing rate of 10° C./min. This operation was performed three times in succession. It was revealed from the result of the second cycle of the DSC measurement that the glass transition point of oFBi(4)Bnf(8) was 101° C., that is, oFBi(4)Bnf(8) was a substance with extremely high heat resistance.

Then, thermogravimetry-differential thermal analysis of oFBi(4)Bnf(8) was performed. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 343° C., which shows that oFBi(4)Bnf(8) is a substance with favorable sublimability.

From the above results, it was found that the organic compound of one embodiment of the present invention has both high heat resistance and favorable sublimability, and can provide an organic optical device (a light-emitting device and a light-receiving device) with high heat resistance and increase the productivity of device manufacturing.

Example 12

In this example, the light-emitting device of one embodiment of the present invention described in the embodiment will be described. The structural formulae of organic compounds used in this example are shown below.

[Chemical Formulae 69]
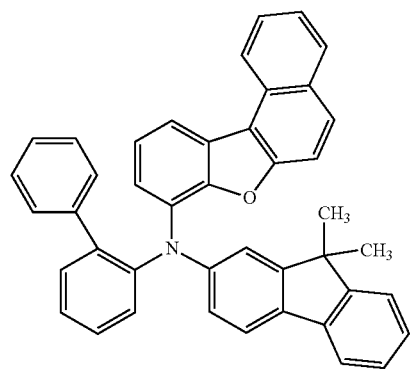
oFBiBnf(8) (xii)
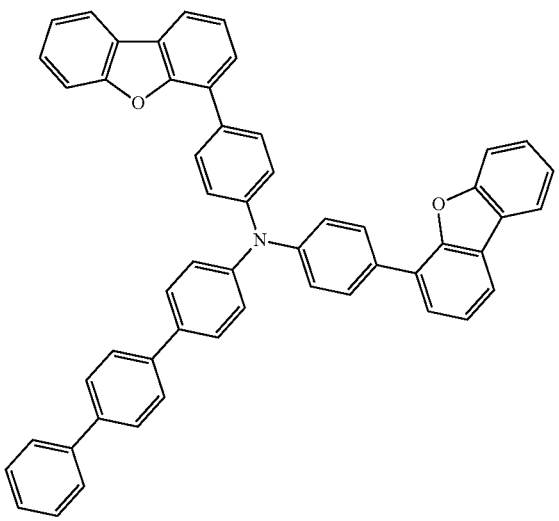
DBfBB1TP (xiii)
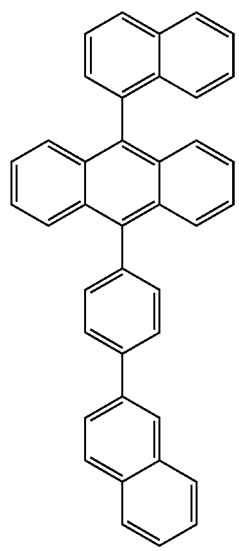
αN-βNPAnth (xiv)
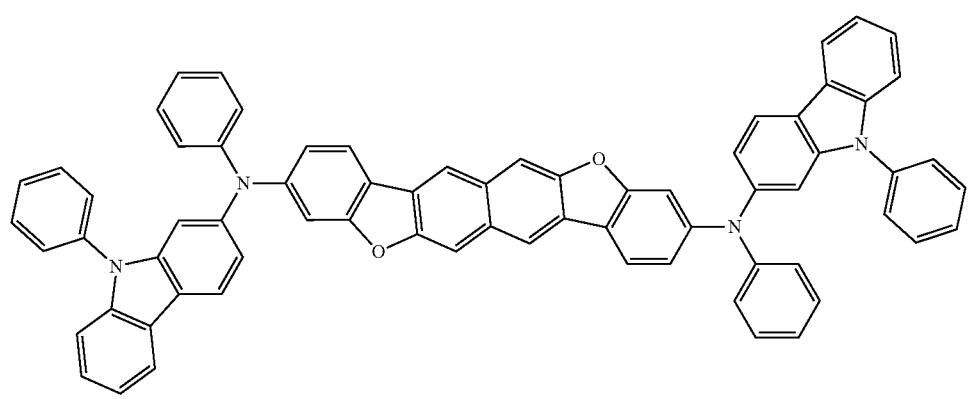
3,10PCA2Nbf(IV)-02 (x)

-continued

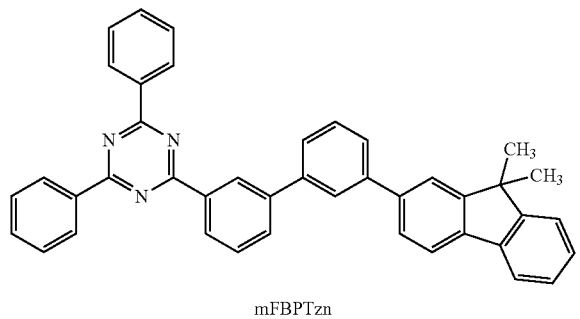

mFBPTzn
(xv)

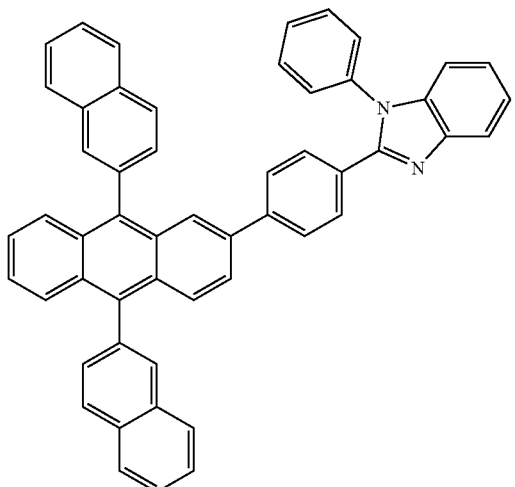

ZADN
(xvi)

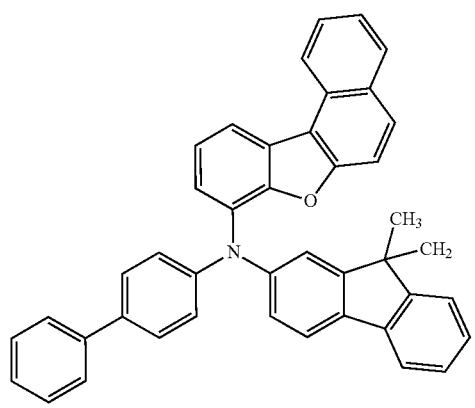

FBiBnf(8)
(xviii)

Liq
(xvii)

(Method for Fabricating Light-Emitting Device 7)

First, indium tin oxide containing silicon oxide (ITSO) was deposited over a glass substrate by a sputtering method, so that the first electrode 101 was formed. Note that the film thickness was 110 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-2-yl)-N-(9,9-dimethyl-9H-fluoren-2-yl)-benzo[b]naphtho[1,2-d]furan-8-amine (abbreviation: oFBiBnf(8)) represented by Structural Formula (xii) above and ALD-MP001Q (manufactured by Analysis Atelier Corporation, material serial No. 1S20180314) were co-evaporated over the first electrode 101 to have a weight ratio of 1:0.1 (=oFBiBnf(8): ALD-MP001Q) to a thickness of 10 nm by an evaporation method using resistance heating, whereby the hole-injection layer 111 was formed.

Subsequently, over the hole-injection layer 111, oFBiBnf (8) was deposited by evaporation to a thickness of 20 nm, and then N,N-bis[4-(dibenzofuran-4-yl)phenyl]-4-amino-p- terphenyl (abbreviation: DBfBB1TP) represented by Structural Formula (xiii) above was deposited by evaporation to a thickness of 10 nm, whereby the hole-transport layer 112 was formed.

Subsequently, 9-(1-naphthyl)-10-[4-(2-naphthyl)phenyl]anthracene (abbreviation: α,N-βNPAnth) represented by Structural Formula (xiv) above and 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02) represented by Structural Formula (x) above were co-evaporated to a thickness of 25 nm at a weight ratio of 1:0.015 (=α,N-βNPAnth: 3,10PCA2Nbf(IV)-02), whereby the light-emitting layer 113 was formed.

After that, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (xv) above was formed to a thickness of 10 nm, and then 2-{4-[9,10-di(naphthalen-2-yl)-2-anthryl]phenyl}-1-phenyl-1H-benzoimidazole (abbreviation: ZADN) represented by Structural Formula (xvi) above and 8-quinolinolatolithium (abbreviation: Liq) represented by Structural Formula (xvii) above were co-evaporated to a thickness of 15 nm at a weight ratio of 1:1, whereby the electron-transport layer 114 was formed.

After the formation of the electron-transport layer 114, aluminum was deposited by evaporation to a thickness of 200 nm to form the second electrode 102, whereby a light-emitting device 7 of this example was fabricated.

(Method for Fabricating Light-Emitting Device 8)

A light-emitting device 8 was fabricated in a manner similar to that of the light-emitting device 7 except that N-(1,1'-biphenyl-4-yl)-N-(9,9-dimethyl-9H-fluoren-2-yl)benzo[b]naphtho[1,2-d]furan-8-amine (abbreviation: FBiBnf(8)) represented by Structural Formula (xvii) above was used instead of oFBiBnf(8) in the light-emitting device 7.

The element structures of the light-emitting devices are listed in the following tables.

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 71:
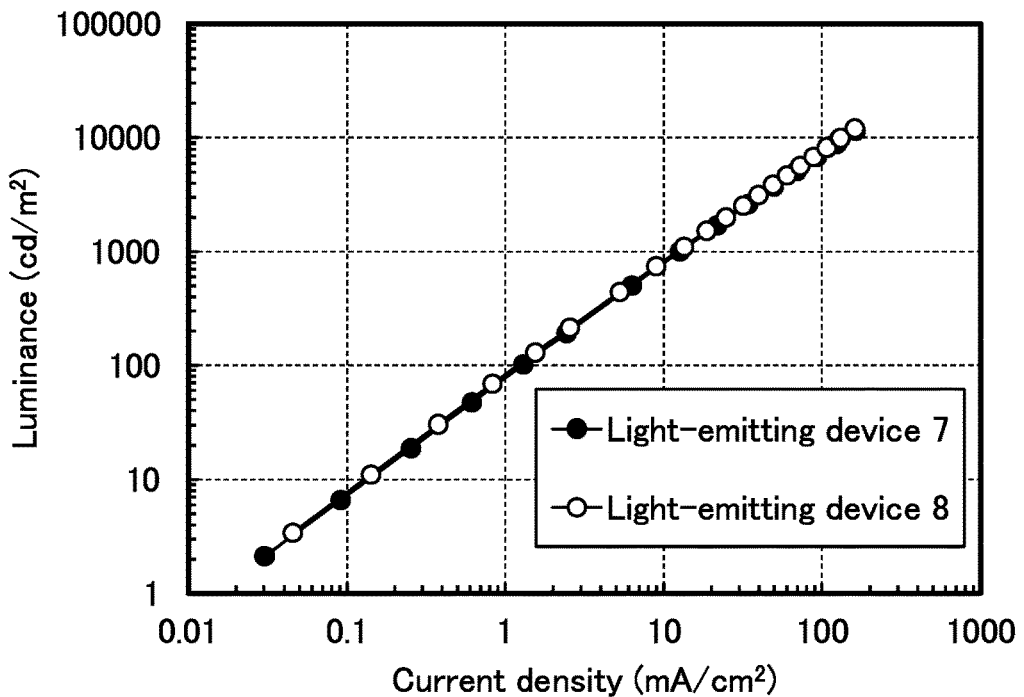
FIG. 71 shows luminance-current density characteristics of a light-emitting device 7 and a light-emitting device 8.
Figure 72:
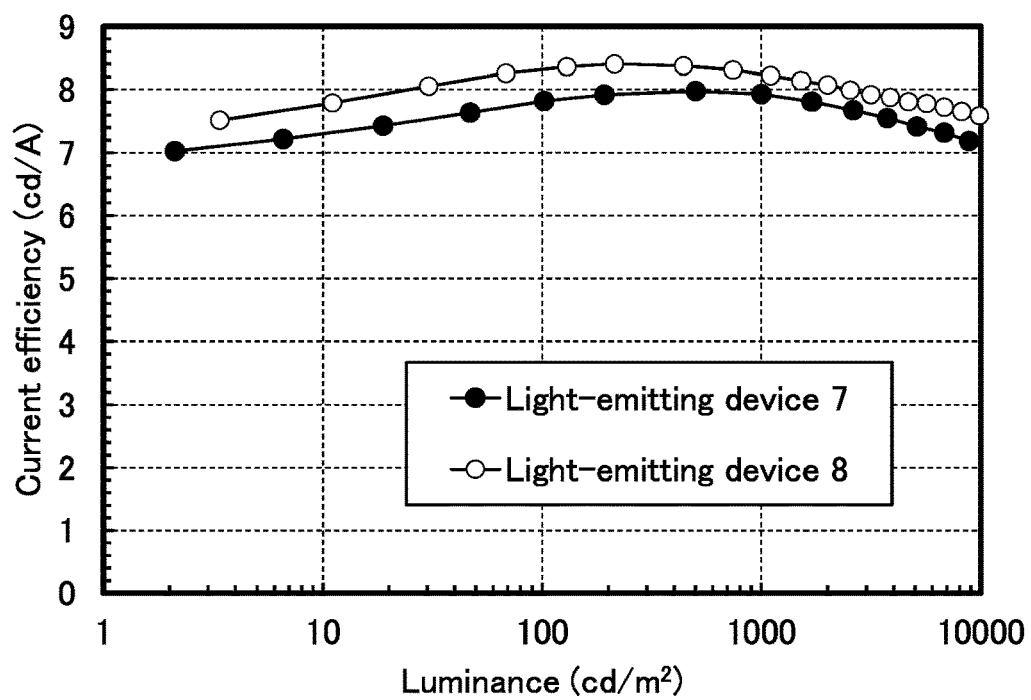
FIG. 72 shows current efficiency-luminance characteristics of the light-emitting device 7 and the light-emitting device 8.
Figure 73:
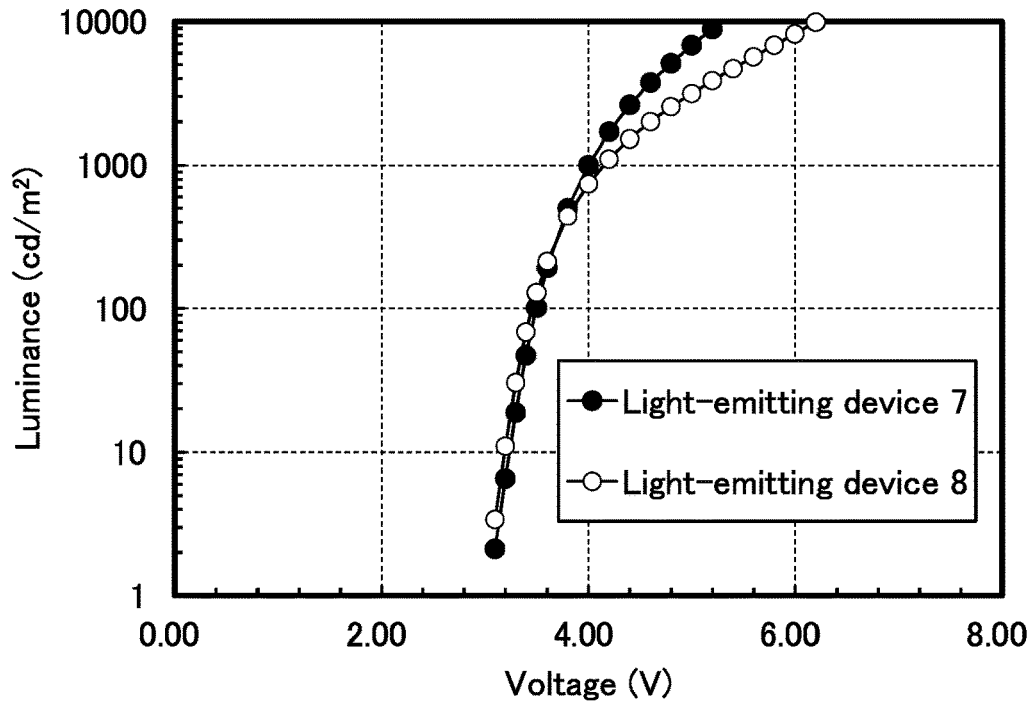
FIG. 73 shows luminance-voltage-characteristics of the light-emitting device 7 and the light-emitting device 8.
Figure 74:
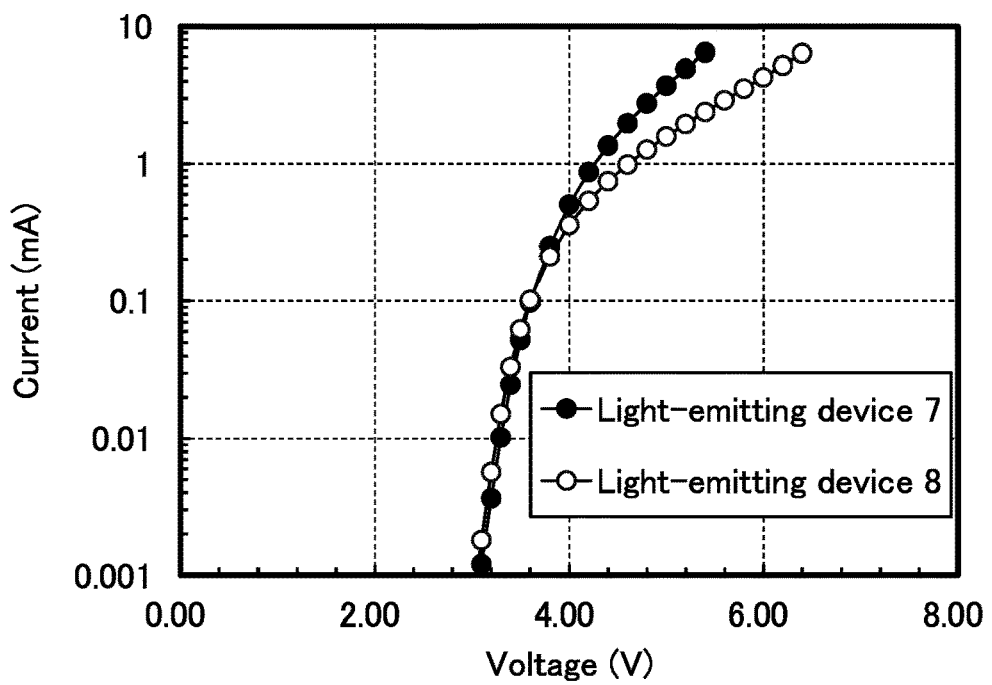
FIG. 74 shows current-voltage characteristics of the light-emitting device 7 and the light-emitting device 8.
Figure 75:
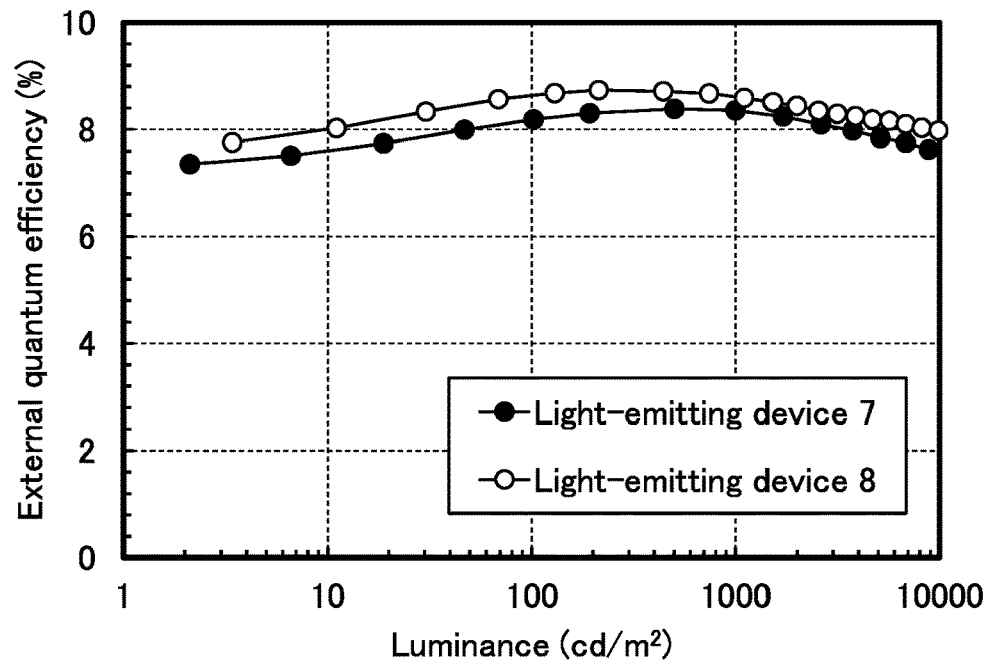
FIG. 75 shows external quantum efficiency-luminance characteristics of the light-emitting device 7 and the light-emitting device 8.
Figure 76:
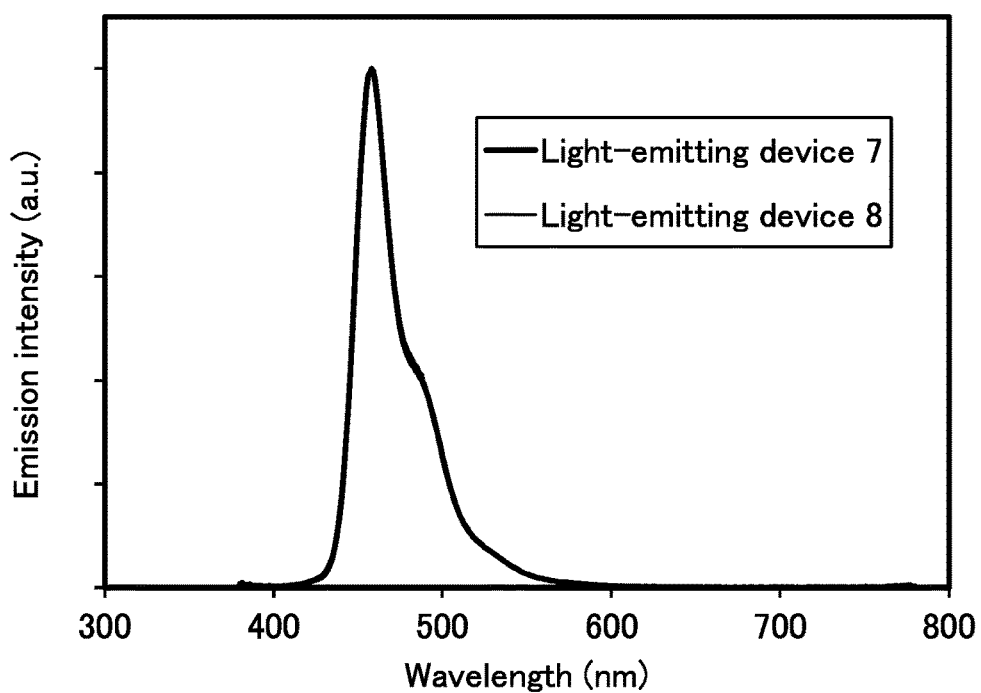
FIG. 76 shows emission spectra of the light-emitting device 7 and the light-emitting device 8.

FIG. 71 shows the luminance-current density characteristics of the light-emitting device 7 and the light-emitting device 8; FIG. 72, the current efficiency-luminance characteristics; FIG. 73, the luminance-voltage characteristics; FIG. 74, the current-voltage characteristics; FIG. 75, the external quantum efficiency-luminance characteristics; and FIG. 76, the emission spectra. Main characteristics of the light-emitting devices at approximately 1000 cd/m$^2$ are listed below.

TABLE 12

|  | voltage (V) | current (mA) | current density (mA/cm$^2$) | chromaticity x | chromaticity y | current efficiency (cd/A) | external quantum efficiency (%) |
|---|---|---|---|---|---|---|---|
| light-emitting device 7 | 4.0 | 0.51 | 12.6 | 0.14 | 0.11 | 7.9 | 8.4 |
| light-emitting device 8 | 4.2 | 0.54 | 13.4 | 0.14 | 0.11 | 8.2 | 8.6 |

It was found from FIG. 71 to FIG. 76 that the light-emitting device 7 and the light-emitting device 8 of embodiments of the present invention are EL devices with high emission efficiency.

Figure 77:
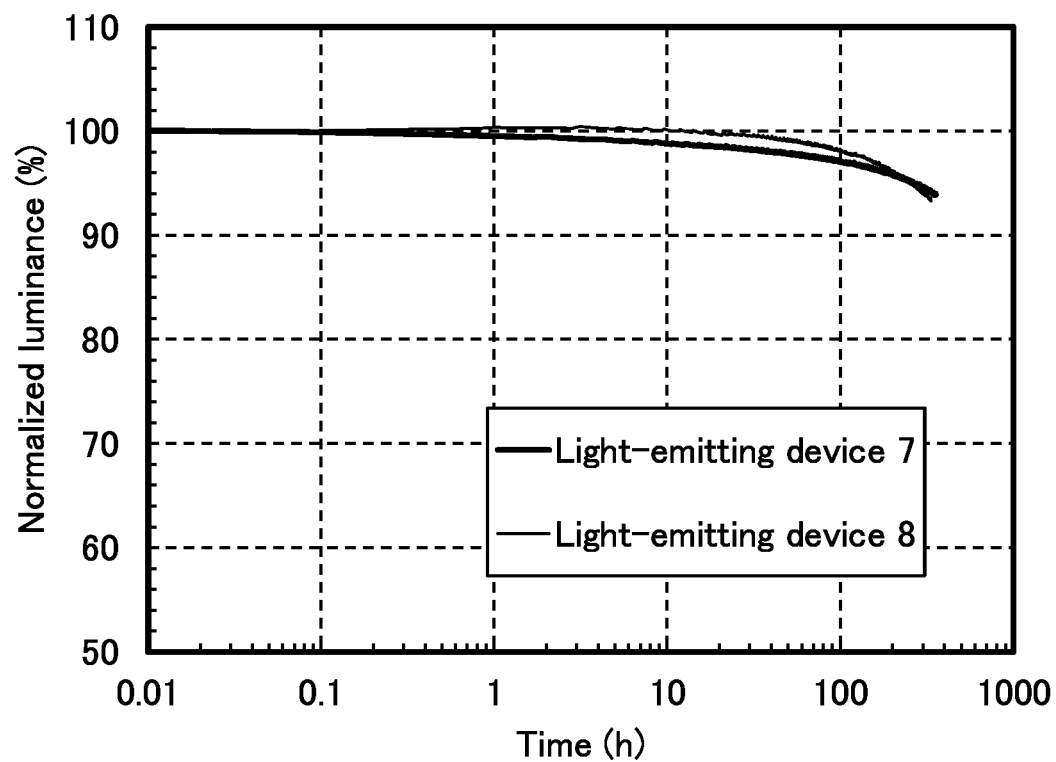
FIG. 77 shows normalized luminance-temporal change characteristics of the light-emitting device 7 and the light-emitting device 8.

FIG. 77 is a graph showing a change in luminance over driving time at a current density of 50 mA/cm$^2$. As shown in FIG. 77, the light-emitting device 7 and the light-emitting device 8, which are the light-emitting devices of embodiments of the present invention, were found to be light-emitting devices with a long lifetime.

Example 13

In this example, the light-emitting device of one embodiment of the present invention described in the embodiment will be described. The structural formulae of organic compounds used in this example are shown below.

TABLE 11

|  | hole-injection layer 10 nm | hole-transport layer 1 20 nm | hole-transport layer 2 10 nm | light-emitting layer 25 nm | electron-transport layer 1 10 nm | electron-transport layer 2 15 nm |
|---|---|---|---|---|---|---|
| light-emitting device 7 | oFBiBnf(8): ALD-MP001Q (1:0.1) | oFBiBnf(8) | DBfBB1TP | αN-βNPAnth: 3,10PCA2Nbf(IV)-02 (1:0.015) | mFBPTzn | ZADN: Liq (1:1) |
| light-emitting device 8 | FBiBnf(8); ALD-MP001Q (1:0.1) | FBiBnf(8) |  |  |  |  |

[Chemical Formulae 70]
(xviii)
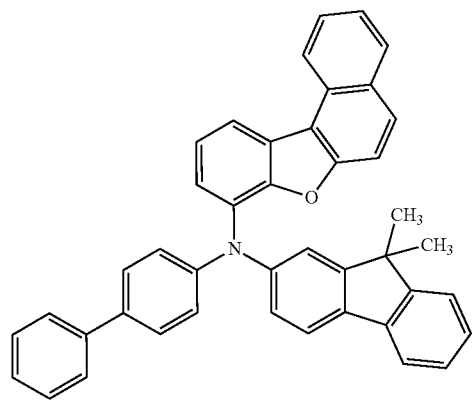
FBiBnf(8)
(ii)
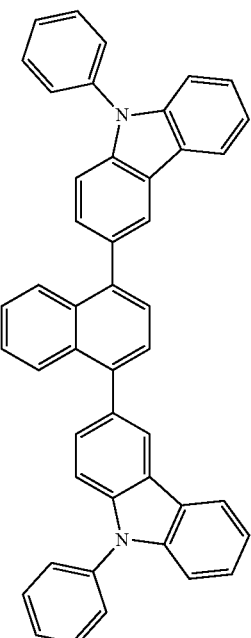
PCzN2
(xiv)
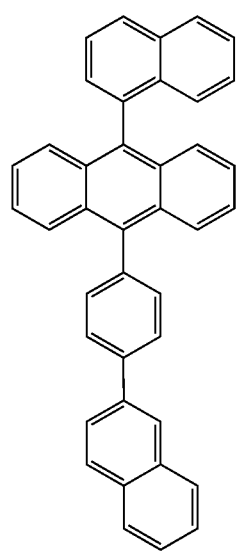
αN-βNPAnth -continued

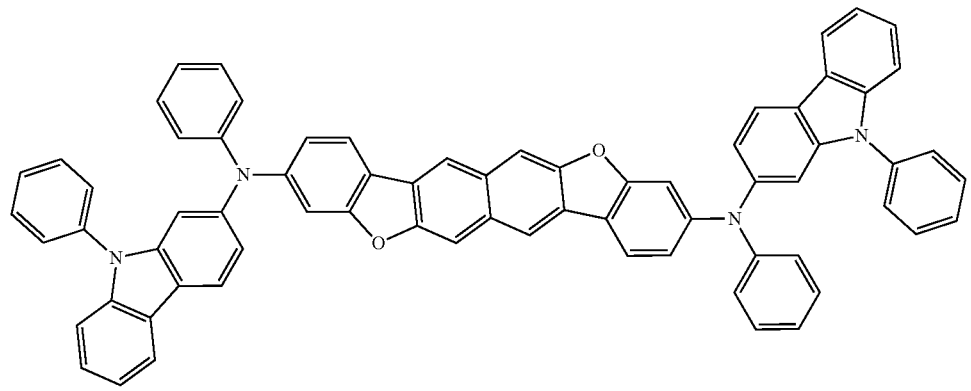

3,10PCA2Nbf(IV)-02

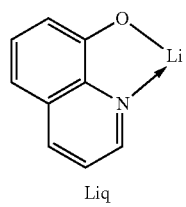

Liq

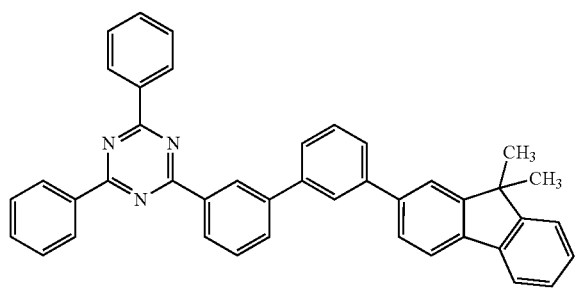

mFBPTzn

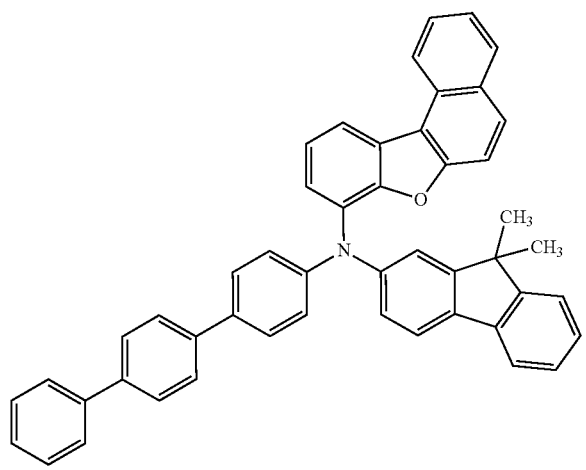

FTPBnf(8)

(Method for Fabricating Light-Emitting Device 9)

First, indium tin oxide containing silicon oxide (ITSO) was deposited over a glass substrate by a sputtering method, so that the first electrode 101 was formed. Note that the film thickness was 110 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately 10-4 Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-4-yl)-N-(9,9-dimethyl-9H-fluoren-2-yl)-benzo[b]naphtho[1,2-d]furan-8-amine (abbreviation: FBiBnf(8)) represented by Structural Formula (xvii) above and ALD-MP001Q (manufactured by Analysis Atelier Corporation, material serial No. 1S20180314) were co-evaporated over the first electrode 101 to have a weight ratio of 1:0.1 (=FBiBnf(8): ALD-MP001Q) to a thickness of 10 nm by an evaporation method using resistance heating, whereby the hole-injection layer 111 was formed.

Subsequently, over the hole-injection layer 111, FBiBnf (8) was deposited by evaporation to a thickness of 90 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Subsequently, 9-(1-naphthyl)-10-[4-(2-naphthyl)phenyl] anthracene (abbreviation: α,N-βNPAnth) represented by Structural Formula (xiv) above and 3,10-bis[N-(9-phenyl-9H-carbazol-2-yl)-N-phenylamino]naphtho[2,3-b; 6,7-b'] bisbenzofuran (abbreviation: 3,10PCA2Nbf(IV)-02) represented by Structural Formula (x) above were co-evaporated to a thickness of 25 nm at a weight ratio of 1:0.015 (=α,N-βNPAnth: 3,10PCA2Nbf(IV)-02), whereby the light-emitting layer 113 was formed.

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 78:
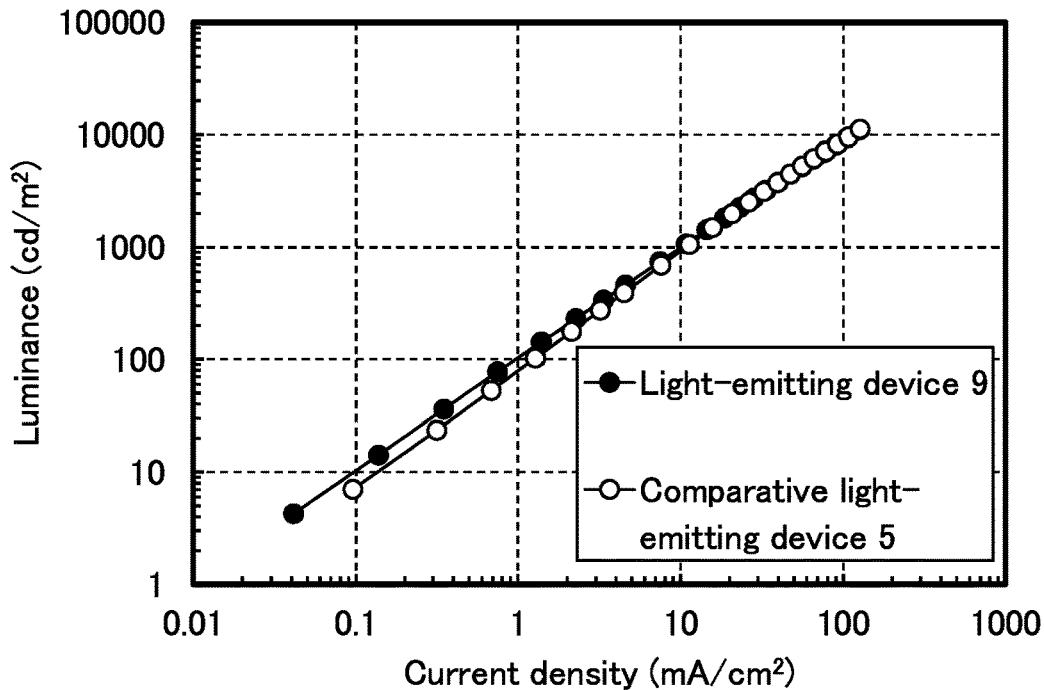
FIG. 78 shows luminance-current density characteristics of a light-emitting device 9 and a comparative light-emitting device 5.
Figure 79:
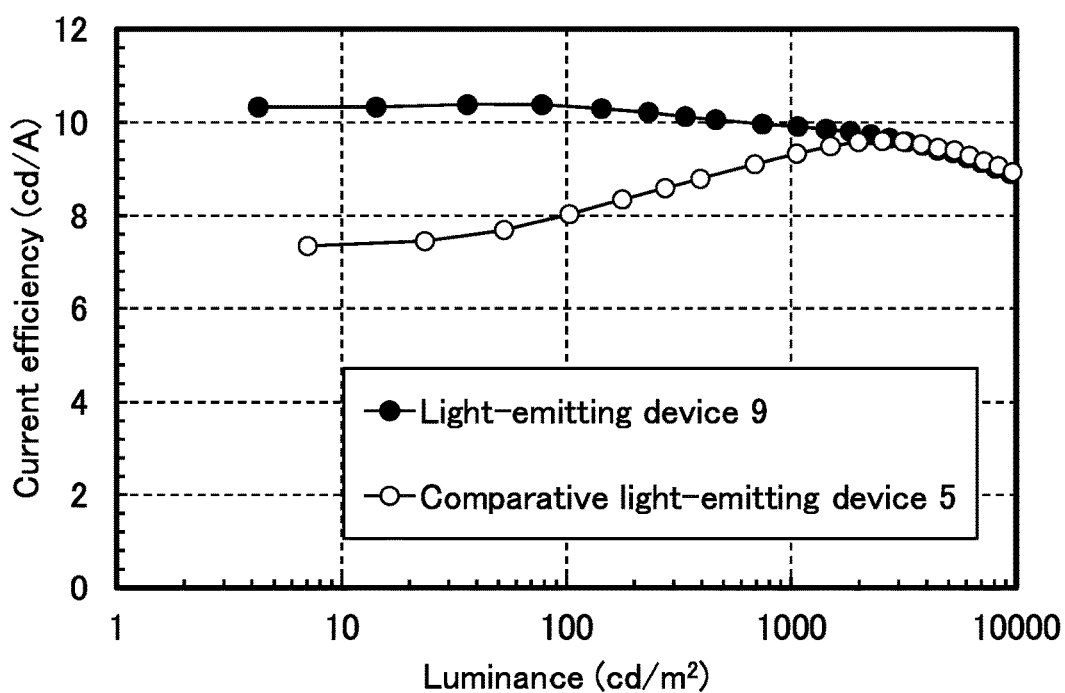
FIG. 79 shows current efficiency-luminance characteristics of the light-emitting device 9 and the comparative light-emitting device 5.
Figure 80:
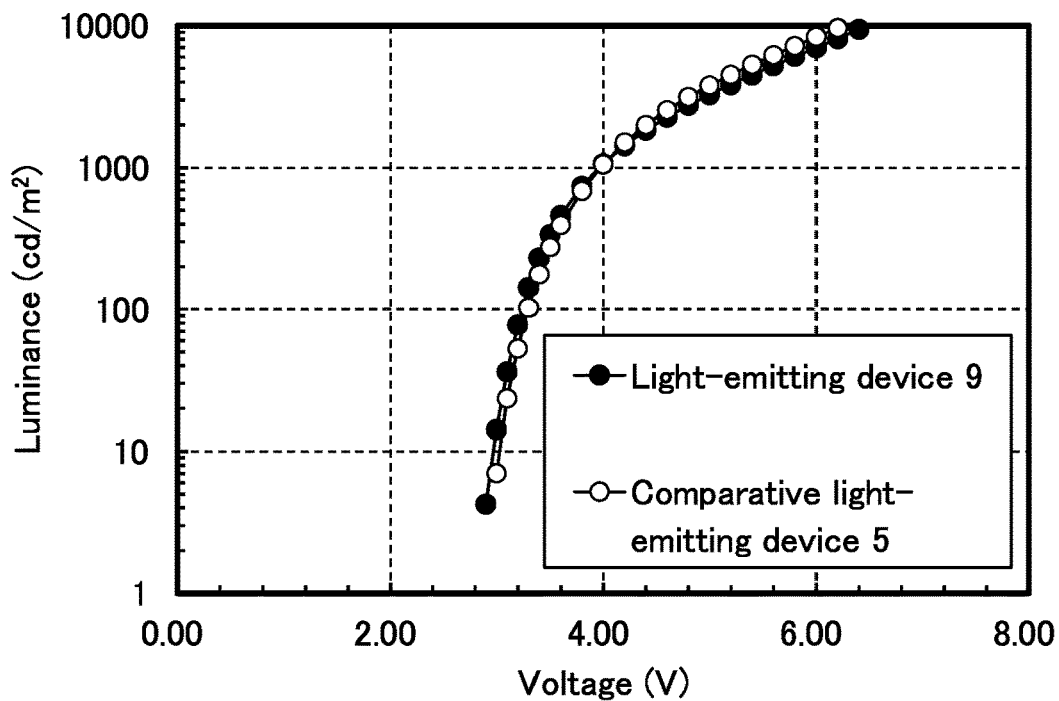
FIG. 80 shows luminance-voltage characteristics of the light-emitting device 9 and the comparative light-emitting device 5.
Figure 81:
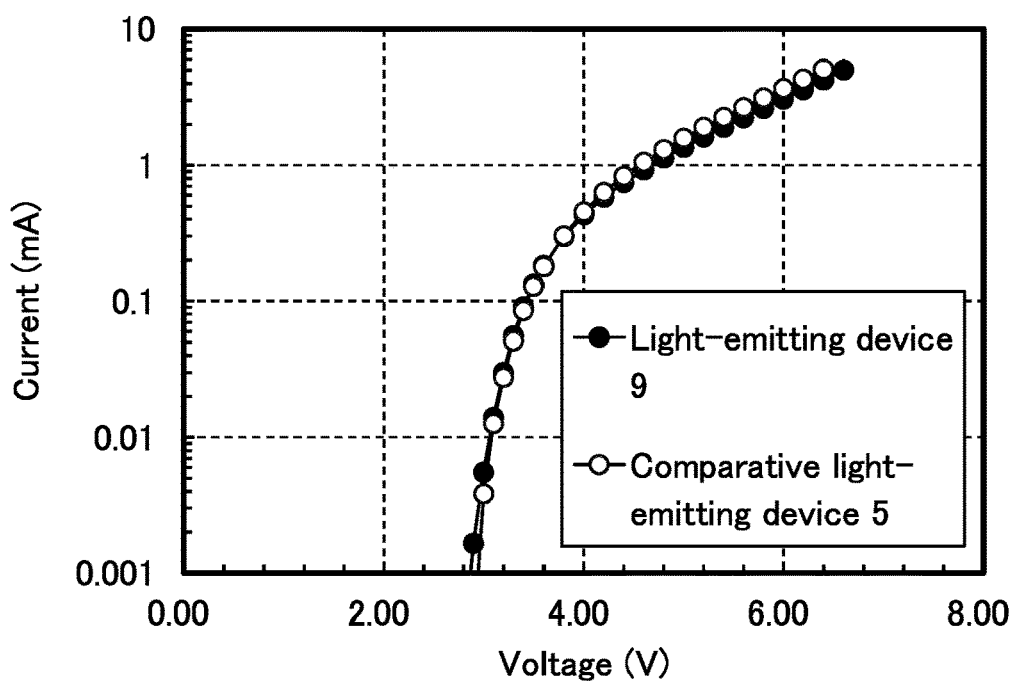
FIG. 81 shows current-voltage characteristics of the light-emitting device 9 and the comparative light-emitting device 5.
Figure 82:
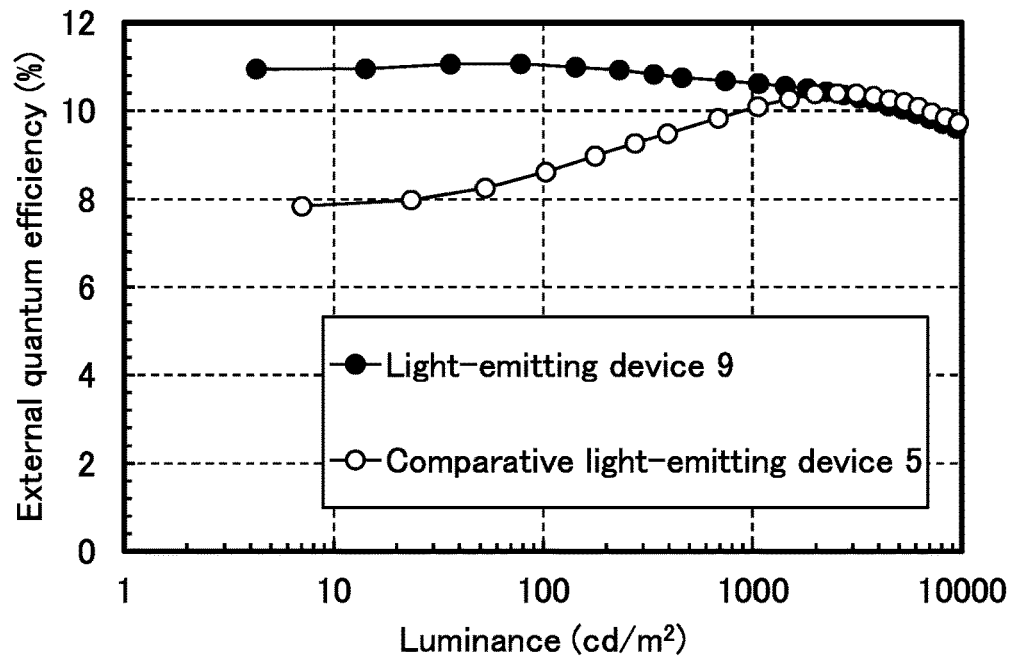
FIG. 82 shows external quantum efficiency-luminance characteristics of the light-emitting device 9 and the comparative light-emitting device 5.
Figure 83:
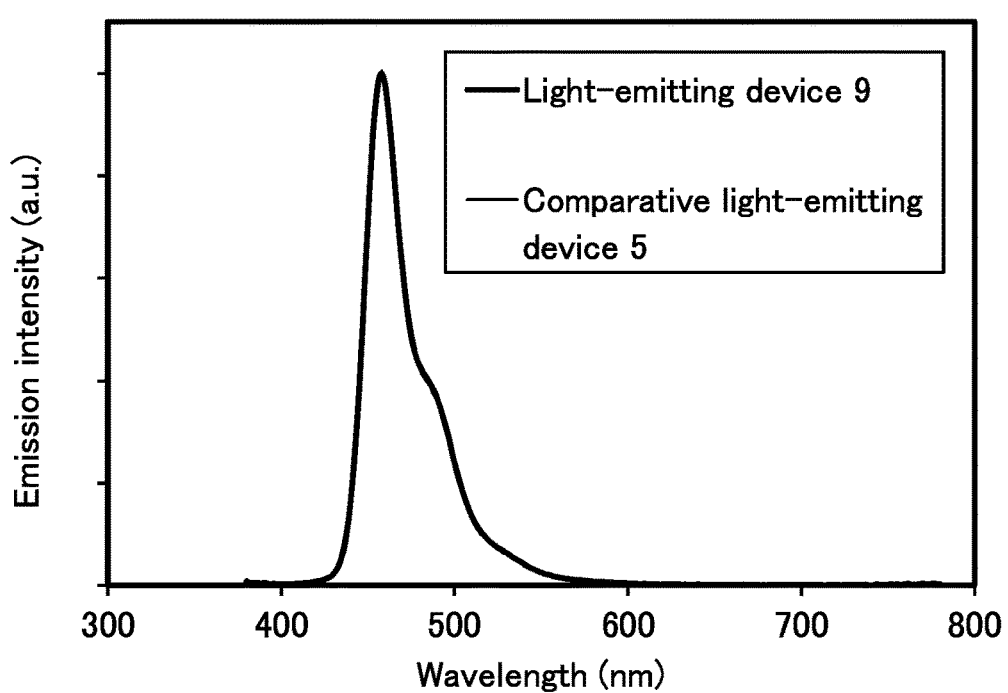
FIG. 83 shows emission spectra of the light-emitting device 9 and the comparative light-emitting device 5.

FIG. 78 shows the luminance-current density characteristics of the light-emitting device 9 and the comparative light-emitting device 5; FIG. 79, the current efficiency-luminance characteristics; FIG. 80, the luminance-voltage characteristics; FIG. 81, the current-voltage characteristics; FIG. 82, the external quantum efficiency-luminance characteristics; and FIG. 83, the emission spectra. Main characteristics of the light-emitting devices at approximately 1000 cd/m$^2$ are listed below.

TABLE 14

| | voltage (V) | current (mA) | current density (mA/cm$^2$) | chromaticity x | chromaticity y | current efficiency (cd/A) | external quantum efficiency (%) |
|---|---|---|---|---|---|---|---|
| light-emitting device 9 | 4.0 | 0.43 | 10.8 | 0.14 | 0.11 | 9.9 | 10.6 |
| comparative light-emitting device 5 | 4.0 | 0.45 | 11.3 | 0.14 | 0.11 | 9.3 | 10.1 |

After that, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (xv) above was formed to a thickness of 10 nm, and then ALD-MC057Q (manufactured by Analysis Atelier Corporation, material serial No. 1S20190330) and 8-hydroxyquinolinolato-lithium (abbreviation: Liq) represented by Structural Formula (xvii) above were co-evaporated to a thickness of 15 nm at a weight ratio of 1:1, whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102, whereby a light-emitting device 9 of this example was fabricated.

(Method for Fabricating Comparative Light-Emitting Device 5)

A comparative light-emitting device 5 was fabricated in a manner similar to that of the light-emitting device 9 except that N-(9,9-dimethyl-9H-fluoren-2-yl)-N-(1,1':4',1''-terphenyl-4-yl)-benzo[b]naphtho[1,2-d]furan-8-amine (abbreviation: FTPBnf(8)) represented by Structural Formula (xix) above was used instead of FBiBnf(8) in the light-emitting device 9.

The element structures of the light-emitting devices are listed in the following tables.

It was found from FIG. 78 to FIG. 83 that the light-emitting device 9 of one embodiment of the present invention is an EL device with high emission efficiency and exhibiting high emission efficiency even in a low-luminance region.

Figure 84:
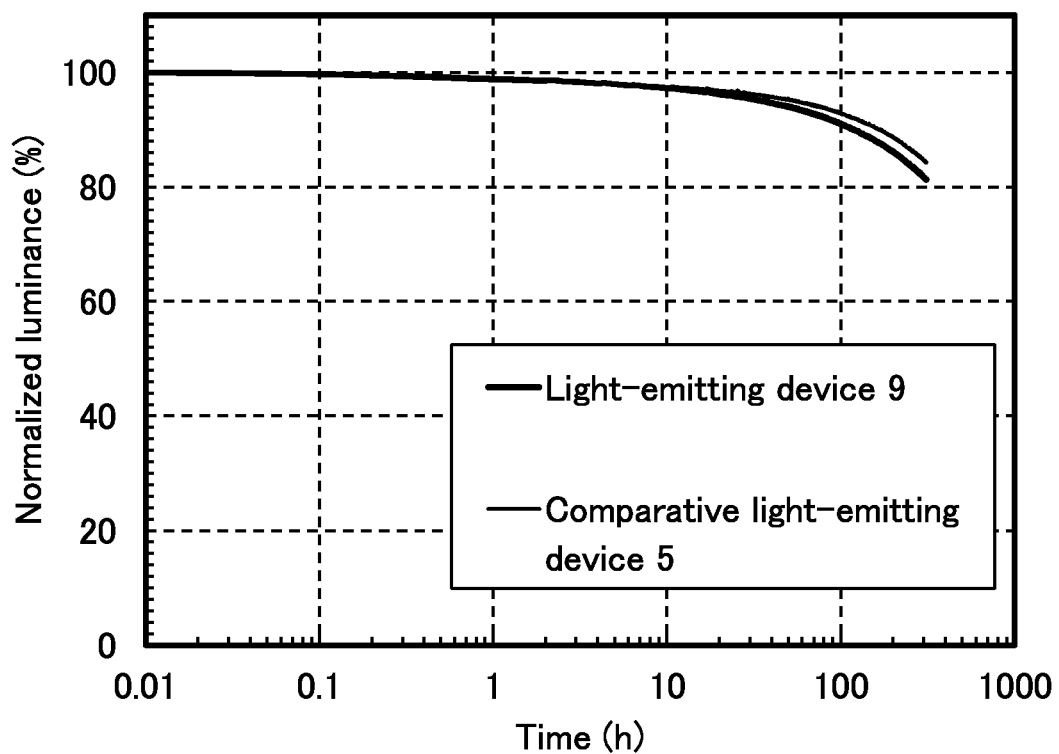
FIG. 84 shows normalized luminance-temporal change characteristics of the light-emitting device 9 and the comparative light-emitting device 5.

FIG. 84 is a graph showing a change in luminance over driving time at a current density of 50 mA/cm$^2$. As shown in FIG. 84, the light-emitting device 9 and the comparative light-emitting device 5 are light-emitting devices with a long lifetime.

Example 14

In this example, the light-emitting device of one embodiment of the present invention described in the embodiment will be described. The structural formulae of organic compounds used in this example are shown below.

TABLE 13

| | hole-injection layer 10 nm | hole-transport layer 1 90 nm | hole-transport layer 2 10 nm | light-emitting layer 25 nm | electron-transport layer hole-injection layer 10 nm | electron-transport layer 1 15 nm |
|---|---|---|---|---|---|---|
| light-emitting device 9 | FBiBnf(8): ALD-MP001Q (1:0.1) | FBiBnf(8) | PCzN2 | αN-βNPAnth: 3,10PCA2Nbf(IV)-02 (1:0.015) | mFBPTzn | ALD-MC057Q: Liq (1:1) |
| comparative light-emitting device 5 | FTPBnf(8): ALD-MP001Q (1:0.1) | FTPBnf(8) | | | | |

[Chemical Formulae 71]
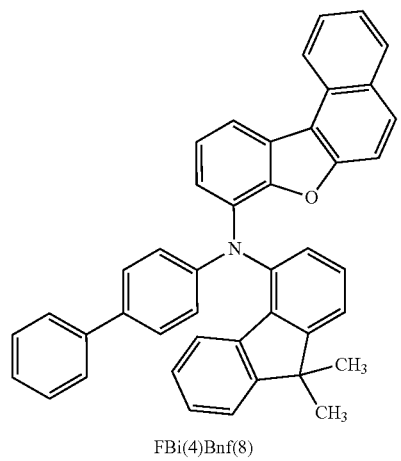
FBi(4)Bnf(8)
(xx)
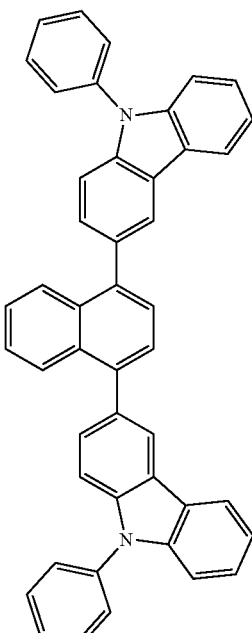
PCzN2
(ii)
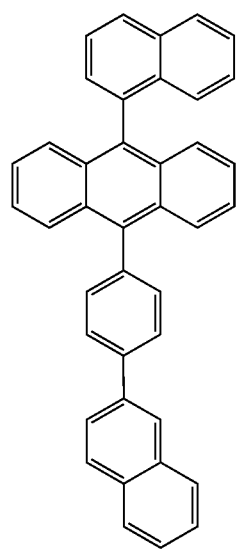
αN-βNPAnth
(xiv)

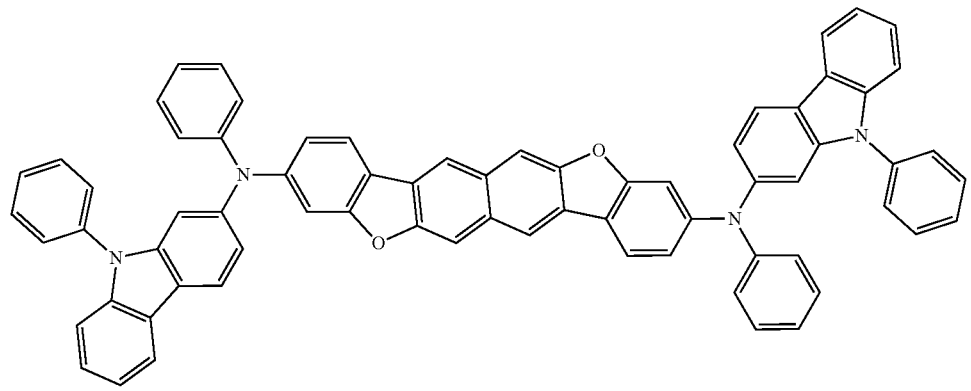

3,10PCA2Nbf(IV)-02 (x)

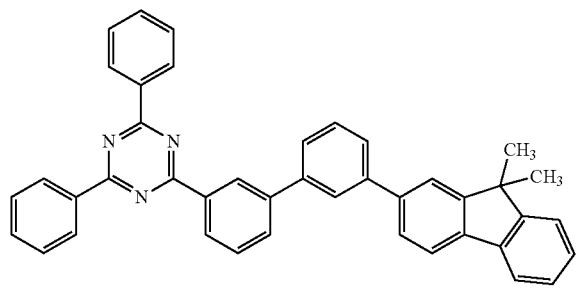

mFBPTzn (xv)

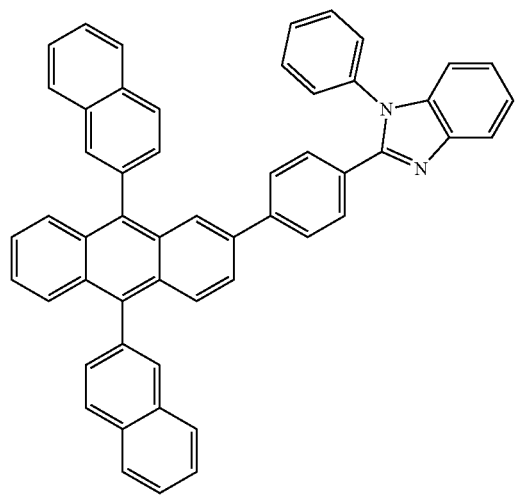

ZADN (xvi)

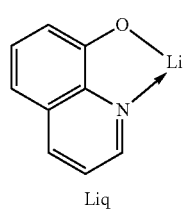

Liq (xvii)

(Method for Fabricating Light-Emitting Device 10)

First, indium tin oxide containing silicon oxide (ITSO) was deposited over a glass substrate by a sputtering method, so that the first electrode 101 was formed. Note that the film thickness was 110 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and N-(1,1'-biphenyl-4-yl)-N-(9,9-dimethyl-9H-fluoren-4-yl)-benzo[b]naphtho[1,2-d]furan-8-amine (abbreviation: FBi(4)Bnf(8)) represented by Structural Formula (xx) above and ALD-MP001Q (manufactured by Analysis Atelier Corporation, material serial No. 1S20180314) were co-evaporated over the first electrode 101 to have a weight ratio of 1:0.1 (=FBi(4)Bnf(8): ALD-MP001Q) to a thickness of 10 nm by an evaporation method using resistance heating, whereby the hole-injection layer 111 was formed.

Subsequently, over the hole-injection layer 111, FBi(4)Bnf(8) was deposited by evaporation to a thickness of 90 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Subsequently, 9-(1-naphthyl)-10-[4-(2-naphthyl)phenyl]anthracene (abbreviation: αN-βNPAnth) represented by Structural Formula (xiv) above and 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02) represented by Structural Formula (x) above were co-evaporated to a thickness of 25 nm at a weight ratio of 1:0.015 (=αN-βNPAnth: 3,10PCA2Nbf(IV)-02), whereby the light-emitting layer 113 was formed.

After that, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (xv) above was formed to a thickness of 10 nm, and then 2-{4-[9,10-di(naphthalen-2-yl)-2-anthryl]phenyl}-1-phenyl-1H-benzoimidazole (abbreviation: ZADN) represented by Structural Formula (xvi) above and 8-hydroxyquinolinolato-lithium (abbreviation: Liq) represented by Structural Formula (xvii) above were co-evaporated to a thickness of 15 nm at a weight ratio of 1:1, whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102, whereby a light-emitting device 10 of this example was fabricated.

The element structure of the light-emitting device 10 is listed in the following table.

REFERENCE NUMERALS

101: first electrode, 102: second electrode, 103: EL layer, 111: hole-injection layer, 112: hole-transport layer, 113: light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: first electrode, 614: insulator, 616: EL layer, 617: second electrode, 618: light-emitting device, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode, 1024R: first electrode, 1024G: first electrode, 1024B: first electrode, 1025: partition, 1028: EL layer, 1029: second electrode, 1031: sealing substrate, 1032: sealant, 1033: transparent base material,

TABLE 15

| | hole-injection layer 10 nm | hole-transport layer | | light-emitting layer 25 nm | electron-transport layer | |
|---|---|---|---|---|---|---|
| | | 1 90 nm | 2 10 nm | | 1 10 nm | 2 15 nm |
| light-emitting device 10 | FBi(4)Bnf(8): ALD-MP001Q (1:0.1) | FBi(4)Bnf(8) | PCzN2 | αN-βNPAnth: 3,10PCA2Nbf(IV)-02 (1:0.015) | mFBPTzn | ZADN: Liq (1:1) |

These light-emitting devices were subjected to sealing with a glass substrate (a sealant was applied to surround the elements, and at the time of sealing, UV treatment was performed first and heat treatment was performed at 80° C. for one hour) in a glove box containing a nitrogen atmosphere so that the light-emitting devices were not exposed to the air. Then, the initial characteristics were measured.

Figure 85:
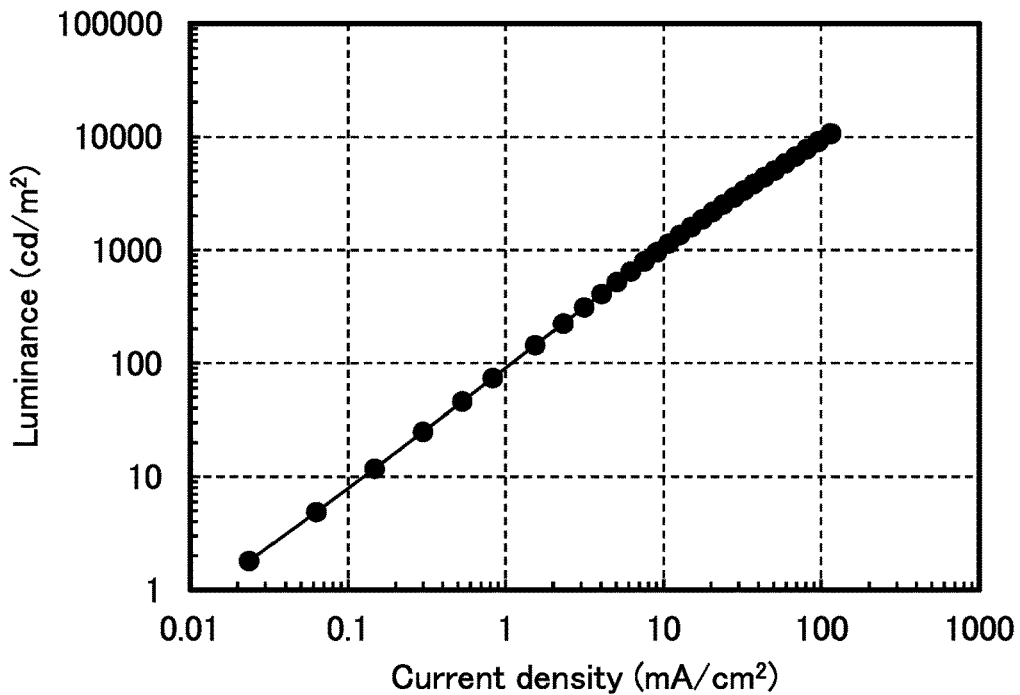
FIG. 85 shows luminance-current density characteristics of a light-emitting device 10.
Figure 86:
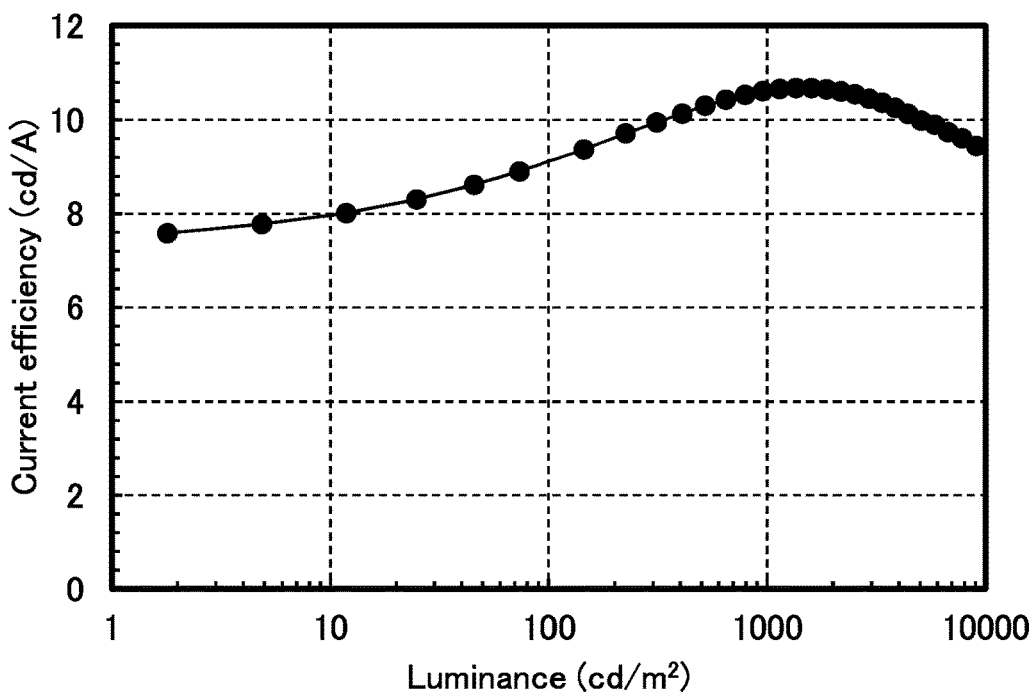
FIG. 86 shows current efficiency-luminance characteristics of the light-emitting device 10.
Figure 87:
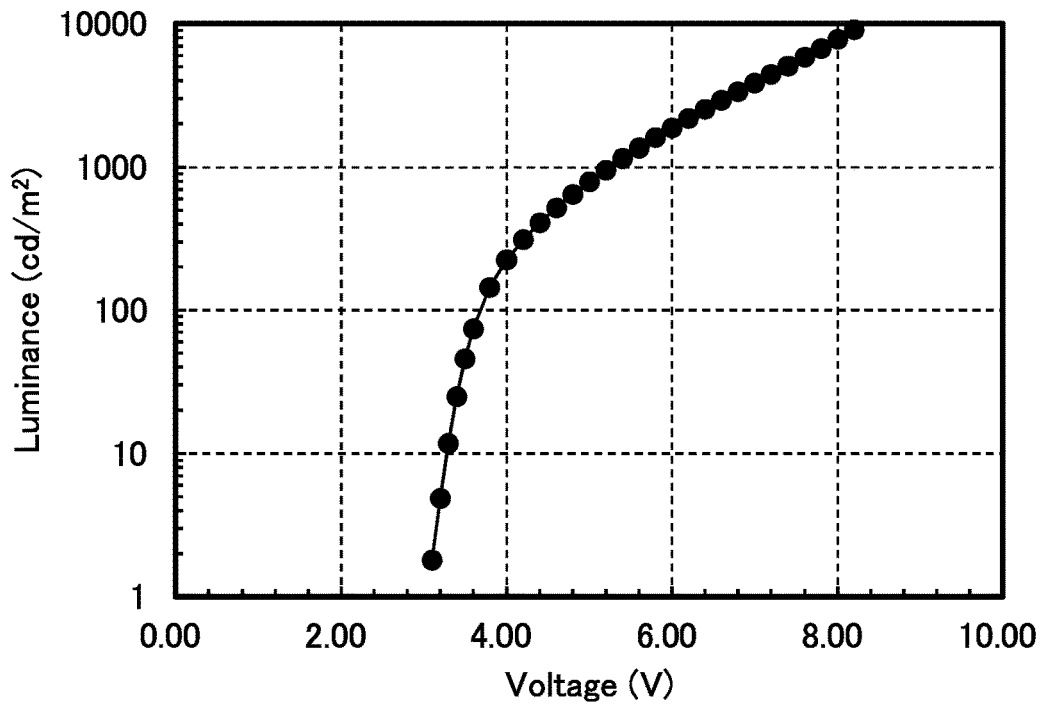
FIG. 87 shows luminance-voltage characteristics of the light-emitting device 10.
Figure 88:
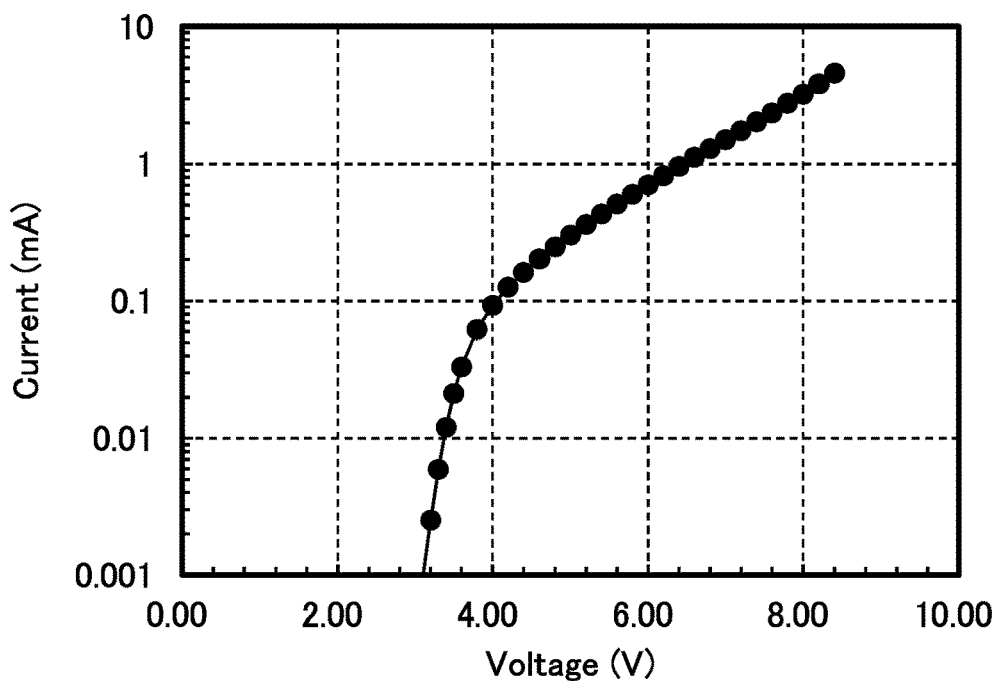
FIG. 88 shows current-voltage characteristics of the light-emitting device 10.
Figure 89:
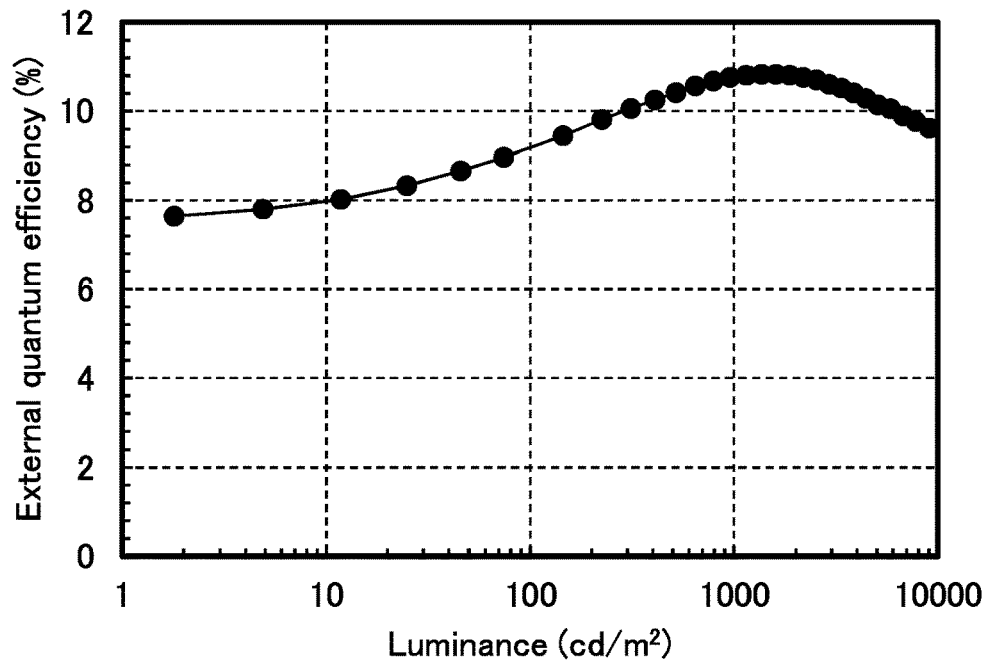
FIG. 89 shows external quantum efficiency-luminance characteristics of the light-emitting device 10.
Figure 90:
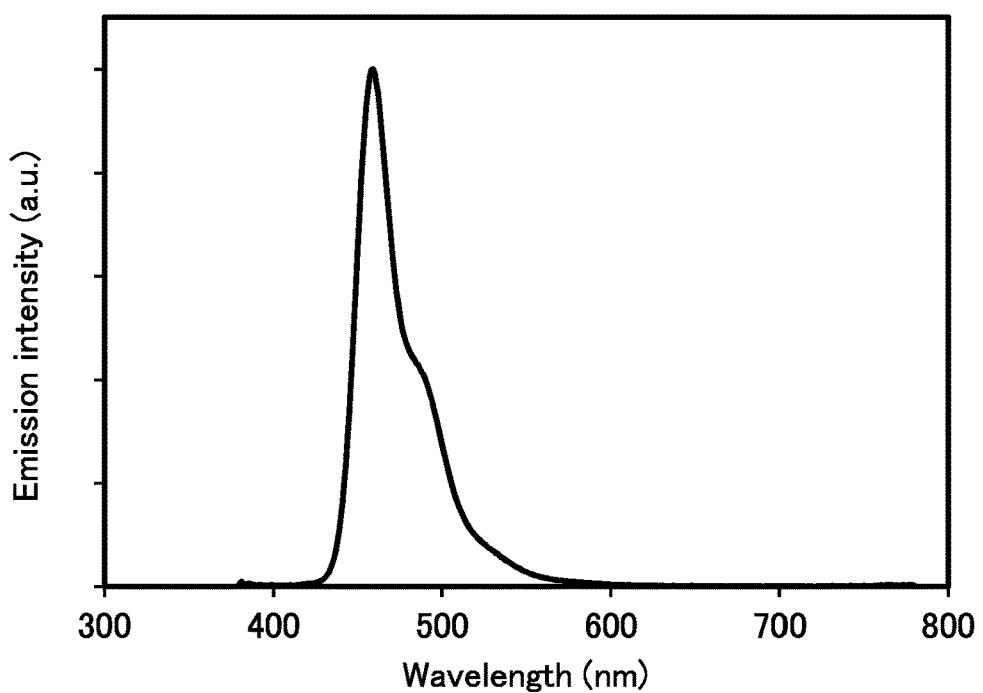
FIG. 90 shows an emission spectrum of the light-emitting device 10.

FIG. 85 shows the luminance-current density characteristics of the light-emitting device 10; FIG. 86, the current efficiency-luminance characteristics; FIG. 87, the luminance-voltage characteristics; FIG. 88, the current-voltage characteristics; FIG. 89, the external quantum efficiency-luminance characteristics; and FIG. 90, the emission spectrum. Main characteristics of the light-emitting device 10 at approximately 1000 cd/m$^2$ are listed below.

1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153:

TABLE 16

| | voltage (V) | current (mA) | current density (mA/cm$^2$) | chromaticity x | chromaticity y | current efficiency (cd/A) | external quantum efficiency (%) |
|---|---|---|---|---|---|---|---|
| light-emitting device 10 | 5.2 | 0.36 | 9.0 | 0.14 | 0.12 | 10.6 | 10.8 |

It was found from FIG. 85 to FIG. 90 that the light-emitting device 10, which is the light-emitting device of one embodiment of the present invention, is an EL device with high emission efficiency.

bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion,

The invention claimed is:

1. An organic compound represented by General Formula (G1),

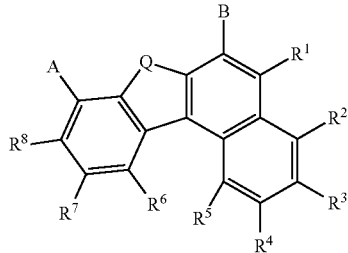

(G1)

wherein:
Q represents an oxygen atom or a sulfur atom,
one of A and B represents a group represented by General Formula (g1-2) and the other represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms,
$R^1$ to $R^8$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms,

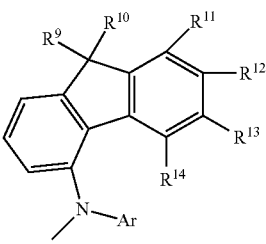

(g1-2)

$R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group,
$R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms, and
Ar represents a substituted or unsubstituted aryl group having 6 to 13 carbon atoms.

2. The organic compound according to claim 1, wherein the General Formula (G1) is represented by General Formula (G1-1),

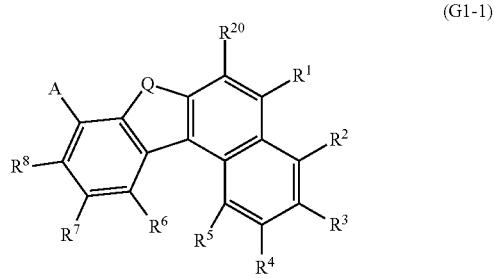

(G1-1)

wherein:
A represents a group represented by General Formula (g1-2), and
$R^{20}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

3. An organic compound represented by General Formula (G1-2),

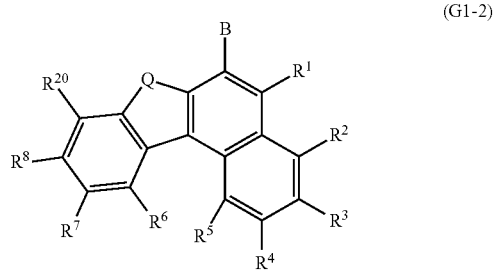

(G1-2)

wherein:
Q represents an oxygen atom or a sulfur atom;
B represents a group represented by General Formula (g1);
$R^{20}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms;
$R^1$ to $R^8$ each independently represent any one of hydrogen, an alkyl group having; to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and an alkyl group of a substituted or unsubstituted aromatic hydrocarbon group having 6 to 60 carbon atoms;

(g1)

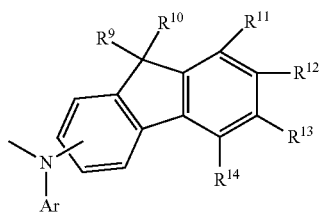

R⁹ and R¹⁰ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group;

R¹¹ to R¹⁴ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms; and Ar represents a substituted or unsubstituted aryl group having 6 to 13 carbon atoms.

4. The organic compound according to claim 1, wherein one of A and B represents hydrogen.

5. The organic compound according to claim 3, wherein the group represented by the General Formula (g1) is a group represented by General Formula (g1-1), (g1-1)

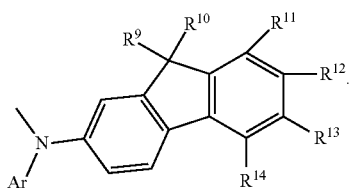

6. The organic compound according to claim 3, wherein the group represented by the General Formula (g1) is a group represented by General Formula (g1-2), (g1-2)

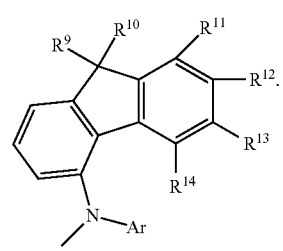

7. The organic compound according to claim 3, wherein Ar is represented by any one of General Formulae (Ar-1) to (Ar-3), and (Ar-1)

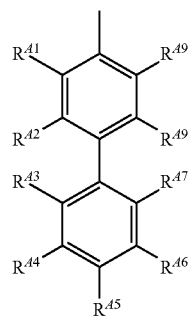

(Ar-2)

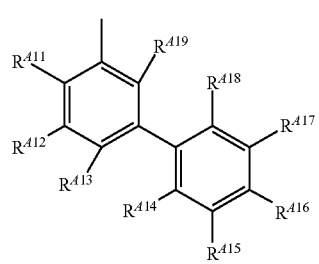

(Ar-3)

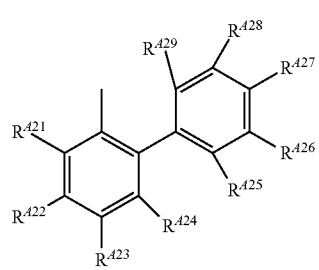

wherein $R^{A1}$ to $R^{A9}$, $R^{A11}$ to $R^{A19}$, and $R^{A21}$ to $R^{A29}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

8. The organic compound according to claim 7, wherein $R^{A1}$ to $R^{A9}$, $R^{A11}$ to $R^{A19}$, and $R^{A21}$ to $R^{A29}$ each represent hydrogen.

9. The organic compound according to claim 1, wherein R⁹ and R¹⁰ each represent a methyl group.

10. The organic compound according to claim 1, wherein R¹ and R⁸ each represent hydrogen.

11. The organic compound according to claim 1, wherein R¹¹ to R¹⁴ each represent hydrogen.

12. The organic compound according to claim 1, wherein Q represents an oxygen atom.

13. The organic compound according to claim 1, wherein Ar is represented by any one of General Formulae (Ar-1) to (Ar-3), and

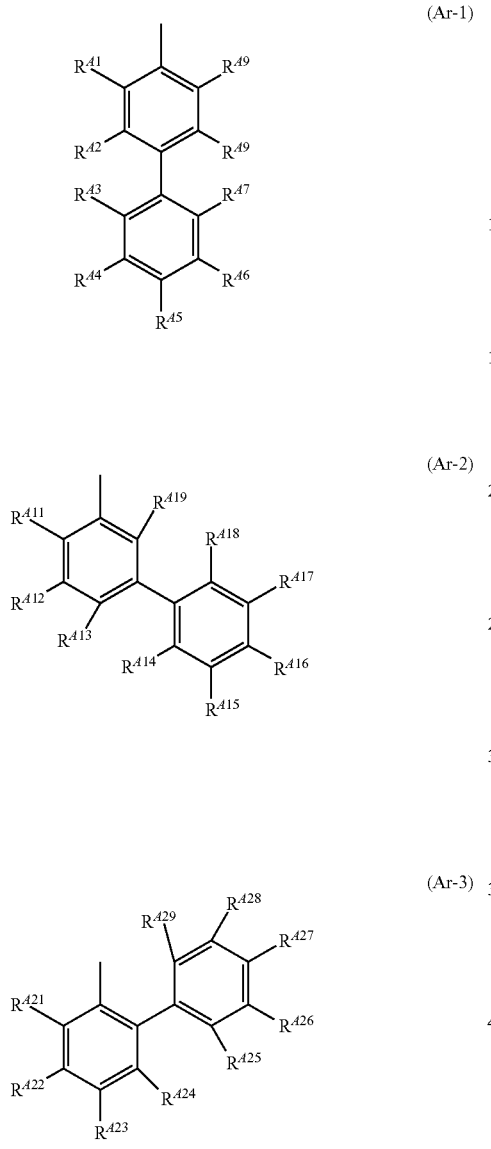

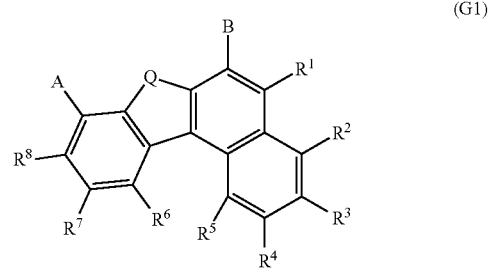

wherein:

Q represents an oxygen atom or a sulfur atom;

one of A and B represents a group represented by General Formula (g1) and the other represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms;

$R^1$ to $R^8$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms;

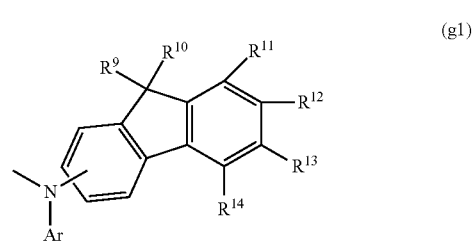

wherein $R^{A1}$ to $R^{A9}$, $R^{A11}$ to $R^{A19}$, and $R^{A21}$ to $R^{A29}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

14. The organic compound according to claim 13, wherein $R^{A1}$ to $R^{A9}$, $R^{A11}$ to $R^{A19}$, and $R^{A21}$ to $R^{A29}$ each represent hydrogen.

15. The organic compound according to claim 3, wherein $R^9$ and $R^{10}$ each represent a methyl group.

16. The organic compound according to claim 3, wherein $R^1$ and $R^8$ each represent hydrogen.

17. The organic compound according to claim 3, wherein Q represents an oxygen atom.

18. An organic compound represented by General Formula (G1), $R^9$ and $R^{10}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted phenyl group;

$R^{11}$ to $R^{14}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms;

Ar is represented by any one of General Formulae (Ar-1) to (Ar-3),

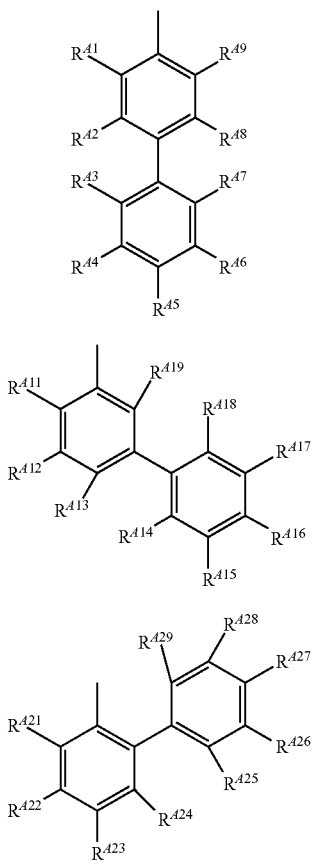

(Ar-1)

(Ar-2)

(Ar-3)

$R^{A1}$ to $R^{A4}$, $R^{A6}$ to $R^{A9}$, $R^{A11}$ to $R^{A19}$, and $R^{A21}$ to $R^{A29}$ each independently represent any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms; and $R^{A5}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, a biphenyl group, and a fluorenyl group.

19. The organic compound according to claim 18, wherein the General Formula (G1) is represented by General Formula (G1-1),

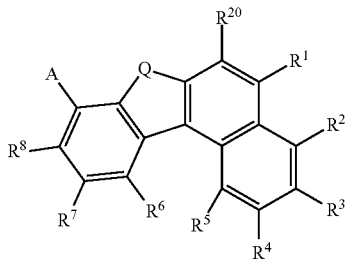

(G1-1)

wherein:

A represents a group represented by General Formula (g1); and $R^{20}$ represents any one of hydrogen, an alkyl group having 1 to 6 carbon atoms, a cyclic hydrocarbon group having 3 to 6 carbon atoms, an alkoxy group having 1 to 6 carbon atoms, a cyano group, a halogen, a haloalkyl group having 1 to 6 carbon atoms, and a substituted or unsubstituted aromatic hydrocarbon group having 6 to 60 carbon atoms.

20. The organic compound according to claim 18, wherein the group represented by the General Formula (g1) is a group represented by General Formula (g1-1),

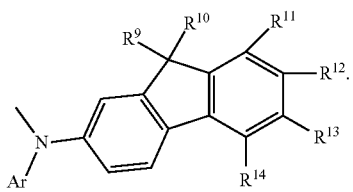

(g1-1)

* * * * *